US011590224B2

(12) United States Patent
Hicklin et al.

(10) Patent No.: US 11,590,224 B2
(45) Date of Patent: *Feb. 28, 2023

(54) ANTI-TIGIT ANTIGEN-BINDING PROTEINS AND METHODS OF USES THEREOF

(71) Applicant: Potenza Therapeutics, Inc., Cambridge, MA (US)

(72) Inventors: Daniel Hicklin, Montclair, NJ (US); William Winston, Marlborough, MA (US); Cynthia S. Dugan, Belmont, MA (US); Nels P. Nielson, Lebanon, NH (US)

(73) Assignee: Potenza Therapeutics, Inc., Cambridge, MA (US)

( * ) Notice: Subject to any disclaimer, the term of this patent is extended or adjusted under 35 U.S.C. 154(b) by 477 days.

This patent is subject to a terminal disclaimer.

(21) Appl. No.: 16/659,797

(22) Filed: Oct. 22, 2019

(65) Prior Publication Data

US 2020/0101158 A1 Apr. 2, 2020

Related U.S. Application Data

(60) Continuation of application No. 15/627,161, filed on Jun. 19, 2017, now Pat. No. 10,507,244, which is a division of application No. 15/430,998, filed on Feb. 13, 2017, now Pat. No. 9,713,641, which is a continuation of application No. PCT/US2016/054484, filed on Sep. 29, 2016.

(60) Provisional application No. 62/235,990, filed on Oct. 1, 2015.

(51) Int. Cl.
 *A61K 39/395* (2006.01)
 *A61K 39/00* (2006.01)
 *C07K 16/28* (2006.01)

(52) U.S. Cl.
 CPC .... *A61K 39/39558* (2013.01); *C07K 16/2803* (2013.01); *C07K 16/2818* (2013.01); *A61K 2039/505* (2013.01); *A61K 2039/507* (2013.01); *A61K 2039/572* (2013.01); *C07K 2317/14* (2013.01); *C07K 2317/21* (2013.01); *C07K 2317/24* (2013.01); *C07K 2317/33* (2013.01); *C07K 2317/55* (2013.01); *C07K 2317/56* (2013.01); *C07K 2317/565* (2013.01); *C07K 2317/76* (2013.01); *C07K 2317/92* (2013.01); *Y02A 50/30* (2018.01)

(58) Field of Classification Search
 CPC ........ C07K 16/00–468; C07K 16/2803; A61K 35/395–39558
 See application file for complete search history.

(56) References Cited

U.S. PATENT DOCUMENTS

| | | | |
|---|---|---|---|
| 8,354,509 B2 | 1/2013 | Carven et al. |
| 8,431,350 B2 | 4/2013 | Baldwin et al. |
| 8,716,254 B2 | 5/2014 | Xiang et al. |
| 8,822,642 B2 | 9/2014 | Levin et al. |
| 9,499,596 B2 | 11/2016 | Clark et al. |
| 9,713,641 B2 | 7/2017 | Hicklin et al. |
| 10,507,244 B2 | 12/2019 | Hicklin et al. |
| 2004/0005560 A1 | 1/2004 | Isogai et al. |
| 2006/0105376 A1 | 5/2006 | Isogai et al. |
| 2007/0041982 A1 | 2/2007 | Ponath et al. |
| 2007/0054360 A1 | 3/2007 | Gao et al. |
| 2008/0038264 A1 | 2/2008 | Bodary et al. |
| 2008/0050809 A1 | 2/2008 | Abuin et al. |
| 2009/0156495 A1 | 6/2009 | Gao et al. |
| 2009/0181024 A1 | 7/2009 | Baldwin et al. |
| 2009/0258013 A1 | 10/2009 | Clark et al. |
| 2010/0316646 A1 | 12/2010 | Gao et al. |
| 2011/0104170 A1 | 5/2011 | Baldwin et al. |
| 2011/0172114 A1 | 7/2011 | Bodary et al. |
| 2012/0219540 A1 | 8/2012 | Gao et al. |
| 2013/0065791 A1 | 3/2013 | Rosenthal et al. |
| 2013/0095102 A1 | 4/2013 | Levin et al. |
| 2014/0010861 A1 | 1/2014 | Bancel et al. |
| 2014/0056890 A1 | 2/2014 | Gurney et al. |
| 2014/0128277 A1 | 5/2014 | Moller et al. |
| 2016/0176963 A1 | 6/2016 | Maurer et al. |
| 2016/0355589 A1 | 12/2016 | Williams et al. |
| 2017/0165366 A1 | 6/2017 | Hicklin et al. |
| 2020/0095324 A1 | 3/2020 | Nielson et al. |

FOREIGN PATENT DOCUMENTS

| | | |
|---|---|---|
| CA | 2994858 A1 | 3/2017 |
| CA | 3055289 A1 | 10/2018 |
| JP | 2011-523034 A | 8/2011 |
| JP | 2016-525117 A | 8/2016 |
| JP | 2018-536698 A | 12/2018 |
| RU | 2015123032 A | 1/2017 |
| WO | WO-2006/124667 A2 | 11/2006 |

(Continued)

OTHER PUBLICATIONS

Vazquez-Lombardi et al., Drug Discovery Today 20(10): 1271-83 (Year: 2015).*
Anderson et al., Lag-3, Tim-3, and TIGIT: Co-inhibitory Receptors with Specialized Functions in Immune Regulation. Immunity. May 1, 20167;44(5):989-1004.
Anderson et al., Preclinical characterization of AB154, a fully humanized anti-TIGIT antibody, for use in combination therapies. Cancer Immunology Research. Abstract A124, retrieved online at: http://cancerimmunolres.aacrjournals.org/content/7/2_Supplement/A124. 2 page, Feb. 2019.

(Continued)

*Primary Examiner* — Jessica H Roark
(74) *Attorney, Agent, or Firm* — McCarter & English, LLP; Maria Laccotripe Zacharakis

(57) ABSTRACT

Provided herein are antigen-binding proteins (ABPs) that selectively bind to TIGIT and its isoforms and homologs, and compositions comprising the ABPs. Also provided are methods of using the ABPs, such as therapeutic and diagnostic methods.

8 Claims, 50 Drawing Sheets

Specification includes a Sequence Listing.

(56) References Cited

FOREIGN PATENT DOCUMENTS

| | | |
|---|---|---|
| WO | WO-2007/073478 A2 | 6/2007 |
| WO | WO-2009/036379 A2 | 3/2009 |
| WO | WO-2009/126688 A2 | 10/2009 |
| WO | WO-2010/105256 A1 | 9/2010 |
| WO | WO-2011/144718 A2 | 11/2011 |
| WO | WO-2011/156356 A1 | 12/2011 |
| WO | WO-2011/161699 A2 | 12/2011 |
| WO | WO-2012/009568 A2 | 1/2012 |
| WO | 2012/058065 A1 | 5/2012 |
| WO | WO-2013/151665 A2 | 10/2013 |
| WO | 2014/089169 A2 | 6/2014 |
| WO | WO-2014/089113 A1 | 6/2014 |
| WO | WO-2014/179363 A1 | 11/2014 |
| WO | WO-2015/009856 A2 | 1/2015 |
| WO | WO-2016/028656 A1 | 2/2016 |
| WO | WO-2016/073282 A1 | 5/2016 |
| WO | WO-2016/106302 A1 | 6/2016 |
| WO | WO-2016/191643 A2 | 12/2016 |
| WO | WO-2017/037707 A1 | 3/2017 |
| WO | WO-2017/059095 A1 | 4/2017 |

OTHER PUBLICATIONS

Aspeslagh et al., Rationale for anti-OX40 cancer immunotherapy. Eur J Cancer. Jan. 2016;52:50-66.

Ayano et al., Increased CD226 Expression on CD8+ T Cells is Associated with Upregulated Cytokine Production and Endothelial Cell Injury in Patients with Systemic Sclerosis. J Immunol. Aug. 1, 2015;195(3):892-900.

Bashir et al., Fusobacterium nucleatum, inflammation, and immunity: the fire within human gut. Tumour Biol. Mar. 2016;37(3):2805-10.

Bi et al., T-cell Ig and ITIM domain regulates natural killer cell activation in murine acute viral hepatitis. Hepatology. May 2014;59(5):1715-25.

Bi et al., TIGIT safeguards liver regeneration through regulating natural killer cell-hepatocyte crosstalk. Hepatology. Oct. 2014;60(4):1389-98.

Bin Dhuban et al., Coexpression of TIGIT and FCRL3 identifies Helios+ human memory regulatory T cells. J Immunol. Apr. 15, 2015;194(8):3687-96.

Blake et al., Molecular Pathways: Targeting CD96 and TIGIT for Cancer Immunotherapy. Clin Cancer Res. Nov. 1, 2016;22(21):5183-5188.

Blake et al., Suppression of Metastases Using a New Lymphocyte Checkpoint Target for Cancer Immunotherapy. Cancer Discov. Apr. 2016;6(4):446-59.

Boerman et al., Role of NKG2D, DNAM-1 and natural cytotoxicity receptors in cytotoxicity toward rhabdomyosarcoma cell lines mediated by resting and IL-15-activated human natural killer cells. Cancer Immunol Immunother. May 2015;64(5):573-83.

Boles et al., A novel molecular interaction for the adhesion of follicular CD4 T cells to follicular DC. Eur J Immunol. Mar. 2009;39(3):695-703.

Bottino et al., Identification of PVR (CD155) and Nectin-2 (CD112) as cell surface ligands for the human DNAM-1 (CD226) activating molecule. J Exp Med. Aug. 18, 2003;198(4):557-67.

Braun et al., Blockade of death receptor-mediated pathways early in the signaling cascade coincides with distinct apoptosis resistance in cutaneous T-cell lymphoma cells. J Invest Dermatol. Oct. 2007;127(10):2425-37.

Burchill et al., Memory re-differentiation and reduced lymphocyte activation in chronic HCV-infected patients receiving direct-acting antivirals. J Viral Hepat. Dec. 2015;22(12):983-91.

Burton et al., Sequential transcriptional changes dictate safe and effective antigen-specific immunotherapy. Nat Commun. Sep. 3, 2014;5:4741. 13 pages.

Butcher et al., Atherosclerosis-Driven Treg Plasticity Results in Formation of a Dysfunctional Subset of Plastic IFN?+ Th1/Tregs. Circ Res. Nov. 11, 2016;119(11):1190-1203.

Chan et al., Receptors that interact with nectin and nectin-like proteins in the immunosurveillance and immunotherapy of cancer. Curr Opin Immunol. Apr. 2012;24(2):246-51.

Chan et al., The receptors CD96 and CD226 oppose each other in the regulation of natural killer cell functions. Nat Immunol. May 2014;15(5):431-8.

Chan et al., Therapeutic antibodies for autoimmunity and inflammation. Nat Rev Immunol. May 2010;10(5):301-16.

Chauvin et al., TIGIT and PD-1 impair tumor antigen-specific CD8? T cells in melanoma patients. J Clin Invest. May 2015;125(5):2046-58.

Chen et al., TIGIT negatively regulates inflammation by altering macrophage phenotype. Immunobiology. Jan. 2016;221(1):48-55.

Chew et al., TIGIT Marks Exhausted T Cells, Correlates with Disease Progression, and Serves as a Target for Immune Restoration in HIV and SIV Infection. PLoS Pathog. Jan. 7, 2016;12(1):e1005349. 28 pages.

Chruscinski et al., Role of Regulatory T Cells (Treg) and the Treg Effector Molecule Fibrinogen-like Protein 2 in Alloimmunity and Autoimmunity. Rambam Maimonides Med J. Jul. 30, 2015;6(3):e0024. 17 pages.

De Andrade et al., DNAM-1 control of natural killer cells functions through nectin and nectin-like proteins. Immunol Cell Biol. Mar. 2014;92(3):237-44.

El-Sherbiny et al., The requirement for DNAM-1, NKG2D, and NKp46 in the natural killer cell-mediated killing of myeloma cells. Cancer Res. Sep. 15, 2007;67(18):8444-9.

Elahi et al., Atorvastatin restricts HIV replication in CD4+ T cells by upregulation of p21. AIDS. Jan. 2016;30(2):171-83.

Elhai et al., Targeting CD226/DNAX accessory molecule-1 (DNAM-1) in collagen-induced arthritis mouse models. J Inflamm (Lond). Feb. 8, 2015;12:9. 12 pages.

Fionda et al., Nitric oxide donors increase PVR/CD155 DNAM-1 ligand expression in multiple myeloma cells: role of DNA damage response activation. BMC Cancer. 2015;15(17):1-14.

Foks et al., Agonistic anti-TIGIT treatment inhibits T cell responses in LDLr deficient mice without affecting atherosclerotic lesion development. PLoS One. Dec. 20, 2013;8(12):e83134. 7 pages.

Fromentin et al., CD4+ T Cells Expressing PD-1, TIGIT and LAG-3 Contribute to HIV Persistence during ART. PLoS Pathog. Jul. 14, 2016;12(7):e1005761. 19 pages.

Fuhrman et al., Divergent Phenotypes of Human Regulatory T Cells Expressing the Receptors TIGIT and CD226. J Immunol. Jul. 1, 2015;195(1):145-55.

Gao et al., Generation and characterization of polyclonal antibodies against mouse T-cell immunoglobulin and immunoreceptor tyrosine-based inhibitory domain by DNA-based immunization. Transplant Proc. Jan.-Feb. 2014;46(1):260-5.

GenBank Accession No. NM_173799.3, *Homo sapiens* T cell immunoreceptor with Ig and ITIM domains (TIGIT), mRNA. Aug. 28, 2016, 5 pages.

Georgiev et al., CD155/CD226-interaction impacts on the generation of innate CD8(+) thymocytes by regulating iNKT-cell differentiation. Eur J Immunol. Apr. 2016;46(4):993-1003.

Georgiev et al., To the editor: TIGIT versus CD226: hegemony or coexistence? Eur J Immunol. Jan. 2014;44(1):307-8.

Godefroy et al., TIGIT-positive circulating follicular helper T cells display robust B-cell help functions: potential role in sickle cell alloimmunization. Haematologica. Nov. 2015;100(11):1415-25.

Goding et al., Restoring immune function of tumor-specific CD4+ T cells during recurrence of melanoma. J Immunol. May 1, 2013;190(9):4899-909.

Grauwet et al., Modulation of CD112 by the alphaherpesvirus gD protein suppresses DNAM-1-dependent NK cell-mediated lysis of infected cells. Proc Natl Acad Sci USA. Nov. 11, 2014;111(45):16118-23.

Grogan et al., TIGIT inhibits CD8+ T cell effector function during chronic viral infection and cancer (TUM7P.933). J Immunol. May 1, 2014;192(Suppl 1):203.15.

Guillerey et al., Immunosurveillance and therapy of multiple myeloma are CD226 dependent. J Clin Invest. May 2015;125(5):2077-89.

(56) References Cited

OTHER PUBLICATIONS

Gur et al., Binding of the Fap2 protein of Fusobacterium nucleatum to human inhibitory receptor TIGIT protectstumors from immune cell attack. Immunity. Feb. 17, 2015;42(2):344-355.
Hosken et al., The effect of antigen dose on CD4+ T helper cell phenotype development in a T cell receptor-alpha beta-transgenic model. J Exp Med. Nov. 1, 1995;182(5):1579-84.
Hou et al., Recombinant soluble CD226 protein directly inhibits cancer cell proliferation in vitro. Int Immunopharmacol. Mar. 2014;19(1):119-26.
Huntington et al., DNAM-1: would the real natural killer cell please stand up! Oncotarget. Oct. 6, 2015;6(30):28537-8.
Iguchi-Manaka et al., Increased Soluble CD155 in the Serum of Cancer Patients. PLoS One. Apr. 6, 2016;11(4):e0152982. 12 pages.
Inozume et al., Melanoma Cells Control Anti-Melanoma CTL Responses via Interaction between TIGIT and CD155 in the Effector Phase. J Invest Dermatol. Jan. 2016;136(1):255-263.
Jariwala et al., TIGIT and Helios are Highly Expressed on CD4(+) T Cells in Sézary Syndrome Patients. J Invest Dermatol. Jan. 2017;137(1):257-260.
Jian et al., Identification and characterization of the CD226 gene promoter. J Biol Chem. Sep. 29, 2006;281(39):28731-6.
Johnston et al., The checkpoint inhibitor TIGIT limits antitumor and antiviral CD8(+) T cell responses. Oncoimmunology. May 27, 2015;4(9):e1036214. 2 pages.
Johnston et al., The immunoreceptor TIGIT regulates antitumor and antiviral CD8(+) T cell effector function. Cancer Cell. Dec. 8, 2014;26(6):923-937.
Joller et al., Cutting edge: TIGIT has T cell-intrinsic inhibitory functions. J Immunol. Feb. 1, 2011;186(3):1338-42.
Joller et al., Immune checkpoints in central nervous system autoimmunity. Immunol Rev. Jul. 2012;248(1):122-39.
Joller et al., Treg cells expressing the coinhibitory molecule TIGIT selectively inhibit proinflammatory Th1 and Th17 cell responses. Immunity. Apr. 17, 2014;40(4):569-81.
Kamran et al., Toll-like receptor ligands induce expression of the costimulatory molecule CD155 on antigen-presenting cells. PLoS One. 2013;8(1):e54406. 13 pages.
Kinosada et al., HTLV-1 bZIP Factor Enhances T-Cell Proliferation by Impeding the Suppressive Signaling of Co-inhibitory Receptors. PLoS Pathog. Jan. 3, 2017;13(1):e1006120. With Correction: HTLV-1 bZIP Factor Enhances T-cell Proliferation by Impeding the Suppressive Signaling of Co-inhibitory Receptors. PLoS Pathog. Feb. 23, 2017;13(2):e1006228.
Klemke et al., Lack of T-cell receptor-induced signaling is crucial for CD95 ligand up-regulation and protects cutaneous T-cell lymphoma cells from activation-induced cell death. Cancer Res. May 15, 2009;69(10):4175-83.
Kong et al., T-Cell Immunoglobulin and ITIM Domain (TIGIT) Associates with CD8+ T-Cell Exhaustion and Poor Clinical Outcome in AML Patients. Clin Cancer Res. Jun. 15, 2016;22(12):3057-66.
Kourepini et al., TIGIT Enhances Antigen-Specific Th2 Recall Responses and Allergic Disease. J Immunol. May 1, 2016;196(9):3570-80.
Kurtulus et al., TIGIT predominantly regulates the immune response via regulatory T cells. J Clin Invest. Nov. 2, 2015;125(11):4053-62.
Le Mercier et al., Beyond CTLA-4 and PD-1, the Generation Z of Negative Checkpoint Regulators. Front Immunol. Aug. 21, 2015;6:418. 15 pages.
Lenac Rovis et al., Inflammatory monocytes and NK cells play a crucial role in DNAM-1-dependent control of cytomegalovirus infection. J Exp Med. Aug. 22, 2016;213(9):1835-50.
Levin et al., Vstm3 is a member of the CD28 family and an important modulator of T-cell function. Eur J Immunol. Apr. 2011;41(4):902-15.
Li et al., CD226 as a genetic adjuvant to enhance immune efficacy induced by Ag85A DNA vaccination. Int Immunopharmacol. Mar. 2015;25(1):10-8.

Li et al., Expression of glucocorticoid induced TNF receptor family related protein (GITR) on peripheral T cells from normal human donors and patients with non-infectious uveitis. J Autoimmun. Aug. 2003;21(1):83-92.
Li et al., T-cell immunoglobulin and ITIM domain (TIGIT) receptor/ poliovirus receptor (PVR) ligand engagement suppresses interferon-? production of natural killer cells via β-arrestin 2-mediated negative signaling. J Biol Chem. Jun. 20, 2014;289(25):17647-57.
Liu et al., Crystal structure of cell adhesion molecule nectin-2/ CD112 and its binding to immune receptor DNAM-1/CD226. J Immunol. Jun. 1, 2012;188(11):5511-20.
Liu et al., Recruitment of Grb2 and SHIP1 by the ITT-like motif of TIGIT suppresses granule polarization and cytotoxicity of NK cells. Cell Death Differ. Mar. 2013;20(3):456-64.
Lozano et al., The TIGIT/CD226 axis regulates human T cell function. J Immunol. Apr. 15, 2012;188(8):3869-75.
Mahnke et al., TIGIT-CD155 Interactions in Melanoma: A Novel Co-Inhibitory Pathway with Potential for Clinical Intervention. J Invest Dermatol. Jan. 2016;136(1):9-11.
Manieri et al., TIGIT: A Key Inhibitor of the Cancer Immunity Cycle. Trends Immunol. Jan. 2017;38(1):20-28.
Martinet et al., Balancing natural killer cell activation through paired receptors. Nat Rev Immunol. Apr. 2015;15(4):243-54.
Martinet et al., DNAM-1 expression marks an alternative program of NK cell maturation. Cell Rep. Apr. 7, 2015;11(1):85-97.
Mirjacic Martinovic et al., Decreased expression of NKG2D, NKp46, DNAM-1 receptors, and intracellular perforin and STAT-1 effector molecules in NK cells and their dim and bright subsets in metastatic melanoma patients. Melanoma Res. Aug. 2014;24(4):295-304.
Moorman et al., Tim-3 pathway controls regulatory and effector T cell balance during hepatitis C virus infection. J Immunol. Jul. 15, 2012;189(2):755-66.
Nagumo et al., Increased CD112 expression in methylcholanthrene-induced tumors in CD155-deficient mice. PLoS One. Nov. 10, 2014;9(11):e112415. 7 pages.
Ni et al., Resistance to activation-induced cell death and bystander cytotoxicity via the Fas/Fas ligand pathway are implicated in the pathogenesis of cutaneous T cell lymphomas. J Invest Dermatol. Apr. 2005;124(4):741-50.
Nishiwada et al., Clinical significance of CD155 expression in human pancreatic cancer. Anticancer Res. Apr. 2015;35(4):2287-97.
Oshima et al., Nectin-2 is a potential target for antibody therapy of breast and ovarian cancers. Mol Cancer. Jun. 12, 2013;12:60. 13 pages.
Panka et al., Variable region framework differences result in decreased or increased affinity of variant anti-digoxin antibodies. Proc Natl Acad Sci USA. May 1988;85(9):3080-4.
Pearson, Tragic drug trial spotlights potent molecule. Nature. Retrieved online at: https://www.nature.com/news/2006/060313/full/060313-17.html. Mar. 17, 2006.
Peng et al., Altered expression of CD226 and CD96 on natural killer cells in patients with pancreatic cancer. Oncotarget. Oct. 11, 2016;7(41):66586-66594.
Piedavent-Salomon et al., Multiple sclerosis associated genetic variants of CD226 impair regulatory T cell function. Brain. Nov. 2015;138(Pt 11):3263-74.
Pirenne, TIGIT-positive circulating follicular helper T cells and sickle cell alloimmunization. Haematologica. Nov. 2015;100(11):1371-3.
Qu et al., Loss of CD155 expression predicts poor prognosis in hepatocellular carcinoma. Histopathology. Apr. 2015;66(5):706-14.
Rudikoff et al., Single amino acid substitution altering antigen-binding specificity. Proc Natl Acad Sci U S A. Mar. 1982;79(6):1979-83.
Rueda et al., Effect of chorioamnionitis on regulatory T cells in moderate/late preterm neonates. Hum Immunol. Jan. 2015;76(1):65-73.
Ruggeri et al., Animal models of disease: pre-clinical animal models of cancer and their applications and utility in drug discovery. Biochem Pharmacol. Jan. 1, 2014;87(1):150-61.
Samanta et al., Nectin family of cell-adhesion molecules: structural and molecular aspects of function and specificity. Cell Mol Life Sci. Feb. 2015;72(4):645-58.

(56) References Cited

OTHER PUBLICATIONS

Samanta et al., Structural, mutational and biophysical studies reveal a canonical mode of molecular recognition between immune receptor TIGIT and nectin-2. Mol Immunol. Jan. 2017;81:151-159.
Sanmamed et al., Agonists of Co-stimulation in Cancer Immunotherapy Directed Against CD137, OX40, GITR, CD27, CD28, and ICOS. Seminars in Oncology. Aug. 2015;42(4):640-655.
Serr et al., Type 1 diabetes vaccine candidates promote human Foxp3(+)Treg induction in humanized mice. Nat Commun. Mar. 15, 2016;7:10991. 18 pages.
Seth et al., Abundance of follicular helper T cells in Peyer's patches is modulated by CD155. Eur J Immunol. Nov. 2009;39(11):3160-70.
Sheiko et al., CD4+ and CD8+ T Cell Activation in Children with Hepatitis C. J Pediatr. Mar. 2016;170:142-8.e1.
Shibuya et al., CD226 (DNAM-1) is involved in lymphocyte function-associated antigen 1 costimulatory signal for naive T cell differentiation and proliferation. J Exp Med. Dec. 15, 2003;198(12):1829-39.
Shibuya et al., DNAM-1, a novel adhesion molecule involved in the cytolytic function of T lymphocytes. Immunity. Jun. 1996;4(6):573-81.
Shon et al., Survivin reduces activation-induced T cell death in G1 phase. Mol Cells. Oct. 31, 2003;16(2):147-53.
Siegel et al., High efficiency recovery and epitope-specific sorting of an scFv yeast display library. J Immunol Methods. Mar. 2004;286(1-2):141-53.
Siew et al., Oxaliplatin regulates expression of stress ligands in ovarian cancer cells and modulates their susceptibility to natural killer cell-mediated cytotoxicity. Int Immunol. Dec. 2015;27(12):621-32.
Smith et al., Sensitivity of dendritic cells to NK-mediated lysis depends on the inflammatory environment and is modulated by CD54/CD226-driven interactions. J Leukoc Biol. Oct. 2016;100(4):781-789.
Solomon et al., TIGIT: a novel immunotherapy target moving from bench to bedside. Cancer Immunol Immunother. Nov. 2018;67(11):1659-1667.
Son et al., Nectin-2 (CD112) is Expressed on Outgrowth Endothelial Cells and Regulates Cell Proliferation and Angiogenic Function. PLoS One. Sep. 27, 2016;11(9):e0163301. 16 pages.
Stanietsky et al., Mouse TIGIT inhibits NK-cell cytotoxicity upon interaction with PVR. Eur J Immunol. Aug. 2013;43(8):2138-50.
Stanietsky et al., Paired NK cell receptors controlling NK cytotoxicity. FEBS Lett. Dec. 15, 2010;584(24):4895-900.
Stanietsky et al., The interaction of TIGIT with PVR and PVRL2 inhibits human NK cell cytotoxicity. Proc Natl Acad Sci U S A. Oct. 20, 2009;106(42):17858-63.
Stein et al., The paired receptors TIGIT and DNAM-1 as targets for therapeutic antibodies. Hum Antibodies. 2017;25(3-4):111-119.
Stengel et al., Structure of TIGIT immunoreceptor bound to poliovirus receptor reveals a cell-cell adhesion and signaling mechanism that requires cis-trans receptor clustering. Proc Natl Acad Sci U S A. Apr. 3, 2012;109(14):5399-404.
Sun et al., Expression regulation of co-inhibitory molecules on human natural killer cells in response to cytokine stimulations. Cytokine. Jan. 2014;65(1):33-41.
Tahara-Hanaoka et al., Functional characterization of DNAM-1 (CD226) interaction with its ligands PVR (CD155) and nectin-2 (PRR-2/CD112). Int Immunol. Apr. 2004;16(4):533-8.
Tassi et al., Early Effector T Lymphocytes Coexpress Multiple Inhibitory Receptors in Primary Non-Small Cell Lung Cancer. Cancer Res. Feb. 15, 2017;77(4):851-861.
Tauriainen et al., Perturbed CD8+ T cell TIGIT/CD226/PVR axis despite early initiation of antiretroviral treatment in HIV infected individuals. Scientific Reports. Jan. 13, 2017;7(40354):1-14.
Vitetta et al., Immunology. Considering therapeutic antibodies. Science. Jul. 21, 2006;313(5785):308-9.
Wang et al., NK cells play a significant role in immunosurveillance at the early stage of MLL-AF9 acute myeloid leukemia via CD226/CD155 interactions. Sci China Life Sci. Dec. 2015;58(12):1288-98.
Wang et al., TIGIT expression levels on human NK cells correlate with functional heterogeneity among healthy individuals. Eur J Immunol. Oct. 2015;45(10):2886-97.
Weinmann, Cancer Immunotherapy: Selected Targets and Small-Molecule Modulators. ChemMedChem. Mar. 4, 2016;11(5):450-66. doi: 10.1002/cmdc.201500566. Epub Feb. 2, 2016. Review. Erratum in: ChemMedChem. Jul. 19, 2016;11(14 ):1576.
White et al., Tr1-Like T Cells—An Enigmatic Regulatory T Cell Lineage. Front Immunol. Sep. 14, 2016;7:355. 7 pages.
Wu et al., DNAM-1-based chimeric antigen receptors enhance T cell effector function and exhibit in vivo efficacy against melanoma. Cancer Immunol Immunother. Apr. 2015;64(4):409-18.
Xie et al., Expression of immune checkpoints in T cells of esophageal cancer patients. Oncotarget. Sep. 27, 2016;7(39):63669-63678.
Xu et al., Addressing polyspecificity of antibodies selected from an in vitro yeast presentation system: a FACS-based, high-throughput selection and analytical tool. Protein Eng Des Sel. Oct. 2013;26(10):663-70.
Yamamoto et al., Comprehensive analysis of FOXP3 mRNA expression in leukemia and transformed cell lines. Leuk Res. Apr. 2008;32(4):651-8.
Yamashita-Kanemaru et al., CD155 (PVR/Necl5) mediates a costimulatory signal in CD4+ T cells and regulates allergic inflammation. J Immunol. Jun. 15, 2015;194(12):5644-53.
Yang et al., DNA methylation and childhood asthma in the inner city. J Allergy Clin Immunol. Jul. 2015;136(1):69-80.
Yano et al., Defucosylated anti CC chemokine receptor 4 monoclonal antibody combined with immunomodulatory cytokines: a novel immunotherapy for aggressive/refractory Mycosis fungoides and Sezary syndrome. Clin Cancer Res. Nov. 1, 2007;13(21):6494-500.
Yasuma et al., HTLV-1 bZIP Factor Impairs Anti-viral Immunity by Inducing Co-inhibitory Molecule, T Cell Immunoglobulin and ITIM Domain (TIGIT). PLoS Pathog. Jan. 6, 2016;12(1):e1005372. 22 pages.
Yu et al., The surface protein TIGIT suppresses T cell activation by promoting the generation of mature immunoregulatory dendritic cells. Nat Immunol. Jan. 2009;10(1):48-57.
Zhang et al., CD226 ligation protects against EAE by promoting IL-10 expression via regulation of CD4+ T cell differentiation. Oncotarget. Apr. 12, 0162;7(15):19251-64.
Zhang et al., DNAM-1 controls NK cell activation via an ITT-like motif. J Exp Med. Nov. 16, 2015;212(12):2165-82.
Zhang et al., Genome-wide DNA methylation analysis identifies hypomethylated genes regulated by FOXP3 in human regulatory T cells. Blood. Oct. 17, 2013;122(16):2823-36.
Zhang et al., Immunoreceptor TIGIT inhibits the cytotoxicity of human cytokine-induced killer cells by interacting with CD155. Cancer Immunol Immunother. Mar. 2016;65(3):305-14.
Zhang et al., Increased expression of TIGIT on CD4+ T cells ameliorates immune-mediated bone marrow failure of aplastic anemia. J Cell Biochem. Nov. 2014;115(11):1918-27.
Zhang et al., MicroRNAs in CD4(+) T cell subsets are markers of disease risk and T cell dysfunction in individuals at risk for type 1 diabetes. J Autoimmun. Apr. 2016;68:52-61.
Zhang et al., Profiling the dynamic expression of checkpoint molecules on cytokine-induced killer cells from non-small-cell lung cancer patients. Oncotarget. Jul. 12, 2016;7(28):43604-43615.
Zhao et al., TIGIT overexpression diminishes the function of CD4 T cells and ameliorates the severity of rheumatoid arthritis in mouse models. Exp Cell Res. Jan. 1, 2016;340(1):132-8.
Zhu et al., Identification of CD112R as a novel checkpoint for human T cells. J Exp Med. Feb. 8, 2016;213(2):167-76.
International Search Report for Application No. PCT/US2016/054484, dated Jan. 25, 2017, 22 pages.
Invitation to Pay Additional Fees for Application No. PCT/US2016/054484, dated Dec. 2, 2016, 11 pages.
U.S. Appl. No. 14/221,160, filed Mar. 20, 2014, 102 pages.
U.S. Appl. No. 14/228,172, filed Mar. 27, 2014,101 pages.
U.S. Appl. No. 14/228,173, filed Mar. 27, 2014, 102 pages.

(56) References Cited

OTHER PUBLICATIONS

U.S. Appl. No. 14/699,845, filed Apr. 29, 2015, 100 pages.
U.S. Office Action for U.S. Appl. No. 15/430,998, dated Mar. 20, 2017, 7 pages.

* cited by examiner

Figure 1B

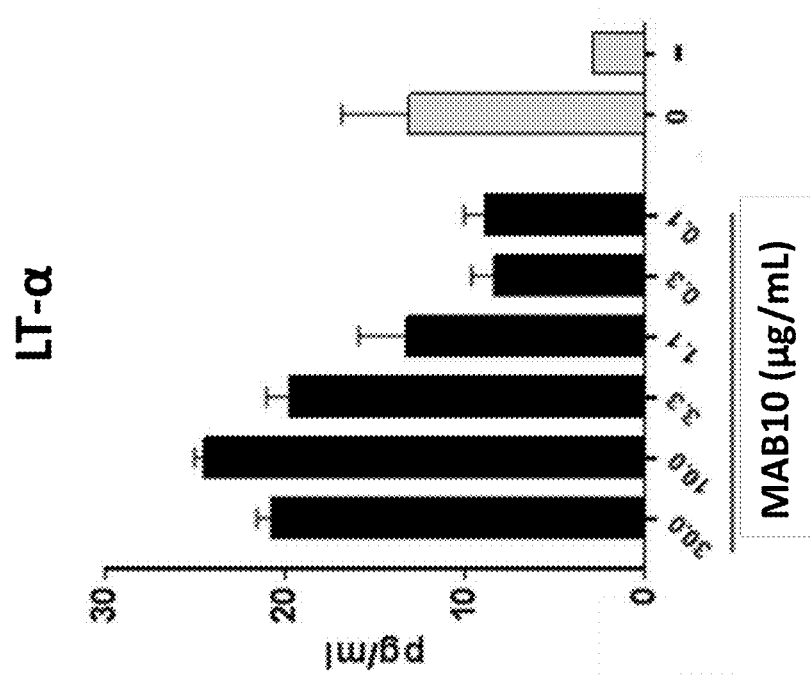

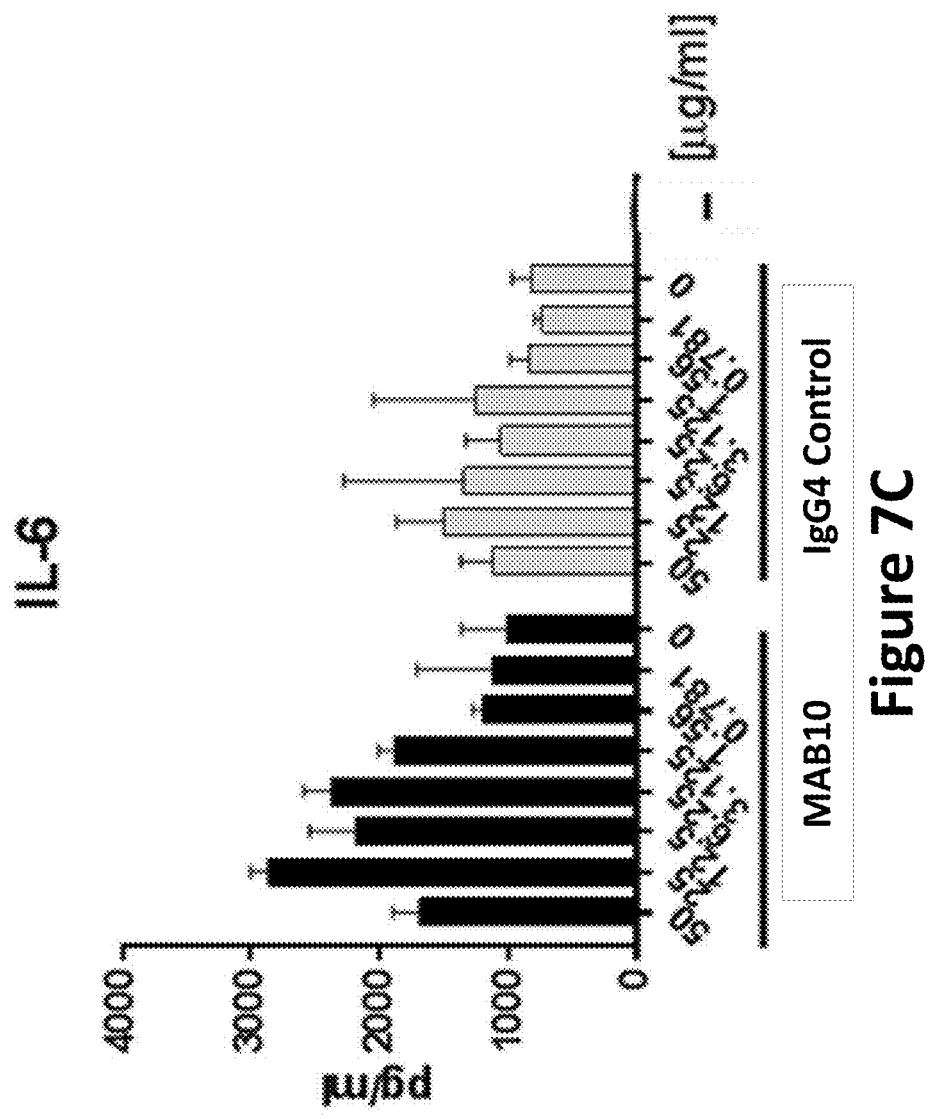

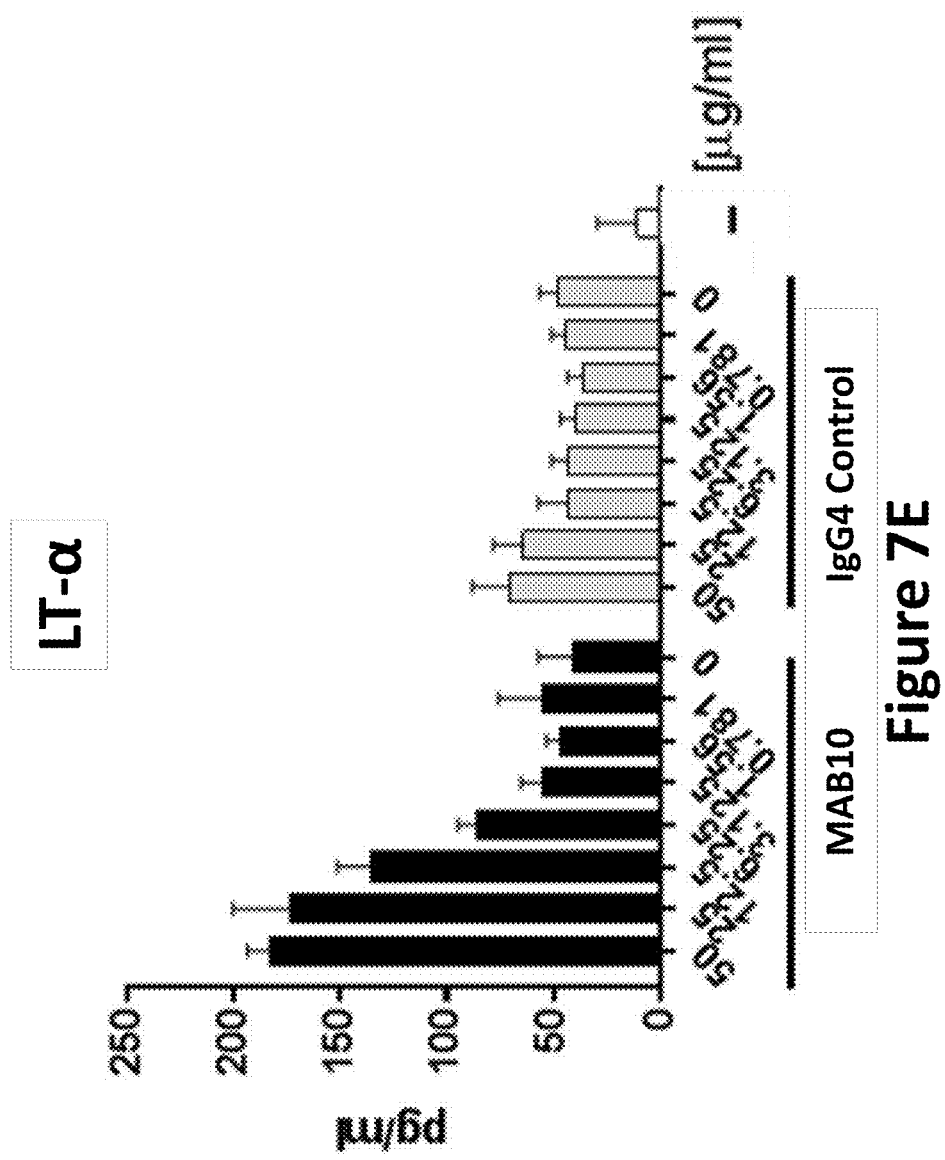

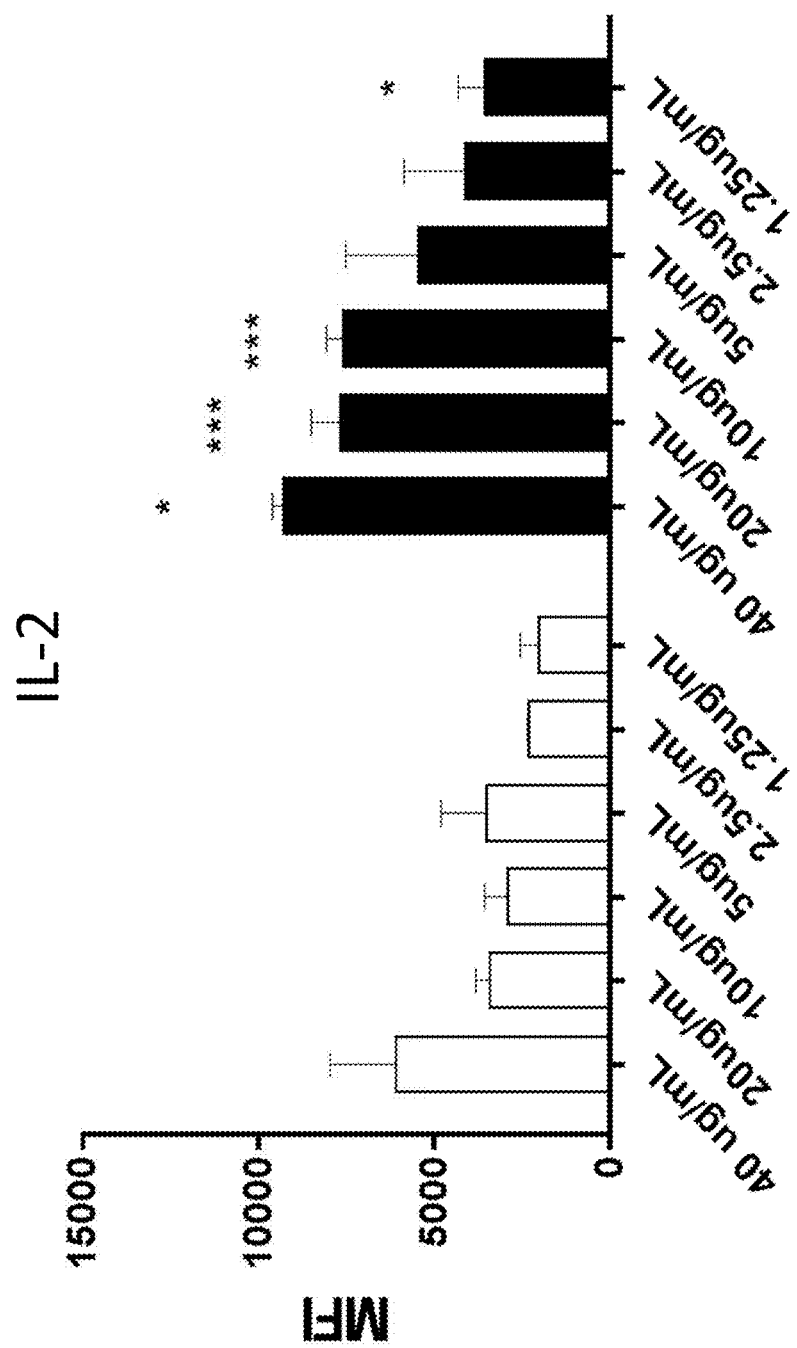

ANTI-TIGIT ANTIGEN-BINDING PROTEINS AND METHODS OF USES THEREOF

This application is a continuation application of U.S. application Ser. No. 15/627,161, filed Jun. 19, 2017, which is a divisional of U.S. application Ser. No. 15/430,998, filed Feb. 13, 2017, now U.S. Pat. No. 9,713,641, issued Jul. 25, 2017, which is a continuation of PCT/US2016/054484, filed Sep. 29, 2016, which claims the benefit of U.S. Provisional Application No. 62/235,990, filed Oct. 1, 2015. The entire contents of each of the foregoing applications are hereby incorporated-herein by reference.

SEQUENCE LISTING

The instant application contains a Sequence Listing which has been submitted electronically in ASCII format and is hereby incorporated by reference in its entirety. Said ASCII copy, created on Oct. 21, 2019, is named 127206-03504_SL.txt and is 261,191 bytes in size.

FIELD

Provided herein are antigen-binding proteins (ABPs) with binding specificity for T cell immunoreceptor with Ig and ITIM domains (TIGIT) and compositions comprising such ABPs, including pharmaceutical compositions, diagnostic compositions, and kits. Also provided are methods of making TIGIT ABPs, and methods of using TIGIT ABPs, for example, for therapeutic purposes, diagnostic purposes, and research purposes.

BACKGROUND

TIGIT has been identified as a co-inhibitory receptor that limits the response of T cells to cancer and chronic infection. See Grogan et al., *J. Immunol.*, 2014, 192: (1 Supplement) 203.15., incorporated by reference in its entirety. Blockade of TIGIT has been shown to contribute to the enhancement CD8+ T cell effector function, and improvement of viral clearance and tumor rejection. See id.

Thus, there is a need for therapeutics that can antagonize TIGIT. Provided herein are ABPs that fulfill this need.

SUMMARY

Provided herein are ABPs that specifically bind TIGIT and methods of using such ABPs.

In some embodiments, the TIGIT is selected from human TIGIT ("hTIGIT", SEQ ID NO: 1), cynomolgus monkey TIGIT ("cTIGIT", SEQ ID NO:2), and murine TIGIT ("mTIGIT", SEQ ID NO:3 or 138).

In some embodiments, the ABP comprises an antibody. In some aspects, the antibody is a monoclonal antibody. In some aspects, the antibody is a chimeric antibody. In some aspects, the antibody is a humanized antibody. In some aspects, the antibody is a human antibody. In some aspects, the ABP comprises an antibody fragment. In some embodiments, the ABP comprises an alternative scaffold.

In some embodiments, the TIGIT is expressed on the surface of a target cell. In some aspects, the ABP antagonizes TIGIT expressed on the surface of the target cell.

In some embodiments, the target cell is selected from an effector T cell, a regulatory T cell, a natural killer (NK) cell, and a natural killer T (NKT) cell. In some aspects, the target cell is an effector T cell selected from a helper (CD4-positive, "CD4+") T cell, a cytotoxic (CD8-positive, "CD8+") T cell, and combinations thereof. In some aspects, the target cell is a regulatory T cell selected from a CD4+CD25+Foxp3+ regulatory T cell, a CD8+CD25+ regulatory T cell, and combinations thereof.

In some embodiments, the ABPs provided herein induce various biological effects associated with inhibition of TIGIT. In some aspects, an ABP provided herein prevents inhibition of an effector T cell. In some aspects, the ABP co-stimulates an effector T cell. In some aspects, the ABP inhibits the suppression of an effector T cell by a regulatory T cell. In some aspects, the ABP increases the number of effector T cells in a tissue or in systemic circulation. In some aspects, the tissue is a tumor. In some aspects, the tissue is a tissue that is infected with a virus.

Also provided are kits comprising one or more of the ABPs provided herein, and instructions for use of the ABPs. Also provided are kits comprising one or more of the pharmaceutical compositions provided herein, and instructions for use of the pharmaceutical composition.

Also provided are isolated polynucleotides encoding the ABPs provided herein, and portions thereof.

Also provided are vectors comprising such polynucleotides.

Also provided are recombinant host cells comprising such polynucleotides and recombinant host cells comprising such vectors.

Also provided are methods of producing an ABP provided herein using the polynucleotides, vectors, or host cells provided herein.

Also provided are pharmaceutical compositions comprising the ABPs provided herein and a pharmaceutically acceptable excipient.

Also provided are methods of treating or preventing a disease or condition in a subject in need thereof, comprising administering to the subject an effective amount of an ABP provided herein, or a pharmaceutical composition comprising such ABP. In some aspects, the disease or condition is a cancer. In some aspects, the disease or condition is a viral infection. In some aspects the method further comprises administering one or more additional therapeutic agents. In some aspects, the additional therapeutic agent is an immunostimulatory agent.

In some embodiments, provided herein is a first family of ABPs, wherein an ABP of such family comprises the following six CDR sequences: (a) a CDR-H3 having the sequence A-R-D-G-V-L-$X_1$-L-N-K-R-S-F-D-I, wherein $X_1$ is A or T (SEQ ID NO: 128); (b) a CDR-H2 having the sequence S-I-Y-Y-S-G-$X_2$-T-Y-Y-N-P-S-L-K-S, wherein $X_2$ is S, Q or G (SEQ ID NO: 129); (c) a CDR-H1 having the sequence G-S-I-$X_3$-S-G-$X_4$-Y-Y-W-G, wherein $X_3$ is E or A, and $X_4$ is L, V or S (SEQ ID NO: 130); (d) a CDR-L3 having the sequence QQHTVRPPLT (SEQ ID NO: 64); (e) a CDR-L2 having the sequence GASSRAT (SEQ ID NO: 68); and (f) a CDR-L1 having the sequence RASQSVSSSYLA (SEQ ID NO: 71). In some embodiments, provided herein is an ABP within such first family.

In some embodiments, an ABP of such first family comprises: (a) a CDR-H3 of SEQ ID NO: 32, a CDR-H2 of SEQ ID NO: 40, a CDR-H1 of SEQ ID NO: 54, a CDR-L3 of SEQ ID NO: 64, a CDR-L2 of SEQ ID NO: 68, and a CDR-L1 of SEQ ID NO: 71; (b) a CDR-H3 of SEQ ID NO: 31, a CDR-H2 of SEQ ID NO: 40, a CDR-H1 of SEQ ID NO: 54, a CDR-L3 of SEQ ID NO: 64, a CDR-L2 of SEQ ID NO: 68, and a CDR-L1 of SEQ ID NO: 71; (c) a CDR-H3 of SEQ ID NO: 31, a CDR-H2 of SEQ ID NO: 39, a CDR-H1 of SEQ ID NO: 51, a CDR-L3 of SEQ ID NO: 64, a CDR-L2 of SEQ ID NO: 68, and a CDR-L1 of SEQ ID NO: 71; (d) a CDR-H3 of SEQ ID NO: 31, a CDR-H2 of SEQ ID NO: 40, a CDR-H1 of SEQ ID NO: 52, a CDR-L3 of SEQ ID NO: 64, a CDR-L2 of SEQ ID NO: 68, and a CDR-L1 of SEQ ID NO: 71; or (e) a CDR-H3 of SEQ ID NO: 31, a CDR-H2 of SEQ ID NO: 41, a CDR-H1 of SEQ ID NO: 53, a CDR-L3 of SEQ ID NO: 64, a CDR-L2 of SEQ ID NO: 68, and a CDR-L1 of SEQ ID NO: 71.

In some embodiments, an ABP of such first family comprises: (a) a $V_H$ sequence of SEQ ID NO: 13 and a $V_L$ sequence of SEQ ID NO: 26; (b) a $V_H$ sequence of SEQ ID NO: 12 and a $V_L$ sequence of SEQ ID NO: 26; (c) a $V_H$ sequence of SEQ ID NO: 14 and a $V_L$ sequence of SEQ ID NO: 26; (d) a $V_H$ sequence of SEQ ID NO: 15 and a $V_L$ sequence of SEQ ID NO: 26; (e) a $V_H$ sequence of SEQ ID NO: 9 and a $V_L$ sequence of SEQ ID NO: 26; (f) a $V_H$ sequence of SEQ ID NO: 10 and a $V_L$ sequence of SEQ ID NO: 26; or (g) a $V_H$ sequence of SEQ ID NO: 11 and a $V_L$ sequence of SEQ ID NO: 26.

In some embodiments, an ABP of such first family comprises: (a) (i) a heavy chain of SEQ ID NO: 99 and a light chain of SEQ ID NO: 92; or (ii) a heavy chain of SEQ ID NO: 100 and a light chain of SEQ ID NO: 92; (b) (i) a heavy chain of SEQ ID NO: 97 and a light chain of SEQ ID NO: 92; or (ii) a heavy chain of SEQ ID NO: 98 and a light chain of SEQ ID NO: 92; (c) (i) a heavy chain of SEQ ID NO: 101 and a light chain of SEQ ID NO: 92; or (ii) a heavy chain of SEQ ID NO: 102 and a light chain of SEQ ID NO: 92; (d) (i) a heavy chain of SEQ ID NO: 103 and a light chain of SEQ ID NO: 92; or (ii) a heavy chain of SEQ ID NO: 104 and a light chain of SEQ ID NO: 92; (e) (i) a heavy chain of SEQ ID NO: 90 and a light chain of SEQ ID NO: 92; or (ii) a heavy chain of SEQ ID NO: 91 and a light chain of SEQ ID NO: 92; (f) (i) a heavy chain of SEQ ID NO: 93 and a light chain of SEQ ID NO: 92; or (ii) a heavy chain of SEQ ID NO: 94 and a light chain of SEQ ID NO: 92; or (g) (i) a heavy chain of SEQ ID NO: 95 and a light chain of SEQ ID NO: 92; or (ii) a heavy chain of SEQ ID NO: 96 and a light chain of SEQ ID NO: 92.

In some embodiments, provided herein is a second family of ABPs, wherein an ABP of such family comprises the following six CDR sequences: (a) a CDR-H3 having the sequence A-R-D-A-N—Y-Y-G-$X_1$-A-W-A-F-D-P, wherein $X_1$ is S or G (SEQ ID NO: 131); (b) a CDR-H2 having the sequence S-I-Y-Y-S-G-$X_2$-T-F-Y-N-P-S-L-K-$X_3$, wherein $X_2$ is S or A, and $X_3$ is S or G (SEQ ID NO: 132); (c) a CDR-H1 having the sequence G-S-I-$X_4$-S-$X_5$-$X_6$-$X_7$-Y-W-G, wherein $X_4$ is S or T, $X_5$ is S or T, $X_6$ is S or K, and $X_7$ is H or Y (SEQ ID NO: 133); (d) a CDR-L3 having the sequence QQHFNLPT (SEQ ID NO: 63); (e) a CDR-L2 having the sequence DASNRAT (SEQ ID NO: 67); and (f) a CDR-L1 having the sequence RASQSVSSYLA (SEQ ID NO: 70). In some embodiments, provided herein is an ABP within such second family.

In some embodiments, an ABP of such second family comprises: (a) a CDR-H3 of SEQ ID NO: 29, a CDR-H2 of SEQ ID NO: 37, a CDR-H1 of SEQ ID NO: 49, a CDR-L3 of SEQ ID NO: 63, a CDR-L2 of SEQ ID NO: 67, and a CDR-L1 of SEQ ID NO: 70; (b) a CDR-H3 of SEQ ID NO: 30, a CDR-H2 of SEQ ID NO: 37, a CDR-H1 of SEQ ID NO: 50, a CDR-L3 of SEQ ID NO: 63, a CDR-L2 of SEQ ID NO: 67, and a CDR-L1 of SEQ ID NO: 70; (c) a CDR-H3 of SEQ ID NO: 29, a CDR-H2 of SEQ ID NO: 38, a CDR-H1 of SEQ ID NO: 50, a CDR-L3 of SEQ ID NO: 63, a CDR-L2 of SEQ ID NO: 67, and a CDR-L1 of SEQ ID NO: 70; (d) a CDR-H3 of SEQ ID NO: 29, a CDR-H2 of SEQ ID NO: 36, a CDR-H1 of SEQ ID NO: 48, a CDR-L3 of SEQ ID NO: 63, a CDR-L2 of SEQ ID NO: 67, and a CDR-L1 of SEQ ID NO: 70; or (e) a CDR-H3 of SEQ ID NO: 29, a CDR-H2 of SEQ ID NO: 37, a CDR-H1 of SEQ ID NO: 50, a CDR-L3 of SEQ ID NO: 63, a CDR-L2 of SEQ ID NO: 67, and a CDR-L1 of SEQ ID NO: 70.

In some embodiments, an ABP of such second family comprises: (a) a $V_H$ sequence of SEQ ID NO: 5 and a $V_L$ sequence of SEQ ID NO: 25; (b) a $V_H$ sequence of SEQ ID NO: 7 and a $V_L$ sequence of SEQ ID NO: 25; (c) a $V_H$ sequence of SEQ ID NO: 8 and a $V_L$ sequence of SEQ ID NO: 25; (d) a $V_H$ sequence of SEQ ID NO: 4 and a $V_L$ sequence of SEQ ID NO: 25; or (e) a $V_H$ sequence of SEQ ID NO: 6 and a $V_L$ sequence of SEQ ID NO: 25.

In some embodiments, an ABP of such second family comprises: (a) (i) a heavy chain of SEQ ID NO: 82 and a light chain of SEQ ID NO: 81; or (ii) a heavy chain of SEQ ID NO: 83 and a light chain of SEQ ID NO: 81; (b) (i) a heavy chain of SEQ ID NO: 86 and a light chain of SEQ ID NO: 81; or (ii) a heavy chain of SEQ ID NO: 87 and a light chain of SEQ ID NO: 81; (c) (i) a heavy chain of SEQ ID NO: 88 and a light chain of SEQ ID NO: 81; or (ii) a heavy chain of SEQ ID NO: 89 and a light chain of SEQ ID NO: 81; (d) (i) a heavy chain of SEQ ID NO: 79 and a light chain of SEQ ID NO: 81; or (ii) a heavy chain of SEQ ID NO: 80 and a light chain of SEQ ID NO: 81; or (e) (i) a heavy chain of SEQ ID NO: 84 and a light chain of SEQ ID NO: 81; or (ii) a heavy chain of SEQ ID NO: 85 and a light chain of SEQ ID NO: 81.

In some embodiments, provided herein is a third family of ABPs, wherein an ABP of such family comprises the following six CDR sequences: (a) a CDR-H3 having the sequence A-R-G-G-R-T-T-W-I-G-A-$X_1$-D-I, wherein $X_1$ is F or L (SEQ ID NO: 134); (b) a CDR-H2 having the sequence I-I-N-P-S-$X_2$-G-L-T-S-Y-A-$X_3$-K-F-Q-G, wherein $X_2$ is L or I, and $X_3$ is Q or R (SEQ ID NO: 135); (c) a CDR-H1 having the sequence Y-T-F-$X_4$-$X_5$-Y-Y-$X_6$-H, wherein $X_4$ is G, P or R, $X_5$ is N, A or E, and $X_6$ is M or I (SEQ ID NO: 136); (d) a CDR-L3 having the sequence QQYVVWPPLT (SEQ ID NO: 65); (e) a CDR-L2 having the sequence GASTRAT (SEQ ID NO: 69); and (f) a CDR-L1 having the sequence RASQSVSSNLA (SEQ ID NO: 72). In some embodiments, provided herein is an ABP within such third family.

In some embodiments, an ABP of such third family comprises: (a) a CDR-H3 of SEQ ID NO: 33, a CDR-H2 of SEQ ID NO: 43, a CDR-H1 of SEQ ID NO: 60, a CDR-L3 of SEQ ID NO: 65, a CDR-L2 of SEQ ID NO: 69, and a CDR-L1 of SEQ ID NO: 72; (b) a CDR-H3 of SEQ ID NO: 34, a CDR-H2 of SEQ ID NO: 43, a CDR-H1 of SEQ ID NO: 60, a CDR-L3 of SEQ ID NO: 65, a CDR-L2 of SEQ ID NO: 69, and a CDR-L1 of SEQ ID NO: 72; (c) a CDR-H3 of SEQ ID NO: 33, a CDR-H2 of SEQ ID NO: 44, a CDR-H1 of SEQ ID NO: 59, a CDR-L3 of SEQ ID NO: 65, a CDR-L2 of SEQ ID NO: 69, and a CDR-L1 of SEQ ID NO: 72; (d) a CDR-H3 of SEQ ID NO: 33, a CDR-H2 of SEQ ID NO: 42, a CDR-H1 of SEQ ID NO: 58, a CDR-L3 of SEQ ID NO: 65, a CDR-L2 of SEQ ID NO: 69, and a CDR-L1 of SEQ ID NO: 72; (e) a CDR-H3 of SEQ ID NO: 33, a CDR-H2 of SEQ ID NO: 42, a CDR-H1 of SEQ ID NO: 59, a CDR-L3 of SEQ ID NO: 65, a CDR-L2 of SEQ ID NO: 69, and a CDR-L1 of SEQ ID NO: 72; or (f) a CDR-H3 of SEQ ID NO: 34, a CDR-H2 of SEQ ID NO: 44, a CDR-H1 of SEQ ID NO: 61, a CDR-L3 of SEQ ID NO: 65, a CDR-L2 of SEQ ID NO: 69, and a CDR-L1 of SEQ ID NO: 72.

In some embodiments, an ABP of such third family comprises: (a) a $V_H$ sequence of SEQ ID NO: 18 and a $V_L$ sequence of SEQ ID NO: 27; (b) a $V_H$ sequence of SEQ ID NO: 19 and a $V_L$ sequence of SEQ ID NO: 27; (c) a $V_H$ sequence of SEQ ID NO: 21 and a $V_L$ sequence of SEQ ID NO: 27; (d) a $V_H$ sequence of SEQ ID NO: 16 and a $V_L$ sequence of SEQ ID NO: 27; (e) a $V_H$ sequence of SEQ ID NO: 17 and a $V_L$ sequence of SEQ ID NO: 27; or (f) a $V_H$ sequence of SEQ ID NO: 20 and a $V_L$ sequence of SEQ ID NO: 27.

In some embodiments, an ABP of such third family comprises: (a) (i) a heavy chain of SEQ ID NO: 110 and a light chain of SEQ ID NO: 107; or (ii) a heavy chain of SEQ ID NO: 111 and a light chain of SEQ ID NO: 107; (b) (i) a heavy chain of SEQ ID NO: 112 and a light chain of SEQ ID NO: 113 and a light chain of SEQ ID NO: 107; (c) (i) a heavy chain of SEQ ID NO: 116 and a light chain of SEQ ID NO: 107; or (ii) a heavy chain of SEQ ID NO: 117 and a light chain of SEQ ID NO: 107; (d) (i) a heavy chain of SEQ ID NO: 105 and a light chain of SEQ ID NO: 107; or (ii) a heavy chain of SEQ ID NO: 106 and a light chain of SEQ ID NO: 107; (e) (i) a heavy chain of SEQ ID NO: 108 and a light chain of SEQ ID NO: 107; or (ii) a heavy chain of SEQ ID NO: 109 and a light chain of SEQ ID NO: 107; or (f) (i) a heavy chain of SEQ ID NO: 114 and a light chain of SEQ ID NO: 107; or (ii) a heavy chain of SEQ ID NO: 115 and a light chain of SEQ ID NO: 107.

In some embodiments, provided herein is a fourth family of ABPs, wherein an ABP of such family comprises the following six CDR sequences: (a) a CDR-H3 having the sequence ARLHVSGSYYPAYLDY (SEQ ID NO: 35); (b) a CDR-H2 having the sequence $X_1$-I-N-P-S-M-G-A-T-S-Y-$X_2$-Q-K-F-$X_3$-G, wherein $X_1$ is V or I, $X_2$ is A or T, and $X_3$ is Q or R (SEQ ID NO: 137); (c) a CDR-H1 having the sequence YTFTSHYMG (SEQ ID NO: 62); (d) a CDR-L3 having the sequence QQYIVFPWT (SEQ ID NO: 66); (e) a CDR-L2 having the sequence GASTRAT (SEQ ID NO: 69); and (f) a CDR-L1 having the sequence RASQSVSSNLA, (SEQ ID NO: 72). In some embodiments, provided herein is an ABP within such fourth family.

In some embodiments, an ABP of such fourth family comprises: (a) a CDR-H3 of SEQ ID NO: 35, a CDR-H2 of SEQ ID NO: 46, a CDR-H1 of SEQ ID NO: 62, a CDR-L3 of SEQ ID NO: 66, a CDR-L2 of SEQ ID NO: 69, and a CDR-L1 of SEQ ID NO: 72; (b) a CDR-H3 of SEQ ID NO: 35, a CDR-H2 of SEQ ID NO: 47, a CDR-H1 of SEQ ID NO: 62, a CDR-L3 of SEQ ID NO: 66, a CDR-L2 of SEQ ID NO: 69, and a CDR-L1 of SEQ ID NO: 72; or (c) a CDR-H3 of SEQ ID NO: 35, a CDR-H2 of SEQ ID NO: 45, a CDR-H1 of SEQ ID NO: 62, a CDR-L3 of SEQ ID NO: 66, a CDR-L2 of SEQ ID NO: 69, and a CDR-L1 of SEQ ID NO: 72.

In some embodiments, an ABP of such fourth family comprises: (a) a $V_H$ sequence of SEQ ID NO: 23 and a $V_L$ sequence of SEQ ID NO: 28; (b) a $V_H$ sequence of SEQ ID NO: 24 and a $V_L$ sequence of SEQ ID NO: 28; or (c) a $V_H$ sequence of SEQ ID NO: 22 and a $V_L$ sequence of SEQ ID NO: 28.

In some embodiments, an ABP of such fourth family comprises: (a) (i) a heavy chain of SEQ ID NO: 121 and a light chain of SEQ ID NO: 120; or (ii) a heavy chain of SEQ ID NO: 122 and a light chain of SEQ ID NO: 120; (b) (i) a heavy chain of SEQ ID NO: 123 and a light chain of SEQ ID NO: 120; or (ii) a heavy chain of SEQ ID NO: 124 and a light chain of SEQ ID NO: 120; or (c) (i) a heavy chain of SEQ ID NO: 118 and a light chain of SEQ ID NO: 120; or (ii) a heavy chain of SEQ ID NO: 119 and a light chain of SEQ ID NO: 120.

In some embodiments, provided herein is an isolated antigen binding protein (ABP) that specifically binds human TIGIT (hTIGIT; SEQ ID NO: 1), comprising: (a) a CDR-H3 having at least about 80% identity to a CDR-H3 of a $V_H$ region selected from SEQ ID NOs: 4-24; (b) a CDR-H2 having at least about 80% identity to a CDR-H2 of a $V_H$ region selected from SEQ ID NOs: 4-24; (c) a CDR-H1 having at least about 80% identity to a CDR-H1 of a $V_H$ region selected from SEQ ID NOs: 4-24; (d) a CDR-L3 having at least about 80% identity to a CDR-L3 of a $V_L$ region selected from SEQ ID NOs: 25-28; (e) a CDR-L2 having at least about 80% identity to a CDR-L2 of a $V_L$ region selected from SEQ ID NOs: 25-28; and (f) a CDR-L1 having at least about 80% identity to a CDR-L1 of a $V_L$ region selected from SEQ ID NOs: 25-28. In some embodiments, the CDR-H3, CDR-H2, CDR-H1, CDR-L3, CDR-L2, and CDR-L1 are each identified according to a numbering scheme selected from the Kabat numbering scheme, the Chothia numbering scheme, or the IMGT numbering scheme. In some embodiments, the CDR-H1 is identified as defined by both the Chothia and Kabat numbering schemes, inclusive of the boundaries of both numbering schemes. In some embodiments: (a) the CDR-H3 comprises a CDR-H3 selected from SEQ ID NOs: 29-35, or a variant thereof having 1, 2, or 3 amino acid substitutions; (b) the CDR-H2 comprises a CDR-H3 selected from SEQ ID NOs: 36-47, or a variant thereof having 1, 2, or 3 amino acid substitutions; (c) the CDR-H1 comprises a CDR-H1 selected from SEQ ID NOs: 48-54 or 58-62, or a variant thereof having 1 or 2 amino acid substitutions; (d) the CDR-L3 comprises a CDR-L3 selected from SEQ ID NOs: 63-66, or a variant thereof having 1 or 2 amino acid substitutions; (e) the CDR-L2 comprises a CDR-L2 selected from SEQ ID NOs: 67-69, or a variant thereof having 1 amino acid substitution; and (f) the CDR-L1 comprises a CDR-L1 selected from SEQ ID NOs: 70-72, or a variant thereof having 1 or 2 amino acid substitutions.

In some embodiments, provided herein is an isolated antigen binding protein (ABP) that specifically binds human TIGIT (hTIGIT; SEQ ID NO: 1), comprising: (a) a $V_H$ region having at least about 90% identity to a $V_H$ region selected from SEQ ID NOs: 4-24; and (b) a $V_L$ region having at least about 90% identity to a $V_L$ region selected from SEQ ID NOs: 25-28. In some embodiments: (a) the a $V_H$ region comprises a $V_H$ region selected from SEQ ID NOs: 4-24, or a variant thereof having 1, 2, 3, 4, 5, 6, 7, 8, 9, 10, 11 or 12 amino acid substitutions; and (b) the a $V_L$ region comprises a $V_L$ region selected from SEQ ID NOs: 25-28, or a variant thereof having 1, 2, 3, 4, 5, 6, 7, 8, 9 or 10 amino acid substitutions. In some embodiments, the amino acid substitutions are conservative amino acid substitutions.

In some embodiments, any of the foregoing ABPs: (a) competes for binding to TIGIT with an antibody selected from MAB1, MAB2, MAB3, MAB4, MAB5, MAB6, MAB7, MAB8, MAB9, MAB10, MAB11, MAB12, MAB13, MAB14, MAB15, MAB16, MAB17, MAB18, MAB19, MAB20, or MAB21, each as provided in Table 5 of this disclosure; (b) inhibits binding of CD155 to TIGIT; (c) inhibits binding of CD112 to TIGIT; (d) inhibits association of CD226 with TIGIT; (e) activates an effector T cell or a natural killer (NK) cell; (f) decreases the number of regulatory T cells in a tissue or in circulation; (g) inhibits the suppression of an effector T cell by a regulatory T cell; (h) does not bind specifically to any of PVRL1, PVRL2, PVRL3, or PVRL4; or (i) is capable of any combination of (a)-(h).

In some embodiments, any of the foregoing ABPs: (a) specifically binds cynomolgus monkey TIGIT (cTIGIT; SEQ ID NO: 2); (b) binds murine TIGIT (mTIGIT; SEQ ID NO: 3) with an affinity lower (as indicated by higher KD) than the affinity of the ABP for hTIGIT, or does not bind mTIGIT; or (c) is capable of any combination of (a)-(b).

In some embodiments, any of the foregoing ABPs: (a) specifically binds cTIGIT (SEQ ID NO: 2); (b) binds mTIGIT (SEQ ID NO: 3) with an affinity lower (as indicated by higher $K_D$) than the affinity of the ABP for hTIGIT and cTIGIT; and (c) inhibits binding of CD155 to TIGIT.

In some embodiments, provided herein is an ABP that competes for binding to TIGIT with any of the foregoing ABPs, wherein the ABP: (a) specifically binds cTIGIT (SEQ ID NO: 2); (b) binds mTIGIT (SEQ ID NO: 3) with an affinity lower (as indicated by higher $K_D$) than the affinity of the ABP for hTIGIT and cTIGIT; and (c) inhibits binding of CD155 to TIGIT.

In some embodiments, any of the foregoing ABPs comprises an antibody. In some embodiments, the antibody is a monoclonal antibody. In some embodiments, the antibody is selected from a human antibody, a humanized antibody or a chimeric antibody.

In some embodiments, any of the foregoing ABPs is multispecific. In some embodiments, the multispecific ABP binds more than one antigen (i.e., TIGIT and a different (non-TIGIT) antigen). In some embodiments, the multispecific ABP binds more than one epitope on a single antigen (i.e., two or more epitopes on TIGIT).

In some embodiments, any of the foregoing ABPs comprises an antibody fragment.

In some embodiments, any of the foregoing ABPs comprises an alternative scaffold.

In some embodiments, any of the foregoing ABPs comprises an immunoglobulin constant region. In some embodiments, the ABP comprises heavy chain constant region of a class selected from IgA, IgD, IgE, IgG, or IgM. In some embodiments, the ABP comprises a heavy chain constant region of the class IgG and a subclass selected from IgG4, IgG1, IgG2, or IgG3.

In some embodiments, any of the foregoing ABPs binds hTIGIT (SEQ ID NO: 1) with a $K_D$ of less than about 10 nM, as measured by biolayer interferometry. In some embodiments, any of the foregoing ABPs binds hTIGIT (SEQ ID NO: 1) with a $K_D$ of less than about 5 nM, as measured by biolayer interferometry. In some embodiments, any of the foregoing ABPs binds hTIGIT (SEQ ID NO: 1) with a $K_D$ of less than about 2 nM, as measured by biolayer interferometry. In some embodiments, any of the foregoing ABPs binds cTIGIT (SEQ ID NO: 2) with a $K_D$ of less than about 100 nM, as measured by biolayer interferometry. In some embodiments, any of the foregoing ABPs binds cTIGIT (SEQ ID NO: 2) with a $K_D$ of less than about 10 nM, as measured by biolayer interferometry. In some embodiments, any of the foregoing ABPs shows no significant binding to mTIGIT in a biolayer interferometry assay. In some embodiments, any of the foregoing ABPs binds to cell surface mTIGIT with a $K_D$ of less than about 50 nM. In some embodiments, mTIGIT comprises SEQ ID NO: 3. In some embodiments, mTIGIT comprises SEQ ID NO: 138.

In some embodiments, any of the foregoing ABPs comprises a polypeptide sequence having a pyroglutamate (pE) residue at its N-terminus. In some embodiments, any of the foregoing ABPs comprises a $V_H$ sequence in which an N-terminal Q is substituted with pE. In some embodiments, any of the foregoing ABPs comprises a $V_L$ sequence in which an N-terminal E is substituted with pE. In some embodiments, any of the foregoing ABPs comprises a heavy chain sequence in which an N-terminal Q is substituted with pE. In some embodiments, any of the foregoing ABPs comprises a light chain sequence in which an N-terminal E is substituted with pE.

In some embodiments, provided herein are any of the foregoing ABPs for use as a medicament. In some embodiments, provided herein are any of the foregoing ABPs for use in the treatment of a cancer or viral infection. In some embodiments, provided herein are any of the foregoing ABPs for use in the treatment of a cancer, wherein the cancer is selected from a solid tumor and a hematological tumor. In some embodiments, provided herein are any of the foregoing ABPs for use as a medicament in the treatment of a disease or condition that was not responsive to a prior therapy. In some embodiments, the prior therapy was a therapy comprising an agent that inhibits the interaction between PD-1 and PD-L1.

In some embodiments, provided herein is an isolated polynucleotide encoding any of the foregoing ABPs, a $V_H$ thereof, a $V_L$ thereof, a light chain thereof, a heavy chain thereof or an antigen-binding portion thereof. In some embodiments, provided herein is a vector comprising the polynucleotide. In some embodiments, provided herein is a host cell comprising the polynucleotide and/or the vector. In some embodiments, provided herein is a method of producing any of the foregoing ABPs, comprising expressing the ABP in the host cell and isolating the expressed ABP.

In some embodiments, provided herein is a pharmaceutical composition comprising any of the foregoing ABPs. In some embodiments, the amount of the ABP in the pharmaceutical composition is sufficient to (a) increase effector T cell activity; (b) increase cytolytic T cell activity; (c) increase NK cell activity; (d) inhibit TIGIT-mediated signaling; (e) inhibit or block the binding of CD155 and or CD112 to TIGIT; or (f) any combination of (a)-(e), in a subject. In some embodiments, the any of the foregoing pharmaceutical compositions further comprises an antibody that antagonizes PD-1 or blocks PD-L1 from interacting with PD-1. In some embodiments, any of the foregoing pharmaceutical compositions is for use as a medicament. In some embodiments, any of the foregoing pharmaceutical compositions is for use in the treatment of a cancer or a viral infection. In some embodiments, any of the foregoing pharmaceutical compositions is for use in the treatment of a cancer, wherein the cancer is selected from a solid tumor and a hematological tumor. In some embodiments, any of the foregoing pharmaceutical compositions is for use as a medicament in the treatment of a disease or condition that was not responsive to a prior therapy. In some embodiments, the prior therapy was a therapy comprising an agent that inhibits the interaction between PD-1 and PD-L1.

In some embodiments, provided herein is a method of treating or preventing a disease or condition in a subject in need thereof, comprising administering to the subject an effective amount of any of the foregoing ABPs or any of the foregoing pharmaceutical compositions. In some embodiments, the disease or condition is a cancer or viral infection. In some embodiments, the disease or condition is a cancer, and the cancer is selected from a solid tumor and a hematological tumor. In some embodiments, provided herein is a method of modulating an immune response in a subject in need thereof, comprising administering to the subject an effective amount of any of the foregoing ABPs or any of the foregoing pharmaceutical compositions. In some embodiments, any of the foregoing methods, further comprise administering one or more additional therapeutic agents to the subject. In some embodiments, the additional therapeutic agent is selected from an agent that inhibits the interaction between PD-1 and PD-L1, a chemotherapy, an immunostimulatory agent, radiation, and combinations thereof.

In some embodiments, the additional therapeutic agent for use in any of the foregoing methods of treatment, uses of an ABP or uses of a pharmaceutical composition is an agent that inhibits the interaction between PD-1 and PD-L1, and wherein the agent that inhibits the interaction between PD-1 and PD-L1 is selected from an antibody, a peptidomimetic, a small molecule or a nucleic acid encoding such agent. In some embodiments, the agent that inhibits the interaction between PD-1 and PD-L1 is selected from is selected from pembrolizumab, nivolumab, atezolizumab, avelumab, durvalumab, BMS-936559, sulfamonomethoxine 1, and sulfamethizole 2.

In some embodiments, the additional therapeutic agent for use in any of the foregoing methods of treatment, uses of an ABP or uses of a pharmaceutical composition is an immunostimulatory agent selected from (a) an agent that blocks signaling of an inhibitory receptor of an immune cell or a ligand thereof or a nucleic acid encoding such agent; (b) an agonist to a stimulatory receptor of an immune cell or a nucleic acid encoding such agonist; (c) a cytokine or a nucleic acid encoding a cytokine; (d) an oncolytic virus or a nucleic acid encoding an oncolytic virus; (e) a T cell expressing a chimeric antigen receptor; (f) a bi- or multi-specific T cell directed antibody or a nucleic acid encoding such antibody; (g) an anti-TGF-β antibody or a nucleic acid encoding such antibody; (h) a TGF-β trap or a nucleic acid encoding such trap; (i) a vaccine to a cancer-associated antigen, including such antigen or a nucleic acid encoding such antigen and (j) combinations thereof. In some embodiments, the additional therapeutic agent is an agent that blocks signaling of an inhibitory receptor of an immune cell or a ligand thereof or a nucleic acid encoding such agent, and the inhibitory receptor or ligand thereof is selected from CTLA-4, PD-1, PD-L1, PD-L2, LAG-3, Tim3, neuritin, BTLA, CECAM-1, CECAM-5, VISTA, LAIR1, CD160, 2B4, TGF-R, KIR, and combinations thereof. In some embodiments, the additional therapeutic agent is an agonist to a stimulatory receptor of an immune cell or a nucleic acid encoding such agonist, and the stimulatory receptor of an immune cell is selected from OX40, CD2, CD27, CDS, ICAM-1, LFA-1 (CD11a/CD18), ICOS (CD278), 4-1BB (CD137), GITR, CD28, CD30, CD40, BAFFR, HVEM, CD7, LIGHT, NKG2C, SLAMF7, NKp80, CD160, B7-H3, CD83 ligand, and combinations thereof. In some embodiments, the additional therapeutic agent is a cytokine or a nucleic acid encoding a cytokine selected from IL-2, IL-5, IL-7, IL-12, IL-15, IL-21, and combinations thereof. In some embodiments, the additional therapeutic agent is an oncolytic virus or a nucleic acid encoding an oncolytic virus selected from herpes simplex virus, vesicular stomatitis virus, adenovirus, Newcastle disease virus, vaccinia virus, a maraba virus, and combinations thereof.

In some embodiments, the additional therapeutic agent is formulated in the same pharmaceutical composition as the ABP. In some embodiments, the additional therapeutic agent is formulated in a different pharmaceutical composition from the ABP. In some embodiments, the additional therapeutic agent is administered prior to administering the ABP. In some embodiments, the additional therapeutic agent is administered after administering the ABP. In some embodiments, the additional therapeutic agent is administered contemporaneously with the ABP.

In some embodiments, the subject is a subject that has been treated with an agent that inhibits the interaction between PD-1 and PD-L1 prior to performing such method.

In some embodiments, the disease or condition afflicting the subject was not responsive to a prior therapy. In some embodiments, the prior therapy was a therapy comprising an agent that inhibits the interaction between PD-1 and PD-L1.

In some embodiments, provided herein is a kit comprising any of the foregoing pharmaceutical compositions, and instructions for the use of such pharmaceutical composition. In some embodiments, the kit further comprises an additional pharmaceutical composition comprising an additional therapeutic agent and instructions for the use of such additional therapeutic agent. In some embodiments, the additional therapeutic agent is selected from an agent that inhibits the interaction between PD-1 and PD-L1, a chemotherapy, an immunostimulatory agent, radiation, and combinations thereof. In some embodiments, the additional therapeutic agent is an agent that inhibits the interaction between PD-1 and PD-L1, and wherein the agent inhibits the interaction between PD-1 and PD-L1 is selected from an antibody, a peptidomimetic, a small molecule or a nucleic acid encoding such agent. In some embodiments, the agent that inhibits the interaction between PD-1 and PD-L1 is selected from is selected from pembrolizumab, nivolumab, atezolizumab, avelumab, durvalumab, BMS-936559, sulfamonomethoxine 1, and sulfamethizole 2. In some embodiments, the additional therapeutic agent is an immunostimulatory agent selected from (a) an agent that blocks signaling of an inhibitory receptor of an immune cell or a ligand thereof or a nucleic acid encoding such agent; (b) an agonist to a stimulatory receptor of an immune cell or a nucleic acid encoding such agonist; (c) a cytokine or a nucleic acid encoding a cytokine; (d) an oncolytic virus or a nucleic acid encoding an oncolytic virus; (e) a T cell expressing a chimeric antigen receptor; (f) a bi- or multi-specific T cell directed antibody or a nucleic acid encoding such antibody; (g) an anti-TGF-β antibody or a nucleic acid encoding such antibody; (h) a TGF-β trap or a nucleic acid encoding such trap; (i) a vaccine to a cancer-associated antigen, including such antigen or a nucleic acid encoding such antigen and (j) combinations thereof. In some embodiments, the additional therapeutic agent is an agent that blocks signaling of an inhibitory receptor of an immune cell or a ligand thereof or a nucleic acid encoding such agent, and the inhibitory receptor or ligand thereof is selected from CTLA-4, PD-1, PD-L1, PD-L2, LAG-3, Tim3, neuritin, BTLA, CECAM-1, CECAM-5, VISTA, LAIR1, CD160, 2B4, TGF-R, KIR, and combinations thereof. In some embodiments, the additional therapeutic agent is an agonist to a stimulatory receptor of an immune cell or a nucleic acid encoding such agonist, and the stimulatory receptor of an immune cell is selected from OX40, CD2, CD27, CDS, ICAM-1, LFA-1 (CD11a/CD18), ICOS (CD278), 4-1BB (CD137), GITR, CD28, CD30, CD40, BAFFR, HVEM, CD7, LIGHT, NKG2C, SLAMF7, NKp80, CD160, B7-H3, CD83 ligand, and combinations thereof. In some embodiments, the additional therapeutic agent is a cytokine or a nucleic acid encoding a cytokine selected from IL-2, IL-5, IL-7, IL-12, IL-15, IL-21, and combinations thereof. In some embodiments, the additional therapeutic agent is an oncolytic virus or a nucleic acid encoding an oncolytic virus selected from herpes simplex virus, vesicular stomatitis virus, adenovirus, Newcastle disease virus, vaccinia virus, a maraba virus, and combinations thereof.

BRIEF DESCRIPTION OF THE DRAWINGS

FIGS. 1A-1B show sequence alignments of various molecules described further in the Examples. FIG. 1A shows sequence alignments of the TIGIT extracellular domains from human (SEQ ID NO: 139), cynomolgus monkey (SEQ ID NO: 140), mouse (residues 17-139 of SEQ ID NO: 3), and rat (SEQ ID NO: 141) TIGIT reference sequences. FIG. 1B shows an alignment of the human TIGIT (SEQ ID NO: 142) and PVRL4 (SEQ ID NO: 139) extracellular domains.

FIG. 5A and FIG. 5B show a series of graphs showing expression analysis of TIGIT, PVR and CD226 on unstimulated (FIG. 5A) and stimulated (FIG. 5B) CD4+ T cells. FIG. 5C shows analysis of TIGIT expression on naïve (positive for CD45RA, a marker of naïve T cells, top right panel) and memory (positive for CD45RO, a marker of activated T cells, bottom right panel) CD4+ T cells.

FIG. 6O shows a graph illustrating the $EC_{50}$ of MAB10 in PBMCs from Donor 1, as measured by IFN-γ production.

FIGS. 7A-7E provide a series of graphs showing the effect of MAB10 on cytokine secretion in sub-optimally stimulated PBMCs from Donor 2, including IFN-γ (FIG. 7A), TNF (FIG. 7B), interleukin 6 (IL-6, FIG. 7C), granulocyte macrophage colony-stimulating factor (GM-CSF, FIG. 7D), and LT-α (FIG. 7E). Data from cells treated with MAB10 are shown as black bars and data from cells treated with the IgG4 isotype control are shown as light gray bars. Antibody concentration for each bar is in µg/mL.

FIG. 8A shows results obtained from CD4+ cells obtained from Donor 1. FIG. 8B shows results obtained from CD4+ cells obtained from Donor 2. FIG. 8C shows results obtained from CD4+ cells obtained from Donor 3. IFN-γ production in cells treated with either MAB10 (black bars) or the IgG4 isotype control (light gray bars) is shown in the left panel of each of FIGS. 8A-8C. The average $EC_{50}$ value for MAB10 in this assay was calculated by determining the concentration of MAB10 required to induce 50% of the increase in IFN-γ signal (plotted in the right panel of each of FIGS. 8A-8C).

As shown in FIG. 9A, only the combination of MAB10 and pembrolizumab ($EC_{50}$ of 5.06 nM) blocked binding sufficiently to induce luciferase activity in the Jurkat cells. In FIGS. 9A and 9B, neither the IgG4 control alone or the IgG4+MAB10 combination induced luciferase activity.

FIGS. 10A-10D are a series of graphs showing the effect of MAB10 on CMV-stimulated CD4+ T-cells from a human donor using intracellular cytokine staining. Incubation of CD4+ cells with MAB10 (black bars) increases the production of the effector cytokines in a dose-dependent matter, including TNF (FIG. 10A), IL-2 (FIG. 10B), and IFN-γ (FIG. 10C) compared to cells incubated with the IgG4 control (white bars). FIG. 10D shows that incubation with MAB10 increases the proportion of antigen-specific activated CD4+ T-cells. In FIG. 10D, cells that were treated with 20 µg/ml of the IgG4 control or MAB10 were analyzed by FACS for expression of CD3 (a marker of mature T-cells) and expression of TNF and IL-2. Statistical differences were calculated between MAB10 and IgG4 control groups (same concentration treatments) using Student's T test (*=p<0.05, =p<0.01, *=p<0.005, ****=p<0.001).

FIG. 11D shows that incubation with MAB10 also increases the proportion of antigen-specific activated CD8+ T-cells. Cells that were treated with 20 µg/ml of the IgG4 control or MAB10 were analyzed by FACS for expression of CD3 and expression of perforin and granzyme B. Statistical differences were calculated between MAB10 and IgG4 control groups (same concentration treatments) using Student's T test (*=p<0.05, =p<0.01, *=p<0.005, ****=p<0.001).

FIG. 12B (perforin+granzyme B+ analysis) and FIG. 12D (IFN-γ+TNF+ analysis) show the proportion of double positive cells comparing cells treated with 20 µg/ml of the control antibody (left panels) or 20 jgg/ml of MAB10 (right panels).

FIG. 14A shows the results of the assay using cells from Donor 1; FIG. 14B shows the results of the assay using cells from Donor 2;

FIG. 14C shows the results of the assay using cells from Donor 3. The addition of MAB10 (black bars) alone or in combination with increasing concentrations of pembrolizumab results in a greater production of TNF compared to control antibody+pembrolizumab group (white bars). Additionally, MAB10 (black bars) in combination with pembrolizumab also resulted in increased activation compared to MAB10 alone. Statistic differences were calculated between MAB10 alone and MAB10+pembro groups using Student T test analysis (*=p<0.05, =p<0.01, *=p<0.005, ****=p<0.001)

DETAILED DESCRIPTION

1. Definitions

Figure 1A:
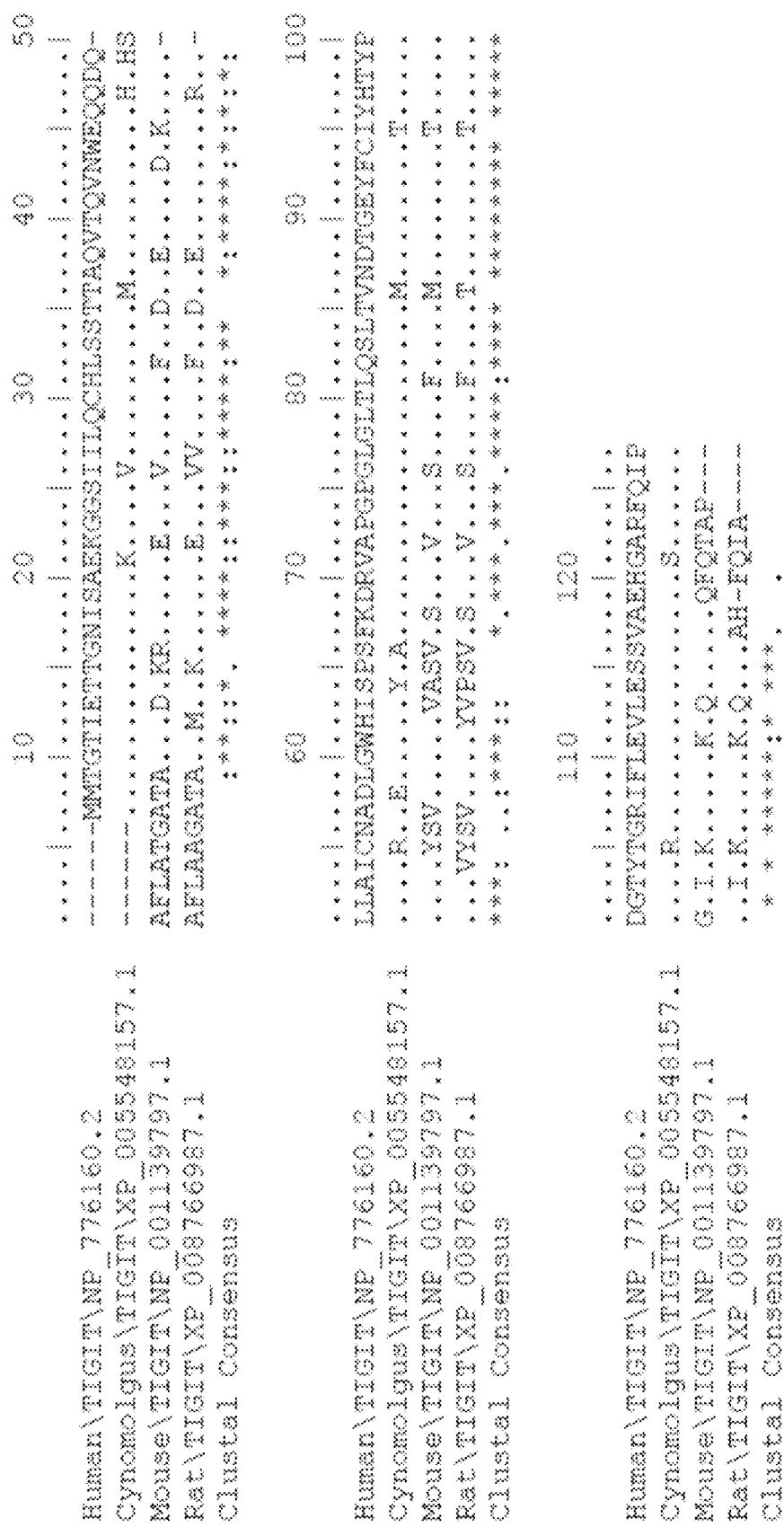

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 4th ed. (2012) Cold Spring Harbor Laboratory Press, Cold Spring Harbor, N.Y. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise. The terms "include," "such as," and the like are intended to convey inclusion without limitation, unless otherwise specifically indicated.

As used herein, the term "comprising" also specifically includes embodiments "consisting of" and "consisting essentially of" the recited elements, unless specifically indicated otherwise. For example, a multispecific ABP "comprising a diabody" includes a multispecific ABP "consisting of a diabody" and a multispecific ABP "consisting essentially of a diabody."

The term "about" indicates and encompasses an indicated value and a range above and below that value. In certain embodiments, the term "about" indicates the designated value ±10%, ±5%, or ±1%. In certain embodiments, where applicable, the term "about" indicates the designated value(s)±one standard deviation of that value(s).

The terms "TIGIT," "TIGIT protein," and "TIGIT antigen" are used interchangeably herein to refer to human TIGIT, or any variants (e.g., splice variants and allelic variants), isoforms, and species homologs of human TIGIT that are naturally expressed by cells, or that are expressed by cells transfected with a tigit gene. In some aspects, the TIGIT protein is a TIGIT protein naturally expressed by a primate (e.g., a monkey or a human), a rodent (e.g., a mouse or a rat), a dog, a camel, a cat, a cow, a goat, a horse, or a sheep. In some aspects, the TIGIT protein is human TIGIT (hTIGIT; SEQ ID NO:1). Without being bound by theory, it is believed that positions 1-21 of SEQ ID NO:1 encode a signal peptide; positions 22-141 of SEQ ID NO:1 encode the extracellular domain of the mature TIGIT protein; positions 142-162 of SEQ ID NO:1 encode a transmembrane domain; and positions 163-244 of SEQ ID NO:1 encode a cytoplasmic domain. See UniProt KB—Q495A1 (TIGIT_HUMAN), at www.uniprot.org/uniprot/Q495A1, accessed Sep. 28, 2015. In some aspects, the TIGIT protein is a cynomolgus monkey TIGIT (cTIGIT; SEQ ID NO:2). In some aspects, the TIGIT protein is a murine TIGIT (mTIGIT) having the sequence provided in SEQ ID NO:3. In some aspects, the TIGIT protein is a murine TIGIT (mTIGIT) having the sequence provided in SEQ ID NO:138. As used herein, if a SEQ ID NO is not specified, the terms "mTIGIT," "murine TIGIT" and "mouse TIGIT mean SEQ ID NO: 3 and/or SEQ ID NO: 138. In some aspects, the TIGIT protein is a full-length or unprocessed TIGIT protein. In some aspects, the TIGIT protein is a truncated or processed TIGIT protein produced by post-translational modification. TIGIT is also known by a variety of synonyms, including WUCAM, VSIG9, and Vstm3.

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, Pa. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antigen-binding protein" (ABP) refers to a protein comprising one or more antigen-binding domains that specifically bind to an antigen or epitope. In some embodiments, the antigen-binding domain binds the antigen or epitope with specificity and affinity similar to that of naturally occurring antibodies. In some embodiments, the ABP comprises an antibody. In some embodiments, the ABP consists of an antibody. In some embodiments, the ABP consists essentially of an antibody. In some embodiments, the ABP comprises an alternative scaffold. In some embodiments, the ABP consists of an alternative scaffold. In some embodiments, the ABP consists essentially of an alternative scaffold. In some embodiments, the ABP comprises an antibody fragment. In some embodiments, the ABP consists of an antibody fragment. In some embodiments, the ABP consists essentially of an antibody fragment. A "TIGIT ABP," "anti-TIGIT ABP," or "TIGIT-specific ABP" is an ABP, as provided herein, which specifically binds to the antigen TIGIT. In some embodiments, the ABP binds the extracellular domain of TIGIT. In certain embodiments, a TIGIT ABP provided herein binds to an epitope of TIGIT that is conserved between or among TIGIT proteins from different species.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies. An antibody is one type of ABP.

The term "alternative scaffold" refers to a molecule in which one or more regions may be diversified to produce one or more antigen-binding domains that specifically bind to an antigen or epitope. In some embodiments, the antigen-binding domain binds the antigen or epitope with specificity and affinity similar to that of an antibody. Exemplary alternative scaffolds include those derived from fibronectin (e.g., Adnectins™), the β-sandwich (e.g., iMab), lipocalin (e.g., Anticalins®), EETI-II/AGRP, BPTI/LACI-D1/ITI-D2 (e.g., Kunitz domains), thioredoxin peptide aptamers, protein A (e.g., Affibody®), ankyrin repeats (e.g., DARPins), gamma-B-crystallin/ubiquitin (e.g., Affilins), $CTLD_3$ (e.g., Tetranectins), Fynomers, and (LDLR-A module) (e.g., Avimers). Additional information on alternative scaffolds is provided in Binz et al., *Nat. Biotechnol.*, 2005 23:1257-1268; Skerra, Current Opin. in Biotech., 2007 18:295-304; and Silacci et al., *J. Biol. Chem.*, 2014, 289:14392-14398; each of which is incorporated by reference in its entirety. An alternative scaffold is one type of ABP.

The term "antigen-binding domain" means the portion of an ABP that is capable of specifically binding to an antigen or epitope. One example of an antigen-binding domain is an antigen-binding domain formed by a $V_H$-$V_L$ dimer of an antibody. Another example of an antigen-binding domain is an antigen-binding domain formed by diversification of certain loops from the tenth fibronectin type III domain of an Adnectin.

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "Fc region" means the C-terminal region of an immunoglobulin heavy chain that, in naturally occurring antibodies, interacts with Fc receptors and certain proteins of the complement system. The structures of the Fc regions of various immunoglobulins, and the glycosylation sites contained therein, are known in the art. See Schroeder and Cavacini, *J. Allergy Clin. Immunol.*, 2010, 125:S41-52, incorporated by reference in its entirety. The Fc region may be a naturally occurring Fc region, or an Fc region modified as described in the art or elsewhere in this disclosure.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, Md., incorporated by reference in its entirety.

The light chain from any vertebrate species can be assigned to one of two types, called kappa (κ) and lambda (λ), based on the sequence of its constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme); each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at www.bioinf.org.uk/abs/abnum/, and described in Abhinandan and Martin, *Immunology*, 2008, 45:3832-3839, incorporated by reference in its entirety.

TABLE 1

Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen-binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with 1-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). Any suitable linker may be used. In some embodiments, the linker is a (GGGGS)$_n$ (SEQ ID NO: 127). In some embodiments, n=1, 2, 3, 4, 5, or 6. See Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG4 Fc domain.

The term "single domain antibody" refers to a molecule in which one variable domain of an antibody specifically binds to an antigen without the presence of the other variable domain. Single domain antibodies, and fragments thereof, are described in Arabi Ghahroudi et al., *FEBS Letters*, 1998, 414:521-526 and Muyldermans et al., *Trends in Biochem. Sci.*, 2001, 26:230-245, each of which is incorporated by reference in its entirety. Single domain antibodies are also known as sdAbs or nanobodies.

A "multispecific ABP" is an ABP that comprises two or more different antigen-binding domains that collectively specifically bind two or more different epitopes. The two or more different epitopes may be epitopes on the same antigen (e.g., a single TIGIT molecule expressed by a cell) or on different antigens (e.g., different TIGIT molecules expressed by the same cell, or a TIGIT molecule and a non-TIGIT molecule). In some aspects, a multi-specific ABP binds two different epitopes (i.e., a "bispecific ABP"). In some aspects, a multi-specific ABP binds three different epitopes (i.e., a "trispecific ABP"). In some aspects, a multi-specific ABP binds four different epitopes (i.e., a "quadspecific ABP"). In some aspects, a multi-specific ABP binds five different epitopes (i.e., a "quintspecific ABP"). In some aspects, a multi-specific ABP binds 6, 7, 8, or more different epitopes. Each binding specificity may be present in any suitable valency. Examples of multispecific ABPs are provided elsewhere in this disclosure.

A "monospecific ABP" is an ABP that comprises one or more binding sites that specifically bind to a single epitope. An example of a monospecific ABP is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated ABP" or "isolated nucleic acid" is an ABP or nucleic acid that has been separated and/or recovered from a component of its natural environment. Components of the natural environment may include enzymes, hormones, and other proteinaceous or nonproteinaceous materials. In some embodiments, an isolated ABP is purified to a degree sufficient to obtain at least 15 residues of N-terminal or internal amino acid sequence, for example by use of a spinning cup sequenator. In some embodiments, an isolated ABP is purified to homogeneity by gel electrophoresis (e.g., SDS-PAGE) under reducing or nonreducing conditions, with detection by Coomassie blue or silver stain. In some embodiments, an isolated ABP may include an ABP in situ within recombinant cells, since at least one component of the ABP's natural environment is not present. In some aspects, an isolated ABP or isolated nucleic acid is prepared by at least one purification step. In some embodiments, an isolated ABP or isolated nucleic acid is purified to at least 80%, 85%, 90%, 95%, or 99% by weight. In some embodiments, an isolated ABP or isolated nucleic acid is purified to at least 80%, 85%, 90%, 95%, or 99% by volume. In some embodiments, an isolated ABP or isolated nucleic acid is provided as a solution comprising at least 85%, 90%, 95%, 98%, 99% to 100% ABP or nucleic acid by weight. In some embodiments, an isolated ABP or isolated nucleic acid is provided as a solution comprising at least 85%, 90%, 95%, 98%, 99% to 100% ABP or nucleic acid by volume.

"Affinity" refers to the strength of the sum total of non-covalent interactions between a single binding site of a molecule (e.g., an ABP) and its binding partner (e.g., an antigen or epitope). Unless indicated otherwise, as used herein, "affinity" refers to intrinsic binding affinity, which reflects a 1:1 interaction between members of a binding pair (e.g., ABP and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

With regard to the binding of an ABP to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the ABP to the target molecule is competitively inhibited by the control molecule. In some aspects, the affinity of a TIGIT ABP for a non-target molecule is less than about 50% of the affinity for TIGIT. In some aspects, the affinity of a TIGIT ABP for a non-target molecule is less than about 40% of the affinity for TIGIT. In some aspects, the affinity of a TIGIT ABP for a non-target molecule is less than about 30% of the affinity for TIGIT. In some aspects, the affinity of a TIGIT ABP for a non-target molecule is less than about 20% of the affinity for TIGIT. In some aspects, the affinity of a TIGIT ABP for a non-target molecule is less than about 10% of the affinity for TIGIT. In some aspects, the affinity of a TIGIT ABP for a non-target molecule is less than about 1% of the affinity for TIGIT. In some aspects, the affinity of a TIGIT ABP for a non-target molecule is less than about 0.1% of the affinity for TIGIT.

The term "$k_d$" (sec$^{-1}$), as used herein, refers to the dissociation rate constant of a particular ABP-antigen interaction. This value is also referred to as the $k_{off}$ value.

The term "$k_a$" (M$^{-1}$×sec$^{-1}$), as used herein, refers to the association rate constant of a particular ABP-antigen interaction. This value is also referred to as the $k_{on}$ value.

The term "$K_D$" (M), as used herein, refers to the dissociation equilibrium constant of a particular ABP-antigen interaction. $K_D = k_d/k_a$. In some embodiments, the affinity of an ABP is described in terms of the $K_D$ for an interaction between such ABP and its antigen. For clarity, as known in the art, a smaller $K_D$ value indicates a higher affinity interaction, while a larger $K_D$ value indicates a lower affinity interaction.

The term "$K_A$" (M$^{-1}$), as used herein, refers to the association equilibrium constant of a particular ABP-antigen interaction. $K_A = k_a/k_d$.

An "affinity matured" ABP is an ABP with one or more alterations (e.g., in one or more CDRs or FRs) relative to a parent ABP (i.e., an ABP from which the altered ABP is derived or designed) that result in an improvement in the affinity of the ABP for its antigen, compared to the parent ABP which does not possess the alteration(s). In some embodiments, an affinity matured ABP has nanomolar or picomolar affinity for the target antigen. Affinity matured ABPs may be produced using a variety of methods known in the art. For example, Marks et al. (*Bio/Technology*, 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.*, 1994, 91:3809-3813); Schier et al., *Gene*, 1995, 169:147-155; Yelton et al., *J. Immunol.*, 1995, 155:1994-2004; Jackson et al., *J. Immunol.*, 1995, 154:3310-33199; and Hawkins et al, *J. Mol. Biol.*, 1992, 226:889-896; each of which is incorporated by reference in its entirety.

An "immunoconjugate" is an ABP conjugated to one or more heterologous molecule(s), such as a therapeutic or diagnostic agent.

"Effector functions" refer to those biological activities mediated by the Fc region of an antibody, which activities may vary depending on the antibody isotype. Examples of antibody effector functions include C1q binding to activate complement dependent cytotoxicity (CDC), Fc receptor binding to activate antibody-dependent cellular cytotoxicity (ADCC), and antibody dependent cellular phagocytosis (ADCP).

When used herein in the context of two or more ABPs, the term "competes with" or "cross-competes with" indicates that the two or more ABPs compete for binding to an antigen (e.g., TIGIT). In one exemplary assay, TIGIT is coated on a surface and contacted with a first TIGIT ABP, after which a second TIGIT ABP is added. In another exemplary assay, a first TIGIT ABP is coated on a surface and contacted with TIGIT, and then a second TIGIT ABP is added. If the presence of the first TIGIT ABP reduces binding of the second TIGIT ABP, in either assay, then the ABPs compete with each other. The term "competes with" also includes combinations of ABPs where one ABP reduces binding of another ABP, but where no competition is observed when the ABPs are added in the reverse order. However, in some embodiments, the first and second ABPs inhibit binding of each other, regardless of the order in which they are added. In some embodiments, one ABP reduces binding of another ABP to its antigen by at least 25%, at least 50%, at least 60%, at least 70%, at least 80%, at least 85%, at least 90%, or at least 95%. A skilled artisan can select the concentrations of the antibodies used in the competition assays based on the affinities of the ABPs for TIGIT and the valency of the ABPs. The assays described in this definition are illustrative, and a skilled artisan can utilize any suitable assay to determine if antibodies compete with each other. Suitable assays are described, for example, in Cox et al., "Immunoassay Methods," in *Assay Guidance Manual* [*Internet*], Updated Dec. 24, 2014 (www.ncbi.nlm.nih.gov/books/NBK92434/; accessed Sep. 29, 2015); Silman et al., *Cytometry*, 2001, 44:30-37; and Finco et al., *J. Pharm. Biomed. Anal.*, 2011, 54:351-358; each of which is incorporated by reference in its entirety.

The term "epitope" means a portion of an antigen that specifically binds to an ABP. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an ABP binds can be determined using known techniques for epitope determination such as, for example, testing for ABP binding to TIGIT variants with different point-mutations, or to chimeric TIGIT variants.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGA-LIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution an amino acid with a chemically or functionally similar amino acid. Conservative substitution tables providing similar amino acids are well known in the art. By way of example, the groups of amino acids provided in Tables 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 3

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 4

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins. Structures and Molecular Properties* 2nd ed. (1993) W. H. Freeman & Co., New York, N.Y. An ABP generated by making one or more conservative substitutions of amino acid residues in a parent ABP is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which an exogenous nucleic acid has been introduced, and the progeny of such cells. Host cells include "transformants" (or "transformed cells") and "transfectants" (or "transfected cells"), which each include the primary transformed or transfected cell and progeny derived therefrom. Such progeny may not be completely identical in nucleic acid content to a parent cell, and may contain mutations.

The term "treating" (and variations thereof such as "treat" or "treatment") refers to clinical intervention in an attempt to alter the natural course of a disease or condition in a subject in need thereof. Treatment can be performed both for prophylaxis and during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

As used herein, the term "therapeutically effective amount" or "effective amount" refers to an amount of an ABP or pharmaceutical composition provided herein that, when administered to a subject, is effective to treat a disease or disorder.

As used herein, the term "subject" means a mammalian subject. Exemplary subjects include humans, monkeys, dogs, cats, mice, rats, cows, horses, camels, goats, rabbits, and sheep. In certain embodiments, the subject is a human. In some embodiments the subject has a disease or condition that can be treated with an ABP provided herein. In some aspects, the disease or condition is a cancer. In some aspects, the disease or condition is a viral infection.

The term "package insert" is used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

The term "cytotoxic agent," as used herein, refers to a substance that inhibits or prevents a cellular function and/or causes cell death or destruction.

A "chemotherapeutic agent" refers to a chemical compound useful in the treatment of cancer. Chemotherapeutic agents include "anti-hormonal agents" or "endocrine therapeutics" which act to regulate, reduce, block, or inhibit the effects of hormones that can promote the growth of cancer.

The term "cytostatic agent" refers to a compound or composition which arrests growth of a cell either in vitro or in vivo. In some embodiments, a cytostatic agent is an agent that reduces the percentage of cells in S phase. In some embodiments, a cytostatic agent reduces the percentage of cells in S phase by at least about 20%, at least about 40%, at least about 60%, or at least about 80%.

The term "tumor" refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein. The terms "cell proliferative disorder" and "proliferative disorder" refer to disorders that are associated with some degree of abnormal cell proliferation. In some embodiments, the cell proliferative disorder is a cancer. In some aspects, the tumor is a solid tumor. In some aspects, the tumor is a hematologic malignancy.

The term "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "agonize" refers to the activation of receptor signaling to induce a biological response associated with activation of the receptor. An "agonist" is an entity that binds to and agonizes a receptor.

The term "antagonize" refers to the inhibition of receptor signaling to inhibit a biological response associated with activation of the receptor. An "antagonist" is an entity that binds to and antagonizes a receptor.

The term "effector T cell" includes T helper (i.e., CD4+) cells and cytotoxic (i.e., CD8+) T cells. CD4+ effector T cells contribute to the development of several immunologic processes, including maturation of B cells into plasma cells and memory B cells, and activation of cytotoxic T cells and macrophages. CD8+ effector T cells destroy virus-infected cells and tumor cells. See Seder and Ahmed, *Nature Immunol.*, 2003, 4:835-842, incorporated by reference in its entirety, for additional information on effector T cells.

The term "regulatory T cell" includes cells that regulate immunological tolerance, for example, by suppressing effector T cells. In some aspects, the regulatory T cell has a CD4+CD25+Foxp3+ phenotype. In some aspects, the regulatory T cell has a CD8+CD25+ phenotype. See Nocentini et al., *Br. J. Pharmacol.*, 2012, 165:2089-2099, incorporated by reference in its entirety, for additional information on regulatory T cells expressing TIGIT.

The term "dendritic cell" refers to a professional antigen-presenting cell capable of activating a naïve T cell and stimulating growth and differentiation of a B cell.

2. TIGIT Antigen-Binding Proteins

2.1. TIGIT Binding and Target Cells

Provided herein are ABPs that specifically bind to TIGIT. In some aspects, the TIGIT is hTIGIT (SEQ ID NO: 1). In some aspects, the TIGIT is cTIGIT (SEQ ID NO:2). In some aspects, the TIGIT is mTIGIT with the sequence provided in SEQ ID NO:3. In some aspects, the TIGIT is mTIGIT with the sequence provided in SEQ ID NO: 138.

In some embodiments, the ABPs provided herein specifically bind to hTIGIT (SEQ ID NO:1), cTIGIT (SEQ ID NO:2), and mTIGIT of SEQ ID NO:3. In some embodiments, the ABPs provided herein specifically bind to hTIGIT (SEQ ID NO: 1), cTIGIT (SEQ ID NO:2), and mTIGIT of SEQ ID NO: 138. In some embodiments, the ABPs provided herein specifically bind to hTIGIT (SEQ ID NO: 1), and cTIGIT (SEQ ID NO:2). In some embodiments, the ABPs provided herein specifically bind to hTIGIT (SEQ ID NO:1). In some embodiments, the ABPs provided herein do not bind mTIGIT of SEQ ID NO:3. In some embodiments, the ABPs provided herein do not bind mTIGIT of SEQ ID NO:138.

In some embodiments, the ABPs provided herein specifically bind to the extracellular domain of TIGIT.

In some embodiments, an ABP provided herein is an antibody. In some embodiments, an ABP provided herein is an antibody fragment. In some embodiments, an ABP provided herein is an alternative scaffold.

The TIGIT may be expressed on the surface of any suitable target cell. In some embodiments, the target cell is a T cell. In some embodiments, the target cell is an effector T cell. In some embodiments, the target cell is a regulatory T cell. In some embodiments, the target cell is a natural killer (NK) cell. In some embodiments, the target cell is a natural killer T (NKT) cell.

In some embodiments, the ABPs provided herein comprise an immunoglobulin molecule. In some embodiments, the ABPs provided herein consist of an immunoglobulin molecule. In some embodiments, the ABPs provided herein consist essentially of an immunoglobulin molecule. In some aspects, the immunoglobulin molecule comprises an antibody. In some aspects, the immunoglobulin molecule consists of an antibody. In some aspects, the immunoglobulin molecule consists essentially of an antibody.

In some embodiments, the ABPs provided herein comprise a light chain. In some aspects, the light chain is a kappa light chain. In some aspects, the light chain is a lambda light chain.

In some embodiments, the ABPs provided herein comprise a kappa light chain comprising SEQ ID NO: 126.

In some embodiments, the ABPs provided herein comprise a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the ABPs provided herein comprise an IgG4 heavy chain comprising a sequence selected from SEQ ID NO:55 and SEQ ID NO:56. In some embodiments, the ABPs provided herein comprise an IgG1 heavy chain comprising a sequence selected from SEQ ID NO:57 and SEQ ID NO: 125.

In some embodiments, the ABPs provided herein comprise an antibody fragment. In some embodiments, the ABPs provided herein consist of an antibody fragment. In some embodiments, the ABPs provided herein consist essentially of an antibody fragment. In some aspects, the antibody fragment is an Fv fragment. In some aspects, the antibody fragment is a Fab fragment. In some aspects, the antibody fragment is a F(ab')$_2$ fragment. In some aspects, the antibody fragment is a Fab' fragment. In some aspects, the antibody fragment is an scFv (sFv) fragment. In some aspects, the antibody fragment is an scFv-Fc fragment. In some aspects, the antibody fragment is a fragment of a single domain antibody.

In some embodiments, an antibody fragment provided herein is derived from an illustrative antibody provided herein. In some embodiments, an antibody fragments provided herein is not derived from an illustrative antibody provided herein and may, for example, be isolated de novo according to the methods provided herein for obtaining antibody fragments.

In some embodiments, an antibody fragment provided specifically binds hTIGIT. In some embodiments, an antibody fragment provided herein specifically binds cTIGIT. In some embodiments, an antibody fragment provided herein specifically binds mTIGIT. In some embodiments, an antibody fragment provided herein specifically binds hTIGIT and cTIGIT. In some embodiments, an antibody fragment provided herein specifically binds hTIGIT and mTIGIT. In some embodiments, an antibody fragment provided herein specifically binds cTIGIT and mTIGIT. In some embodiments, an antibody fragment provided herein specifically binds hTIGIT, cTIGIT and mTIGIT.

In some embodiments, an antibody fragment derived from an antibody provided herein retains affinity, as measured by $K_D$, for hTIGIT that is within about 1.5-fold, about 2-fold, about 3-fold, about 4-fold, about 5-fold, about 6-fold, about 7-fold, about 8-fold, about 9-fold or about 10-fold the affinity of such antibody. In some embodiments, an antibody fragment derived from an antibody provided herein retains affinity, as measured by $K_D$, for cTIGIT that is within about 1.5-fold, about 2-fold, about 3-fold, about 4-fold, about 5-fold, about 6-fold, about 7-fold, about 8-fold, about 9-fold or about 10-fold the affinity of such antibody. In some embodiments, an antibody fragment derived from an antibody provided herein retains affinity, as measured by $K_D$, for mTIGIT that is within about 1.5-fold, about 2-fold, about 3-fold, about 4-fold, about 5-fold, about 6-fold, about 7-fold, about 8-fold, about 9-fold or about 10-fold the affinity of such antibody. In some embodiments, an antibody fragment derived from an antibody provided herein retains affinity, as measured by $K_D$, for both hTIGIT and cTIGIT that is within about 1.5-fold, about 2-fold, about 3-fold, about 4-fold, about 5-fold, about 6-fold, about 7-fold, about 8-fold, about 9-fold or about 10-fold the affinity of such antibody. In some embodiments, an antibody fragment derived from an antibody provided herein retains affinity, as measured by $K_D$, for both hTIGIT and mTIGIT that is within about 1.5-fold, about 2-fold, about 3-fold, about 4-fold, about 5-fold, about 6-fold, about 7-fold, about 8-fold, about 9-fold or about 10-fold the affinity of such antibody. In some embodiments, an antibody fragment derived from an antibody provided herein retains affinity, as measured by $K_D$, for both cTIGIT and mTIGIT that is within about 1.5-fold, about 2-fold, about 3-fold, about 4-fold, about 5-fold, about 6-fold, about 7-fold, about 8-fold, about 9-fold or about 10-fold the affinity of such antibody. In some embodiments, an antibody fragment derived from an antibody provided herein retains affinity, as measured by $K_D$, for all three of hTIGIT, cTIGIT and mTIGIT that is within about 1.5-fold, about 2-fold, about 3-fold, about 4-fold, about 5-fold, about 6-fold, about 7-fold, about 8-fold, about 9-fold or about 10-fold the affinity of such antibody.

In some embodiments, an antibody fragment provided herein retains the ability to antagonize TIGIT, as measured by one or more assays or biological effects described herein. In some embodiments, an antibody fragment provided herein retains the ability to prevent TIGIT from interacting with one or more of its ligands, as described herein.

In some embodiments, an antibody fragment provided herein competes for binding to TIGIT with an antibody selected from MAB1, MAB2, MAB3, MAB4, MAB5, MAB6, MAB7, MAB8, MAB9, MAB10, MAB11, MAB12, MAB13, MAB14, MAB15, MAB16, MAB17, MAB18, MAB19, MAB20, or MAB21, each as provided in Table 5 of this disclosure.

In some embodiments, an antibody fragment provided herein inhibits binding of CD155 to TIGIT. In some embodiments, an antibody fragment provided herein inhibits binding of CD112 to TIGIT. In some embodiments, an antibody fragment provided herein inhibits association of CD226 with TIGIT.

In some embodiments, an antibody fragment provided herein activates an effector T cell or a natural killer (NK) cell. In some embodiments, an antibody fragment provided herein decreases the number of regulatory T cells in a tissue or in circulation. In some embodiments, an antibody fragment provided herein inhibits the suppression of an effector T cell by a regulatory T cell.

In some embodiments, an antibody fragment provided herein does not bind specifically to any of PVRL1, PVRL2, PVRL3, or PVRL4.

In some embodiments, an antibody fragment provided herein binds murine TIGIT (mTIGIT; SEQ ID NO: 3) with an affinity lower (as indicated by higher $K_D$) than the affinity of the antibody fragment for hTIGIT, or does not bind mTIGIT.

In some embodiments, a fragment of an antibody provided herein binds the same epitope of TIGIT as such antibody.

In some embodiments, the ABPs provided herein are monoclonal antibodies. In some embodiments, the ABPs provided herein are polyclonal antibodies.

In some embodiments, the ABPs provided herein comprise a chimeric antibody. In some embodiments, the ABPs provided herein consist of a chimeric antibody. In some embodiments, the ABPs provided herein consist essentially of a chimeric antibody. In some embodiments, the ABPs provided herein comprise a humanized antibody. In some embodiments, the ABPs provided herein consist of a humanized antibody. In some embodiments, the ABPs provided herein consist essentially of a humanized antibody. In some embodiments, the ABPs provided herein comprise a human antibody. In some embodiments, the ABPs provided herein consist of a human antibody. In some embodiments, the ABPs provided herein consist essentially of a human antibody.

In some embodiments, the ABPs provided herein are affinity matured. In some aspects, the affinity matured ABPs are affinity matured ABPs derived from an illustrative ABP provided herein.

In some embodiments, the ABPs provided herein comprise an alternative scaffold. In some embodiments, the ABPs provided herein consist of an alternative scaffold. In some embodiments, the ABPs provided herein consist essentially of an alternative scaffold. Any suitable alternative scaffold may be used. In some aspects, the alternative scaffold is selected from an Adnectin™, an iMab, an Anticalin®, an EETI-II/AGRP, a Kunitz domain, a thioredoxin peptide aptamer, an Affibody®, a DARPin, an Affilin, a Tetranectin, a Fynomer, and an Avimer.

In some embodiments, an ABP provided herein inhibits binding of TIGIT to one or more ligands of TIGIT. In some aspects, the ligand of TIGIT is selected from one or more of poliovirus receptor (PVR; CD155) and nectin-2 (CD112, PVRL2). In some aspects, the ABP inhibits binding of TIGIT to one or more ligands of TIGIT by at least about 50%. In some aspects, the ABP inhibits binding of TIGIT to one or more ligands of TIGIT by at least about 75%. In some aspects, the ABP inhibits binding of TIGIT to one or more ligands of TIGIT by at least about 90%. In some aspects, the ABP inhibits binding of TIGIT to one or more ligands of TIGIT by at least about 95%.

In some embodiments, an ABP of the invention is an ABP that competes with an illustrative ABP provided herein. In some aspects, the ABP that competes with the illustrative ABP provided herein binds the same epitope as an illustrative ABP provided herein.

In some embodiments, an ABP provided herein does not bind PVRL4.

It is known that when an antibody is expressed in cells, the antibody is modified after translation. Examples of the posttranslational modification include cleavage of lysine at the C terminal of the heavy chain by a carboxypeptidase; modification of glutamine or glutamic acid at the N terminal of the heavy chain and the light chain to pyroglutamic acid by pyroglutamylation; glycosylation; oxidation; deamidation; and glycation, and it is known that such posttranslational modifications occur in various antibodies (See Journal of Pharmaceutical Sciences, 2008, Vol. 97, p. 2426-2447, incorporated by reference in its entirety). In some embodiments, an ABP of the invention is an antibody or antigen-binding fragment thereof which has undergone posttranslational modification. Examples of an antibody or antigen-binding fragment thereof which have undergone posttranslational modification include an antibody or antigen-binding fragments thereof which have undergone pyroglutamylation at the N terminal of the heavy chain variable region and/or deletion of lysine at the C terminal of the heavy chain. It is known in the art that such posttranslational modification due to pyroglutamylation at the N terminal and deletion of lysine at the C terminal does not have any influence on the activity of the antibody or fragment thereof (Analytical Biochemistry, 2006, Vol. 348, p. 24-39, incorporated by reference in its entirety).

2.2. Sequences of TIGIT Antigen-Binding Proteins 2.2.1. $V_H$ Domains

In some embodiments, an ABP provided herein comprises a $V_H$ sequence selected from SEQ ID NOs: 4-24. In some embodiments an ABP provided herein comprises a $V_H$ sequence of SEQ ID NO:4. In some embodiments an ABP provided herein comprises a $V_H$ sequence of SEQ ID NO:5. In some embodiments an ABP provided herein comprises a $V_H$ sequence of SEQ ID NO:6. In some embodiments an ABP provided herein comprises a $V_H$ sequence of SEQ ID NO:7. In some embodiments an ABP provided herein comprises a $V_H$ sequence of SEQ ID NO:8. In some embodiments an ABP provided herein comprises a $V_H$ sequence of SEQ ID NO:9. In some embodiments an ABP provided herein comprises a $V_H$ sequence of SEQ ID NO:10. In some embodiments an ABP provided herein comprises a $V_H$ sequence of SEQ ID NO:11. In some embodiments an ABP provided herein comprises a $V_H$ sequence of SEQ ID NO:12. In some embodiments an ABP provided herein comprises a $V_H$ sequence of SEQ ID NO:13. In some embodiments an ABP provided herein comprises a $V_H$ sequence of SEQ ID NO:14. In some embodiments an ABP provided herein comprises a $V_H$ sequence of SEQ ID NO:15. In some embodiments an ABP provided herein comprises a $V_H$ sequence of SEQ ID NO:16. In some embodiments an ABP provided herein comprises a $V_H$ sequence of SEQ ID NO:17. In some embodiments an ABP provided herein comprises a $V_H$ sequence of SEQ ID NO:18. In some embodiments an ABP provided herein comprises a $V_H$ sequence of SEQ ID NO:19. In some embodiments an ABP provided herein comprises a $V_H$ sequence of SEQ ID NO:20. In some embodiments an ABP provided herein comprises a $V_H$ sequence of SEQ ID NO:21. In some embodiments an ABP provided herein comprises a $V_H$ sequence of SEQ ID NO:22. In some embodiments an ABP provided herein comprises a $V_H$ sequence of SEQ ID NO:23. In some embodiments an ABP provided herein comprises a $V_H$ sequence of SEQ ID NO:24.

In some embodiments, an ABP provided herein comprises a $V_H$ sequence having at least about 50%, 60%, 70%, 80%, 90%, 95%, or 99% identity to an illustrative $V_H$ sequence provided in SEQ ID NOs: 4-24. In some embodiments, an ABP provided herein comprises a $V_H$ sequence provided in SEQ ID NOs: 4-24, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

2.2.2. $V_L$ Domains

In some embodiments, an ABP provided herein comprises a $V_L$ sequence selected from SEQ ID NOs: 25-28. In some embodiments an ABP provided herein comprises a $V_L$ sequence of SEQ ID NO:25. In some embodiments an ABP provided herein comprises a $V_L$ sequence of SEQ ID NO:26. In some embodiments an ABP provided herein comprises a $V_L$ sequence of SEQ ID NO:27. In some embodiments an ABP provided herein comprises a $V_L$ sequence of SEQ ID NO:28.

In some embodiments, an ABP provided herein comprises a $V_L$ sequence having at least about 50%, 60%, 70%, 80%, 90%, 95%, or 99% identity to an illustrative $V_L$ sequence provided in SEQ ID NOs: 25-28. In some embodiments, an ABP provided herein comprises a $V_L$ sequence provided in SEQ ID NOs: 25-28, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

2.2.3. $V_H$-$V_L$ Combinations

In some embodiments, an ABP provided herein comprises a $V_H$ sequence selected from SEQ ID NOs: 4-24 and a $V_L$ sequence selected from SEQ ID NOs: 25-28.

In some embodiments, an ABP provided herein comprises a $V_H$ sequence of SEQ ID NO:4 and a $V_L$ sequence of SEQ ID NO:25. In some embodiments, an ABP provided herein comprises a $V_H$ sequence of SEQ ID NO:5 and a $V_L$ sequence of SEQ ID NO:25. In some embodiments, an ABP provided herein comprises a $V_H$ sequence of SEQ ID NO:6 and a $V_L$ sequence of SEQ ID NO:25. In some embodiments, an ABP provided herein comprises a $V_H$ sequence of SEQ ID NO:7 and a $V_L$ sequence of SEQ ID NO:25. In some embodiments, an ABP provided herein comprises a $V_H$ sequence of SEQ ID NO:8 and a $V_L$ sequence of SEQ ID NO:25. In some embodiments, an ABP provided herein comprises a $V_H$ sequence of SEQ ID NO:9 and a $V_L$ sequence of SEQ ID NO:26. In some embodiments, an ABP provided herein comprises a $V_H$ sequence of SEQ ID NO:10 and a $V_L$ sequence of SEQ ID NO:26. In some embodiments, an ABP provided herein comprises a $V_H$ sequence of SEQ ID NO:11 and a $V_L$ sequence of SEQ ID NO:26. In some embodiments, an ABP provided herein comprises a $V_H$ sequence of SEQ ID NO: 12 and a $V_L$ sequence of SEQ ID NO:26. In some embodiments, an ABP provided herein comprises a $V_H$ sequence of SEQ ID NO:13 and a $V_L$ sequence of SEQ ID NO:26. In some embodiments, an ABP provided herein comprises a $V_H$ sequence of SEQ ID NO:14 and a $V_L$ sequence of SEQ ID NO:26. In some embodiments, an ABP provided herein comprises a $V_H$ sequence of SEQ ID NO: 15 and a $V_L$ sequence of SEQ ID NO:26. In some embodiments, an ABP provided herein comprises a $V_H$ sequence of SEQ ID NO:16 and a $V_L$ sequence of SEQ ID NO:27. In some embodiments, an ABP provided herein comprises a $V_H$ sequence of SEQ ID NO:17 and a $V_L$ sequence of SEQ ID NO:27. In some embodiments, an ABP provided herein comprises a $V_H$ sequence of SEQ ID NO: 18 and a $V_L$ sequence of SEQ ID NO:27. In some embodiments, an ABP provided herein comprises a $V_H$ sequence of SEQ ID NO:19 and a $V_L$ sequence of SEQ ID NO:27. In some embodiments, an ABP provided herein comprises a $V_H$ sequence of SEQ ID NO:20 and a $V_L$ sequence of SEQ ID NO:27. In some embodiments, an ABP provided herein comprises a $V_H$ sequence of SEQ ID NO:21 and a $V_L$ sequence of SEQ ID NO:27. In some embodiments, an ABP provided herein comprises a $V_H$ sequence of SEQ ID NO:22 and a $V_L$ sequence of SEQ ID NO:28. In some embodiments, an ABP provided herein comprises a $V_H$ sequence of SEQ ID NO:23 and a $V_L$ sequence of SEQ ID NO:28. In some embodiments, an ABP provided herein comprises a $V_H$ sequence of SEQ ID NO:24 and a $V_L$ sequence of SEQ ID NO:28.

In some embodiments, an ABP provided herein comprises a $V_H$ sequence of SEQ ID NO:4 and a $V_L$ sequence of SEQ ID NO:26. In some embodiments, an ABP provided herein comprises a $V_H$ sequence of SEQ ID NO:4 and a $V_L$ sequence of SEQ ID NO:27. In some embodiments, an ABP provided herein comprises a $V_H$ sequence of SEQ ID NO:4 and a $V_L$ sequence of SEQ ID NO:28.

In some embodiments, an ABP provided herein comprises a $V_H$ sequence of SEQ ID NO:5 and a $V_L$ sequence of SEQ ID NO:26. In some embodiments, an ABP provided herein comprises a $V_H$ sequence of SEQ ID NO:5 and a $V_L$ sequence of SEQ ID NO:27. In some embodiments, an ABP provided herein comprises a $V_H$ sequence of SEQ ID NO:5 and a $V_L$ sequence of SEQ ID NO:28.

In some embodiments, an ABP provided herein comprises a $V_H$ sequence of SEQ ID NO:6 and a $V_L$ sequence of SEQ ID NO:26. In some embodiments, an ABP provided herein comprises a $V_H$ sequence of SEQ ID NO:6 and a $V_L$ sequence of SEQ ID NO:27. In some embodiments, an ABP provided herein comprises a $V_H$ sequence of SEQ ID NO:6 and a $V_L$ sequence of SEQ ID NO:28.

In some embodiments, an ABP provided herein comprises a $V_H$ sequence of SEQ ID NO:7 and a $V_L$ sequence of SEQ ID NO:26. In some embodiments, an ABP provided herein comprises a $V_H$ sequence of SEQ ID NO:7 and a $V_L$ sequence of SEQ ID NO:27. In some embodiments, an ABP provided herein comprises a $V_H$ sequence of SEQ ID NO:7 and a $V_L$ sequence of SEQ ID NO:28.

In some embodiments, an ABP provided herein comprises a $V_H$ sequence of SEQ ID NO:8 and a $V_L$ sequence of SEQ ID NO:26. In some embodiments, an ABP provided herein comprises a $V_H$ sequence of SEQ ID NO:8 and a $V_L$ sequence of SEQ ID NO:27. In some embodiments, an ABP provided herein comprises a $V_H$ sequence of SEQ ID NO:8 and a $V_L$ sequence of SEQ ID NO:28.

In some embodiments, an ABP provided herein comprises a $V_H$ sequence of SEQ ID NO:9 and a $V_L$ sequence of SEQ ID NO:25. In some embodiments, an ABP provided herein comprises a $V_H$ sequence of SEQ ID NO:9 and a $V_L$ sequence of SEQ ID NO:27. In some embodiments, an ABP provided herein comprises a $V_H$ sequence of SEQ ID NO:9 and a $V_L$ sequence of SEQ ID NO:28.

In some embodiments, an ABP provided herein comprises a $V_H$ sequence of SEQ ID NO:10 and a $V_L$ sequence of SEQ ID NO:25. In some embodiments, an ABP provided herein comprises a $V_H$ sequence of SEQ ID NO:10 and a $V_L$ sequence of SEQ ID NO:27. In some embodiments, an ABP provided herein comprises a $V_H$ sequence of SEQ ID NO: 10 and a $V_L$ sequence of SEQ ID NO:28.

In some embodiments, an ABP provided herein comprises a $V_H$ sequence of SEQ ID NO:11 and a $V_L$ sequence of SEQ ID NO:25. In some embodiments, an ABP provided herein comprises a $V_H$ sequence of SEQ ID NO:11 and a $V_L$ sequence of SEQ ID NO:27. In some embodiments, an ABP provided herein comprises a $V_H$ sequence of SEQ ID NO:11 and a $V_L$ sequence of SEQ ID NO:28.

In some embodiments, an ABP provided herein comprises a $V_H$ sequence of SEQ ID NO:12 and a $V_L$ sequence of SEQ ID NO:25. In some embodiments, an ABP provided herein comprises a $V_H$ sequence of SEQ ID NO:12 and a $V_L$ sequence of SEQ ID NO:27. In some embodiments, an ABP provided herein comprises a $V_H$ sequence of SEQ ID NO: 12 and a $V_L$ sequence of SEQ ID NO:28.

In some embodiments, an ABP provided herein comprises a $V_H$ sequence of SEQ ID NO:13 and a $V_L$ sequence of SEQ ID NO:25. In some embodiments, an ABP provided herein comprises a $V_H$ sequence of SEQ ID NO:13 and a $V_L$ sequence of SEQ ID NO:27. In some embodiments, an ABP provided herein comprises a $V_H$ sequence of SEQ ID NO: 13 and a $V_L$ sequence of SEQ ID NO:28.

In some embodiments, an ABP provided herein comprises a $V_H$ sequence of SEQ ID NO:14 and a $V_L$ sequence of SEQ ID NO:25. In some embodiments, an ABP provided herein comprises a $V_H$ sequence of SEQ ID NO:14 and a $V_L$ sequence of SEQ ID NO:27. In some embodiments, an ABP provided herein comprises a $V_H$ sequence of SEQ ID NO: 14 and a $V_L$ sequence of SEQ ID NO:28.

In some embodiments, an ABP provided herein comprises a $V_H$ sequence of SEQ ID NO:15 and a $V_L$ sequence of SEQ ID NO:25. In some embodiments, an ABP provided herein comprises a $V_H$ sequence of SEQ ID NO:15 and a $V_L$ sequence of SEQ ID NO:27. In some embodiments, an ABP provided herein comprises a $V_H$ sequence of SEQ ID NO: 15 and a $V_L$ sequence of SEQ ID NO:28.

In some embodiments, an ABP provided herein comprises a $V_H$ sequence of SEQ ID NO:16 and a $V_L$ sequence of SEQ ID NO:25. In some embodiments, an ABP provided herein comprises a $V_H$ sequence of SEQ ID NO:16 and a $V_L$ sequence of SEQ ID NO:26. In some embodiments, an ABP provided herein comprises a $V_H$ sequence of SEQ ID NO: 16 and a $V_L$ sequence of SEQ ID NO:28.

In some embodiments, an ABP provided herein comprises a $V_H$ sequence of SEQ ID NO:17 and a $V_L$ sequence of SEQ ID NO:25. In some embodiments, an ABP provided herein comprises a $V_H$ sequence of SEQ ID NO:17 and a $V_L$ sequence of SEQ ID NO:26. In some embodiments, an ABP provided herein comprises a $V_H$ sequence of SEQ ID NO: 17 and a $V_L$ sequence of SEQ ID NO:28.

In some embodiments, an ABP provided herein comprises a $V_H$ sequence of SEQ ID NO:18 and a $V_L$ sequence of SEQ ID NO:25. In some embodiments, an ABP provided herein comprises a $V_H$ sequence of SEQ ID NO:18 and a $V_L$ sequence of SEQ ID NO:26. In some embodiments, an ABP provided herein comprises a $V_H$ sequence of SEQ ID NO: 18 and a $V_L$ sequence of SEQ ID NO:28.

In some embodiments, an ABP provided herein comprises a $V_H$ sequence of SEQ ID NO:19 and a $V_L$ sequence of SEQ ID NO:25. In some embodiments, an ABP provided herein comprises a $V_H$ sequence of SEQ ID NO:19 and a $V_L$ sequence of SEQ ID NO:26. In some embodiments, an ABP provided herein comprises a $V_H$ sequence of SEQ ID NO: 19 and a $V_L$ sequence of SEQ ID NO:28.

In some embodiments, an ABP provided herein comprises a $V_H$ sequence of SEQ ID NO:20 and a $V_L$ sequence of SEQ ID NO:25. In some embodiments, an ABP provided herein comprises a $V_H$ sequence of SEQ ID NO:20 and a $V_L$ sequence of SEQ ID NO:26. In some embodiments, an ABP provided herein comprises a $V_H$ sequence of SEQ ID NO:20 and a $V_L$ sequence of SEQ ID NO:28.

In some embodiments, an ABP provided herein comprises a $V_H$ sequence of SEQ ID NO:21 and a $V_L$ sequence of SEQ ID NO:25. In some embodiments, an ABP provided herein comprises a $V_H$ sequence of SEQ ID NO:21 and a $V_L$ sequence of SEQ ID NO:26. In some embodiments, an ABP provided herein comprises a $V_H$ sequence of SEQ ID NO:21 and a $V_L$ sequence of SEQ ID NO:28.

In some embodiments, an ABP provided herein comprises a $V_H$ sequence of SEQ ID NO:22 and a $V_L$ sequence of SEQ ID NO:25. In some embodiments, an ABP provided herein comprises a $V_H$ sequence of SEQ ID NO:22 and a $V_L$ sequence of SEQ ID NO:26. In some embodiments, an ABP provided herein comprises a $V_H$ sequence of SEQ ID NO:22 and a $V_L$ sequence of SEQ ID NO:27.

In some embodiments, an ABP provided herein comprises a $V_H$ sequence of SEQ ID NO:23 and a $V_L$ sequence of SEQ ID NO:25. In some embodiments, an ABP provided herein comprises a $V_H$ sequence of SEQ ID NO:23 and a $V_L$ sequence of SEQ ID NO:26. In some embodiments, an ABP provided herein comprises a $V_H$ sequence of SEQ ID NO:23 and a $V_L$ sequence of SEQ ID NO:27.

In some embodiments, an ABP provided herein comprises a $V_H$ sequence of SEQ ID NO:24 and a $V_L$ sequence of SEQ ID NO:25. In some embodiments, an ABP provided herein comprises a $V_H$ sequence of SEQ ID NO:24 and a $V_L$ sequence of SEQ ID NO:26. In some embodiments, an ABP provided herein comprises a $V_H$ sequence of SEQ ID NO:24 and a $V_L$ sequence of SEQ ID NO:27.

In some embodiments, an ABP provided herein comprises a $V_H$ sequence having at least about 50%, 60%, 70%, 80%, 90%, 95%, or 99% identity to an illustrative $V_H$ sequence provided in SEQ ID NOs: 4-24, and a $V_L$ sequence having at least about 50%, 60%, 70%, 80%, 90%, 95%, or 99% identity to an illustrative $V_L$ sequence provided in SEQ ID NOs: 25-28. In some embodiments, an ABP provided herein comprises a $V_H$ sequence provided in SEQ ID NOs: 4-24, with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a $V_L$ sequence provided in SEQ ID NOs: 25-28, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

2.2.4. CDRs

In some embodiments, an ABP provided herein comprises one to three CDRs of a $V_H$ domain selected from SEQ ID NOs: 4-24. In some embodiments, an ABP provided herein comprises two to three CDRs of a $V_H$ domain selected from SEQ ID NOs: 4-24. In some embodiments, an ABP provided herein comprises three CDRs of a $V_H$ domain selected from SEQ ID NOs: 4-24. In some aspects, the CDRs are Kabat CDRs. In some aspects, the CDRs are Chothia CDRs. In some aspects, the CDRs are IMGT CDRs.

In some embodiments, the CDRs are CDRs having at least about 50%, 75%, 80%, 85%, 90%, or 95% identity with a CDR-H1, CDR-H2, or CDR-H3 of SEQ ID NOs: 4-24. In some embodiments, the CDR-H1 is a CDR-H1 of a $V_H$ domain selected from SEQ ID NOs: 4-24, with up to 1, 2, 3, 4, or 5 amino acid substitutions. In some embodiments, the CDR-H2 is a CDR-H2 of a $V_H$ domain selected from SEQ ID NOs: 4-24, with up to 1, 2, 3, 4, 5, 6, 7, or 8 amino acid substitutions. In some embodiments, the CDR-H3 is a CDR-H3 of a $V_H$ domain selected from SEQ ID NOs: 4-24, with up to 1, 2, 3, 4, 5, 6, 7, or 8 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises one to three CDRs of a $V_L$ domain selected from SEQ ID NOs: 25-28. In some embodiments, an ABP provided herein comprises two to three CDRs of a $V_L$ domain selected from SEQ ID NOs: 25-28. In some embodiments, an ABP provided herein comprises three CDRs of a $V_L$ domain selected from SEQ ID NOs: 25-28. In some aspects, the CDRs are Kabat CDRs. In some aspects, the CDRs are Chothia CDRs. In some aspects, the CDRs are IMGT CDRs.

In some embodiments, the CDRs are CDRs having at least about 50%, 75%, 80%, 85%, 90%, or 95% identity with a CDR-L1, CDR-L2, or CDR-L3 of SEQ ID NOs: 25-28. In some embodiments, the CDR-L1 is a CDR-L1 of a $V_L$ domain selected from SEQ ID NOs: 25-28, with up to 1, 2, 3, 4, 5, or 6 amino acid substitutions. In some embodiments, the CDR-L2 is a CDR-L2 of a $V_L$ domain selected from SEQ ID NOs: 25-28, with up to 1, 2, 3, or 4 amino acid substitutions. In some embodiments, the CDR-L3 is a CDR-L3 of a $V_L$ domain selected from SEQ ID NOs: 25-28, with up to 1, 2, 3, 4, or 5 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises one to three CDRs of a $V_H$ domain selected from SEQ ID NOs: 4-24 and one to three CDRs of a $V_L$ domain selected from SEQ ID NOs: 25-28. In some embodiments, an ABP provided herein comprises two to three CDRs of a $V_H$ domain selected from SEQ ID NOs: 4-24 and two to three CDRs of a $V_L$ domain selected from SEQ ID NOs: 25-28. In some embodiments, an ABP provided herein comprises three CDRs of a $V_H$ domain selected from SEQ ID NOs: 4-24 and three CDRs of a $V_L$ domain selected from SEQ ID NOs: 25-28. In some aspects, the CDRs are Kabat CDRs. In some aspects, the CDRs are Chothia CDRs. In some aspects, the CDRs are IMGT CDRs.

In some embodiments, the CDRs are CDRs having at least about 50%, 75%, 80%, 85%, 90%, or 95% identity with a CDR-H1, CDR-H2, or CDR-H3 of SEQ ID NOs: 4-24 and at least about 50%, 75%, 80%, 85%, 90%, or 95% identity with a CDR-L1, CDR-L2, or CDR-L3 of SEQ ID NOs: 25-28. In some embodiments, the CDR-H1 is a CDR-H1 of a $V_H$ domain selected from SEQ ID NOs: 4-24, with up to 1, 2, 3, 4, or 5 amino acid substitutions; the CDR-H2 is a CDR-H2 of a $V_H$ domain selected from SEQ ID NOs: 4-24, with up to 1, 2, 3, 4, 5, 6, 7, or 8 amino acid substitutions; the CDR-H3 is a CDR-H3 of a $V_H$ domain selected from SEQ ID NOs: 4-24, with up to 1, 2, 3, 4, 5, 6, 7, or 8 amino acid substitutions; the CDR-L1 is a CDR-L1 of a $V_L$ domain selected from SEQ ID NOs: 25-28, with up to 1, 2, 3, 4, 5, or 6 amino acid substitutions; the CDR-L2 is a CDR-L2 of a $V_L$ domain selected from SEQ ID NOs: 25-28, with up to 1, 2, 3, or 4 amino acid substitutions; and the CDR-L3 is a CDR-L3 of a $V_L$ domain selected from SEQ ID NOs: 25-28, with up to 1, 2, 3, 4, or 5 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-H3 selected from SEQ ID NOs: 29-35. In some aspects, the CDR-H3 has at least about 50%, 75%, 80%, 85%, 90%, or 95% identity with a CDR-H3 of SEQ ID NOs: 29-35. In some aspects, the CDR-H3 is a CDR-H3 according to the IMGT numbering system. In some embodiments, the CDR-H3 is a CDR-H3 selected from SEQ ID NOs: 29-35, with up to 1, 2, 3, 4, 5, 6, 7, or 8 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-H2 selected from SEQ ID NOs: 36-47. In some aspects, the CDR-H2 has at least about 50%, 75%, 80%, 85%, 90%, or 95% identity with a CDR-H2 of SEQ ID NOs: 36-47. In some aspects, the CDR-H2 is a CDR-H2 according to the Kabat numbering system. In some embodiments, the CDR-H2 is a CDR-H2 selected from SEQ ID NOs: 36-47, with up to 1, 2, 3, 4, 5, 6, 7, or 8 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-H1 selected from SEQ ID NOs: 48-54 or 58-62. In some aspects, the CDR-H1 has at least about 50%, 75%, 80%, 85%, 90%, or 95% identity with a CDR-H1 of SEQ ID NOs: 48-54 or 58-62. In some aspects, the CDR-H1 is a CDR-H1 that spans the CDR-H1 as defined by both the Chothia and Kabat numbering systems. In some embodiments, the CDR-H1 is a CDR-H1 selected from SEQ ID NOs: 48-54 or 58-62, with up to 1, 2, 3, 4, or 5 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-H3 selected from SEQ ID NOs: 29-35 and a CDR-H2 selected from SEQ ID NOs: 36-47. In some embodiments, an ABP provided herein comprises a CDR-H3 selected from SEQ ID NOs: 29-35, a CDR-H2 selected from SEQ ID NOs: 36-47, and a CDR-H1 selected from SEQ ID NOs: 48-54 or 58-62. In some embodiments, the CDR-H3 has at least about 50%, 75%, 80%, 85%, 90%, or 95% identity with a CDR-H3 of SEQ ID NOs: 29-35, the CDR-H2 has at least about 50%, 75%, 80%, 85%, 90%, or 95% identity with a CDR-H2 of SEQ ID NOs: 36-47, and the CDR-H1 has at least about 50%, 75%, 80%, 85%, 90%, or 95% identity with a CDR-H1 of SEQ ID NOs: 48-54 or 58-62. In some embodiments, the CDR-H3 is a CDR-H3 selected from SEQ ID NOs: 29-35, with up to 1, 2, 3, 4, 5, 6, 7, or 8 amino acid substitutions; the CDR-H2 is a CDR-H2 selected from SEQ ID NOs: 36-47, with up to 1, 2, 3, 4, 5, 6, 7, or 8 amino acid substitutions; and the CDR-H1 is a CDR-H1 selected from SEQ ID NOs: 48-54 or 58-62, with up to 1, 2, 3, 4, or 5 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-L3 selected from SEQ ID NOs: 63-66. In some aspects, the CDR-L3 has at least about 50%, 75%, 80%, 85%, 90%, or 95% identity with a CDR-L3 of SEQ ID NOs: 63-66. In some aspects, the CDR-L3 is a CDR-L3 according to the Kabat, Chothia, and IMGT numbering systems. In some embodiments, the CDR-L3 is a CDR-L3 selected from SEQ ID NOs: 63-66, with up to 1, 2, 3, 4, or 5 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-L2 selected from SEQ ID NOs: 67-69. In some aspects, the CDR-L2 has at least about 50%, 75%, 80%, 85%, 90%, or 95% identity with a CDR-L2 of SEQ ID NOs: 67-69. In some aspects, the CDR-L2 is a CDR-L2 according to the Kabat and Chothia numbering systems. In some embodiments, the CDR-L2 is a CDR-L2 selected from SEQ ID NOs: 67-69, with up to 1, 2, 3, or 4 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-L1 selected from SEQ ID NOs: 70-72. In some aspects, the CDR-L1 has at least about 50%, 75%, 80%, 85%, 90%, or 95% identity with a CDR-L1 of SEQ ID NOs: 70-72. In some aspects, the CDR-L1 is a CDR-L1 according to the Kabat and Chothia numbering systems. In some embodiments, the CDR-L1 is a CDR-L1 selected from SEQ ID NOs: 70-72, with up to 1, 2, 3, 4, 5, or 6 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-L3 selected from SEQ ID NOs: 63-66 and a CDR-L2 selected from SEQ ID NOs: 67-69. In some embodiments, an ABP provided herein comprises a CDR-L3 selected from SEQ ID NOs: 63-66, a CDR-L2 selected from SEQ ID NOs: 67-69, and a CDR-L1 selected from SEQ ID NOs: 70-72. In some embodiments, the CDR-L3 has at least about 50%, 75%, 80%, 85%, 90%, or 95% identity with a CDR-L3 of SEQ ID NOs: 63-66, the CDR-L2 has at least about 50%, 75%, 80%, 85%, 90%, or 95% identity with a CDR-L2 of SEQ ID NOs: 67-69, and the CDR-L1 has at least about 50%, 75%, 80%, 85%, 90%, or 95% identity with a CDR-L1 of SEQ ID NOs: 70-72. In some embodiments, the CDR-L3 is a CDR-L3 selected from SEQ ID NOs: 63-66, with up to 1, 2, 3, 4, or 5 amino acid substitutions; the CDR-L2 is a CDR-L2 selected from SEQ ID NOs: 67-69, with up to 1, 2, 3, or 4 amino acid substitutions; and the CDR-L1 is a CDR-L1 selected from SEQ ID NOs: 70-72, with up to 1, 2, 3, 4, 5, or 6 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-H3 selected from SEQ ID NOs: 29-35, a CDR-H2 selected from SEQ ID NOs: 36-47, a CDR-H1 selected from SEQ ID NOs: 48-54 or 58-62, a CDR-L3 selected from SEQ ID NOs: 63-66, a CDR-L2 selected from SEQ ID NOs: 67-69, and a CDR-L1 selected from SEQ ID NOs: 70-72. In some embodiments, the CDR-H3 has at least about 50%, 75%, 80%, 85%, 90%, or 95% identity with a CDR-H3 of SEQ ID NOs: 29-35, the CDR-H2 has at least about 50%, 75%, 80%, 85%, 90%, or 95% identity with a CDR-H2 of SEQ ID NOs: 36-47, the CDR-H1 has at least about 50%, 75%, 80%, 85%, 90%, or 95% identity with a CDR-H1 of SEQ ID NOs: 48-54 or 58-62, the CDR-L3 has at least about 50%, 75%, 80%, 85%, 90%, or 95% identity with a CDR-L3 of SEQ ID NOs: 63-66, the CDR-L2 has at least about 50%, 75%, 80%, 85%, 90%, or 95% identity with a CDR-L2 of SEQ ID NOs: 67-69, and the CDR-L1 has at least about 50%, 75%, 80%, 85%, 90%, or 95% identity with a CDR-L1 of SEQ ID NOs: 70-72. In some embodiments, the CDR-H3 is a CDR-H3 selected from SEQ ID NOs: 29-35, with up to 1, 2, 3, 4, 5, 6, 7, or 8 amino acid substitutions; the CDR-H2 is a CDR-H2 selected from SEQ ID NOs: 36-47, with up to 1, 2, 3, 4, 5, 6, 7, or 8 amino acid substitutions; the CDR-H1 is a CDR-H1 selected from SEQ ID NOs: 48-54 or 58-62, with up to 1, 2, 3, 4, or 5 amino acid substitutions; the CDR-L3 is a CDR-L3 selected from SEQ ID NOs: 63-66, with up to 1, 2, 3, 4, or 5 amino acid substitutions; the CDR-L2 is a CDR-L2 selected from SEQ ID NOs: 67-69, with up to 1, 2, 3, or 4 amino acid substitutions; and the CDR-L1 is a CDR-L1 selected from SEQ ID NOs: 70-72, with up to 1, 2, 3, 4, 5, or 6 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-H3 of SEQ ID NO:29, a CDR-H2 of SEQ ID NO:36, a CDR-H1 of SEQ ID NO:48, a CDR-L3 of SEQ ID NO:63, a CDR-L2 of SEQ ID NO:67, and a CDR-L1 of SEQ ID NO:70.

In some embodiments, an ABP provided herein comprises a CDR-H3 of SEQ ID NO:29, a CDR-H2 of SEQ ID NO:37, a CDR-H1 of SEQ ID NO:49, a CDR-L3 of SEQ ID NO:63, a CDR-L2 of SEQ ID NO:67, and a CDR-L1 of SEQ ID NO:70.

In some embodiments, an ABP provided herein comprises a CDR-H3 of SEQ ID NO:29, a CDR-H2 of SEQ ID NO:37, a CDR-H1 of SEQ ID NO:50, a CDR-L3 of SEQ ID NO:63, a CDR-L2 of SEQ ID NO:67, and a CDR-L1 of SEQ ID NO:70.

In some embodiments, an ABP provided herein comprises a CDR-H3 of SEQ ID NO:30, a CDR-H2 of SEQ ID NO:37, a CDR-H1 of SEQ ID NO:50, a CDR-L3 of SEQ ID NO:63, a CDR-L2 of SEQ ID NO:67, and a CDR-L1 of SEQ ID NO:70.

In some embodiments, an ABP provided herein comprises a CDR-H3 of SEQ ID NO:29, a CDR-H2 of SEQ ID NO:38, a CDR-H1 of SEQ ID NO:50, a CDR-L3 of SEQ ID NO:63, a CDR-L2 of SEQ ID NO:67, and a CDR-L1 of SEQ ID NO:70.

In some embodiments, an ABP provided herein comprises a CDR-H3 of SEQ ID NO:31, a CDR-H2 of SEQ ID NO:39, a CDR-H1 of SEQ ID NO:51, a CDR-L3 of SEQ ID NO:64, a CDR-L2 of SEQ ID NO:68, and a CDR-L1 of SEQ ID NO:71.

In some embodiments, an ABP provided herein comprises a CDR-H3 of SEQ ID NO:31, a CDR-H2 of SEQ ID NO:40, a CDR-H1 of SEQ ID NO:52, a CDR-L3 of SEQ ID NO:64, a CDR-L2 of SEQ ID NO:68, and a CDR-L1 of SEQ ID NO:71.

In some embodiments, an ABP provided herein comprises a CDR-H3 of SEQ ID NO:31, a CDR-H2 of SEQ ID NO:41, a CDR-H1 of SEQ ID NO:53, a CDR-L3 of SEQ ID NO:64, a CDR-L2 of SEQ ID NO:68, and a CDR-L1 of SEQ ID NO:71.

In some embodiments, an ABP provided herein comprises a CDR-H3 of SEQ ID NO:31, a CDR-H2 of SEQ ID NO:40, a CDR-H1 of SEQ ID NO:54, a CDR-L3 of SEQ ID NO:64, a CDR-L2 of SEQ ID NO:68, and a CDR-L1 of SEQ ID NO:71.

In some embodiments, an ABP provided herein comprises a CDR-H3 of SEQ ID NO:32, a CDR-H2 of SEQ ID NO:40, a CDR-H1 of SEQ ID NO:54, a CDR-L3 of SEQ ID NO:64, a CDR-L2 of SEQ ID NO:68, and a CDR-L1 of SEQ ID NO:71.

In some embodiments, an ABP provided herein comprises a CDR-H3 of SEQ ID NO:32, a CDR-H2 of SEQ ID NO:40, a CDR-H1 of SEQ ID NO:54, a CDR-L3 of SEQ ID NO:64, a CDR-L2 of SEQ ID NO:68, and a CDR-L1 of SEQ ID NO:71.

In some embodiments, an ABP provided herein comprises a CDR-H3 of SEQ ID NO:32, a CDR-H2 of SEQ ID NO:40, a CDR-H1 of SEQ ID NO:54, a CDR-L3 of SEQ ID NO:64, a CDR-L2 of SEQ ID NO:68, and a CDR-L1 of SEQ ID NO:71.

In some embodiments, an ABP provided herein comprises a CDR-H3 of SEQ ID NO:33, a CDR-H2 of SEQ ID NO:42, a CDR-H1 of SEQ ID NO:58, a CDR-L3 of SEQ ID NO:65, a CDR-L2 of SEQ ID NO:69, and a CDR-L1 of SEQ ID NO:72.

In some embodiments, an ABP provided herein comprises a CDR-H3 of SEQ ID NO:33, a CDR-H2 of SEQ ID NO:42, a CDR-H1 of SEQ ID NO:59, a CDR-L3 of SEQ ID NO:65, a CDR-L2 of SEQ ID NO:69, and a CDR-L1 of SEQ ID NO:72.

In some embodiments, an ABP provided herein comprises a CDR-H3 of SEQ ID NO:33, a CDR-H2 of SEQ ID NO:43, a CDR-H1 of SEQ ID NO:60, a CDR-L3 of SEQ ID NO:65, a CDR-L2 of SEQ ID NO:69, and a CDR-L1 of SEQ ID NO:72.

In some embodiments, an ABP provided herein comprises a CDR-H3 of SEQ ID NO:34, a CDR-H2 of SEQ ID NO:43, a CDR-H1 of SEQ ID NO:60, a CDR-L3 of SEQ ID NO:65, a CDR-L2 of SEQ ID NO:69, and a CDR-L1 of SEQ ID NO:72.

In some embodiments, an ABP provided herein comprises a CDR-H3 of SEQ ID NO:34, a CDR-H2 of SEQ ID NO:44, a CDR-H1 of SEQ ID NO:61, a CDR-L3 of SEQ ID NO:65, a CDR-L2 of SEQ ID NO:69, and a CDR-L1 of SEQ ID NO:72.

In some embodiments, an ABP provided herein comprises a CDR-H3 of SEQ ID NO:33, a CDR-H2 of SEQ ID NO:44, a CDR-H1 of SEQ ID NO:59, a CDR-L3 of SEQ ID NO:65, a CDR-L2 of SEQ ID NO:69, and a CDR-L1 of SEQ ID NO:72.

In some embodiments, an ABP provided herein comprises a CDR-H3 of SEQ ID NO:35, a CDR-H2 of SEQ ID NO:45, a CDR-H1 of SEQ ID NO:62, a CDR-L3 of SEQ ID NO:66, a CDR-L2 of SEQ ID NO:69, and a CDR-L1 of SEQ ID NO:72.

In some embodiments, an ABP provided herein comprises a CDR-H3 of SEQ ID NO:35, a CDR-H2 of SEQ ID NO:46, a CDR-H1 of SEQ ID NO:62, a CDR-L3 of SEQ ID NO:66, a CDR-L2 of SEQ ID NO:69, and a CDR-L1 of SEQ ID NO:72.

In some embodiments, an ABP provided herein comprises a CDR-H3 of SEQ ID NO:35, a CDR-H2 of SEQ ID NO:47, a CDR-H1 of SEQ ID NO:62, a CDR-L3 of SEQ ID NO:66, a CDR-L2 of SEQ ID NO:69, and a CDR-L1 of SEQ ID NO:72.

2.2.5. Heavy Chains and Light Chains

In some embodiments, an ABP provided herein comprises a $V_H$ selected from a $V_H$ of SEQ ID NO:4-24 (or a variant described herein) and a constant region selected from SEQ ID NOs: 55-57 or 125. In some embodiments, an ABP provided herein comprises a $V_L$ selected from a $V_L$ of SEQ ID NO:25-28 (or a variant described herein) and a constant region of SEQ ID NO: 126.

In some embodiments, an ABP provided herein comprises a heavy chain of SEQ ID NO:79. In some embodiments, an ABP provided herein comprises a heavy chain of SEQ ID NO:80. In some embodiments, an ABP provided herein comprises a light chain of SEQ ID NO:81. In some embodiments, an APB provided herein comprises a heavy chain of SEQ ID NO:79 and a light chain of SEQ ID NO: 81. In some embodiments, an APB provided herein comprises a heavy chain of SEQ ID NO:80 and a light chain of SEQ ID NO: 81.

In some embodiments, an ABP provided herein comprises a heavy chain of SEQ ID NO:82. In some embodiments, an ABP provided herein comprises a heavy chain of SEQ ID NO:83. In some embodiments, an APB provided herein comprises a heavy chain of SEQ ID NO:82 and a light chain of SEQ ID NO: 81. In some embodiments, an APB provided herein comprises a heavy chain of SEQ ID NO:83 and a light chain of SEQ ID NO: 81.

In some embodiments, an ABP provided herein comprises a heavy chain of SEQ ID NO:84. In some embodiments, an ABP provided herein comprises a heavy chain of SEQ ID NO:85. In some embodiments, an APB provided herein comprises a heavy chain of SEQ ID NO:84 and a light chain of SEQ ID NO: 81. In some embodiments, an APB provided herein comprises a heavy chain of SEQ ID NO:85 and a light chain of SEQ ID NO: 81.

In some embodiments, an ABP provided herein comprises a heavy chain of SEQ ID NO:86. In some embodiments, an ABP provided herein comprises a heavy chain of SEQ ID NO:87. In some embodiments, an APB provided herein comprises a heavy chain of SEQ ID NO:86 and a light chain of SEQ ID NO: 81. In some embodiments, an APB provided herein comprises a heavy chain of SEQ ID NO:87 and a light chain of SEQ ID NO: 81.

In some embodiments, an ABP provided herein comprises a heavy chain of SEQ ID NO:88. In some embodiments, an ABP provided herein comprises a heavy chain of SEQ ID NO:89. In some embodiments, an APB provided herein comprises a heavy chain of SEQ ID NO:88 and a light chain of SEQ ID NO: 81. In some embodiments, an APB provided herein comprises a heavy chain of SEQ ID NO:89 and a light chain of SEQ ID NO: 81.

In some embodiments, an ABP provided herein comprises a heavy chain of SEQ ID NO:90. In some embodiments, an ABP provided herein comprises a heavy chain of SEQ ID NO:91. In some embodiments, an APB provided herein comprises a light chain of SEQ ID NO:92. In some embodiments, an APB provided herein comprises a heavy chain of SEQ ID NO:90 and a light chain of SEQ ID NO:92. In some embodiments, an APB provided herein comprises a heavy chain of SEQ ID NO:91 and a light chain of SEQ ID NO:92.

In some embodiments, an ABP provided herein comprises a heavy chain of SEQ ID NO:93. In some embodiments, an ABP provided herein comprises a heavy chain of SEQ ID NO:94. In some embodiments, an APB provided herein comprises a heavy chain of SEQ ID NO:93 and a light chain of SEQ ID NO:92. In some embodiments, an APB provided herein comprises a heavy chain of SEQ ID NO:94 and a light chain of SEQ ID NO:92.

In some embodiments, an ABP provided herein comprises a heavy chain of SEQ ID NO:95. In some embodiments, an ABP provided herein comprises a heavy chain of SEQ ID NO:96. In some embodiments, an APB provided herein comprises a heavy chain of SEQ ID NO:95 and a light chain of SEQ ID NO:92. In some embodiments, an APB provided herein comprises a heavy chain of SEQ ID NO:96 and a light chain of SEQ ID NO:92.

In some embodiments, an ABP provided herein comprises a heavy chain of SEQ ID NO:97. In some embodiments, an ABP provided herein comprises a heavy chain of SEQ ID NO:98. In some embodiments, an APB provided herein comprises a heavy chain of SEQ ID NO:97 and a light chain of SEQ ID NO:92. In some embodiments, an APB provided herein comprises a heavy chain of SEQ ID NO:98 and a light chain of SEQ ID NO:92.

In some embodiments, an ABP provided herein comprises a heavy chain of SEQ ID NO:99. In some embodiments, an ABP provided herein comprises a heavy chain of SEQ ID NO: 100. In some embodiments, an APB provided herein comprises a heavy chain of SEQ ID NO:99 and a light chain of SEQ ID NO:92. In some embodiments, an APB provided herein comprises a heavy chain of SEQ ID NO: 100 and a light chain of SEQ ID NO:92.

In some embodiments, an ABP provided herein comprises a heavy chain of SEQ ID NO: 101. In some embodiments, an ABP provided herein comprises a heavy chain of SEQ ID NO: 102. In some embodiments, an APB provided herein comprises a heavy chain of SEQ ID NO:101 and a light chain of SEQ ID NO:92. In some embodiments, an APB provided herein comprises a heavy chain of SEQ ID NO: 102 and a light chain of SEQ ID NO:92.

In some embodiments, an ABP provided herein comprises a heavy chain of SEQ ID NO: 103. In some embodiments, an ABP provided herein comprises a heavy chain of SEQ ID NO: 104. In some embodiments, an APB provided herein comprises a heavy chain of SEQ ID NO: 103 and a light chain of SEQ ID NO:92. In some embodiments, an APB provided herein comprises a heavy chain of SEQ ID NO: 104 and a light chain of SEQ ID NO:92.

In some embodiments, an ABP provided herein comprises a heavy chain of SEQ ID NO: 105. In some embodiments, an ABP provided herein comprises a heavy chain of SEQ ID NO: 106. In some embodiments, an APB provided herein comprises a light chain of SEQ ID NO:107. In some embodiments, an APB provided herein comprises a heavy chain of SEQ ID NO: 105 and a light chain of SEQ ID NO: 107. In some embodiments, an APB provided herein comprises a heavy chain of SEQ ID NO: 106 and a light chain of SEQ ID NO: 107.

In some embodiments, an ABP provided herein comprises a heavy chain of SEQ ID NO: 108. In some embodiments, an ABP provided herein comprises a heavy chain of SEQ ID NO: 109. In some embodiments, an APB provided herein comprises a heavy chain of SEQ ID NO: 108 and a light chain of SEQ ID NO: 107. In some embodiments, an APB provided herein comprises a heavy chain of SEQ ID NO: 109 and a light chain of SEQ ID NO: 107.

In some embodiments, an ABP provided herein comprises a heavy chain of SEQ ID NO:110. In some embodiments, an ABP provided herein comprises a heavy chain of SEQ ID NO:111. In some embodiments, an APB provided herein comprises a heavy chain of SEQ ID NO:110 and a light chain of SEQ ID NO: 107. In some embodiments, an APB provided herein comprises a heavy chain of SEQ ID NO:111 and a light chain of SEQ ID NO:107.

In some embodiments, an ABP provided herein comprises a heavy chain of SEQ ID NO: 112. In some embodiments, an ABP provided herein comprises a heavy chain of SEQ ID NO: 113. In some embodiments, an APB provided herein comprises a heavy chain of SEQ ID NO: 112 and a light chain of SEQ ID NO: 107. In some embodiments, an APB provided herein comprises a heavy chain of SEQ ID NO:113 and a light chain of SEQ ID NO:107.

In some embodiments, an ABP provided herein comprises a heavy chain of SEQ ID NO: 114. In some embodiments, an ABP provided herein comprises a heavy chain of SEQ ID NO: 115. In some embodiments, an APB provided herein comprises a heavy chain of SEQ ID NO: 114 and a light chain of SEQ ID NO: 107. In some embodiments, an APB provided herein comprises a heavy chain of SEQ ID NO: 115 and a light chain of SEQ ID NO: 107.

In some embodiments, an ABP provided herein comprises a heavy chain of SEQ ID NO: 116. In some embodiments, an ABP provided herein comprises a heavy chain of SEQ ID NO: 117. In some embodiments, an APB provided herein comprises a heavy chain of SEQ ID NO: 116 and a light chain of SEQ ID NO: 107. In some embodiments, an APB provided herein comprises a heavy chain of SEQ ID NO: 117 and a light chain of SEQ ID NO: 107.

In some embodiments, an ABP provided herein comprises a heavy chain of SEQ ID NO:118. In some embodiments, an ABP provided herein comprises a heavy chain of SEQ ID NO: 119. In some embodiments, an ABP provided herein comprises a light chain of SEQ ID NO:120. In some embodiments, an APB provided herein comprises a heavy chain of SEQ ID NO: 118 and a light chain of SEQ ID NO: 120. In some embodiments, an APB provided herein comprises a heavy chain of SEQ ID NO: 119 and a light chain of SEQ ID NO: 120.

In some embodiments, an ABP provided herein comprises a heavy chain of SEQ ID NO:121. In some embodiments, an ABP provided herein comprises a heavy chain of SEQ ID NO: 122. In some embodiments, an APB provided herein comprises a heavy chain of SEQ ID NO: 121 and a light chain of SEQ ID NO: 120. In some embodiments, an APB provided herein comprises a heavy chain of SEQ ID NO: 122 and a light chain of SEQ ID NO: 120.

In some embodiments, an ABP provided herein comprises a heavy chain of SEQ ID NO: 123. In some embodiments, an ABP provided herein comprises a heavy chain of SEQ ID NO: 124. In some embodiments, an APB provided herein comprises a heavy chain of SEQ ID NO: 123 and a light chain of SEQ ID NO: 120. In some embodiments, an APB provided herein comprises a heavy chain of SEQ ID NO: 124 and a light chain of SEQ ID NO: 120.

2.2.6. Consensus Sequences

In some embodiments, provided herein is a first family of ABPs, wherein an ABP of such family comprises the following six CDR sequences: (a) a CDR-H3 having the sequence A-R-D-G-V-L-$X_1$-L-N-K-R-S-F-D-I, wherein $X_1$ is A or T (SEQ ID NO: 128); (b) a CDR-H2 having the sequence S-I-Y-Y-S-G-$X_2$-T-F-Y-N-P-S-L-K-S, wherein $X_2$ is S, Q or G (SEQ ID NO: 129); (c) a CDR-H1 having the sequence G-S-I-$X_3$-S-G-$X_4$-Y-Y-W-G, wherein $X_3$ is E or A, and $X_4$ is L, V or S (SEQ ID NO: 130); (d) a CDR-L3 having the sequence QQHTVRPPLT (SEQ ID NO: 64); (e) a CDR-L2 having the sequence GASSRAT (SEQ ID NO: 68); and (f) a CDR-L1 having the sequence RASQSVSSSYLA (SEQ ID NO: 71). In some embodiments, provided herein is an ABP within such first family.

In some embodiments, provided herein is a second family of ABPs, wherein an ABP of such family comprises the following six CDR sequences: (a) a CDR-H3 having the sequence A-R-D-A-N—Y-Y-G-$X_1$-A-W-A-F-D-P, wherein $X_1$ is S or G (SEQ ID NO: 131); (b) a CDR-H2 having the sequence S-I-Y-Y-S-G-$X_2$-T-F-Y-N-P-S-L-K-$X_3$, wherein $X_2$ is S or A, and $X_3$ is S or G (SEQ ID NO: 132); (c) a CDR-H1 having the sequence G-S-I-$X_4$-S-$X_5$-$X_6$-$X_7$-Y-W-G, wherein $X_4$ is S or T, $X_5$ is S or T, $X_6$ is S or K, and $X_7$ is H or Y (SEQ ID NO: 133); (d) a CDR-L3 having the sequence QQHFNLPT (SEQ ID NO: 63); (e) a CDR-L2 having the sequence DASNRAT (SEQ ID NO: 67); and (f) a CDR-L1 having the sequence RASQSVSSYLA (SEQ ID NO: 70). In some embodiments, provided herein is an ABP within such second family.

In some embodiments, provided herein is a third family of ABPs, wherein an ABP of such family comprises the following six CDR sequences: (a) a CDR-H3 having the sequence A-R-G-G-R-T-T-W-I-G-A-$X_1$-D-I, wherein $X_1$ is F or L (SEQ ID NO: 134); (b) a CDR-H2 having the sequence I—I-N-P-S-$X_2$-G-L-T-S-Y-A-$X_3$-K-F-Q-G, wherein $X_2$ is L or I, and $X_3$ is Q or R (SEQ ID NO: 135); (c) a CDR-H1 having the sequence Y-T-F-$X_4$-$X_5$-Y-Y-$X_6$-H, wherein $X_4$ is G, P or R, $X_5$ is N, A or E, and $X_6$ is M or I (SEQ ID NO: 136); (d) a CDR-L3 having the sequence QQYVVWPPLT (SEQ ID NO:65); (e) a CDR-L2 having the sequence GASTRAT (SEQ ID NO:69); and (f) a CDR-L1 having the sequence RASQSVSSNLA (SEQ ID NO:72). In some embodiments, provided herein is an ABP within such third family.

In some embodiments, provided herein is a fourth family of ABPs, wherein an ABP of such family comprises the following six CDR sequences: (a) a CDR-H3 having the sequence ARLHVSGSYYPAYLDY (SEQ ID NO: 35); (b) a CDR-H2 having the sequence $X_1$-I-N-P-S-M-G-A-T-S-Y-$X_2$-Q-K-F-$X_3$-G, wherein $X_1$ is V or I, $X_2$ is A or T, and $X_3$ is Q or R (SEQ ID NO: 137); (c) a CDR-H1 having the sequence YTFTSHYMG (SEQ ID NO: 62); (d) a CDR-L3 having the sequence QQYIVFPWT (SEQ ID NO: 66); (e) a CDR-L2 having the sequence GASTRAT (SEQ ID NO: 69); and (f) a CDR-L1 having the sequence RASQSVSSNLA, (SEQ ID NO: 72). In some embodiments, provided herein is an ABP within such fourth family.

2.2.7. Functional Properties of ABP Variants

As described above, and elsewhere in this disclosure, provided herein are ABP variants defined based on percent identity to an illustrative ABP sequence provided herein, or substitution of amino acid residues in comparison to an illustrative ABP sequence provided herein.

In some embodiments, a variant of an ABP provided herein has specificity for hTIGIT. In some embodiments, a variant of an ABP provided herein has specificity for cTIGIT. In some embodiments, a variant of an ABP provided herein has specificity for mTIGIT. In some embodiments, a variant of an ABP provided herein has specificity for hTIGIT and cTIGIT. In some embodiments, a variant of an ABP provided herein has specificity for hTIGIT and mTIGIT. In some embodiments, a variant of an ABP provided herein has specificity for cTIGIT and mTIGIT. In some embodiments, a variant of an ABP provided herein has specificity for hTIGIT, cTIGIT and mTIGIT.

In some embodiments, a variant of an ABP that is derived from an illustrative ABP sequence provided herein retains affinity, as measured by $K_D$, for hTIGIT that is within about 1.5-fold, about 2-fold, about 3-fold, about 4-fold, about 5-fold, about 6-fold, about 7-fold, about 8-fold, about 9-fold or about 10-fold the affinity of such illustrative ABP. In some embodiments, a variant of an ABP that is derived from an illustrative ABP sequence provided herein retains affinity, as measured by $K_D$, for cTIGIT that is within about 1.5-fold, about 2-fold, about 3-fold, about 4-fold, about 5-fold, about 6-fold, about 7-fold, about 8-fold, about 9-fold or about 10-fold the affinity of such illustrative ABP. In some embodiments, a variant of an ABP that is derived from an illustrative ABP sequence provided herein retains affinity, as measured by $K_D$, for mTIGIT that is within about 1.5-fold, about 2-fold, about 3-fold, about 4-fold, about 5-fold, about 6-fold, about 7-fold, about 8-fold, about 9-fold or about 10-fold the affinity of such illustrative ABP. In some embodiments, a variant of an ABP that is derived from an illustrative ABP sequence provided herein retains affinity, as measured by $K_D$, for both hTIGIT and cTIGIT that is within about 1.5-fold, about 2-fold, about 3-fold, about 4-fold, about 5-fold, about 6-fold, about 7-fold, about 8-fold, about 9-fold or about 10-fold the affinity of such illustrative ABP. In some embodiments, a variant of an ABP that is derived from an illustrative ABP sequence provided herein retains affinity, as measured by $K_D$, for both hTIGIT and mTIGIT that is within about 1.5-fold, about 2-fold, about 3-fold, about 4-fold, about 5-fold, about 6-fold, about 7-fold, about 8-fold, about 9-fold or about 10-fold the affinity of such illustrative ABP. In some embodiments, a variant of an ABP that is derived from an illustrative ABP sequence provided herein retains affinity, as measured by $K_D$, for both cTIGIT and mTIGIT that is within about 1.5-fold, about 2-fold, about 3-fold, about 4-fold, about 5-fold, about 6-fold, about 7-fold, about 8-fold, about 9-fold or about 10-fold the affinity of such illustrative ABP. In some embodiments, a variant of an ABP that is derived from an illustrative ABP sequence provided herein retains affinity, as measured by $K_D$, for all three of hTIGIT, cTIGIT and mTIGIT that is within about 1.5-fold, about 2-fold, about 3-fold, about 4-fold, about 5-fold, about 6-fold, about 7-fold, about 8-fold, about 9-fold or about 10-fold the affinity of such illustrative ABP.

In some embodiments, a variant of an ABP provided herein retains the ability to antagonize TIGIT, as measured by one or more assays or biological effects described herein. In some embodiments, a variant of an ABP provided herein retains the ability to prevent TIGIT from interacting with one or more of its ligands, as described herein.

In some embodiments, a variant of an ABP provided herein competes for binding to TIGIT with an antibody selected from MAB1, MAB2, MAB3, MAB4, MAB5, MAB6, MAB7, MAB8, MAB9, MAB10, MAB11, MAB12, MAB13, MAB14, MAB15, MAB16, MAB17, MAB18, MAB19, MAB20, or MAB21, each as provided in Table 5 of this disclosure.

In some embodiments, a variant of an ABP provided herein inhibits binding of CD155 to TIGIT. In some embodiments, a variant of an ABP provided herein inhibits binding of CD112 to TIGIT. In some embodiments, a variant of an ABP provided herein inhibits association of CD226 with TIGIT.

In some embodiments, a variant of an ABP provided herein activates an effector T cell or a natural killer (NK) cell. In some embodiments, a variant of an ABP provided herein decreases the number of regulatory T cells in a tissue or in circulation. In some embodiments, a variant of an ABP provided herein inhibits the suppression of an effector T cell by a regulatory T cell.

In some embodiments, a variant of an ABP provided herein does not bind specifically to any of PVRL1, PVRL2, PVRL3, or PVRL4.

In some embodiments, a variant of an ABP provided herein binds murine TIGIT (SEQ ID NO: 3) with an affinity lower (as indicated by higher $K_D$) than the affinity of the ABP for hTIGIT, or does not bind mTIGIT. In some embodiments, a variant of an ABP provided herein binds murine TIGIT (SEQ ID NO: 138) with an affinity lower (as indicated by higher $K_D$) than the affinity of the ABP for hTIGIT, or does not bind mTIGIT.

In some embodiments, a variant of an ABP provided herein binds the same epitope of TIGIT as such ABP.

2.2.8. Other Functional Properties of ABPs

In some embodiments, an ABP provided herein has one or more of the characteristics listed in the following (a)-(j): (a) competes for binding to TIGIT with an antibody selected from MAB1, MAB2, MAB3, MAB4, MAB5, MAB6, MAB7, MAB8, MAB9, MAB10, MAB11, MAB12, MAB13, MAB14, MAB15, MAB16, MAB17, MAB18, MAB19, MAB20, or MAB21, each as provided in Table 5 of this disclosure; (b) inhibits binding of CD155 to TIGIT; (c) inhibits binding of CD112 to TIGIT; (d) inhibits association of CD226 with TIGIT; (e) activates an effector T cell or a natural killer (NK) cell; (f) decreases the number of regulatory T cells in a tissue or in circulation; (g) inhibits the suppression of an effector T cell by a regulatory T cell; (h) does not bind specifically to any of PVRL1, PVRL2, PVRL3, or PVRL4; (i) specifically binds cynomolgus monkey TIGIT (cTIGIT; SEQ ID NO: 2); or (j) binds murine TIGIT (mTIGIT; SEQ ID NO: 3) with an affinity lower (as indicated by higher $K_D$) than the affinity of the ABP for hTIGIT, or does not bind mTIGIT. In some embodiments, an ABP provided herein has two or more of the characteristics listed in the foregoing (a)-(j). In some embodiments, an ABP provided herein has three or more of the characteristics listed in the foregoing (a)-(j). In some embodiments, an ABP provided herein has four or more of the characteristics listed in the foregoing (a)-(j). In some embodiments, an ABP provided herein has five or more of the characteristics listed in the foregoing (a)-(j). In some embodiments, an ABP provided herein has six or more of the characteristics listed in the foregoing (a)-(j). In some embodiments, an ABP provided herein has seven or more of the characteristics listed in the foregoing (a)-(j). In some embodiments, an ABP provided herein has eight or more of the characteristics listed in the foregoing (a)-(j). In some embodiments, an ABP provided herein has nine or more of the characteristics listed in the foregoing (a)-(j). In some embodiments, an ABP provided herein has all ten of the characteristics listed in the foregoing (a)-(j).

In some embodiments, an ABP provided herein exhibits a combination of the characteristics listed in the following (a)-(j): (a) competes for binding to TIGIT with an antibody selected from MAB1, MAB2, MAB3, MAB4, MAB5, MAB6, MAB7, MAB8, MAB9, MAB10, MAB11, MAB12, MAB13, MAB14, MAB15, MAB16, MAB17, MAB18, MAB19, MAB20, or MAB21, each as provided in Table 5 of this disclosure; (b) inhibits binding of CD155 to TIGIT; (c) inhibits binding of CD112 to TIGIT; (d) inhibits association of CD226 with TIGIT; (e) activates an effector T cell or a natural killer (NK) cell; (f) decreases the number of regulatory T cells in a tissue or in circulation; (g) inhibits the suppression of an effector T cell by a regulatory T cell; (h) does not bind specifically to any of PVRL1, PVRL2, PVRL3, or PVRL4; (i) specifically binds cynomolgus monkey TIGIT (cTIGIT; SEQ ID NO: 2); or (j) binds murine TIGIT (mTIGIT; SEQ ID NO: 3) with an affinity lower (as indicated by higher $K_D$) than the affinity of the ABP for hTIGIT, or does not bind mTIGIT. In some embodiments, such ABP exhibits a combination of the characteristics selected from (a and b), (a and c), (a and d), (a and e), (a and f), (a and g), (a and h), (a and i), (a and j), (b and a), (b and c), (b and d), (b and e), (b and f), (b and g), (b and h), (b and i), (b and j), (c and a), (c and b), (c and d), (c and e), (c and f), (c and g), (c and h), (c and i), (c and j), (d and a), (d and b), (d and c), (d and e), (d and f), (d and g), (d and h), (d and i), (d and j), (e and a), (e and b), (e and c), (e and d), (e and f), (e and g), (e and h), (e and i), (e and j), (f and a), (f and b), (f and c), (f and d), (f and e), (f and g), (f and h), (f and i), (f and j), (g and a), (g and b), (g and c), (g and d), (g and e), (g and f), (g and h), (g and i), (g and j), (h and a), (h and b), (h and c), (h and d), (h and e), (h and f), (h and g), (h and i), (h and j), (i and a), (i and b), (i and c), (i and d), (i and e), (i and f), (i and g), (i and h), (i and j), (j and a), (j and b), (j and c), (j and d), (j and e), (j and f), (j and g), (j and h), and (j and i). In some embodiments, such ABP exhibits a combination of the characteristics selected from (a and b and c), (a and b and d), (a and b and e), (a and b and f), (a and b and g), (a and b and h), (a and b and i), (a and b and j), (a and c and b), (a and c and d), (a and c and e), (a and c and f), (a and c and g), (a and c and h), (a and c and i), (a and c and j), (a and d and b), (a and d and c), (a and d and e), (a and d and f), (a and d and g), (a and d and h), (a and d and i), (a and d and j), (a and e and b), (a and e and c), (a and e and d), (a and e and f), (a and e and g), (a and e and h), (a and e and i), (a and e and j), (a and f and b), (a and f and c), (a and f and d), (a and f and e), (a and f and g), (a and f and h), (a and f and i), (a and f and j), (a and g and b), (a and g and c), (a and g and d), (a and g and e), (a and g and f), (a and g and h), (a and g and i), (a and g and j), (a and h and b), (a and h and c), (a and h and d), (a and h and e), (a and h and f), (a and h and g), (a and h and i), (a and h and j), (a and i and b), (a and i and c), (a and i and d), (a and i and e), (a and i and f), (a and i and g), (a and i and h), (a and i and j), (a and j and b), (a and j and c), (a and j and d), (a and j and e), (a and j and f), (a and j and g), (a and j and h), (a and j and i), (b and a and j), (b and a and c), (b and a and d), (b and a and e), (b and a and f), (b and a and g), (b and a and h), (b and a and i), (b and c and j), (b and c and a), (b and c and d), (b and c and e), (b and c and f), (b and c and g), (b and c and h), (b and c and i), (b and d and j), (b and d and a), (b and d and c), (b and d and e), (b and d and f), (b and d and g), (b and d and h), (b and d and i), (b and e and j), (b and e and a), (b and e and c), (b and e and d), (b and e and f), (b and e and g), (b and e and h), (b and e and i), (b and f and j), (b and f and a), (b and f and c), (b and f and d), (b and f and e), (b and f and g), (b and f and h), (b and f and i), (b and g and j), (b and g and a), (b and g and c), (b and g and d), (b and g and e), (b and g and f), (b and g and h), (b and g and i), (b and h and j), (b and h and a), (b and h and c), (b and h and d), (b and h and e), (b and h and f), (b and h and g), (b and h and i), (b and i and j), (b and i and a), (b and i and c), (b and i and d), (b and i and e), (b and i and f), (b and i and g), (b and i and h), (b and j and i), (b and j and a), (b and j and c), (b and j and d), (b and j and e), (b and j and f), (b and j and g), (b and j and h), (c and a and i), (c and a and j), (c and a and b), (c and a and d), (c and a and e), (c and a and f), (c and a and g), (c and a and h), (c and b and i), (c and b and j), (c and b and a), (c and b and d), (c and b and e), (c and b and f), (c and b and g), (c and b and h), (c and d and i), (c and d and j), (c and d and a), (c and d and b), (c and d and e), (c and d and f), (c and d and g), (c and d and h), (c and e and i), (c and e and j), (c and e and a), (c and e and b), (c and e and d), (c and e and f), (c and f and g), (c and f and h), (c and f and i), (c and f and j), (c and f and a), (c and f and b), (c and f and d), (c and f and e), (c and f and g), (c and f and h), (c and g and i), (c and g and j), (c and g and a), (c and g and b), (c and g and d), (c and g and e), (c and g and f), (c and g and h), (c and h and i), (c and h and j), (c and h and a), (c and h and b), (c and h and d), (c and h and e), (c and h and f), (c and h and g), (c and i and h), (c and i and j), (c and i and a), (c and i and b), (c and i and d), (c and i and e), (c and i and f), (c and i and g), (c and j and h), (c and j and i), (c and j and a), (c and j and b), (c and j and d), (c and j and e), (c and j and f), (c and j and g), (d and a and h), (d and a and i), (d and a and j), (d and a and b), (d and a and c), (d and a and e), (d and a and f), (d and a and g), (d and b and h), (d and b and i), (d and b and j), (d and b and a), (d and b and c), (d and b and e), (d and b and f), (d and b and g), (d and c and h), (d and c and i), (d and c and j), (d and c and a), (d and c and b), (d and c and e), (d and c and f), (d and c and g), (d and e and h), (d and e and i), (d and e and j), (d and e and a), (d and e and b), (d and e and c), (d and e and f), (d and e and g), (d and f and h), (d and f and i), (d and f and j), (d and f and a), (d and f and b), (d and f and c), (d and f and e), (d and f and g), (d and g and h), (d and g and i), (d and g and j), (d and g and a), (d and g and b), (d and g and c), (d and g and e), (d and g and f), (d and h and g), (d and h and i), (d and h and j), (d and h and a), (d and h and b), (d and h and c), (d and h and e), (d and h and f), (d and i and g), (d and i and h), (d and i and j), (d and i and a), (d and i and b), (d and i and c), (d and i and e), (d and i and f), (d and j and g), (d and j and h), (d and j and i), (d and j and a), (d and j and b), (d and j and c), (d and j and e), (d and j and f), (e and a and g), (e and a and h), (e and a and i), (e and a and j), (e and a and b), (e and a and c), (e and a and d), (e and a and f), (e and b and g), (e and b and h), (e and b and i), (e and b and j), (e and b and a), (e and b and c), (e and b and d), (e and b and f), (e and c and g), (e and c and h), (e and c and i), (e and c and j), (e and c and a), (e and c and b), (e and c and d), (e and c and f), (e and d and g), (e and d and h), (e and d and i), (e and d and j), (e and d and a), (e and d and b), (e and d and c), (e and d and f), (e and f and g), (e and f and h), (e and f and i), (e and f and j), (e and f and a), (e and f and b), (e and f and c), (e and f and d), (e and g and f), (e and g and h), (e and g and i), (e and g and j), (e and g and a), (e and g and b), (e and g and c), (e and g and d), (e and h and f), (e and h and g), (e and h and i), (e and h and j), (e and h and a), (e and h and b), (e and h and c), (e and h and d), (e and i and f), (e and i and g), (e and i and h), (e and i and j), (e and i and a), (e and i and b), (e and i and c), (e and i and d), (e and j and f), (e and j and g), (e and j and h), (e and j and i), (e and j and a), (e and j and b), (e and j and c), (e and j and d), (f and a and e), (f and a and g), (f and a and h), (f and a and i), (f and a and j), (f and a and b), (f and a and c), (f and a and d), (f and b and e), (f and b and g), (f and b and h), (f and b and i), (f and b and j), (f and b and a), (f and b and c), (f and b and d), (f and c and e), (f and c and g), (f and c and h), (f and c and i), (f and c and j), (f and c and a), (f and c and b), (f and c and d), (f and d and e), (f and d and g), (f and d and h), (f and d and i), (f and d and j), (f and d and a), (f and d and b), (f and d and c), (f and e and d), (f and e and g), (f and e and h), (f and e and i), (f and e and j), (f and e and a), (f and e and b), (f and e and c), (f and g and d), (f and g and e), (f and g and h), (f and g and i), (f and g and j), (f and g and a), (f and g and b), (f and g and c), (f and h and d), (f and h and e), (f and h and g), (f and h and i), (f and h and j), (f and h and a), (f and h and b), (f and h and c), (f and i and d), (f and i and e), (f and i and g), (f and i and h), (f and i and j), (f and i and a), (f and i and b), (f and i and c), (f and j and d), (f and j and e), (f and j and g), (f and j and h), (f and j and i), (f and j and a), (f and j and b), (f and j and c), (g and a and d), (g and a and e), (g and a and f), (g and a and h), (g and a and i), (g and a and j), (g and a and b), (g and a and c), (g and b and d), (g and b and e), (g and b and f), (g and b and h), (g and b and i), (g and b and j), (g and b and a), (g and b and c), (g and c and d), (g and c and e), (g and c and f), (g and c and h), (g and c and i), (g and c and j), (g and c and a), (g and c and b), (g and d and c), (g and d and e), (g and d and f), (g and d and h), (g and d and i), (g and d and j), (g and d and a), (g and d and b), (g and e and c), (g and e and d), (g and e and f), (g and e and h), (g and e and i), (g and e and j), (g and e and a), (g and e and b), (g and f and c), (g and f and d), (g and f and e), (g and f and h), (g and f and i), (g and f and j), (g and f and a), (g and f and b), (g and h and c), (g and h and d), (g and h and e), (g and h and f), (g and h and i), (g and h and j), (g and h and a), (g and h and b), (g and i and c), (g and i and d), (g and i and e), (g and i and f), (g and i and h), (g and i and j), (g and i and a), (g and i and b), (g and j and c), (g and j and d), (g and j and e), (g and j and f), (g and j and h), (g and j and i), (g and j and a), (g and j and b), (h and a and c), (h and a and d), (h and a and e), (h and a and f), (h and a and g), (h and a and i), (h and a and j), (h and a and b), (h and b and c), (h and b and d), (h and b and e), (h and b and f), (h and b and g), (h and b and i), (h and b and j), (h and b and a), (h and c and b), (h and c and d), (h and c and e), (h and c and f), (h and c and g), (h and c and i), (h and c and j), (h and c and a), (h and d and b), (h and d and c), (h and d and e), (h and d and f), (h and d and g), (h and d and i), (h and d and j), (h and d and a), (h and e and b), (h and e and c), (h and e and d), (h and e and f), (h and e and g), (h and e and i), (h and e and j), (h and e and a), (h and f and b), (h and f and c), (h and f and d), (h and f and e), (h and f and g), (h and f and i), (h and f and j), (h and f and a), (h and g and b), (h and g and c), (h and g and d), (h and g and e), (h and g and f), (h and g and i), (h and g and j), (h and g and a), (h and i and b), (h and i and c), (h and i and d), (h and i and e), (h and i and f), (h and i and g), (h and i and j), (h and i and a), (h and j and b), (h and j and c), (h and j and d), (h and j and e), (h and j and f), (h and j and g), (h and j and i), (h and j and a), (i and a and b), (i and a and c), (i and a and d), (i and a and e), (i and a and f), (i and a and g), (i and a and h), (i and a and j), (i and b and a), (i and b and c), (i and b and d), (i and b and e), (i and b and f), (i and b and g), (i and b and h), (i and b and j), (i and c and a), (i and c and b), (i and c and d), (i and c and e), (i and c and f), (i and c and g), (i and c and h), (i and c and j), (i and d and a), (i and d and b), (i and d and c), (i and d and e), (i and d and f), (i and d and g), (i and d and h), (i and d and j), (i and e and a), (i and e and b), (i and e and c), (i and e and d), (i and e and f), (i and e and g), (i and e and h), (i and e and j), (i and f and a), (i and f and b), (i and f and c), (i and f and d), (i and f and e), (i and f and g), (i and f and h), (i and f and j), (i and g and a), (i and g and b), (i and g and c), (i and g and d), (i and g and e), (i and g and f), (i and g and h), (i and g and j), (i and h and a), (i and h and b), (i and h and c), (i and h and d), (i and h and e), (i and h and f), (i and h and g), (i and h and j), (i and j and a), (i and j and b), (i and j and c), (i and j and d), (i and j and e), (i and j and f), (i and j and g), (i and j and h), (j and a and i), (j and a and b), (j and a and c), (j and a and d), (j and a and e), (j and a and f), (j and a and g), (j and a and h), (j and b and i), (j and b and a), (j and b and c), (j and b and d), (j and b and e), (j and b and f), (j and b and g), (j and b and h), (j and c and i), (j and c and a), (j and c and b), (j and c and d), (j and c and e), (j and c and f), (j and c and g), (j and c and h), (j and d and i), (j and d and a), (j and d and b), (j and d and c), (j and d and e), (j and d and f), (j and d and g), (j and d and h), (j and e and i), (j and e and a), (j and e and b), (j and e and c), (j and e and d), (j and e and f), (j and e and g), (j and e and h), (j and f and i), (j and f and a), (j and f and b), (j and f and c), (j and f and d), (j and f and e), (j and f and g), (j and f and h), (j and g and i), (j and g and a), (j and g and b), (j and g and c), (j and g and d), (j and g and e), (j and g and f), (j and g and h), (j and h and i), (j and h and a), (j and h and b), (j and h and c), (j and h and d), (j and h and e), (j and h and f), (j and h and g), (j and i and h), (j and i and a), (j and i and b), (j and i and c), (j and i and d), (j and i and e), (j and i and f), and (j and i and g).

2.3. Germlines

The ABPs provided herein may comprise any suitable $V_H$ and $V_L$ germline sequences.

In some embodiments, the $V_H$ region of an ABP provided herein is from the VH4 germline. In some embodiments, the $V_H$ region of an ABP provided herein is from the VH1 germline.

In some embodiments, the $V_H$ region of an ABP provided herein is from the VH4-39 germline. In some embodiments, the $V_H$ region of an ABP provided herein is from the VH4-31 germline. In some embodiments, the $V_H$ region of an ABP provided herein is from the VH1-46 germline.

In some embodiments, the $V_L$ region of an ABP provided herein is from the VK3 germline.

In some embodiments, the $V_L$ region of an ABP provided herein is from the VK3-11 germline. In some embodiments, the $V_L$ region of an ABP provided herein is from the VK3-20 germline. In some embodiments, the $V_L$ region of an ABP provided herein is from the VK3-15 germline.

2.4. Monospecific and Multispecific TIGIT Antigen-Binding Proteins

In some embodiments, the ABPs provided herein are monospecific ABPs.

In some embodiments, the ABPs provided herein are multispecific ABPs.

In some embodiments, a multispecific ABP provided herein binds more than one antigen. In some embodiments, a multispecific antibody binds 2 antigens. In some embodiments, a multispecific antibody binds 3 antigens. In some embodiments, a multispecific antibody binds 4 antigens. In some embodiments, a multispecific antibody binds 5 antigens.

In some embodiments, a multispecific antibody provided herein binds more than one epitope on a TIGIT antigen. In some embodiments, a multispecific antibody binds 2 epitopes on a TIGIT antigen. In some embodiments, a multispecific antibody binds 3 epitopes on a TIGIT antigen.

Many multispecific ABP constructs are known in the art, and the ABPs provided herein may be provided in the form of any suitable multispecific suitable construct.

In some embodiments, the multispecific ABP comprises an immunoglobulin comprising at least two different heavy chain variable regions each paired with a common light chain variable region (i.e., a "common light chain antibody"). The common light chain variable region forms a distinct antigen-binding domain with each of the two different heavy chain variable regions. See Merchant et al., *Nature Biotechnol.*, 1998, 16:677-681, incorporated by reference in its entirety.

In some embodiments, the multispecific ABP comprises an immunoglobulin comprising an antibody or fragment thereof attached to one or more of the N- or C-termini of the heavy or light chains of such immunoglobulin. See Coloma and Morrison, Nature *Biotechnol.*, 1997, 15:159-163, incorporated by reference in its entirety. In some aspects, such ABP comprises a tetravalent bispecific antibody.

In some embodiments, the multispecific ABP comprises a hybrid immunoglobulin comprising at least two different heavy chain variable regions and at least two different light chain variable regions. See Milstein and Cuello, *Nature*, 1983, 305:537-540; and Staerz and Bevan, *Proc. Natl. Acad. Sci. USA*, 1986, 83:1453-1457; each of which is incorporated by reference in its entirety.

In some embodiments, the multispecific ABP comprises immunoglobulin chains with alterations to reduce the formation of side products that do not have multispecificity. In some aspects, the ABPs comprise one or more "knobs-into-holes" modifications as described in U.S. Pat. No. 5,731,168, incorporated by reference in its entirety.

In some embodiments, the multispecific ABP comprises immunoglobulin chains with one or more electrostatic modifications to promote the assembly of Fc hetero-multimers. See WO 2009/089004, incorporated by reference in its entirety.

In some embodiments, the multispecific ABP comprises a bispecific single chain molecule. See Traunecker et al., *EMBO J.*, 1991, 10:3655-3659; and Gruber et al., *J. Immunol.*, 1994, 152:5368-5374; each of which is incorporated by reference in its entirety.

In some embodiments, the multispecific ABP comprises a heavy chain variable domain and a light chain variable domain connected by a polypeptide linker, where the length of the linker is selected to promote assembly of multispecific ABPs with the desired multispecificity. For example, monospecific scFvs generally form when a heavy chain variable domain and light chain variable domain are connected by a polypeptide linker of more than 12 amino acid residues. See U.S. Pat. Nos. 4,946,778 and 5,132,405, each of which is incorporated by reference in its entirety. In some embodiments, reduction of the polypeptide linker length to less than 12 amino acid residues prevents pairing of heavy and light chain variable domains on the same polypeptide chain, thereby allowing pairing of heavy and light chain variable domains from one chain with the complementary domains on another chain. The resulting ABPs therefore have multispecificity, with the specificity of each binding site contributed by more than one polypeptide chain. Polypeptide chains comprising heavy and light chain variable domains that are joined by linkers between 3 and 12 amino acid residues form predominantly dimers (termed diabodies). With linkers between 0 and 2 amino acid residues, trimers (termed triabodies) and tetramers (termed tetrabodies) are favored. However, the exact type of oligomerization appears to depend on the amino acid residue composition and the order of the variable domain in each polypeptide chain (e.g., $V_H$-linker-$V_L$ vs. $V_L$-linker-$V_H$), in addition to the linker length. A skilled person can select the appropriate linker length based on the desired multispecificity.

In some embodiments, the multispecific ABP comprises a diabody. See Hollinger et al., *Proc. Natl. Acad. Sci. USA*, 1993, 90:6444-6448, incorporated by reference in its entirety. In some embodiments, the multispecific ABP comprises a triabody. See Todorovska et al., *J. Immunol. Methods*, 2001, 248:47-66, incorporated by reference in its entirety. In some embodiments, the multispecific ABP comprises a tetrabody. See id., incorporated by reference in its entirety.

In some embodiments, the multispecific ABP comprises a trispecific F(ab')3 derivative. See Tutt et al. *J. Immunol.*, 1991, 147:60-69, incorporated by reference in its entirety.

In some embodiments, the multispecific ABP comprises a cross-linked antibody. See U.S. Pat. No. 4,676,980; Brennan et al., *Science*, 1985, 229:81-83; Staerz, et al. *Nature*, 1985, 314:628-631; and EP 0453082; each of which is incorporated by reference in its entirety.

In some embodiments, the multispecific ABP comprises antigen-binding domains assembled by leucine zippers. See Kostelny et al., *J. Immunol.*, 1992, 148:1547-1553, incorporated by reference in its entirety.

In some embodiments, the multispecific ABP comprises complementary protein domains. In some aspects, the complementary protein domains comprise an anchoring domain (AD) and a dimerization and docking domain (DDD). In some embodiments, the AD and DDD bind to each other and thereby enable assembly of multispecific ABP structures via the "dock and lock" (DNL) approach. ABPs of many specificities may be assembled, including bispecific ABPs, trispecific ABPs, tetraspecific ABPs, quintspecific ABPs, and hexaspecific ABPs. Multispecific ABPs comprising complementary protein domains are described, for example, in U.S. Pat. Nos. 7,521,056; 7,550,143; 7,534,866; and 7,527,787; each of which is incorporated by reference in its entirety.

In some embodiments, the multispecific ABP comprises a dual action Fab (DAF) antibody as described in U.S. Pat. Pub. No. 2008/0069820, incorporated by reference in its entirety.

In some embodiments, the multispecific ABP comprises an antibody formed by reduction of two parental molecules followed by mixing of the two parental molecules and reoxidation to assembly a hybrid structure. See Carlring et al., *PLoS One*, 2011, 6:e22533, incorporated by reference in its entirety.

In some embodiments, the multispecific ABP comprises a DVD-Ig™. A DVD-Ig™ is a dual variable domain immunoglobulin that can bind to two or more antigens. DVD-Igs™ are described in U.S. Pat. No. 7,612,181, incorporated by reference in its entirety.

In some embodiments, the multispecific ABP comprises a DART™. DARTs™ are described in Moore et al., *Blood*, 2011, 117:454-451, incorporated by reference in its entirety.

In some embodiments, the multispecific ABP comprises a DuoBody®. DuoBodies® are described in Labrijn et al., *Proc. Natl. Acad. Sci. USA*, 2013, 110:5145-5150; Gramer et al., mAbs, 2013, 5:962-972; and Labrijn et al., *Nature Protocols*, 2014, 9:2450-2463; each of which is incorporated by reference in its entirety.

In some embodiments, the multispecific ABP comprises an antibody fragment attached to another antibody or fragment. The attachment can be covalent or non-covalent. When the attachment is covalent, it may be in the form of a fusion protein or via a chemical linker. Illustrative examples of multispecific ABPs comprising antibody fragments attached to other antibodies include tetravalent bispecific antibodies, where an scFv is fused to the C-terminus of the $C_{H3}$ from an IgG. See Coloma and Morrison, Nature *Biotechnol.*, 1997, 15:159-163. Other examples include antibodies in which a Fab molecule is attached to the constant region of an immunoglobulin. See Miler et al., *J. Immunol.*, 2003, 170:4854-4861, incorporated by reference in its entirety. Any suitable fragment may be used, including any of the fragments described herein or known in the art.

In some embodiments, the multispecific ABP comprises a CovX-Body. CovX-Bodies are described, for example, in Doppalapudi et al., *Proc. Natl. Acad. Sci. USA*, 2010, 107:22611-22616, incorporated by reference in its entirety.

In some embodiments, the multispecific ABP comprises an Fcab antibody, where one or more antigen-binding domains are introduced into an Fc region. Fcab antibodies are described in Wozniak-Knopp et al., *Protein Eng. Des. Sel.*, 2010, 23:289-297, incorporated by reference in its entirety.

In some embodiments, the multispecific ABP comprises an TandAb® antibody. TandAb® antibodies are described in Kipriyanov et al., *J. Mol. Biol.*, 1999, 293:41-56 and Zhukovsky et al., *Blood*, 2013, 122:5116, each of which is incorporated by reference in its entirety.

In some embodiments, the multispecific ABP comprises a tandem Fab. Tandem Fabs are described in WO 2015/103072, incorporated by reference in its entirety.

In some embodiments, the multispecific ABP comprises a Zybody™. Zybodies™ are described in LaFleur et al., mAbs, 2013, 5:208-218, incorporated by reference in its entirety.

2.5. TIGIT Antagonism

In some embodiments, the ABPs provided herein antagonize TIGIT upon binding.

Figure 2:
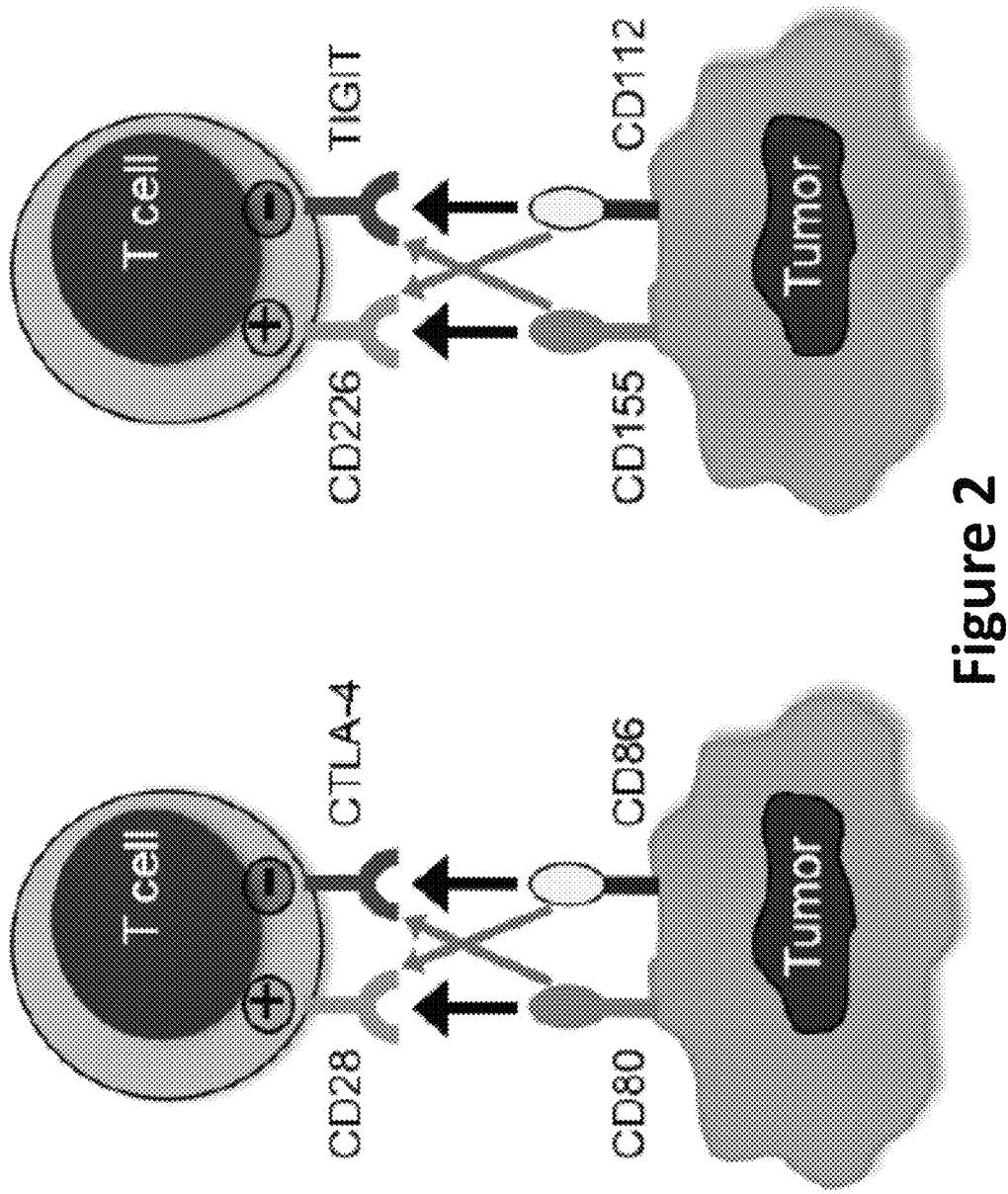
FIG. 2 is an illustration of the similarity between the CD28-CTLA4 and CD226-TIGIT pathways and thus the utility of TIGIT as an immune checkpoint target. The CD226/TIGIT costimulation/coinhibition biology is analogous to that of CD28/CTLA4; TIGIT provides an inhibitory signal to T cells while CD226 provides a costimulation signal to T cells. TIGIT ligands CD155 and CD112 are widely expressed in tumors providing an immune suppressive environment.

In some embodiments, antagonism of TIGIT by an ABP provided herein results in dimerization and/or activation of CD226 (also known as DNAM-1), a co-stimulatory receptor whose dimerization and function is impaired by direct interaction with TIGIT. See Grogan et al., *J. Immunol.*, 2014, 192 (1 Supplement) 2013.15, incorporated by reference in its entirety. FIG. 2 provides an illustration of the CD226-TIGIT pathway in comparison to the CD28/CTLA4 pathway, which has similar costimulation/coinhibition biology.

In some embodiments, antagonism of TIGIT by an ABP provided herein increases the amount of CD226 and CD155 that interact in comparison to the amount that interact in the absence of the ABP.

In some embodiments, antagonism of TIGIT by an ABP provided herein results in activation of an effector T cell. In some aspects, the effector T cell is a CD8+ T cell. In some aspects, the effector T cell is a CD4+ T cell.

In some embodiments, antagonism of TIGIT by an ABP provided herein results in activation of an NK cell. In some embodiments, antagonism of TIGIT by an ABP provided herein results in activation of an NKT cell.

In some embodiments, antagonism of TIGIT by an ABP provided herein results in a reduction of the inhibitory activity of a regulatory T cell toward an effector T cell.

In some embodiments, antagonism of TIGIT by an ABP provided herein results in increased secretion of IL-2, IL-6, GM-CSF, TNF, LT-$\alpha$, and/or IFN-$\gamma$ by a target cell.

In some embodiments, antagonism of TIGIT by an ABP provided herein increases the proliferation, survival, and/or function of an effector T cell. In some aspects the effector T cell is a CD4+ effector T cell. In some aspects, the effector T cell is a CD8+ effector T cell.

In some embodiments, antagonism of TIGIT by an ABP provided herein abrogates suppression of an effector T cell by a regulatory T cell. In some aspects, the regulatory T cell is a CD4+CD25+Foxp3+ regulator T cell. In some aspects, the regulatory T cell is a CD8+CD25+ regulatory T cell.

In some embodiments, antagonism of TIGIT by an ABP provided herein results in an enhancement of an immune response.

In some embodiments, antagonism of TIGIT by an ABP provided herein results in the prevention of a tumor. In some embodiments, antagonism of TIGIT by an ABP provided herein results in the delay of onset of a tumor. In some embodiments, antagonism of TIGIT by an ABP provided herein results in a reduction of the size of a tumor. In some embodiments, antagonism of TIGIT by an ABP provided herein results in elimination of a tumor. In some embodiments, antagonism of TIGIT by an ABP provided herein results in a reduction in the number of metastases.

In some embodiments, antagonism of TIGIT by an ABP provided herein results in the prevention of a viral disease. In some embodiments, antagonism of TIGIT by an ABP provided herein results in the delay of onset of a viral disease. In some embodiments, antagonism of TIGIT by an ABP provided herein results in a reduction of the viral load in a subject. In some embodiments, antagonism of TIGIT by an ABP provided herein results in the elimination of a viral infection.

2.6. Affinity and Kinetics of Antigen-Binding Proteins for TIGIT; Potency

In some embodiments, the affinity of an ABP provided herein for TIGIT as indicated by $K_D$, is less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M. In some embodiments, the affinity of the ABP is between about $10^{-7}$ M and $10^{-12}$ M. In some embodiments, the affinity of the ABP is between about $10^{-7}$ M and $10^{-11}$ M. In some embodiments, the affinity of the ABP is between about $10^{-7}$ M and $10^{-10}$ M. In some embodiments, the affinity of the ABP is between about $10^{-7}$ M and $10^{-9}$ M. In some embodiments, the affinity of the ABP is between about $10^{-7}$ M and $10^{-8}$ M. In some embodiments, the affinity of the ABP is between about $10^{-8}$ M and $10^{-12}$ M. In some embodiments, the affinity of the ABP is between about $10^{-8}$ M and $10^{-11}$ M. In some embodiments, the affinity of the ABP is between about $10^{-9}$ M and $10^{-11}$ M. In some embodiments, the affinity of the ABP is between about $10^{-10}$ M and $10^{-11}$ M.

In some embodiments, the affinity of an ABP provided herein for hTIGIT as indicated by $K_D$ measured by ForteBio, as set forth in Example 4 is selected from about $5.24 \times 10^{-10}$ M, about $4.57 \times 10^{-10}$ M, about $3.32 \times 10^{-10}$ M, about $2.46 \times 10^{-10}$ M, about $1.96 \times 10^{-10}$ M, about $3.11 \times 10^{-9}$ M, about $2.54 \times 10^{-9}$ M, about $3.13 \times 10^{-9}$ M, about $2.83 \times 10^{-9}$ M, about $1.71 \times 10^{-9}$ M, about $2.47 \times 10^{-9}$ M, about $2.35 \times 10^{-9}$ M, about $1.44 \times 10^{-9}$ M, about $1.23 \times 10^{-9}$ M, about $5.26 \times 10^{-10}$ M, about $3.78 \times 10^{-10}$ M, about $4.29 \times 10^{-10}$ M, or about $4.48 \times 10^{-10}$ M. In some embodiments, such affinity ranges from about $3.13 \times 10^{-9}$ M to about $1.96 \times 10^{-10}$ M. In some embodiments, such $K_D$ is about $3.13 \times 10^{-9}$ M or less.

In some embodiments, the affinity of an ABP provided herein for cTIGIT as indicated by $K_D$ measured by ForteBio, as set forth in Example 4 is selected from about $2.64 \times 10^{-9}$ M, about $6.55 \times 10^{-9}$ M, about $8.14 \times 10^{-9}$ M, about $6.57 \times 10^{-9}$ M, about $7.94 \times 10^{-8}$ M, about $7.04 \times 10^{-8}$ M, about $1.10 \times 10^{-7}$ M, about $7.20 \times 10^{-8}$ M, about $1.57 \times 10^{-9}$ M, about $8.02 \times 10^{-10}$ M, about $3.67 \times 10^{-10}$ M, about $8.98 \times 10^{-10}$ M, about $1.75 \times 10^{-8}$ M, or about $2.58 \times 10^{-8}$ M, about $9.35 \times 10^{-9}$ M. In some embodiments, such affinity ranges from about $1.10 \times 10^{-7}$ M to about $3.69 \times 10^{-10}$ M. In some embodiments, such $K_D$ is about $1.10 \times 10^{-7}$ M or less.

In some embodiments, the affinity of an ABP provided herein for hTIGIT as indicated by $K_D$ measured by solution equilibrium methods (MSD-SET), as set forth in Example 4 is selected from about $5.40 \times 10^{-11}$ M, about $1.10 \times 10^{-10}$ M, about $1.50 \times 10^{-10}$ M, about $5.60 \times 10^{-11}$ M, about $4.00 \times 10^{-10}$ M, about $3.80 \times 10^{-10}$ M, about $2.10 \times 10^{-10}$ M, about $7.00 \times 10^{-11}$ M, about $4.10 \times 10^{-11}$ M, about $2.50 \times 10^{-11}$ M, about $3.00 \times 10^{-11}$ M, about $8.00 \times 10^{-11}$ M, about $8.10 \times 10^{-12}$ M, about $5.00 \times 10^{-12}$ M, or about $4.90 \times 10^{-12}$ M. In some embodiments, such affinity ranges from about $4.00 \times 10^{-10}$ M to about $4.90 \times 10^{-12}$ M. In some embodiments, such $K_D$ is about $4.00 \times 10^{-10}$ M or less.

In some embodiments, the affinity of an ABP provided herein for cTIGIT as indicated by $K_D$ measured by MSD-SET, as set forth in Example 4 is selected from about $3.20 \times 10^{-10}$ M, about $2.30 \times 10^{-10}$ M, about $3.50 \times 10^{-11}$ M, about $1.50 \times 10^{-11}$ M, or about $4.60 \times 10^{-11}$ M. In some embodiments, such affinity ranges from about $3.20 \times 10^{-10}$ M to about $1.50 \times 10^{-11}$ M. In some embodiments, such $K_D$ is about $3.20 \times 10^{-10}$ M or less.

In some embodiments, the affinity of an ABP provided herein for hTIGIT as indicated by $K_D$ measured by ForteBio, as set forth in Example 6 is selected from about $7.1 \times 10^{-10}$ M, about $8.1 \times 10^{-11}$ M, about $1.9 \times 10^{-10}$ M, about $5.6 \times 10^{-10}$ M, about $2.4 \times 10^{-10}$ M, about $2.8 \times 10^{-10}$ M, about $1.6 \times 10^{-10}$ M, about $5.8 \times 10^{-10}$ M, about $1.1 \times 10^{-9}$ M, about $8.1 \times 10^{-10}$ M, about $4.6 \times 10^{-10}$ M, or about $3.6 \times 10^{-10}$ M. In some embodiments, such affinity ranges from about $1.1 \times 10^{-9}$ M to about $8.1 \times 10^{-11}$ M. In some embodiments, such $K_D$ is about $1.1 \times 10^{-9}$ M or less.

In some embodiments, the affinity of an ABP provided herein for hTIGIT as indicated by $K_D$ measured by ForteBio, as set forth in Example 6, is about $2.4 \times 10^{-10}$ M. In some embodiments, the affinity of an ABP provided herein for cTIGIT as indicated by $K_D$ measured by ForteBio, as set forth in Example 6, is about $6.2 \times 10^{-9}$ M. In some embodiments, such $K_D$ is about $6.2 \times 10^{-9}$ M or less.

In some embodiments, the affinity of an ABP provided herein for hTIGIT expressed on the surface of a Jurkat cell, as indicated by $K_D$, described in Example 6 is about $5.1 \times 10^{-10}$ M. In some embodiments, such $K_D$ is about $5.1 \times 10^{-10}$ M or less.

In some embodiments, the affinity of an ABP provided herein for cTIGIT expressed on the surface of a Jurkat cell, as indicated by $K_D$, described in Example 6 is about $4.0 \times 10^{-10}$ M. In some embodiments, such $K_D$ is about $4.0 \times 10^{-10}$ M or less.

In some embodiments, the affinity of an ABP provided herein for mTIGIT (SEQ ID NO: 3) expressed on the surface of a Jurkat cell, as indicated by $K_D$, described in Example 6 is about $9.8 \times 10^{-9}$ M. In some embodiments, such $K_D$ is about $9.8 \times 10^{-9}$ M or less. In some embodiments, such $K_D$ is about $9.8 \times 10^{-9}$ M or greater.

In some embodiments, the affinity of an ABP provided herein for hTIGIT expressed on the surface of a human CD8+ T cell, as indicated by $K_D$, described in Example 6 is about $1.3 \times 10^{-9}$ M. In some embodiments, such $K_D$ is about $1.3 \times 10^{-9}$ M or less.

In some embodiments, the affinity of an ABP provided herein for cTIGIT expressed on the surface of a cynomolgus monkey CD8+ T cell, as indicated by $K_D$, described in Example 6 is about $2.8 \times 10^{-9}$ M. In some embodiments, such $K_D$ is about $2.8 \times 10^{-9}$ M or less.

In some embodiments, the affinity of an ABP provided herein for mTIGIT expressed on the surface of a murine T regulatory cell (i.e., mTIGIT as it naturally occurs on such cells, whether or not such mTIGIT is of SEQ ID NOs: 3 or 138, but inclusive of such SEQ ID NOs), as indicated by $K_D$, described in Example 6 is about $2.5 \times 10^{-8}$ M. In some embodiments, such $K_D$ is about $2.5 \times 10^{-8}$ M or less.

In some embodiments, the ABPs provided herein specifically bind to hTIGIT (SEQ ID NO: 1) with a $K_D$ of X and to cTIGIT (SEQ ID NO:2) or mTIGIT (SEQ ID NO:3 or 138) with a $K_D$ of ≤10X. In some embodiments, the ABPs provided herein specifically bind to hTIGIT (SEQ ID NO: 1) with a $K_D$ of X and to cTIGIT (SEQ ID NO:2) or mTIGIT (SEQ ID NO:3 or 138) with a $K_D$ of ≤5X. In some embodiments, the ABPs provided herein specifically bind to hTIGIT (SEQ ID NO: 1) with a $K_D$ of X and to cTIGIT (SEQ ID NO:2) or mTIGIT (SEQ ID NO:3 or 138) with a $K_D$ of ≤2X. In some aspects, X is any $K_D$ described in this disclosure. In some aspects, X is 0.01 nM, 0.1 nM, 1 nM, 10 nM, 20 nM, 50 nM, or 100 nM.

In some embodiments, the ratio of $K_{D(hTIGIT)}:K_{D(cTIGIT)}$ for an ABP provided herein, as measured by ForteBio as set forth in Example 4, is selected from about $1.98 \times 10^{-1}$, about $2.61 \times 10^{-1}$, about $3.03 \times 10^{-1}$, about $3.58 \times 10^{-1}$, about $6.62 \times 10^{-3}$, about $1.98 \times 10^{-1}$, about $5.37 \times 10^{-3}$, about $3.90 \times 10^{-3}$, about $6.22 \times 10^{-3}$, about $2.91 \times 10^{-1}$, about $4.14 \times 10^{-1}$, about $6.67 \times 10^{-1}$, about $2.18 \times 10^{-1}$, about $1.78 \times 10^{-1}$, about $1.21 \times 10^{-1}$, or about $3.03 \times 10^{-1}$. In some embodiments, such ratio ranges from about $3.90 \times 10^{-3}$ to about $6.67 \times 10^{-1}$.

In some embodiments, the ratio of $K_{D(hTIGIT)}:K_{D(cTIGIT)}$ for an ABP provided herein, as measured by ForteBio as set forth in Example, is about $3.87 \times 10^{-2}$.

In some embodiments, the ratio of $K_{D(hTIGIT)}:K_{D(cTIGIT)}$ for an ABP provided herein, as measured by MSD-SET as set forth in Example 4, is selected from about $3.33 \times 10^{-1}$, about $2.31 \times 10^{-1}$, about $1.09 \times 10^{-1}$, about $1.07 \times 10^{-1}$, or about $1.69 \times 10^{-}$. In some embodiments, such ratio ranges from about $1.07 \times 10^{-1}$ M to about $3.33 \times 10^{-1}$ M.

In some embodiments an ABP provided herein has a $k_a$ of at least about $10^4$ $M^{-1} \times sec^{-1}$. In some embodiments the ABP has a $k_a$ of at least about $10^5$ $M^{-1} \times sec^{-1}$. In some embodiments the ABP has a $k_a$ of at least about $10^6$ $M^{-1} \times sec^{-1}$. In some embodiments the ABP has a $k_a$ of between about $10^4$ $M^{-1} \times sec^{-1}$ and about $10^5$ $M^{-1} \times sec^{-1}$. In some embodiments the ABP has a $k_a$ of between about $10^5$ $M^{-1} \times sec^{-1}$ and about $10^6$ $M^{-1} \times sec^{-1}$. In some embodiments, such $k_a$ is at least about $10^5$ $M^{-1} \times sec^{-1}$.

In some embodiments, an ABP provided herein has a $k_a$ for hTIGIT, as measured by ForteBio as set forth in Example 6, selected from about $3.2 \times 10^5$ $M^{-1} \times sec^{-1}$, about $7.0 \times 10^5$ $M^{-1} \times sec^{-1}$, about $7.7 \times 10^5$ $M^{-1} \times sec^{-1}$, about $1.6 \times 10^6$ $M^{-1} \times sec^{-1}$, about $2.0 \times 10^6$ $M^{-1} \times sec^{-1}$, about $1.3 \times 10^6$ $M^{-1} \times sec^{-1}$, about $1.5 \times 10^6$ $M^{-1} \times sec^{-1}$, about $1.1 \times 10^6$ $M^{-1} \times sec^{-1}$, about $4.5 \times 10^5$ $M^{-1} \times sec^{-1}$, about $7.5 \times 10^5$ $M^{-1} \times sec^{-1}$, about $8.9 \times 10^5$ $M^{-1} \times sec^{-1}$, or about $1.4 \times 10^6$ $M^{-1} \times sec^{-1}$. In some embodiments, such $k_a$ ranges from about $3.2 \times 10^5$ $M^{-1} \times sec^{-1}$ to about $2.0 \times 10^6$ $M^{-1} \times sec^{-1}$. In some embodiments, such $k_d$ is about $2.0 \times 10^6$ M or less.

In some embodiments, an ABP provided herein has a $k_a$ for hTIGIT, as measured by ForteBio as set forth in Example 6, of about $2.0 \times 10^6$ $M^{-1} \times sec^{-1}$. In some embodiments, such $k_a$ is at least about $2.0 \times 10^6$ $M^{-1} \times sec^{-1}$.

In some embodiments, an ABP provided herein has a $k_a$ for cTIGIT, as measured by ForteBio as set forth in Example 6, of about $7.9 \times 10^5$ $M^{-1} \times sec^{-1}$. In some embodiments, such $k_a$ is at least about $7.9 \times 10^5$ $M^{-1} \times sec^{-1}$.

In some embodiments an ABP provided herein has a $k_d$ of about $10^{-5}$ $sec^{-1}$ or less. In some embodiments the ABP has a $k_d$ of about $10^4$ $sec^{-1}$ or less. In some embodiments the ABP has a $k_d$ of about $10^3$ $sec^{-1}$ or less. In some embodiments the ABP has a $k_d$ of between about $10^{-2}$ $sec^{-1}$ and about $10^{-5}$ $sec^{-1}$. In some embodiments the ABP has a $k_d$ of between about $10^{-2}$ $sec^{-1}$ and about $10^{-4}$ $sec^{-1}$. In some embodiments the ABP has a $k_d$ of between about $10^{-4}$ $sec^{-1}$ and about $105$ $sec^{-1}$.

In some embodiments, an ABP provided herein has a $k_d$, for hTIGIT, as measured by ForteBio as set forth in Example 6, selected from about $2.3 \times 10^4$ $sec^{-1}$, about $6.3 \times 10^{-5}$ $sec^{-1}$, about $1.4 \times 10^4$ $sec^{-1}$, about $8.5 \times 10^4$ $sec^{-1}$, about $3.8 \times 10^4$ $sec^{-1}$, about $3.5 \times 10^4$ $sec^{-1}$, about $2.4 \times 10^4$ sec 1, about $6.6 \times 10^{-4}$ $sec^{-1}$, about $5.9 \times 10^{-4}$ $sec^{-1}$, or about $5.0 \times 10^{-4}$ $sec^{-1}$. In some embodiments, such $k_d$ ranges from about $6.3 \times 10^{-5}$ sec$^{-1}$ to about $8.5 \times 10^{-4}$ sec$^{-1}$. In some embodiments, such $k_d$ is less than about $8.5 \times 10^{-4}$ sec$^{-1}$.

In some embodiments, an ABP provided herein has a $k_d$ for hTIGIT, as measured by ForteBio as set forth in Example 6, of about $3.8 \times 10^{-4}$ sec$^{-1}$. In some embodiments, such $k_d$ is less than about $3.8 \times 10^{-4}$ sec$^{-1}$.

In some embodiments, an ABP provided herein has a $k_d$ for cTIGIT, as measured by ForteBio as set forth in Example 6, of about $4.6 \times 10^{-3}$ sec$^{-1}$. In some embodiments, such $k_d$ is less than about $4.6 \times 10^{-3}$ sec$^{-1}$.

In some embodiments, an ABP provided herein has a $k_a$ for hTIGIT of about $3.2 \times 10^5$ M$^{-1} \times$sec$^{-1}$, a $k_d$ for hTIGIT of about $2.3 \times 10^{-4}$ sec$^{-1}$, and a $K_D$ for hTIGIT of about $7.1 \times 10^{-10}$ M. In some embodiments, an ABP provided herein has a $k_a$ for hTIGIT of about $7.0 \times 10^5$ M$^{-1} \times$sec$^{-1}$, a $k_d$ for hTIGIT of about $6.3 \times 10^{-5}$ sec$^{-1}$, and a $K_D$ for hTIGIT of about $8.1 \times 10^{-11}$ M. In some embodiments, an ABP provided herein has a $k_a$ for hTIGIT of about $7.7 \times 10^5$ M$^{-1} \times$sec$^{-1}$, a $k_d$ for hTIGIT of about $1.4 \times 10^{-4}$ sec$^{-1}$, and a $K_D$ for hTIGIT of about $1.9 \times 10^{-10}$ M. In some embodiments, an ABP provided herein has a $k_a$ for hTIGIT of about $1.6 \times 10^6$ M$^{-1} \times$sec$^{-1}$, a $k_d$ for hTIGIT of about $8.5 \times 10^4$ sec$^{-1}$, and a $K_D$ for hTIGIT of about $5.6 \times 10^{-10}$ M. In some embodiments, an ABP provided herein has a $k_a$ for hTIGIT of about $2.0 \times 10^6$ M$^{-1} \times$sec$^{-1}$, a $k_d$ for hTIGIT of about $3.8 \times 10^4$ sec$^{-1}$, and a $K_D$ for hTIGIT of about $2.4 \times 10^{-10}$ M. In some embodiments, an ABP provided herein has a $k_a$ for hTIGIT of about $1.3 \times 10^6$ M$^{-1} \times$sec$^{-1}$, a $k_d$ for hTIGIT of about $3.5 \times 10^{-4}$ sec$^{-1}$ and a $K_D$ for hTIGIT of about $2.8 \times 10^{-10}$ M. In some embodiments, an ABP provided herein has a $k_a$ for hTIGIT of about $1.5 \times 10^6$ M$^{-1} \times$sec$^{-1}$, a $k_d$ for hTIGIT of about $2.4 \times 10^{-4}$ sec$^{-1}$, and a $K_D$ for hTIGIT of about $1.6 \times 10^{-10}$ M. In some embodiments, an ABP provided herein has a $k_a$ for hTIGIT of about $1.1 \times 10^6$ M$^{-1} \times$sec$^{-1}$, a $k_d$ for hTIGIT of about $6.6 \times 10^{-4}$ sec$^{-1}$, and a $K_D$ for hTIGIT of about $5.8 \times 10^{-10}$ M. In some embodiments, an ABP provided herein has a $k_a$ for hTIGIT of about $4.5 \times 10^5$ M$^{-1} \times$sec$^{-1}$, a $k_d$ for hTIGIT of about $3.5 \times 10^{-4}$ sec$^{-1}$, and a $K_D$ for hTIGIT of about $1.1 \times 10^{-9}$ M. In some embodiments, an ABP provided herein has a $k_a$ for hTIGIT of about $7.5 \times 10^5$ M$^{-1} \times$sec$^{-1}$, a $k_d$ for hTIGIT of about $5.9 \times 10^4$ sec$^{-1}$, and a $K_D$ for hTIGIT of about $8.1 \times 10^{-10}$ M. In some embodiments, an ABP provided herein has a $k_a$ for hTIGIT of about $8.9 \times 10^5$ M$^{-1} \times$sec$^{-1}$, a $k_d$ for hTIGIT of about $3.8 \times 10^4$ sec$^{-1}$, and a $K_D$ for hTIGIT of about $4.6 \times 10^{-10}$ M. In some embodiments, an ABP provided herein has a $k_a$ for hTIGIT of about $1.4 \times 10^6$ M$^{-1} \times$sec$^{-1}$, a $k_d$ for hTIGIT of about $5.0 \times 10^4$ sec$^{-1}$, and a $K_D$ for hTIGIT of about $3.6 \times 10^{-10}$ M. In some embodiments, such $k_a$, $k_d$ and $K_D$ are determined according to the methods provided in Example 6.

In some embodiments, an ABP provided herein has a $k_a$ for hTIGIT of about $2.0 \times 10^6$ M$^{-1} \times$sec$^{-1}$, a $k_d$ for hTIGIT of about $3.8 \times 10^{-4}$ sec$^{-1}$, a $K_D$ for hTIGIT of about $2.4 \times 10^{-10}$ M, a $k_a$ for cTIGIT of about $7.9 \times 10^5$ M$^{-1} \times$sec$^{-1}$, a $k_d$ for cTIGIT of about $4.6 \times 10^3$ sec$^{-1}$, a $K_D$ for cTIGIT of about $6.2 \times 10^{-9}$ M, and a $K_D$ for mTIGIT (SEQ ID NO: 3) of greater than about $7.0 \times 10^{-7}$ M. In some embodiments, such $k_a$, $k_d$ and $K_D$ are determined according to the methods provided in Example 6.

In some embodiments, $K_D$, $k_a$, and $k_d$ are determined using surface plasmon resonance (SPR). In some aspects, the SPR analysis utilizes a BIACORE® instrument. In some aspects, the antigen is immobilized on a carboxymethylated dextran biosensor chip (CM4 or CM5) and contacted with an ABP provided herein. Association and dissociation rate constants may be calculated using the BIAevaluation® software and a one-to-one Langmuir binding model. In some aspects, the assay is performed at 25° C. In some aspects, the assay is performed at 37° C.

In some embodiments, $K_D$, $k_a$, and $k_d$ are determined using biolayer interferometry (BLI). Any suitable BLI method may be used. In some aspects, the BLI analysis utilizes a FORTEBIO® instrument. In some aspects, an anti-human IgG Fc capture (AHC) biosensor is used to capture ABPs onto the surface of a sensor. Subsequently, association of the ABP and antigen is monitored by contacting the immobilized ABP with different concentrations of TIGIT. Dissociation of the antigen and ABP is then measured in a buffer without TIGIT. Association and dissociation rate constants are calculated using the kinetic modules of the FORTEBIO® Analysis Software. In some aspects, the assay is performed at 30° C.

In other embodiments, $K_D$ may be determined by a radiolabeled antigen-binding assay, as described in Chen et al. *J. Mol. Biol.*, 1999, 293:865-881, incorporated by reference in its entirety.

In other embodiments, $K_D$ may be determined by using MSD-SET, as described in Example 4.

In some embodiments, an ABP provided herein has an $EC_{50}$, as measured by IL-2 production in a human TIGIT Jurkat co-culture assay as described in Example 7, of about 0.22 nM, about 0.31 nM, about 0.33 nM, about 0.34 nM, about 0.25 nM, about 0.24 nM, about 0.11 nM, about 0.06 nM, about 0.14 nM, about 0.16 nM, about 1.40 nM, about 0.71 nM, about 0.21 nM, about 1.11 nM, about 0.13 nM, about 0.20 nM, about 0.68 nM, or about 0.61 nM. In some embodiments, such $EC_{50}$ ranges from about 0.06 nM to about 1.40 nM. In some embodiments, such $EC_{50}$ is about 1.40 nM or less.

In some embodiments, an ABP provided herein has an $EC_{50}$, as measured by IL-2 production in a cynomolgus monkey TIGIT Jurkat co-culture assay as described in Example 7, of about 2.87 nM. In some embodiments, such $EC_{50}$ is about 2.87 nM or less. In some embodiments, the ratio of $EC_{50(cTIGIT)}:EC_{50(hTIGIT)}$ in such assay ranges from about 2.05 to about 47.8.

In some embodiments, an ABP provided herein has an $EC_{10}$, as measured by TNF production in PBMCs isolated from a human donor and treated as described in Example 9, in a range of about 5.02 nM to about 18.86 nM. In some embodiments, such $EC_{10}$ is about 18.86 nM or less.

In some embodiments, an ABP provided herein has an $EC_{50}$, as measured by TNF production in PBMCs isolated from a human donor and treated as described in Example 9, in a range of about 12.60 nM to about 20.60 nM. In some embodiments, such $EC_{50}$ is about 20.60 nM or less.

In some embodiments, an ABP provided herein has an $EC_{90}$, as measured by TNF production in PBMCs isolated from a human donor and treated as described in Example 9, in a range of about 22.49 nM to about 31.59 nM. In some embodiments, such $EC_{90}$ is about 31.59 nM or less.

In some embodiments, an ABP provided herein has an $EC_{10}$ in a range of about 5.02 nM to about 18.86 nM, an $EC_{50}$ in a range of about 12.60 nM to about 20.60 nM, and $EC_{90}$ in a range of about 22.49 nM to about 31.59 nM, in each cases as measured by TNF production in PBMCs isolated from a human donor and treated as described in Example 9.

In some embodiments, an ABP provided herein has an $EC_{10}$ of about 11.94 nM or less, an $EC_{50}$ of about 16.60 nM or less, and $EC_{90}$ of about 27.04 nM or less, in each cases as measured by TNF production in PBMCs isolated from a human donor and treated as described in Example 9.

In some embodiments, an ABP provided herein has an $EC_{10}$ of about 18.86 nM or less, an $EC_{50}$ of about 20.06 nM or less, and $EC_{90}$ of about 31.59 nM or less, in each cases as measured by TNF production in PBMCs isolated from a human donor and treated as described in Example 9.

In some embodiments, an ABP provided herein has an $EC_{10}$ of about 5.02 nM or less, an $EC_{50}$ of about 12.60 nM or less, and $EC_{90}$ of about 22.49 nM or less, in each cases as measured by TNF production in PBMCs isolated from a human donor and treated as described in Example 9.

In some embodiments, an ABP provided herein has an $EC_{10}$, as measured by IFN-γ production in CD4+ T cells isolated from a human donor and treated as described in Example 9, in a range of about 0.37 nM to about 1.05 nM. In some embodiments, such $EC_{10}$ is about 1.05 nM or less.

In some embodiments, an ABP provided herein has an $EC_{50}$, as measured by IFN-γ production in CD4+ T cells isolated from a human donor and treated as described in Example 9, in a range of about 0.94 nM to about 1.12 nM. In some embodiments, such $EC_{50}$ is about 1.12 nM or less.

In some embodiments, an ABP provided herein has an $EC_{90}$, as measured by IFN-γ production in CD4+ T cells isolated from a human donor and treated as described in Example 9, in a range of about 1.04 nM to about 2.72 nM. In some embodiments, such $EC_{90}$ is about 2.72 nM or less.

In some embodiments, an ABP provided herein has an $EC_{10}$ in a range of about 0.37 nM to about 1.05 nM, an $EC_{50}$ in a range of about 0.94 nM to about 1.12 nM, and $EC_{90}$ in a range of about 1.04 nM to about 2.72 nM, in each cases as measured by IFN-γ production in PBMCs isolated from a human donor and treated as described in Example 9.

In some embodiments, an ABP provided herein has an $EC_{10}$ of about 0.37 nM or less, an $EC_{50}$ of about 1.00 nM or less, and $EC_{90}$ of about 2.72 nM or less, in each cases as measured by IFN-γ production in PBMCs isolated from a human donor and treated as described in Example 9.

In some embodiments, an ABP provided herein has an $EC_{10}$ of about 0.85 nM or less, an $EC_{50}$ of about 0.94 nM or less, and $EC_{90}$ of about 1.04 nM or less, in each cases as measured by IFN-γ production in PBMCs isolated from a human donor and treated as described in Example 9.

In some embodiments, an ABP provided herein has an $EC_{10}$ of about 1.05 nM or less, an $EC_{50}$ of about 1.12 nM or less, and $EC_{90}$ of about 1.19 nM or less, in each cases as measured by IFN-γ production in PBMCs isolated from a human donor and treated as described in Example 9.

In some embodiments, an ABP provided herein has an $EC_{10}$ of about 0.75 nM or less, an $EC_{50}$ of about 1.02 nM or less, and $EC_{90}$ of about 1.65 nM or less, in each cases as measured by IFN-γ production in PBMCs isolated from a human donor and treated as described in Example 9.

In some embodiments, an ABP provided herein binds hTIGIT with a $K_D$ of about $5.24 \times 10^{-10}$ M (as determined by ForteBio), cTIGIT with a $K_D$ of about $2.64 \times 10^{-9}$ M (as determined by ForteBio), hTIGIT with a $K_D$ of about $5.40 \times 10^{-11}$ M (as determined by MSD-SET), and cTIGIT with a $K_D$ of about $3.20 \times 10^{-10}$ M (as determined by MSD-SET), in each case determined according to the methods provided in Example 4.

In some embodiments, an ABP provided herein binds hTIGIT with a $K_D$ of about $4.57 \times 10^{-10}$ M (as determined by ForteBio), cTIGIT with a $K_D$ of about $1.57 \times 10^{-9}$ M (as determined by ForteBio), hTIGIT with a $K_D$ of about $2.50 \times 10^{-11}$ M (as determined by MSD-SET), and cTIGIT with a $K_D$ of about $2.30 \times 10^{-10}$ M (as determined by MSD-SET), in each case determined according to the methods provided in Example 4.

In some embodiments, an ABP provided herein binds hTIGIT with a $K_D$ of about $3.32 \times 10^{-10}$ M (as determined by ForteBio), cTIGIT with a $K_D$ of about $8.02 \times 10^{-10}$ M (as determined by ForteBio), hTIGIT with a $K_D$ of about $8.10 \times 10^{-12}$ M (as determined by MSD-SET), and cTIGIT with a $K_D$ of about $3.50 \times 10^{-1}$ M (as determined by MSD-SET), in each case determined according to the methods provided in Example 4.

In some embodiments, an ABP provided herein binds hTIGIT with a $K_D$ of about $2.46 \times 10^{-10}$ M (as determined by ForteBio), cTIGIT with a $K_D$ of about $3.69 \times 10^{-10}$ M (as determined by ForteBio), hTIGIT with a $K_D$ of about $5.00 \times 10^{-12}$ M (as determined by MSD-SET), and cTIGIT with a $K_D$ of about $1.50 \times 10^{-11}$ M (as determined by MSD-SET), in each case determined according to the methods provided in Example 4.

In some embodiments, an ABP provided herein binds hTIGIT with a $K_D$ of about $1.96 \times 10^{-10}$ M (as determined by ForteBio), cTIGIT with a $K_D$ of about $8.98 \times 10^{-10}$ M (as determined by ForteBio), hTIGIT with a $K_D$ of about $4.90 \times 10^{-12}$ M (as determined by MSD-SET), and cTIGIT with a $K_D$ of about $4.60 \times 10^{-11}$ M (as determined by MSD-SET), in each case determined according to the methods provided in Example 4.

In some embodiments, an ABP provided herein binds hTIGIT with a $K_D$ of about $3.11 \times 10^{-9}$ M (as determined by ForteBio) and cTIGIT with a $K_D$ of about $1.75 \times 10^{-8}$ M (as determined by ForteBio), in each case determined according to the methods provided in Example 4.

In some embodiments, an ABP provided herein binds hTIGIT with a $K_D$ of about $2.54 \times 10^{-9}$ M, as determined by ForteBio according to the methods provided in Example 4.

In some embodiments, an ABP provided herein binds hTIGIT with a $K_D$ of about $3.13 \times 10^{-9}$ M (as determined by ForteBio) and cTIGIT with a $K_D$ of about $2.58 \times 10^{-8}$ M (as determined by ForteBio), in each case determined according to the methods provided in Example 4.

In some embodiments, an ABP provided herein binds hTIGIT with a $K_D$ of about $2.83 \times 10^{-9}$ M (as determined by ForteBio) and cTIGIT with a $K_D$ of about $9.35 \times 10^{-9}$ M (as determined by ForteBio), in each case determined according to the methods provided in Example 4.

In some embodiments, an ABP provided herein binds hTIGIT with a $K_D$ of about $1.71 \times 10^{-9}$ M (as determined by ForteBio), cTIGIT with a $K_D$ of about $6.55 \times 10^{-9}$ M (as determined by ForteBio), and hTIGIT with a $K_D$ of about $1.10 \times 10^{-10}$ M (as determined by MSD-SET), in each case determined according to the methods provided in Example 4.

In some embodiments, an ABP provided herein binds hTIGIT with a $K_D$ of about $2.47 \times 10^{-9}$ M (as determined by ForteBio), cTIGIT with a $K_D$ of about $8.14 \times 10^{-9}$ M (as determined by ForteBio), and hTIGIT with a $K_D$ of about $1.50 \times 10^{-10}$ M (as determined by MSD-SET), in each case determined according to the methods provided in Example 4.

In some embodiments, an ABP provided herein binds hTIGIT with a $K_D$ of about $2.35 \times 10^{-9}$ M (as determined by ForteBio), cTIGIT with a $K_D$ of about $6.57 \times 10^{-9}$ M (as determined by ForteBio), and hTIGIT with a $K_D$ of about $5.60 \times 10^{-11}$ M (as determined by MSD-SET), in each case determined according to the methods provided in Example 4.

In some embodiments, an ABP provided herein binds hTIGIT with a $K_D$ of about $1.44 \times 10^{-9}$ M (as determined by ForteBio) and hTIGIT with a $K_D$ of about $4.00 \times 10^{-10}$ M (as determined by MSD-SET), in each case determined according to the methods provided in Example 4.

In some embodiments, an ABP provided herein binds hTIGIT with a $K_D$ of about $1.23 \times 10^{-9}$ M (as determined by ForteBio) and hTIGIT with a $K_D$ of about $3.80 \times 10^{-10}$ M (as determined by MSD-SET), in each case determined according to the methods provided in Example 4.

In some embodiments, an ABP provided herein binds hTIGIT with a $K_D$ of about $5.26 \times 10^{-10}$ M (as determined by ForteBio), cTIGIT with a $K_D$ of about $7.94 \times 10^{-8}$ M (as determined by ForteBio), and hTIGIT with a $K_D$ of about $2.10 \times 10^{-10}$ M (as determined by MSD-SET), in each case determined according to the methods provided in Example 4.

In some embodiments, an ABP provided herein binds hTIGIT with a $K_D$ of about $3.78 \times 10^{-10}$ M (as determined by ForteBio), cTIGIT with a $K_D$ of about $7.04 \times 10^{-8}$ M (as determined by ForteBio), and hTIGIT with a $K_D$ of about $7.00 \times 10^{-11}$ M (as determined by MSD-SET), in each case determined according to the methods provided in Example 4.

In some embodiments, an ABP provided herein binds hTIGIT with a $K_D$ of about $4.29 \times 10^{-10}$ M (as determined by ForteBio), cTIGIT with a $K_D$ of about $1.10 \times 10^{-7}$ M (as determined by ForteBio), and hTIGIT with a $K_D$ of about $4.10 \times 10^{-11}$ M (as determined by MSD-SET), in each case determined according to the methods provided in Example 4.

In some embodiments, an ABP provided herein binds hTIGIT with a $K_D$ of about $4.48 \times 10^{-10}$ M (as determined by ForteBio) and cTIGIT with a $K_D$ of about $7.20 \times 10^{-8}$ M (as determined by ForteBio), in each case determined according to the methods provided in Example 4.

In some embodiments, an ABP provided herein binds hTIGIT with a $K_D$ of about $3.00 \times 10^{-11}$ M, as determined by MSD-SET according to the methods provided in Example 4.

In some embodiments, an ABP provided herein binds hTIGIT with a $K_D$ of about $8.00 \times 10^{-11}$ M, as determined by MSD-SET according to the methods provided in Example 4.

In some embodiments, an ABP provided herein inhibits binding of PVR to TIGIT with an $IC_{50}$ of about 2.2 nM, about 2.3 nM, about 1.6 nM, about 1.9 nM, about 1.7 nM, about 3.2 nM, about 2.6 nM, about 2.9 nM, about 3.3 nM, about 2 nM, about 2.2 nM, about 2.1 nM, about 1.8 nM, about 6.4 nM, or about 1 nM. In some embodiments, such $IC_{50}$ ranges from about 1 nM to about 6.4 nM. In some embodiments, such $IC_{50}$ is about 6.4 nM or less. In some embodiments, such $IC_{50}$ is determined as described in Example 5.

In some embodiments, an ABP provided herein inhibits binding of PVRL2 to TIGIT with an $IC_{50}$ of about 1.4 nM, about 1.3 nM, about 1.2 nM, about 1.6 nM, about 2 nM, about 1.2 nM, about 1.1 nM, about 1 nM, about 1.8 nM, about 1.9 nM, about 2 nM, or about 0.8 nM. In some embodiments, such $IC_{50}$ ranges from about 0.8 nM to about 2 nM. In some embodiments, such $IC_{50}$ is about 2 nM or less. In some embodiments, such $IC_{50}$ is determined as described in Example 5.

In some embodiments, an ABP provided herein inhibits binding of PVR to TIGIT with an $IC_{50}$ of about 2.2 nM and inhibits binding of PVRL2 to TIGIT with an $IC_{50}$ of about 1.4 nM. In some embodiments, an ABP provided herein inhibits binding of PVR to TIGIT with an $IC_{50}$ of about 2.3 nM and inhibits binding of PVRL2 to TIGIT with an $IC_{50}$ of about 1.3 nM. In some embodiments, an ABP provided herein inhibits binding of PVR to TIGIT with an $IC_{50}$ of about 1.6 nM and inhibits binding of PVRL2 to TIGIT with an $IC_{50}$ of about 1.2 nM. In some embodiments, an ABP provided herein inhibits binding of PVR to TIGIT with an $IC_{50}$ of about 1.9 nM and inhibits binding of PVRL2 to TIGIT with an $IC_{50}$ of about 1.6 nM. In some embodiments, an ABP provided herein inhibits binding of PVR to TIGIT with an $IC_{50}$ of about 1.7 nM and inhibits binding of PVRL2 to TIGIT with an $IC_{50}$ of about 1.4 nM. In some embodiments, an ABP provided herein inhibits binding of PVR to TIGIT with an $IC_{50}$ of about 3.2 nM and inhibits binding of PVRL2 to TIGIT with an $IC_{50}$ of about 1.4 nM. In some embodiments, an ABP provided herein inhibits binding of PVR to TIGIT with an $IC_{50}$ of about 2.6 nM and inhibits binding of PVRL2 to TIGIT with an $IC_{50}$ of about 2 nM. In some embodiments, an ABP provided herein inhibits binding of PVR to TIGIT with an $IC_{50}$ of about 2.9 nM and inhibits binding of PVRL2 to TIGIT with an $IC_{50}$ of about 1.2 nM. In some embodiments, an ABP provided herein inhibits binding of PVR to TIGIT with an $IC_{50}$ of about 1.9 nM and inhibits binding of PVRL2 to TIGIT with an $IC_{50}$ of about 1.1 nM. In some embodiments, an ABP provided herein inhibits binding of PVR to TIGIT with an $IC_{50}$ of about 3.3 nM and inhibits binding of PVRL2 to TIGIT with an $IC_{50}$ of about 1 nM. In some embodiments, an ABP provided herein inhibits binding of PVR to TIGIT with an $IC_{50}$ of about 2 nM and inhibits binding of PVRL2 to TIGIT with an $IC_{50}$ of about 1.2 nM. In some embodiments, an ABP provided herein inhibits binding of PVR to TIGIT with an $IC_{50}$ of about 1.7 nM and inhibits binding of PVRL2 to TIGIT with an $IC_{50}$ of about 1.2 nM. In some embodiments, an ABP provided herein inhibits binding of PVR to TIGIT with an $IC_{50}$ of about 2.1 nM and inhibits binding of PVRL2 to TIGIT with an $IC_{50}$ of about 1.8 nM. In some embodiments, an ABP provided herein inhibits binding of PVR to TIGIT with an $IC_{50}$ of about 2.6 nM and inhibits binding of PVRL2 to TIGIT with an $IC_{50}$ of about 1.6 nM. In some embodiments, an ABP provided herein inhibits binding of PVR to TIGIT with an $IC_{50}$ of about 2.2 nM and inhibits binding of PVRL2 to TIGIT with an $IC_{50}$ of about 1.1 nM. In some embodiments, an ABP provided herein inhibits binding of PVR to TIGIT with an $IC_{50}$ of about 2.1 nM and inhibits binding of PVRL2 to TIGIT with an $IC_{50}$ of about 1.3 nM. In some embodiments, an ABP provided herein inhibits binding of PVR to TIGIT with an $IC_{50}$ of about 2.6 nM and inhibits binding of PVRL2 to TIGIT with an $IC_{50}$ of about 1.9 nM. In some embodiments, an ABP provided herein inhibits binding of PVR to TIGIT with an $IC_{50}$ of about 1.8 nM and inhibits binding of PVRL2 to TIGIT with an $IC_{50}$ of about 1.9 nM. In some embodiments, an ABP provided herein inhibits binding of PVR to TIGIT with an $IC_{50}$ of about 6.4 nM and inhibits binding of PVRL2 to TIGIT with an $IC_{50}$ of about 2 nM. In some embodiments, an ABP provided herein inhibits binding of PVR to TIGIT with an $IC_{50}$ of about 2.3 nM and inhibits binding of PVRL2 to TIGIT with an $IC_{50}$ of about 1.9 nM. In some embodiments, an ABP provided herein inhibits binding of PVR to TIGIT with an $IC_{50}$ of about 1 nM and inhibits binding of PVRL2 to TIGIT with an $IC_{50}$ of about 0.8 nM. In some embodiments, such $IC_{50}$ is about 2 nM or less. In some embodiments, such $IC_{50}$ is determined as described in Example 5.

2.6.1. Glycosylation Variants

In certain embodiments, an ABP provided herein may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to or from an ABP provided herein may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an ABP.

In some embodiments, an ABP provided herein comprises a glycosylation motif that is different from a naturally occurring ABP. Any suitable naturally occurring glycosylation motif can be modified in the ABPs provided herein. The structural and glycosylation properties of immunoglobulins, for example, are known in the art and summarized, for example, in Schroeder and Cavacini, *J. Allergy Clin. Immunol.*, 2010, 125:S41-52, incorporated by reference in its entirety.

In some embodiments, an ABP provided herein comprises an IgG1 Fc region with modification to the oligosaccharide attached to asparagine 297 (Asn 297). Naturally occurring IgG1 antibodies produced by mammalian cells typically comprise a branched, biantennary oligosaccharide that is generally attached by an N-linkage to Asn 297 of the $C_{H2}$ domain of the Fc region. See Wright et al., *TIBTECH*, 1997, 15:26-32, incorporated by reference in its entirety. The oligosaccharide attached to Asn 297 may include various carbohydrates such as mannose, N-acetyl glucosamine (GlcNAc), galactose, and sialic acid, as well as a fucose attached to a GlcNAc in the "stem" of the biantennary oligosaccharide structure.

In some embodiments, the oligosaccharide attached to Asn 297 is modified to create ABPs having altered ADCC. In some embodiments, the oligosaccharide is altered to improve ADCC. In some embodiments, the oligosaccharide is altered to reduce ADCC.

In some aspects, an ABP provided herein comprises an IgG1 domain with reduced fucose content at position Asn 297 compared to a naturally occurring IgG1 domain. Such Fc domains are known to have improved ADCC. See Shields et al., *J. Biol. Chem.*, 2002, 277:26733-26740, incorporated by reference in its entirety. In some aspects, such ABPs do not comprise any fucose at position Asn 297. The amount of fucose may be determined using any suitable method, for example as described in WO 2008/077546, incorporated by reference in its entirety.

In some embodiments, an ABP provided herein comprises a bisected oligosaccharide, such as a biantennary oligosaccharide attached to the Fc region of the ABP that is bisected by GlcNAc. Such ABP variants may have reduced fucosylation and/or improved ADCC function. Examples of such ABP variants are described, for example, in WO 2003/011878; U.S. Pat. No. 6,602,684; and U.S. Pat. Pub. No. 2005/0123546; each of which is incorporated by reference in its entirety.

Other illustrative glycosylation variants which may be incorporated into the ABPs provided herein are described, for example, in U.S. Pat. Pub. Nos. 2003/0157108, 2004/0093621, 2003/0157108, 2003/0115614, 2002/0164328, 2004/0093621, 2004/0132140, 2004/0110704, 2004/0110282, 2004/0109865; International Pat. Pub. Nos. 2000/61739, 2001/29246, 2003/085119, 2003/084570, 2005/035586, 2005/035778; 2005/053742, 2002/031140; Okazaki et al., *J. Mol. Biol.*, 2004, 336:1239-1249; and Yamane-Ohnuki et al., *Biotech. Bioeng.*, 2004, 87: 614-622; each of which is incorporated by reference in its entirety.

In some embodiments, an ABP provided herein comprises an Fc region with at least one galactose residue in the oligosaccharide attached to the Fc region. Such ABP variants may have improved CDC function. Examples of such ABP variants are described, for example, in WO 1997/30087; WO 1998/58964; and WO 1999/22764; each of which his incorporated by reference in its entirety.

Examples of cell lines capable of producing defucosylated ABPs include Lec13 CHO cells, which are deficient in protein fucosylation (see Ripka et al., *Arch. Biochem. Biophys.*, 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., *Biotech. Bioeng.*, 2004, 87: 614-622; Kanda et al., *Biotechnol. Bioeng.*, 2006, 94:680-688; and WO 2003/085107; each of which is incorporated by reference in its entirety).

In some embodiments, an ABP provided herein is an aglycosylated ABP. An aglycosylated ABP can be produced using any method known in the art or described herein. In some aspects, an aglycosylated ABP is produced by modifying the ABP to remove all glycosylation sites. In some aspects, the glycosylation sites are removed only from the Fc region of the ABP. In some aspects, an aglycosylated ABP is produced by expressing the ABP in an organism that is not capable of glycosylation, such as *E. coli*, or by expressing the ABP in a cell-free reaction mixture.

In some embodiments, an ABP provided herein has a constant region with reduced effector function compared to a native IgG1 antibody. In some embodiments, the affinity of a constant region of an Fc region of an ABP provided herein for Fc receptor is less than the affinity of a native IgG1 constant region for such Fc receptor.

2.7. Fc Region Amino Acid Sequence Variants

In certain embodiments, an ABP provided herein comprises an Fc region with one or more amino acid substitutions, insertions, or deletions in comparison to a naturally occurring Fc region. In some aspects, such substitutions, insertions, or deletions yield ABPs with altered stability, glycosylation, or other characteristics. In some aspects, such substitutions, insertions, or deletions yield aglycosylated ABPs.

In some aspects, the Fc region of an ABP provided herein is modified to yield an ABP with altered affinity for an Fc receptor, or an ABP that is more immunologically inert. In some embodiments, the ABP variants provided herein possess some, but not all, effector functions. Such ABPs may be useful, for example, when the half-life of the ABP is important in vivo, but when certain effector functions (e.g., complement activation and ADCC) are unnecessary or deleterious.

In some embodiments, the Fc region of an ABP provided herein is a human IgG4 Fc region comprising one or more of the hinge stabilizing mutations S228P and L235E. See Aalberse et al., *Immunology*, 2002, 105:9-19, incorporated by reference in its entirety. In some embodiments, the IgG4 Fc region comprises one or more of the following mutations: E233P, F234V, and L235A. See Armour et al., *Mol. Immunol.,* 2003, 40:585-593, incorporated by reference in its entirety. In some embodiments, the IgG4 Fc region comprises a deletion at position G236.

In some embodiments, the Fc region of an ABP provided herein is a human IgG1 Fc region comprising one or more mutations to reduce Fc receptor binding. In some aspects, the one or more mutations are in residues selected from S228 (e.g., S228A), L234 (e.g., L234A), L235 (e.g., L235A), D265 (e.g., D265A), and N297 (e.g., N297A). In some aspects, the ABP comprises a PVA236 mutation. PVA236 means that the amino acid sequence ELLG, from amino acid position 233 to 236 of IgG1 or EFLG of IgG4, is replaced by PVA. See U.S. Pat. No. 9,150,641, incorporated by reference in its entirety.

In some embodiments, the Fc region of an ABP provided herein is modified as described in Armour et al., *Eur. J. Immunol.,* 1999, 29:2613-2624; WO 1999/058572; and/or U.K. Pat. App. No. 98099518; each of which is incorporated by reference in its entirety.

In some embodiments, the Fc region of an ABP provided herein is a human IgG2 Fc region comprising one or more of mutations A330S and P331S.

In some embodiments, the Fc region of an ABP provided herein has an amino acid substitution at one or more positions selected from 238, 265, 269, 270, 297, 327 and 329. See U.S. Pat. No. 6,737,056, incorporated by reference in its entirety. Such Fc mutants include Fc mutants with substitutions at two or more of amino acid positions 265, 269, 270, 297 and 327, including the so-called "DANA" Fc mutant with substitution of residues 265 and 297 with alanine. See U.S. Pat. No. 7,332,581, incorporated by reference in its entirety. In some embodiments, the ABP comprises an alanine at amino acid position 265. In some embodiments, the ABP comprises an alanine at amino acid position 297.

In certain embodiments, an ABP provided herein comprises an Fc region with one or more amino acid substitutions which improve ADCC, such as a substitution at one or more of positions 298, 333, and 334 of the Fc region. In some embodiments, an ABP provided herein comprises an Fc region with one or more amino acid substitutions at positions 239, 332, and 330, as described in Lazar et al., *Proc. Natl. Acad. Sci. USA,* 2006,103:4005-4010, incorporated by reference in its entirety.

In some embodiments, an ABP provided herein comprises one or more alterations that improves or diminishes C1q binding and/or CDC. See U.S. Pat. No. 6,194,551; WO 99/51642; and Idusogie et al., *J. Immunol.,* 2000, 164:4178-4184; each of which is incorporated by reference in its entirety.

In some embodiments, an ABP provided herein comprises one or more alterations to increase half-life. ABPs with increased half-lives and improved binding to the neonatal Fc receptor (FcRn) are described, for example, in Hinton et al., *J. Immunol.,* 2006, 176:346-356; and U.S. Pat. Pub. No. 2005/0014934; each of which is incorporated by reference in its entirety. Such Fc variants include those with substitutions at one or more of Fc region residues: 238, 250, 256, 265, 272, 286, 303, 305, 307, 311, 312, 314, 317, 340, 356, 360, 362, 376, 378, 380, 382, 413, 424, 428, and 434 of an IgG.

In some embodiments, an ABP provided herein comprises one or more Fc region variants as described in U.S. Pat. Nos. 7,371,826, 5,648,260, and 5,624,821; Duncan and Winter, *Nature,* 1988, 322:738-740; and WO 94/29351; each of which is incorporated by reference in its entirety.

2.8. Pyroglutamate

As is known in the art, both glutamate (E) and glutamine (Q) at the N-termini of recombinant proteins can cyclize spontaneously to form pyroglutamate (pE) in vitro and in vivo. See Liu et al., *J. Biol. Chem.,* 2011, 286:11211-11217, incorporated by reference in its entirety.

In some embodiments, provided herein are ABPs comprising a polypeptide sequence having a pE residue at the N-terminal position. In some embodiments, provided herein are ABPs comprising a polypeptide sequence in which the N-terminal residue has been converted from Q to pE. In some embodiments, provided herein are ABPs comprising a polypeptide sequence in which the N-terminal residue has been converted from E to pE.

In some embodiments, provided herein are ABPs comprising $V_H$ sequences having a pE residue at the N-terminal position. In some embodiments, provided herein are ABPs comprising a $V_H$ sequence in which the N-terminal residue has been converted from Q to pE. In some embodiments, provided herein is an ABP comprising a $V_H$ sequence selected from SEQ ID NOs: 4-24, wherein the N-terminal Q residue has been converted to pE. In some embodiments, provided herein is a composition comprising an ABP, wherein the ABP comprises a $V_H$ selected from SEQ ID NOs: 4-24, in which at least about 20%, at least about 40%, at least about 60%, at least about 80%, at least about 90%, at least about 95%, or at least about 99% of the N-terminal residues of such $V_H$ in such composition have been converted from Q to pE.

In some embodiments, provided herein are ABPs comprising $V_L$ sequences having a pE residue at the N-terminal position. In some embodiments, provided herein are ABPs comprising a $V_L$ sequence in which the N-terminal residue has been converted from E to pE. In some embodiments, provided herein is an ABP comprising a $V_L$ sequence selected from SEQ ID NOs: 25-28, wherein the N-terminal E residue has been converted to pE. In some embodiments, provided herein is a composition comprising an ABP, wherein the ABP comprises a $V_L$ selected from SEQ ID NOs: 25-28, in which at least about 20%, at least about 40%, at least about 60%, at least about 80%, at least about 90%, at least about 95%, or at least about 99% of the N-terminal residues of such $V_L$ in such composition have been converted from E to pE.

In some embodiments, provided herein are ABPs comprising heavy chain sequences having a pE residue at the N-terminal position. In some embodiments, provided herein are ABPs comprising a heavy chain sequence in which the N-terminal residue has been converted from Q to pE. In some embodiments, provided herein is an ABP comprising a heavy chain sequence selected from SEQ ID NOs: 79, 80, 82, 83, 84, 85, 86, 87, 88, 89, 90, 91, 93, 94, 95, 96, 97, 98, 99, 100, 101, 102, 103, 104, 105, 106, 108, 109, 110, 111, 112, 113, 114, 115, 116, 117, 118, 119, 121, 122, 123 or 124, wherein the N-terminal Q residue has been converted to pE. In some embodiments, provided herein is a composition comprising an ABP, wherein the ABP comprises a heavy chain selected from SEQ ID NOs: 79, 80, 82, 83, 84, 85, 86, 87, 88, 89, 90, 91, 93, 94, 95, 96, 97, 98, 99, 100, 101, 102, 103, 104, 105, 106, 108, 109, 110, 111, 112, 113, 114, 115, 116, 117, 118, 119, 121, 122, 123 or 124, in which at least about 20%, at least about 40%, at least about 60%, at least about 80%, at least about 90%, at least about 95%, or at least about 99% of the N-terminal residues of such heavy chain in such composition have been converted from Q to pE.

In some embodiments, provided herein are ABPs comprising light chain sequences having a pE residue at the N-terminal position. In some embodiments, provided herein are ABPs comprising a light chain sequence in which the N-terminal residue has been converted from E to pE. In some embodiments, provided herein is an ABP comprising a light chain sequence selected from SEQ ID NOs: 81, 92, 107 or 120, wherein the N-terminal E residue has been converted to pE. In some embodiments, provided herein is a composition comprising an ABP, wherein the ABP comprises a light chain selected from SEQ ID NOs: 81, 92, 107 or 120, in which at least about 20%, at least about 40%, at least about 60%, at least about 80%, at least about 90%, at least about 95%, or at least about 99% of the N-terminal residues of such light chain in such composition have been converted from E to pE.

2.9. Cysteine Engineered Antigen-Binding Protein Variants

In certain embodiments, provided herein are cysteine engineered ABPs, also known as "thioMAbs," in which one or more residues of the ABP are substituted with cysteine residues. In particular embodiments, the substituted residues occur at solvent accessible sites of the ABP. By substituting such residues with cysteine, reactive thiol groups are introduced at solvent accessible sites of the ABP and may be used to conjugate the ABP to other moieties, such as drug moieties or linker-drug moieties, for example, to create an immunoconjugate.

In certain embodiments, any one or more of the following residues may be substituted with cysteine: V205 of the light chain; A118 of the heavy chain Fc region; and S400 of the heavy chain Fc region. Cysteine engineered ABPs may be generated as described, for example, in U.S. Pat. No. 7,521,541, which is incorporated by reference in its entirety.

2.9.1. Immunoconjugates 2.9.1.1. Antigen-Binding Protein-Polymer Conjugates

In some embodiments, an ABP provided herein is derivatized by conjugation with a polymer. Any suitable polymer may be conjugated to the ABP.

In some embodiments, the polymer is a water soluble polymer. Illustrative examples of water soluble polymers include polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl pyrrolidone)-co-polyethylene glycol, propropylene glycol homopolymers, polypropylene oxide/ethylene oxide co-polymers, polyoxyethylated polyols (e.g., glycerol), polyvinyl alcohol, and mixtures thereof. In some aspects, polyethylene glycol propionaldehyde may be useful for manufacturing purposes due to its stability in water.

The polymer may be of any molecular weight, and may be branched or unbranched. The number of polymers attached to each ABP may vary, and if more than one polymer is attached, they may be the same polymer or different polymers. In general, the number and/or type of polymers used for derivatization can be determined based on considerations including the particular properties or functions of the ABP to be improved and the intended use of the ABP.

2.9.1.2. Antigen-Binding Protein-Drug Conjugates

In some embodiments, the ABPs provided herein are conjugated to one or more therapeutic agents. Any suitable therapeutic agent may be conjugated to the ABP. Exemplary therapeutic agents include cytokines, chemokines, and other agents that induce a desired T cell activity, such as OX40L, 4-1BBL, TNF-alpha (as used herein, "TNF"), IL-2, IL-15 fusion, CXCL9, CXCL10, IL-10 trap, IL-27 trap, and IL-35 trap. Cytokine traps and their use are known in the art and described, for example, in Economides et al., *Nature Medicine*, 2003, 9:47-52, incorporated by reference in its entirety.

3. Methods of Making TIGIT Antigen-Binding Proteins 3.1. TIGIT Antigen Preparation The TIGIT antigen used for isolation of the ABPs provided herein may be intact TIGIT or a fragment of TIGIT. The TIGIT antigen may be, for example, in the form of an isolated protein or a protein expressed on the surface of a cell.

In some embodiments, the TIGIT antigen is a non-naturally occurring variant of TIGIT, such as a TIGIT protein having an amino acid sequence or post-translational modification that does not occur in nature.

In some embodiments, the TIGIT antigen is truncated by removal of, for example, intracellular or membrane-spanning sequences, or signal sequences. In some embodiments, the TIGIT antigen is fused at its C-terminus to a human IgG1 Fc domain or a polyhistidine tag.

3.2. Methods of Making Monoclonal Antibodies

Monoclonal antibodies may be obtained, for example, using the hybridoma method first described by Kohler et al., *Nature*, 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage or yeast-based libraries. See e.g., U.S. Pat. Nos. 8,258,082 and 8,691,730, each of which is incorporated by reference in its entirety.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* 3rd ed. (1986) Academic Press, San Diego, Calif., incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, *J. Immunol.*, 1984, 133:3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

3.3. Methods of Making Chimeric Antibodies

Illustrative methods of making chimeric antibodies are described, for example, in U.S. Pat. No. 4,816,567; and Morrison et al., *Proc. Natl. Acad. Sci. USA*, 1984, 81:6851-6855; each of which is incorporated by reference in its entirety. In some embodiments, a chimeric antibody is made by using recombinant techniques to combine a non-human variable region (e.g., a variable region derived from a mouse, rat, hamster, rabbit, or non-human primate, such as a monkey) with a human constant region.

3.4. Methods of Making Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature*, 1991, 349:293-299; Rader et al., *Proc. Nat. Acad. Sci. U.S.A.*, 1998, 95:8910-8915; Steinberger et al., *J. Biol. Chem.*, 2000, 275:36073-36078; Queen et al., *Proc. Natl. Acad. Sci. U.S.A.*, 1989, 86:10029-10033; and U.S. Pat. Nos. 5,585,089, 5,693,761, 5,693,762, and 6,180,370; each of which is incorporated by reference in its entirety.

3.5. Methods of Making Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.*, 1993, 90:2551; Jakobovits et al., *Nature*, 1993, 362:255-258; Bruggermann et al., *Year in Immuno.*, 1993, 7:33; and U.S. Pat. Nos. 5,591,669, 5,589,369 and 5,545,807; each of which is incorporated by reference in its entirety. Human antibodies can also be derived from phage-display libraries (see e.g., Hoogenboom et al., *J. Mol. Biol.*, 1991, 227:381-388; Marks et al., *J. Mol. Biol.*, 1991, 222:581-597; and U.S. Pat. Nos. 5,565,332 and 5,573,905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. No. 8,691,730, incorporated by reference in its entirety).

3.6. Methods of Making Antibody Fragments

The antibody fragments provided herein may be made by any suitable method, including the illustrative methods described herein or those known in the art. Suitable methods include recombinant techniques and proteolytic digestion of whole antibodies. Illustrative methods of making antibody fragments are described, for example, in Hudson et al., *Nat. Med.*, 2003, 9:129-134, incorporated by reference in its entirety. Methods of making scFv antibodies are described, for example, in Plückthun, in *The Pharmacology of Monoclonal Antibodies*, vol. 113, Rosenburg and Moore eds., Springer-Verlag, New York, pp. 269-315 (1994); WO 93/16185; and U.S. Pat. Nos. 5,571,894 and 5,587,458; each of which is incorporated by reference in its entirety.

3.7. Methods of Making Alternative Scaffolds

The alternative scaffolds provided herein may be made by any suitable method, including the illustrative methods described herein or those known in the art. For example, methods of preparing Adnectins™ are described in Emanuel et al., mAbs, 2011, 3:38-48, incorporated by reference in its entirety. Methods of preparing iMabs are described in U.S. Pat. Pub. No. 2003/0215914, incorporated by reference in its entirety. Methods of preparing Anticalins® are described in Vogt and Skerra, *Chem. Biochem.*, 2004, 5:191-199, incorporated by reference in its entirety. Methods of preparing Kunitz domains are described in Wagner et al., *Biochem. & Biophys. Res. Comm.*, 1992, 186:118-1145, incorporated by reference in its entirety. Methods of preparing thioredoxin peptide aptamers are provided in Geyer and Brent, *Meth. Enzymol.*, 2000, 328:171-208, incorporated by reference in its entirety. Methods of preparing Affibodies are provided in Fernandez, Curr. Opinion in Biotech., 2004, 15:364-373, incorporated by reference in its entirety. Methods of preparing DARPins are provided in Zahnd et al., *J. Mol. Biol.*, 2007, 369:1015-1028, incorporated by reference in its entirety. Methods of preparing Affilins are provided in Ebersbach et al., *J. Mol. Biol.*, 2007, 372:172-185, incorporated by reference in its entirety. Methods of preparing Tetranectins are provided in Graversen et al., *J. Biol. Chem.*, 2000, 275:37390-37396, incorporated by reference in its entirety. Methods of preparing Avimers are provided in Silverman et al., *Nature Biotech.*, 2005, 23:1556-1561, incorporated by reference in its entirety. Methods of preparing Fynomers are provided in Silacci et al., *J. Biol. Chem.*, 2014, 289:14392-14398, incorporated by reference in its entirety.

Further information on alternative scaffolds is provided in Binz et al., *Nat. Biotechnol.*, 2005 23:1257-1268; and Skerra, Current Opin. in Biotech., 2007 18:295-304, each of which is incorporated by reference in its entirety.

3.8. Methods of Making Multispecific ABPs

The multispecific ABPs provided herein may be made by any suitable method, including the illustrative methods described herein or those known in the art. Methods of making common light chain antibodies are described in Merchant et al., *Nature Biotechnol.*, 1998, 16:677-681, incorporated by reference in its entirety. Methods of making tetravalent bispecific antibodies are described in Coloma and Morrison, Nature *Biotechnol.*, 1997, 15:159-163, incorporated by reference in its entirety. Methods of making hybrid immunoglobulins are described in Milstein and Cuello, *Nature*, 1983, 305:537-540; and Staerz and Bevan, *Proc. Natl. Acad. Sci. USA*, 1986, 83:1453-1457; each of which is incorporated by reference in its entirety. Methods of making immunoglobulins with knobs-into-holes modification are described in U.S. Pat. No. 5,731,168, incorporated by reference in its entirety. Methods of making immunoglobulins with electrostatic modifications are provided in WO 2009/089004, incorporated by reference in its entirety. Methods of making bispecific single chain antibodies are described in Traunecker et al., *EMBO J.*, 1991, 10:3655-3659; and Gruber et al., *J. Immunol.*, 1994, 152:5368-5374; each of which is incorporated by reference in its entirety. Methods of making single-chain antibodies, whose linker length may be varied, are described in U.S. Pat. Nos. 4,946,778 and 5,132,405, each of which is incorporated by reference in its entirety. Methods of making diabodies are described in Hollinger et al., *Proc. Natl. Acad. Sci. USA*, 1993, 90:6444-6448, incorporated by reference in its entirety. Methods of making triabodies and tetrabodies are described in Todorovska et al., *J. Immunol. Methods*, 2001, 248:47-66, incorporated by reference in its entirety. Methods of making trispecific F(ab')3 derivatives are described in Tutt et al. *J. Immunol.*, 1991, 147:60-69, incorporated by reference in its entirety. Methods of making cross-linked antibodies are described in U.S. Pat. No. 4,676,980; Brennan et al., *Science*, 1985, 229:81-83; Staerz, et al. *Nature*, 1985, 314:628-631; and EP 0453082; each of which is incorporated by reference in its entirety. Methods of making antigen-binding domains assembled by leucine zippers are described in Kostelny et al., *J. Immunol.*, 1992, 148:1547-1553, incorporated by reference in its entirety. Methods of making ABPs via the DNL approach are described in U.S. Pat. Nos. 7,521,056; 7,550,143; 7,534,866; and 7,527,787; each of which is incorporated by reference in its entirety. Methods of making hybrids of antibody and non-antibody molecules are described in WO 93/08829, incorporated by reference in its entirety, for examples of such ABPs. Methods of making DAF antibodies are described in U.S. Pat. Pub. No. 2008/0069820, incorporated by reference in its entirety. Methods of making ABPs via reduction and oxidation are described in Carlring et al., *PLoS One*, 2011, 6:e22533, incorporated by reference in its entirety. Methods of making DVD-Igs™ are described in U.S. Pat. No. 7,612,181, incorporated by reference in its entirety. Methods of making DARTs™ are described in Moore et al., *Blood*, 2011, 117:454-451, incorporated by reference in its entirety. Methods of making DuoBodies® are described in Labrijn et al., *Proc. Natl. Acad. Sci. USA*, 2013, 110:5145-5150; Gramer et al., mAbs, 2013, 5:962-972; and Labrijn et al., *Nature Protocols*, 2014, 9:2450-2463; each of which is incorporated by reference in its entirety. Methods of making antibodies comprising scFvs fused to the C-terminus of the $C_{H3}$ from an IgG are described in Coloma and Morrison, Nature *Biotechnol.*, 1997, 15:159-163, incorporated by reference in its entirety. Methods of making antibodies in which a Fab molecule is attached to the constant region of an immunoglobulin are described in Miler et al., *J. Immunol.*, 2003, 170:4854-4861, incorporated by reference in its entirety. Methods of making CovX-Bodies are described in Doppalapudi et al., *Proc. Natl. Acad. Sci. USA*, 2010, 107:22611-22616, incorporated by reference in its entirety. Methods of making Fcab antibodies are described in Wozniak-Knopp et al., *Protein Eng. Des. Sel.*, 2010, 23:289-297, incorporated by reference in its entirety. Methods of making TandAb® antibodies are described in Kipriyanov et al., *J. Mol. Biol.*, 1999, 293:41-56 and Zhukovsky et al., *Blood*, 2013, 122:5116, each of which is incorporated by reference in its entirety. Methods of making tandem Fabs are described in WO 2015/103072, incorporated by reference in its entirety. Methods of making Zybodies™ are described in LaFleur et al., mAbs, 2013, 5:208-218, incorporated by reference in its entirety.

3.9. Methods of Making Variants

In some embodiments, an ABP provided herein is an affinity matured variant of a parent ABP, which may be generated, for example, using phage display-based affinity maturation techniques. Briefly, one or more CDR residues may be mutated and the variant ABPs, or portions thereof, displayed on phage and screened for affinity. Such alterations may be made in CDR "hotspots," or residues encoded by codons that undergo mutation at high frequency during the somatic maturation process (see Chowdhury, *Methods Mol. Biol.*, 2008, 207:179-196, incorporated by reference in its entirety), and/or residues that contact the antigen.

Any suitable method can be used to introduce variability into a polynucleotide sequence(s) encoding an ABP, including error-prone PCR, chain shuffling, and oligonucleotide-directed mutagenesis such as trinucleotide-directed mutagenesis (TRIM). In some aspects, several CDR residues (e.g., 4-6 residues at a time) are randomized. CDR residues involved in antigen binding may be specifically identified, for example, using alanine scanning mutagenesis or modeling. CDR-H3 and CDR-L3 in particular are often targeted for mutation.

The introduction of diversity into the variable regions and/or CDRs can be used to produce a secondary library. The secondary library is then screened to identify ABP variants with improved affinity. Affinity maturation by constructing and reselecting from secondary libraries has been described, for example, in Hoogenboom et al., *Methods in Molecular Biology*, 2001, 178:1-37, incorporated by reference in its entirety.

3.10. Vectors, Host Cells, and Recombinant Methods

Also provided are isolated nucleic acids encoding TIGIT ABPs, vectors comprising the nucleic acids, and host cells comprising the vectors and nucleic acids, as well as recombinant techniques for the production of the ABPs.

For recombinant production of an ABP, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells are provided below. These host cells are not meant to be limiting, and any suitable host cell may be used to produce the ABPs provided herein.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are also suitable.

In addition to prokaryotes, eukaryotic microbes such as filamentous fungi or yeast are also suitable cloning or expression hosts for TIGIT ABP-encoding vectors. *Saccharomyces cerevisiae*, or common baker's yeast, is a commonly used lower eukaryotic host microorganism. However, a number of other genera, species, and strains are available and useful, such as *Schizosaccharomyces pombe, Kluyveromyces* (*K. lactis, K. fragilis, K. bulgaricus K. wickeramii, K.*

*waltii, K. drosophilarum, K. thermotolerans*, and *K. marxianus*), *Yarrowia, Pichia pastoris, Candida* (*C. albicans*), *Trichoderma reesia, Neurospora crassa, Schwanniomyces* (*S. occidentalis*), and filamentous fungi such as, for example *Penicillium, Tolypocladium*, and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the TIGIT ABP of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.*, 1979, 58:44; Barnes et al., *Anal. Biochem.*, 1980, 102:255; and U.S. Pat. Nos. 4,767,704, 4,657,866, 4,927,762, 4,560,655, and 5,122,469; or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the ABP can be produced intracellularly, in the periplasmic space, or directly secreted into the medium. If the ABP is produced intracellularly, as a first step, the particulate debris, either host cells or lysed fragments, is removed, for example, by centrifugation or ultrafiltration. For example, Carter et al. (*Bio/Technology*, 1992, 10:163-167, incorporated by reference in its entirety) describes a procedure for isolating ABPs which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the ABP is produced in a cell-free system. In some aspects, the cell-free system is an in vitro transcription and translation system as described in Yin et al., mAbs, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the ABP may be useful, for example, where the ABP accumulates in a cell as an insoluble aggregate, or where yields from periplasmic expression are low.

Where the ABP is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The ABP composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the ABP. Protein A can be used to purify ABPs that comprise human γ1, γ2, or γ4 heavy chains (Lindmark et al., *J. Immunol. Meth.*, 1983, 62:1-13, incorporated by reference in its entirety). Protein G is useful for all mouse isotypes and for human γ3 (Guss et al., *EMBO J.*, 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the ABP comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the ABP of interest and contaminants may be subjected to low pH hydrophobic interaction chromatography using an elution buffer at a pH between about 2.5 to about 4.5, generally performed at low salt concentrations (e.g., from about 0 to about 0.25 M salt).

4. Assays

A variety of assays known in the art may be used to identify and characterize the TIGIT ABPs provided herein.

4.1. Binding, Competition, and Epitope Mapping Assays

Specific antigen-binding activity of the ABPs provided herein may be evaluated by any suitable method, including using SPR, BLI, RIA and MSD-SET, as described elsewhere in this disclosure. Additionally, antigen-binding activity may be evaluated by ELISA assays and Western blot assays.

Assays for measuring competition between two ABPs, or an ABP and another molecule (e.g., one or more ligands of TIGIT) are described elsewhere in this disclosure and, for example, in Harlow and Lane, *Antibodies: A Laboratory Manual* ch. 14, 1988, Cold Spring Harbor Laboratory, Cold Spring Harbor, N.Y., incorporated by reference in its entirety.

Assays for mapping the epitopes to which the ABPs provided herein bind are described, for example, in Morris "Epitope Mapping Protocols," in *Methods in Molecular Biology* vol. 66, 1996, Humana Press, Totowa, N.J., incorporated by reference in its entirety. In some embodiments, the epitope is determined by peptide competition. In some embodiments, the epitope is determined by mass spectrometry. In some embodiments, the epitope is determined by crystallography.

4.2. TIGIT Antagonism Assays

In some embodiments, the ABPs provided herein are screened to identify or characterize ABPs with antagonistic activity against TIGIT. Any suitable assay may be used to identify or characterize such ABPs. In some aspects, the assay measures the amount of a cytokine secreted by an effector T cell after contacting the effector T cell with an ABP provided herein. In some aspects, the cytokine is selected from IL-2, IL-6, LT-α, TNF, GM-CSF, IFNγ, and combinations thereof. In some aspects, the cytokine is selected from sCD40L, VEGF, TGF-α, RANTES, PDGF-AB/BB, PDGF-AA, MIP-1β, MIP-1α, MDC (CCL22), MCP-3, MCP-1, IP-10, IL-17A, IL-2Rα, IL-15, IL-13, IL-12 (p70), IL-12 (p40), IL-10, IL-9, IL-8, IL-7, IL-5, IL-4, IL-3, IL-2, IL-2Rα, IL-1RA, IL-1β, IL-1α, IFNγ, IFNα2, GRO, GM-CSF, G-CSF, fractalkine, Flt-3 ligand, FGF-2, eotaxin, EGF, and combinations thereof.

In some embodiments, the effector cells are co-stimulated with an agonist of CD3, to promote the secretion of cytokines by the effector cell. In some aspects, the CD3 agonist is provided at a submaximal level.

In some aspects, such assays may measure the proliferation of an effector T cell after contacting the effector T cell with an ABP provided herein. In some aspects, proliferation of the effector T cell is measured by dilution of a dye (e.g., carboxyfluorescein diacetate succinimidyl ester; CFSE), by tritiated thymidine uptake, by luminescent cell viability assays, or by other assays known in the art.

In some aspects, such assays may measure the differentiation, cytokine production, viability (e.g., survival), proliferation, or suppressive activity of a regulatory T cell after contacting the regulatory T cell with an ABP provided herein.

In some aspects, such assays may measure the cytotoxic activity of an NK cell after contacting the NK cell with an ABP provided herein. In some aspects, the cytotoxic activity of the NK cell is measured using a cytotoxicity assay that quantifies NK-mediated killing of target cells (e.g., a K562 cell line). See Jang et al., *Ann. Clin. Lab. Sci.*, 2012, 42:42-49, incorporated by reference in its entirety.

In some aspects, such assays may measure the amount of granzyme B. In some aspects, such assays may measure the amount of perforin.

4.3. Assays for Effector Functions

Effector function following treatment with the ABPs provided herein may be evaluated using a variety of in vitro and in vivo assays known in the art, including those described in Ravetch and Kinet, *Annu. Rev. Immunol.,* 1991, 9:457-492; U.S. Pat. Nos. 5,500,362, 5,821,337; Hellstrom et al., *Proc. Nat'l Acad. Sci.* USA, 1986, 83:7059-7063; Hellstrom et al., *Proc. Nat'l Acad. Sci.* USA, 1985, 82:1499-1502; Bruggemann et al., *J. Exp. Med.,* 1987, 166:1351-1361; Clynes et al., *Proc. Nat'l Acad. Sci.* USA, 1998, 95:652-656; WO 2006/029879; WO 2005/100402; Gazzano-Santoro et al., *J. Immunol. Methods,* 1996, 202:163-171; Cragg et al., *Blood,* 2003, 101:1045-1052; Cragg et al. *Blood,* 2004, 103:2738-2743; and Petkova et al., *Int'l. Immunol.,* 2006, 18:1759-1769; each of which is incorporated by reference in its entirety.

5. Pharmaceutical Compositions

The ABPs provided herein can be formulated in any appropriate pharmaceutical composition and administered by any suitable route of administration. Suitable routes of administration include, but are not limited to, the intraarterial, intradermal, intramuscular, intraperitoneal, intravenous, nasal, parenteral, pulmonary, and subcutaneous routes.

The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a cosolvent. Illustrative examples of cosolvents include ethanol, poly(ethylene) glycol, butylene glycol, dimethylacetamide, glycerin, propylene glycol, and combinations thereof.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, monosodium glutamate, and combinations thereof.

In some embodiments, the pharmaceutical composition comprises a carrier or filler. Illustrative examples of carriers or fillers include lactose, maltodextrin, mannitol, sorbitol, chitosan, stearic acid, xanthan gum, guar gum, and combinations thereof.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, vitamin E polyethylene(glycol) succinate, and combinations thereof.

In some embodiments, the pharmaceutical composition comprises an anti-caking agent. Illustrative examples of anti-caking agents include calcium phosphate (tribasic), hydroxymethyl cellulose, hydroxypropyl cellulose, magnesium oxide, and combinations thereof.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, sugars, and combinations thereof. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an ABP, since water can facilitate the degradation of some ABPs.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

5.1. Parenteral Dosage Forms

In certain embodiments, the ABPs provided herein are formulated as parenteral dosage forms. Parenteral dosage forms can be administered to subjects by various routes including, but not limited to, subcutaneous, intravenous (including infusions and bolus injections), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry (e.g., lyophilized) products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the ABPs disclosed herein can also be incorporated into the parenteral dosage forms.

In some embodiments, the parenteral dosage form is lyophilized. Exemplary lyophilized formulations are described, for example, in U.S. Pat. Nos. 6,267,958 and 6,171,586; and WO 2006/044908; each of which is incorporated by reference in its entirety.

6. Dosage and Unit Dosage Forms

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic ABPs.

The amount of the ABP or composition which will be effective in the prevention or treatment of a disorder or one or more symptoms thereof will vary with the nature and severity of the disease or condition, and the route by which the ABP is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the ABP per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the ABP provided herein, based on weight of the ABP, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. It may be necessary to use dosages of the ABP outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the ABPs provided herein are also encompassed by the dosage amounts and dose frequency schedules provided herein. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an ABP or composition provided herein followed by one or more maintenance doses.

In certain embodiments, a dose of an ABP or composition provided herein can be administered to achieve a steady-state concentration of the ABP in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months.

As discussed in more detail elsewhere in this disclosure, an ABP provided herein may optionally be administered with one or more additional agents useful to prevent or treat a disease or disorder. The effective amount of such additional agents may depend on the amount of ABP present in the formulation, the type of disorder or treatment, and the other factors known in the art or described herein.

7. Therapeutic Applications

For therapeutic applications, the ABPs of the invention are administered to a mammal, generally a human, in a pharmaceutically acceptable dosage form such as those known in the art and those discussed above. For example, the ABPs of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The ABPs also are suitably administered by peritumoral, intralesional, or perilesional routes, to exert local as well as systemic therapeutic effects. The intraperitoneal route may be particularly useful, for example, in the treatment of ovarian tumors.

The ABPs provided herein may be useful for the treatment of any disease or condition involving TIGIT. In some embodiments, the disease or condition is a disease or condition that can benefit from treatment with an anti-TIGIT ABP. In some embodiments, the disease or condition is a tumor. In some embodiments, the disease or condition is a cell proliferative disorder. In some embodiments, the disease or condition is a cancer. In some embodiments, the disease or condition is a viral infection.

In some embodiments, the ABPs provided herein are provided for use as a medicament. In some embodiments, the ABPs provided herein are provided for use in the manufacture or preparation of a medicament. In some embodiments, the medicament is for the treatment of a disease or condition that can benefit from an anti-TIGIT ABP. In some embodiments, the disease or condition is a tumor. In some embodiments, the disease or condition is a cell proliferative disorder. In some embodiments, the disease or condition is a cancer. In some embodiments, the disease or condition is a viral infection.

In some embodiments, provided herein is a method of treating a disease or condition in a subject in need thereof by administering an effective amount of an ABP provided herein to the subject. In some aspects, the disease or condition is a cancer. In some aspects, the disease or condition is a viral infection.

Any suitable cancer may be treated with the ABPs provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

Any suitable virus may be treated with the ABPs provided herein. Illustrative suitable viruses include, for example, adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, cowpox virus, Coxsackievirus, Crimean-Congo hemorrhagic fever virus, Dengue virus, Dhori virus, Dugbe virus, Duvenhage virus, eastern equine encephalitis virus, ebolavirus, echovirus, encephalomyocarditis virus, Epstein-Barr virus, European bat lyssavirus, GB virus C/Hepatitis G virus, Hantaan virus, Hendra virus, hepatitis A virus, hepatitis B virus, hepatitis C virus, hepatitis E virus, hepatitis delta virus, horsepox virus, human adenovirus, human astrovirus, human coronavirus, human cytomegalovirus, human enterovirus, human herpesvirus 1, human herpesvirus 2, human herpesvirus 6, human herpesvirus 7, human herpesvirus 8, human immunodeficiency virus, human papillomavirus 1, human papillomavirus 2, human papillomavirus, human parainfluenza, human parvovirus B19, human respiratory syncytial virus, human rhinovirus, human SARS coronavirus, human spumaretrovirus, human T-lymphotropic virus, human torovirus, influenza A virus, influenza B virus, influenza C virus, Isfahan virus, JC polyomavirus, Japanese encephalitis virus, Junin arenavirus, KI polyomavirus, Kunjin virus, Lagos bat virus, Lake Victoria marburgvirus, Langat virus, Lassa virus, Lordsdale virus, Louping ill virus, lymphocytic choriomeningitis virus, Machupo virus, Mayaro virus, MERS coronavirus, measles virus, Mengo encephalomyocarditis virus, Merkel cell polyomavirus, Mokola virus, molluscum contagiosum virus, monkeypox virus, mumps virus, Murray valley encephalitis virus, New York virus, Nipah virus, Norwalk virus, O'nyong-nyong virus, Orf virus, Oropouche virus, Pichinde virus, poliovirus, Punta toro phlebovirus, Puumala virus, rabies virus, Rift Valley fever virus, Rosavirus A, Ross River virus, rotavirus A, rotavirus B, rotavirus C, rubella virus, Sagiyama virus, salivirus A, sandfly fever Sicilian virus, Sapporo virus, Semliki Forest virus, Seoul virus, simian foamy virus, simian virus 5, Sindbis virus, Southampton virus, St. Louis encephalitis virus, tick-borne powassan virus, torque teno virus, Toscana virus, Uukuniemi virus, vaccinia virus, varicella-zoster virus, variola virus, Venezuelan equine encephalitis virus, vesicular stomatitis virus, western equine encephalitis virus, WU polyomavirus, West Nile virus, Yaba monkey tumor virus, Yaba-like disease virus, yellow fever virus, and Zika virus.

In some embodiments, provided herein is a method of antagonizing TIGIT in a target cell of a subject in need thereof by administering an effective amount of an ABP provided herein to the subject. In some aspects, antagonism of TIGIT by an ABP provided herein results in increased secretion of IL-2, LT-α, IL-6, TNF, GM-CSF, IFNγ or combinations thereof by a target cell.

In some embodiments, provided herein is a method of increasing the proliferation, survival, and/or function of an effector T cell in a subject in need thereof by administering an effective amount of an ABP provided herein to the subject. In some aspects the effector T cell is a CD4+ effector T cell. In some aspects, the effector T cell is a CD8+ effector T cell.

In some embodiments, provided herein is a method of abrogating suppression of an effector T cell by a regulatory T cell in a subject in need thereof by administering an effective amount of an ABP provided herein to the subject. In some aspects, the regulatory T cell is a CD4+CD25+ Foxp3+ regulator T cell. In some aspects, the regulatory T cell is a CD8+CD25+ regulatory T cell.

In some embodiments, provided herein is a method of increasing the activity of a natural killer (NK) or natural killer T (NKT) cell in a subject in need thereof by administering an effective amount of an ABP provided herein to the subject.

In some embodiments, provided herein is a method of enhancing an immune response in a subject in need thereof by administering an effective amount of an ABP provided herein to the subject.

In some embodiments, provided herein is a method delaying the onset of a tumor in a subject in need thereof by administering an effective amount of an ABP provided herein to the subject.

In some embodiments, provided herein is a method preventing the onset of a tumor in a subject in need thereof by administering an effective amount of an ABP provided herein to the subject.

In some embodiments, provided herein is a method of delaying the onset of a cancer in a subject in need thereof by administering an effective amount of an ABP provided herein to the subject.

In some embodiments, provided herein is a method of preventing the onset of a cancer in a subject in need thereof by administering an effective amount of an ABP provided herein to the subject.

In some embodiments, provided herein is a method of reducing the size of a tumor in a subject in need thereof by administering an effective amount of an ABP provided herein to the subject.

In some embodiments, provided herein is a method of reducing the number of metastases in a subject in need thereof by administering an effective amount of an ABP provided herein to the subject.

In some embodiments, provided herein is a method of delaying the onset of a viral infection in a subject in need thereof by administering an effective amount of an ABP provided herein to the subject.

In some embodiments, provided herein is a method of preventing the onset of a viral infection in a subject in need thereof by administering an effective amount of an ABP provided herein to the subject.

In some embodiments, provided herein is a method of reducing viral titer a subject in need thereof by administering an effective amount of an ABP provided herein to the subject.

In some embodiments, provided herein is a method of eliminating a virus from subject in need thereof by administering an effective amount of an ABP provided herein to the subject.

In some embodiments, provided herein is a method for extending the period of overall survival, median survival time, or progression-free survival in a subject in need thereof by administering an effective amount of an ABP provided herein to the subject.

In some embodiments, provided herein is a method for treating a subject who has become resistant to a standard of care therapeutic by administering an effective amount of an ABP provided herein to the subject. In some embodiments, the standard-of-care therapeutic to which the subject has become resistant is a PD-1 inhibitor. In other embodiments, the standard-of-care therapeutic to which the subject has become resistant is a PD-L1 inhibitor. In other embodiments, the standard-of-care therapeutic to which the subject has become resistant is a CTLA-4 inhibitor.

8. Combination Therapies

In some embodiments, an ABP provided herein is administered with at least one additional therapeutic agent. Any suitable additional therapeutic agent may be administered with an ABP provided herein. In some aspects, the additional therapeutic agent is selected from radiation, a cytotoxic agent, a chemotherapeutic agent, a cytostatic agent, an anti-hormonal agent, an EGFR inhibitor, an immunostimulatory agent, an anti-angiogenic agent, and combinations thereof.

In some embodiments, the additional therapeutic agent comprises an immunostimulatory agent.

In some embodiments, the immunostimulatory agent is an agent that blocks signaling of an inhibitory receptor of an immune cell, or a ligand thereof. In some aspects, the inhibitory receptor or ligand is selected from CTLA-4, PD-1, PD-L1, LAG-3, Tim3, TIGIT, neuritin, BTLA, KIR, and combinations thereof. In some aspects, the agent is selected from an anti-PD-1 antibody (e.g., pembrolizumab or nivolumab), and anti-PD-L1 antibody (e.g., atezolizumab), an anti-CTLA-4 antibody (e.g., ipilimumab), and combinations thereof. In some aspects, the agent is pembrolizumab. In some aspects, the agent is nivolumab. In some aspects, the agent is atezolizumab.

In some embodiments, the additional therapeutic agent is an agent that inhibits the interaction between PD-1 and PD-L1. In some aspects, the additional therapeutic agent that inhibits the interaction between PD-1 and PD-L1 is selected from an antibody, a peptidomimetic and a small molecule. In some aspects, the additional therapeutic agent that inhibits the interaction between PD-1 and PD-L1 is selected from pembrolizumab, nivolumab, atezolizumab, avelumab, durvalumab, BMS-936559, sulfamonomethoxine 1, and sulfamethizole 2. In some embodiments, the additional therapeutic agent that inhibits the interaction between PD-1 and PD-L1 is any therapeutic known in the art to have such activity, for example as described in Weinmann et al., *Chem Med Chem*, 2016, 14:1576 (DOI: 10.1002/cmdc.201500566), incorporated by reference in its entirety. In some embodiments, the agent that inhibits the interaction between PD-1 and PD-L1 is formulated in the same pharmaceutical composition an ABP provided herein. In some embodiments, the agent that inhibits the interaction between PD-1 and PD-L1 is formulated in a different pharmaceutical composition from an ABP provided herein. In some embodiments, the agent that inhibits the interaction between PD-1 and PD-L1 is administered prior to administration of an ABP provided herein. In some embodiments, the agent that inhibits the interaction between PD-1 and PD-L1 is administered after administration of an ABP provided herein. In some embodiments, the agent that inhibits the interaction between PD-1 and PD-L1 is administered contemporaneously with an ABP provided herein, but the agent and ABP are administered in separate pharmaceutical compositions.

In some embodiments, the immunostimulatory agent is an agonist of a co-stimulatory receptor of an immune cell. In some aspects, the co-stimulatory receptor is selected from OX40, ICOS, CD27, CD28, 4-1BB, or CD40. In some embodiments, the agonist is an antibody.

In some embodiments, the immunostimulatory agent is a cytokine. In some aspects, the cytokine is selected from IL-2, IL-5, IL-7, IL-12, IL-15, IL-21, and combinations thereof.

In some embodiments, the immunostimulatory agent is an oncolytic virus. In some aspects, the oncolytic virus is selected from a herpes simplex virus, a vesicular stomatitis virus, an adenovirus, a Newcastle disease virus, a vaccinia virus, and a maraba virus.

In some embodiments, the immunostimulatory agent is a T cell with a chimeric antigen receptor (CAR-T cell). In some embodiments, the immunostimulatory agent is a bi- or multi-specific T cell directed antibody. In some embodiments, the immunostimulatory agent is an anti-TGF-antibody. In some embodiments, the immunostimulatory agent is a TGF-β trap.

In some embodiments, the additional therapeutic agent is a vaccine to a tumor antigen. Any suitable antigen may be targeted by the vaccine, provided that it is present in a tumor treated by the methods provided herein. In some aspects, the tumor antigen is a tumor antigen that is overexpressed in comparison its expression levels in normal tissue. In some aspects, the tumor antigen is selected from cancer testis antigen, differentiation antigen, NY-ESO-1, MAGE-A1, MART, and combinations thereof.

Further examples of additional therapeutic agents include a taxane (e.g., paclitaxel or docetaxel); a platinum agent (e.g., carboplatin, oxaliplatin, and/or cisplatin); a topoisomerase inhibitor (e.g., irinotecan, topotecan, etoposide, and/or mitoxantrone); folinic acid (e.g., leucovorin); or a nucleoside metabolic inhibitor (e.g., fluorouracil, capecitabine, and/or gemcitabine). In some embodiments, the additional therapeutic agent is folinic acid, 5-fluorouracil, and/or oxaliplatin. In some embodiments, the additional therapeutic agent is 5-fluorouracil and irinotecan. In some embodiments, the additional therapeutic agent is a taxane and a platinum agent. In some embodiments, the additional therapeutic agent is paclitaxel and carboplatin. In some embodiments, the additional therapeutic agent is pemetrexate. In some embodiments, the additional therapeutic agent is a targeted therapeutic such as an EGFR, RAF or MEK-targeted agent.

The additional therapeutic agent may be administered by any suitable means. In some embodiments, an ABP provided herein and the additional therapeutic agent are included in the same pharmaceutical composition. In some embodiments, an ABP provided herein and the additional therapeutic agent are included in different pharmaceutical compositions.

In embodiments where an ABP provided herein and the additional therapeutic agent are included in different pharmaceutical compositions, administration of the ABP can occur prior to, simultaneously, and/or following, administration of the additional therapeutic agent. In some aspects, administration of an ABP provided herein and the additional therapeutic agent occur within about one month of each other. In some aspects, administration of an ABP provided herein and the additional therapeutic agent occur within about one week of each other. In some aspects, administration of an ABP provided herein and the additional therapeutic agent occur within about one day of each other. In some aspects, administration of an ABP provided herein and the additional therapeutic agent occur within about twelve hours of each other. In some aspects, administration of an ABP provided herein and the additional therapeutic agent occur within about one hour of each other.

9. Diagnostic Methods

Also provided are methods for detecting the presence of TIGIT on cells from a subject. Such methods may be used, for example, to predict and evaluate responsiveness to treatment with an ABP provided herein.

In some embodiments, a blood sample is obtained from a subject and the fraction of cells expressing TIGIT is determined. In some aspects, the relative amount of TIGIT expressed by such cells is determined. The fraction of cells expressing TIGIT and the relative amount of TIGIT expressed by such cells can be determined by any suitable method. In some embodiments, flow cytometry is used to make such measurements. In some embodiments, fluorescence assisted cell sorting (FACS) is used to make such measurement. See Li et al., *J. Autoimmunity*, 2003, 21:83-92 for methods of evaluating expression of TIGIT in peripheral blood.

10. Kits

Also provided are kits comprising the ABPs provided herein. The kits may be used for the treatment, prevention, and/or diagnosis of a disease or disorder, as described herein.

In some embodiments, the kit comprises a container and a label or package insert on or associated with the container. Suitable containers include, for example, bottles, vials, syringes, and IV solution bags. The containers may be formed from a variety of materials, such as glass or plastic. The container holds a composition that is by itself, or when combined with another composition, effective for treating, preventing and/or diagnosing a disease or disorder. The container may have a sterile access port. For example, if the container is an intravenous solution bag or a vial, it may have a port that can be pierced by a needle. At least one active agent in the composition is an ABP provided herein. The label or package insert indicates that the composition is used for treating the selected condition.

In some embodiments, the kit comprises (a) a first container with a first composition contained therein, wherein the first composition comprises an ABP provided herein; and (b) a second container with a second composition contained therein, wherein the second composition comprises a further therapeutic agent. The kit in this embodiment of the invention may further comprise a package insert indicating that the compositions can be used to treat a particular condition.

Alternatively, or additionally, the kit may further comprise a second (or third) container comprising a pharmaceutically-acceptable excipient. In some aspects, the excipient is

11. Other Illustrative Embodiments

The embodiments provided below are non-limiting and provided by way of illustration of certain embodiments and aspects of the invention, in addition to those described throughout this disclosure.

Embodiment 1

An antigen binding protein that binds specifically to a human TIGIT (hTIGIT) and is capable of at least one of the following: a) inhibits binding of hTIGIT to CD155 and CD112; b) increases a T effector cell function; c) increases a natural killer (NK) cell function; d) decreases the number of regulatory T cells in tissues or in circulation; e) suppresses a regulatory T cell or a regulatory T cell activity; f) inhibits association of TIGIT and CD226; and does not bind specifically to Nectin-4 (also known as poliovirus-receptor-like 4, PVRL4).

Embodiment 2

The antigen binding protein of Embodiment 1, wherein the antigen binding protein has one or more of the following characteristics: a) is a monoclonal antibody; b) is a human antibody, a humanized antibody, or a chimeric antibody; c) is a bispecific antibody, a multispecific antibody, a diabody, or a multivalent antibody; d) is of the IgG1, IgG2, IgG3, the IgG4 type, or the IgG4 isotype with a S228P substitution; e) is an antigen-binding antibody fragment; f) is a Fab fragment, a Fab' fragment, a F(ab')2 fragment, or an Fv fragment; g) is a single chain antibody, a single domain antibody, or a nanobody.

Embodiment 3

A pharmaceutical composition comprising an effective amount of an antibody which binds to hTIGIT and: (a) increases cell-mediated immunity; (b) increases T-cell activity; (c) increases cytolytic T-cell (CTL) activity; (d) increases natural killer (NK) cell activity; (e) is an antagonist of TIGIT-mediated signaling; (f) inhibits TIGIT signaling; (g) inhibits or blocks the interaction between PVR and TIGIT; (h) inhibits or blocks the interaction of TIGIT and CD155 ligand and/or CD112; but does not inhibit the interaction between PVR and CD226.

Embodiment 4

A pharmaceutical composition comprising the antigen-binding protein of Embodiment 1 or Embodiment 2.

Embodiment 5

The pharmaceutical composition of Embodiment 4, further comprising an effective amount of an anti-PD-1 antibody.

Embodiment 6

The antigen binding protein of Embodiment 1, wherein the antigen binding protein has one or more of the following characteristics: a) binds to a human TIGIT polypeptide or a variant thereof, or as otherwise provided herein with a $K_D$ of less than about 20 nM; or b) binds to a cynomolgus monkey (also "cynomolgus" or "cyno") TIGIT polypeptide or a variant thereof, or as otherwise provided herein, with a $K_D$ of less than about 200 nM; c) binds to a murine TIGIT polypeptide or a variant thereof, or as otherwise provided herein, with a $K_D$ of less than about 200 nM; or d) a combination of at least 2 of a), b), and c).

Embodiment 7

An antigen binding protein that competes or is capable of competing for binding to human TIGIT with a reference antigen binding protein, wherein the reference antigen binding protein is the antigen binding protein of Embodiment 1.

Embodiment 8

The antigen binding protein of Embodiment 7, wherein the antigen binding protein and the reference antibody cross-compete or are capable of cross-competing for binding to a human TIGIT.

Embodiment 9

The antigen binding protein of Embodiment 1, comprising a heavy chain constant region comprising a human heavy chain constant region or fragment or a variant thereof, wherein the constant region variant comprises up to 20 conservatively modified amino acid substitutions.

Embodiment 10

The antigen binding protein of Embodiment 1, that competes or is capable of competing for binding to human TIGIT with a CD155 protein and/or a CD112 protein.

Embodiment 11

The antigen binding protein of Embodiment 1, that is capable of antagonizing TIGIT signaling in a T cell-specific manner.

Embodiment 12

An isolated antibody molecule capable of binding to human TIGIT (hTIGIT), comprising a heavy chain variable region (VH) comprising a VHCDR1 amino acid sequence of SEQ ID NOs: 48-62, a VHCDR2 amino acid sequence of SEQ ID NO:36-47, and a VHCDR3 amino acid sequence of SEQ ID NO:29-35; and a light chain variable region (VL) comprising a VLCDR1 amino acid sequence of SEQ ID NO:70-72, a VLCDR2 amino acid sequence of SEQ ID NO:67-69, and a VLCDR3 amino acid sequence of SEQ ID NO:63-66.

Embodiment 13

An isolated nucleic acid encoding an antigen binding protein according to Embodiment 1.

Embodiment 14

An expression vector comprising the nucleic acid according to Embodiment 13.

Embodiment 15

A prokaryotic or eukaryotic host cell comprising a vector of Embodiment 14.

Embodiment 16

A method for the production of a recombinant protein comprising the steps of expressing a nucleic acid according to Embodiment 13 in a prokaryotic or eukaryotic host cell and recovering said protein from said cell or the cell culture supernatant.

Embodiment 17

A method for treatment of a subject suffering from cancer or from an inflammatory disease, comprising the step of administering to the subject a pharmaceutical composition comprising an effective amount of the antigen binding protein of Embodiment 1.

Embodiment 18

The method of Embodiment 17, wherein the cancer is a solid cancer.

Embodiment 19

The method of Embodiment 17, wherein the cancer is a hematological cancer.

Embodiment 20

A method for modulating immune system function in a human subject in need thereof, comprising the step of contacting a population of T cells of the human subject with a pharmaceutical composition comprising an effective amount of the antigen binding protein of Embodiment 1, under conditions such that the immune system is modulated.

Embodiment 21

A method for inducing or enhancing an immune response in a subject, comprising the step of administering to the subject a pharmaceutical composition comprising an antigen binding protein or a bispecific antibody or a complexing antigen binding protein, of any of the preceding embodiments, wherein the immune response is generated against a tumor antigen.

Embodiment 22

The method of Embodiment 21, wherein the antigen binding protein, bispecific antibody or the complexing antigen binding protein is administered in an amount sufficient to achieve one or more of the following in the subject: a) reduce regulatory T cells suppression of activity of effector T cells; b) decrease levels of regulatory T cells; c) activation of effector T cells; d) induce or enhance effector T cell proliferation; e) inhibit tumor growth; and f) induce tumor regression.

Embodiment 23

The method of Embodiment 22, wherein the method further comprises one or more of the following a) administering chemotherapy; b) administering radiation therapy; or c) administering one or more additional therapeutic agents.

Embodiment 24

The method of Embodiment 23, wherein the additional therapeutic agent comprises an immunostimulatory agent.

Embodiment 25

The method of Embodiment 24, wherein the immunostimulatory agent comprises an antagonist to an inhibitory receptor of an immune cell.

Embodiment 26

The method of Embodiment 25, wherein the inhibitory receptor is CTLA-4, PD-1, PD-L1, PD-L2, LAG-3, Tim3, neuritin, BTLA, CECAM-1, CECAM-5, VISTA, LAIR1, CD160, 2B4, TGF-R, or a KIR.

Embodiment 27

The method of Embodiment 24, wherein the immunostimulatory agent comprises an agonist of co-stimulatory receptor of an immune cell.

Embodiment 28

The method of Embodiment 27, wherein the co-stimulatory receptor is OX40, CD2, CD27, CDS, ICAM-1, LFA-1 (CD11a/CD18), ICOS (CD278), 4-1BB (CD137), GITR, CD28, CD30, CD40, BAFFR, HVEM, CD7, LIGHT, NKG2C, SLAMF7, NKp80, CD160, B7-H3 or CD83 ligand.

Embodiment 29

The method of Embodiment 24, wherein the immunostimulatory agent comprises a cytokine.

Embodiment 30

The method of Embodiment 29, wherein the cytokine is IL-2, IL-5, IL-7, IL-12, IL-15 or IL-21.

Embodiment 31

The method of Embodiment 24, wherein the immunostimulatory agent comprises an oncolytic virus.

Embodiment 32

The method of Embodiment 31, wherein the oncolytic virus is a Herpes simplex virus, a Vesicular stomatitis virus, an adenovirus, a Newcastle disease virus, a vaccinia virus, or a maraba virus.

Embodiment 33

The method of Embodiment 24, wherein the immunostimulatory agent comprises a chimeric antigen engineered T cell.

Embodiment 34

The method of Embodiment 24, wherein the immunostimulatory agent comprises a bi- or multispecific T cell directed antibody.

Embodiment 35

The method of Embodiment 23, wherein the additional therapeutic agent comprises an anti-TGF-beta antibody or a TGFβ receptor trap.

Embodiment 36

The method of any one of Embodiments 20-35, wherein administration of the pharmaceutical composition results in induction or enhancement of proliferation of a T-effector cell, or modulation of I-κB and/or NF-κB in the T cell, or modulation of TIGIT activity in the T cell, or T cell receptor induced signaling in a T-effector cell, or a combination thereof.

Embodiment 37

A method of screening for test compounds comprising an antigen binding protein of Embodiment 1 that are capable of inhibiting the interaction of a TIGIT ligand with TIGIT, comprising the steps of: contacting a sample containing a TIGIT ligand and TIGIT with the compound; and determining whether the interaction of a TIGIT ligand with TIGIT in the sample is decreased relative to the interaction of a TIGIT ligand with TIGIT in a sample not contacted with the compound, whereby a decrease in the interaction of a TIGIT ligand with TIGIT in the sample contacted with the compound identifies the compound as one that inhibits the interaction of a TIGIT ligand with TIGIT.

Embodiment 38

The antigen binding protein of Embodiment 1, that is capable of inhibiting phosphorylation of the ITIM domain of the TIGIT polypeptide.

Embodiment 1A

An isolated antigen-binding protein (ABP) that specifically binds to TIGIT, wherein the antibody: (a) competes for binding to TIGIT with an antibody selected from MAB1, MAB2, MAB3, MAB4, MAB5, MAB6, MAB7, MAB8, MAB9, MAB10, MAB11, MAB12, MAB13, MAB14, MAB15, MAB16, MAB17, MAB18, MAB19, MAB20, or MAB21, each as provided in Table 5 of this disclosure; (b) inhibits binding of CD155 to TIGIT; (c) inhibits binding of CD112 to TIGIT; (d) inhibits association of CD226 with TIGIT; (e) activates an effector T cell or an NK cell; (f) decreases the number of regulatory T cells in a tissue or in circulation; (g) inhibits the suppression of an effector T cell by a regulatory T cell; (h) does not bind specifically to any of PVRL1, PVRL2, PVRL3, or PVRL4; or (i) is capable of any combination of (a)-(h).

Embodiment 2A

The ABP of Embodiment 1A, wherein the ABP comprises a CDR-H3 of a $V_H$ region selected from SEQ ID NOs: 4-24, or a CDR-H3 having at least about 80% identity to a CDR-H3 of a $V_H$ region selected from SEQ ID NOs: 4-24.

Embodiment 3A

The ABP of Embodiment 2A, wherein the CDR-H3 is identified according to the Kabat, Chothia, or IMGT numbering schemes.

Embodiment 4A

The ABP of any of Embodiments 2A-3A, wherein the CDR-H3 is selected from SEQ ID NOs: 29-35.

Embodiment 5A

The ABP of any of Embodiments 1A-4A, wherein the ABP comprises a CDR-H2 of a $V_H$ region selected from SEQ ID NOs: 4-24, or a CDR-H2 having at least about 80% identity to a CDR-H2 of a $V_H$ region selected from SEQ ID NOs: 4-24

Embodiment 6A

The ABP of Embodiment 5A, wherein the CDR-H2 is identified according to the Kabat, Chothia, or IMGT numbering schemes.

Embodiment 7A

The ABP of any of Embodiments 5A-6A, wherein the CDR-H2 is selected from SEQ ID NOs: 36-47.

Embodiment 8A

The ABP of any of Embodiments 1A-7A, wherein the ABP comprises a CDR-H1 of a $V_H$ region selected from SEQ ID NOs: 4-24, or a CDR-H1 having at least about 80% identity to a CDR-H1 of a $V_H$ region selected from SEQ ID NOs: 4-24

Embodiment 9A

The ABP of Embodiment 8A, wherein the CDR-H1 is identified according to the Kabat, Chothia, Kabat plus Chothia, or IMGT numbering schemes.

Embodiment 10A

The ABP of any of Embodiments 8A-9A, wherein the CDR-H1 is selected from SEQ ID NOs: 48-54 and 58-62.

Embodiment 11A

The ABP of any of Embodiments 1A-10A, wherein the ABP comprises a CDR-L3 of a $V_L$ region selected from SEQ ID NOs: 25-28, or a CDR-L3 having at least about 80% identity to a CDR-L3 of a $V_L$ region selected from SEQ ID NOs: 25-28.

Embodiment 12A

The ABP of Embodiment 11A, wherein the CDR-L3 is identified according to the Kabat, Chothia, or IMGT numbering schemes.

Embodiment 13A

The ABP of any of Embodiments 11A-12A, wherein the CDR-L3 is selected from SEQ ID NOs: 63-66.

Embodiment 14A

The ABP of any of Embodiments 1A-13A, wherein the ABP comprises a CDR-L2 of a $V_L$ region selected from SEQ ID NOs: 25-28, or a CDR-L2 having at least about 80% identity to a CDR-L2 of a $V_L$ region selected from SEQ ID NOs: 25-28.

Embodiment 15A

The ABP of Embodiment 14A, wherein the CDR-L2 is identified according to the Kabat, Chothia, or IMGT numbering schemes.

Embodiment 16A

The ABP of any of Embodiments 14A-15A, wherein the CDR-L2 is selected from SEQ ID NOs: 67-69.

Embodiment 17A

The ABP of any of Embodiments 1A-16A, wherein the ABP comprises a CDR-L1 of a $V_L$ region selected from SEQ ID NOs: 25-28, or a CDR-L1 having at least about 80% identity to a CDR-L1 of a $V_L$ region selected from SEQ ID NOs: 25-28.

Embodiment 18A

The ABP of Embodiment 17A, wherein the CDR-L1 is identified according to the Kabat, Chothia, or IMGT numbering schemes.

Embodiment 19A

The ABP of any of Embodiments 17A-18A, wherein the CDR-L1 is selected from SEQ ID NOs: 70-72.

Embodiment 20A

The ABP of any of Embodiments 1A-19A, wherein the ABP comprises a $V_H$ region selected from SEQ ID NOs: 4-24.

Embodiment 21A

The ABP of any of Embodiments 1A-20A, wherein the ABP comprises a $V_L$ region selected from SEQ ID NOs: 25-28.

Embodiment 22A

The ABP of any of Embodiments 1A-21A, wherein the TIGIT is selected from hTIGIT (SEQ ID NO: 1), cTIGIT (SEQ ID NO: 2), and mTIGIT (SEQ ID NOs: 3 or 138).

Embodiment 23A

The ABP of any of Embodiments 1A-22A, wherein the ABP comprises an antibody.

Embodiment 24A

The ABP of Embodiment 23A, wherein the antibody comprises a $V_H$ and $V_L$ paired as provided for an antibody selected from MAB1, MAB2, MAB3, MAB4, MAB5, MAB6, MAB7, MAB8, MAB9, MAB10, MAB11, MAB12, MAB13, MAB14, MAB15, MAB16, MAB17, MAB18, MAB19, MAB20, or MAB21, each as provided in Table 5 of this disclosure.

Embodiment 25A

The ABP of Embodiment 24A, wherein the ABP is an antibody selected from MAB1, MAB2, MAB3, MAB4, MAB5, MAB6, MAB7, MAB8, MAB9, MAB10, MAB11, MAB12, MAB13, MAB14, MAB15, MAB16, MAB17, MAB18, MAB19, MAB20, or MAB21, each as provided in Table 5 of this disclosure.

Embodiment 26A

The ABP of any of Embodiments 23A-25A, wherein the antibody is a monoclonal antibody.

Embodiment 27A

The ABP of any of Embodiments 23A-26A, wherein the antibody is a chimeric, humanized, or human antibody.

Embodiment 28A

The ABP of any of Embodiments 1A-27A, wherein the ABP is multispecific.

Embodiment 29A

The ABP of any of Embodiments 1A-28A, wherein the ABP comprises an antibody fragment.

Embodiment 30A

The ABP of any of Embodiments 1A-29A, wherein the ABP comprises an alternative scaffold.

Embodiment 31A

The ABP of any of Embodiments 1A-30A, wherein the ABP comprises an immunoglobulin constant region.

Embodiment 32A

The ABP of any of Embodiments 1A-31A, wherein the ABP comprises an antibody selected from an IgA, an IgD, an IgE, an IgG, or an IgM.

Embodiment 33A

The ABP of Embodiment 32A, wherein the ABP comprises an IgG selected from an IgG4, an IgG1, an IgG2, or an IgG3.

Embodiment 34A

The ABP of any of Embodiments 1A-33A, wherein the ABP binds hTIGIT (SEQ ID NO: 1) with an affinity of less than about 20 nM.

Embodiment 35A

The ABP of any of Embodiments 1A-34A, wherein the ABP binds cTIGIT (SEQ ID NO: 2) with an affinity of less than about 200 nM.

Embodiment 36A

The ABP of any of Embodiments 1A-35A, wherein the ABP binds mTIGIT (SEQ ID NO: 3 or 138) with an affinity of less than about 200 nM.

Embodiment 37A

An isolated polynucleotide encoding an ABP of any of Embodiments 1A-36A, a $V_H$ or $V_L$ thereof, or an antigen-binding portion thereof.

Embodiment 38A

A vector comprising the polynucleotide of Embodiment 37A.

Embodiment 39A

A host cell comprising the vector of Embodiment 38A.

Embodiment 40A

A method of producing an ABP of any of Embodiments 1A-36A, comprising expressing the ABP in the host cell of Embodiment 39A and isolating the expressed ABP.

Embodiment 41A

A pharmaceutical composition comprising an ABP of any of Embodiments 1A-36A.

Embodiment 42A

The pharmaceutical composition of Embodiment 41A, wherein the amount of the ABP in the pharmaceutical composition is sufficient to (a) increase effector T cell activity; (b) increase cytolytic T cell activity; (c) increase NK cell activity; (d) inhibit TIGIT-mediated signaling; (e) inhibit or block the binding of CD155 and or CD112 to TIGIT; or (f) any combination of (a)-(e), in a subject.

Embodiment 43A

The pharmaceutical composition of any of Embodiments 41A-42A, further comprising an antibody that antagonizes PD-1.

Embodiment 44A

A method of treating or preventing a disease or condition in a subject in need thereof, comprising administering to the subject an effective amount of an ABP of any of Embodiments 1A-36A or a pharmaceutical composition of any of Embodiments 41A-43A.

Embodiment 45A

The method of Embodiment 44A, wherein the disease or condition is a cancer or viral infection.

Embodiment 46A

A method of modulating an immune response in a subject in need thereof, comprising administering to the subject an effective amount of an ABP of any of Embodiments 1A-36A or a pharmaceutical composition of any of Embodiments 41A-43A.

Embodiment 47A

The method of any of Embodiments 44A-46A, further comprising administering one or more additional therapeutic agents to the subject.

Embodiment 48A

The method of Embodiment 47A, wherein the additional therapeutic agent is selected from a PD-1 antagonist antibody, a chemotherapy, an immunostimulatory agent, and radiation.

Embodiment 49A

The method of Embodiments 47A, wherein the additional therapeutic agent is an immunostimulatory agent that blocks signaling of an inhibitory receptor of an immune cell or a ligand thereof.

Embodiment 50A

The method of Embodiment 49A, wherein the inhibitory receptor or ligand thereof is selected from CTLA-4, PD-1, PD-L1, PD-L2, LAG-3, Tim3, neuritin, BTLA, CECAM-1, CECAM-5, VISTA, LAIR1, CD160, 2B4, TGF-R, KIR, and combinations thereof.

Embodiment 51A

The method of Embodiment 48A, wherein the additional therapeutic agent is an immunostimulatory agent that is an agonist to a stimulatory receptor of an immune cell.

Embodiment 52A

The method of Embodiment 51A, wherein the stimulatory receptor of an immune cell is selected from OX40, CD2, CD27, CDS, ICAM-1, LFA-1 (CD11a/CD18), ICOS (CD278), 4-1BB (CD137), GITR, CD28, CD30, CD40, BAFFR, HVEM, CD7, LIGHT, NKG2C, SLAMF7, NKp80, CD160, B7-H3, CD83 ligand, and combinations thereof.

Embodiment 53A

The method of Embodiment 48A, wherein the additional therapeutic agent is an immunostimulatory agent that is a cytokine.

Embodiment 54A

The method of Embodiment 53A, wherein the cytokine is selected from IL-2, IL-5, IL-7, IL-12, IL-15, IL-21, and combinations thereof.

Embodiment 55A

The method of Embodiment 48A, wherein the additional therapeutic agent is an immunostimulatory agent that is an oncolytic virus.

Embodiment 56A

The method of Embodiment 55A, wherein the oncolytic virus is selected from herpes simplex virus, vesicular stomatitis virus, adenovirus, Newcastle disease virus, vaccinia virus, a maraba virus, and combinations thereof.

Embodiment 57A

The method of Embodiment 48A, wherein the immunostimulatory agent comprises a T cell expressing a chimeric antigen receptor.

Embodiment 58A

The method of Embodiment 48A, wherein the immunostimulatory agent comprises a bi- or multi-specific T cell directed antibody.

Embodiment 59A

The method of Embodiment 48A, wherein the immunostimulatory agent comprises an anti-TGF-β antibody, a TGF-β trap, or a combination thereof.

Embodiment 60A

The method of Embodiment 48A, wherein the immunostimulatory agent comprises a vaccine to a cancer-associated antigen.

Embodiment 61A

A method of screening for ABPs capable of inhibiting the interaction of a ligand of TIGIT with TIGIT, comprising (a) contacting a sample comprising a ligand of TIGIT and TIGIT with an ABP of any of Embodiments 1A-36A, and (b) determining if the binding of the ligand of TIGIT to TIGIT is decreased in the presence of the ABP, in comparison to the binding of the ligand of TIGIT to TIGIT in the absence of the ABP.

EXAMPLES

The following are examples of methods and compositions of the invention. It is understood that various other embodiments may be practiced, given the general description provided herein.

Example 1: Selection of TIGIT Antigen-Binding Proteins

TIGIT ABPs were selected from a synthetic library of human antibodies expressed and displayed on the surface of yeast cells in IgG format, as generally described, e.g., in WO2009036379; WO2010105256; WO2012009568; and Xu et al., *Protein Eng. Des. Sel.*, 2013, 26:663-670 (each incorporated by reference in its entirety), and more specifically as provided below. The sequences and characteristics of the ABPs isolated from the recombinant library are provided in Table 5.

Eight naïve human synthetic yeast libraries each of ~$10^9$ diversity were propagated as described in WO2009036379; WO2010105256; WO2012009568; and Xu et al., *Protein Eng. Des. Sel.*, 2013, 26:663-670; each incorporated by reference in its entirety. For the first two rounds of selection, a magnetic bead sorting technique utilizing the Miltenyi MACS® system was performed, as described in Siegel et al., *J. Immunol. Meth.*, 2004, 286:141-153. Briefly, yeast cells (~$10^{10}$ cells/library) were incubated with biotinylated TIGIT-Fc antigen in FACS wash buffer (phosphate-buffered saline (PBS)/0.1% bovine serum albumin (BSA)). After washing once with 50 ml ice-cold wash buffer, the cell pellet was resuspended in 40 mL wash buffer, and 500 μl streptavidin MicroBeads™ (Miltenyi Biotec) were added to the yeast and incubated for 15 min at 4° C. Next, the yeast were pelleted, resuspended in 5 mL wash buffer, and loaded onto a Miltenyi LS column. After the 5 mL was loaded, the column was washed 3 times with 3 ml FACS wash buffer. The column was then removed from the magnetic field, and the yeast were eluted with 5 mL of growth media and then grown overnight. The following rounds of sorting were performed using flow cytometry. Approximately $1 \times 10^8$ yeast were pelleted, washed three times with wash buffer, and incubated with decreasing concentrations of biotinylated TIGIT-Fc fusion antigen (100 to 1 nM) under equilibrium conditions at room temperature. Yeast were then washed twice and stained with LC-FITC (diluted 1:100) and either SA-633 (diluted 1:500) or EA-PE (diluted 1:50) secondary reagents for 15 min at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences) and sort gates were assigned to select for specific binders relative to a background control. Subsequent rounds of selection were employed in order to reduce the number of non-specific binders utilizing soluble membrane proteins from CHO cells (see WO2014179363 and Xu et al., *Protein Eng. Des. Sel.,* 2013, 26:663-670, each incorporated by reference in its entirety), and identify binders with improved affinity to TIGIT using the TIGIT-Fc antigen. After the final round of sorting, yeast were plated and individual colonies were picked for characterization and for nomination of clones for affinity maturation.

Example 2: Affinity Maturation

Optimization of naïve clones was carried out utilizing three maturation strategies: light chain diversification; diversification of CDR-H1 and CDR-H2; and performing VH mutagenesis.

Light Chain Diversification:

Heavy chain plasmids were extracted from naïve outputs (described above) and transformed into a light chain library with a diversity of $1 \times 10^6$. Selections were performed as described above with one round of MACS sorting and two rounds of FACS sorting using 10 nM or 1 nM biotinylated TIGIT-Fc antigen for respective rounds.

CDR-H1 and CDR-H2 Selection:

The CDR-H3s from clones selected from the light chain diversification procedure were recombined into a premade library with CDR-H1 and CDR-H2 variants of a diversity of $1 \times 10^8$ and selections were performed using monomeric HIS-TIGIT antigen. Affinity pressures were applied by using decreasing concentrations of biotinylated HIS-TIGIT antigen (100 to 1 nM) under equilibrium conditions at room temperature.

$V_H$mut Selection:

Clones obtained from the CDR-H1 and CDR-H2 selection procedure were subject to additional rounds of affinity maturation via error prone PCR-based mutagenesis of the heavy chain. Selections were performed using HIS-TIGIT as antigen generally as described above but with the addition of employing FACS sorting for all selection rounds.

Example 3: Antibody Production and Purification

In order to produce sufficient amounts of selected antibodies for further characterization, the yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect® (GE Healthcare LifeSciences).

Antibodies were also produced by transient transfection of Expi293 cells according to the manufacturer's protocol (Thermo Fisher), transient transfection of CHO cells, or stable expression of CHO cells. Antibodies were purified by Protein A chromatography.

TABLE 5

Sequences and germlines (GL) of TIGIT ABPs.

| Ab | VH GL | CDR-H1[1] | CDR-H2[2] | CDR-H3[3] | VH Protein | VL GL | CDR-L1[4] | CDR-L2[5] | CDR-L3[6] | VL Protein |
|---|---|---|---|---|---|---|---|---|---|---|
| MAB1-IgG4 | VH4-39 | GSITSSSYYWG (SEQ ID NO: 48) | SIYYSGATFYNPSLKS (SEQ ID NO: 36) | ARDANYYGSAWAFDP (SEQ ID NO: 29) | QLQLQESGPGLVKPSETLSLTCTVSGGSITSSSYYWGWIRQPPGKGLEWIGSIYYSGATFYNPSLKSRVTISVDTSKNQFSLKLSSVTAADTAVYYCARDANYYGSAWAFDPWGQGTLVTVSS (SEQ ID NO: 4) | VK3-11 | RASQSVSSYLA (SEQ ID NO: 70) | DASNRAT (SEQ ID NO: 67) | QQHFNLPT (SEQ ID NO: 63) | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK (SEQ ID NO: 25) |
| MAB2-IgG4 | VH4-39 | GSISSSKYYWG (SEQ ID NO: 49) | SIYYSGSTFYNPSLKS (SEQ ID NO: 37) | ARDANYYGSAWAFDP (SEQ ID NO: 29) | QLQLQESGPGLVKPSETLSLTCTVSGGSISSSKYYWGWIRQPPGKGLEWIGSIYYSGSTFYNPSLKSRVTISVDTSKNQFSLKLSSVTAADTAVYYCARDANYYGSAWAFDPWGQGTLVTVSS (SEQ ID NO: 5) | VK3-11 | RASQSVSSYLA (SEQ ID NO: 70) | DASNRAT (SEQ ID NO: 67) | QQHFNLPT (SEQ ID NO: 63) | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK (SEQ ID NO: 25) |
| MAB3-IgG4 | VH4-39 | GSISSTSHYWG (SEQ ID NO: 50) | SIYYSGSTFYNPSLKS (SEQ ID NO: 37) | ARDANYYGSAWAFDP (SEQ ID NO: 29) | QLQLQESGPGLVKPSETLSLTCTVSGGSISSTSHYWGWIRQPPGKGLEWIGSIYYSGSTFYNPSLKSRVTISVDTSKNQFSLKLSSVTAADTAVYYCARDANYYGSAWAFDPWGQGTLVTVSS (SEQ ID NO: 6) | VK3-11 | RASQSVSSYLA (SEQ ID NO: 70) | DASNRAT (SEQ ID NO: 67) | QQHFNLPT (SEQ ID NO: 63) | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK (SEQ ID NO: 25) |
| MAB4-IgG4 | VH4-39 | GSISSTSHYWG (SEQ ID NO: 50) | SIYYSGSTFYNPSLKS (SEQ ID NO: 37) | ARDANYYGGAWAFDP (SEQ ID NO: 30) | QLQLQESGPGLVKPSETLSLTCTVSGGSISSTSHYWGWIRQPPGKGLEWIGSIYYSGSTFYNPSLKSRVTISVDTSKNQFSLKLSSVTAADTAVYYCARDANYYGGAWAFDPWGQGTLVTVSS (SEQ ID NO: 7) | VK3-11 | RASQSVSSYLA (SEQ ID NO: 70) | DASNRAT (SEQ ID NO: 67) | QQHFNLPT (SEQ ID NO: 63) | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK (SEQ ID NO: 25) |
| MAB5-IgG4 | VH4-39 | GSISSTSHYWG (SEQ ID NO: 50) | SIYYSGSTFYNPSLKG (SEQ ID NO: 38) | ARDANYYGSAWAFDP (SEQ ID NO: 29) | QLQLQESGPGLVKPSETLSLTCTVSGGSISSTSHYWGWIRQPPGKGLEWIGSIYYSGSTFYNPSLKGRVTISVDTSKNQFSLKLSSVTAADTAVYYCARDANYYGSAWAFDPWGQGTLVTVSS (SEQ ID NO: 8) | VK3-11 | RASQSVSSYLA (SEQ ID NO: 70) | DASNRAT (SEQ ID NO: 67) | QQHFNLPT (SEQ ID NO: 63) | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK (SEQ ID NO: 25) |
| MAB6-IgG4 | VH4-39 | GSIESGSYYWG (SEQ ID NO: 51) | SIYYSGGTYYNPSLKS (SEQ ID NO: 39) | ARDGVLTLNKRSFDI (SEQ ID NO: 31) | QLQLQESGPGLVKPSETLSLTCTVSGGSIESGSYYWGWIRQPPGKGLEWIGSIYYSGGTYYNPSLKSRVTISVDTSKNQFSLKLSSVTAADTAVYYCARDGVLTLNKRSFDIWGQGTMVTVSS (SEQ ID NO: 9) | VK3-20 | RASQSVSSSYLA (SEQ ID NO: 71) | GASSRAT (SEQ ID NO: 68) | QQHTVRPPLT (SEQ ID NO: 64) | EIVLTQSPGTLSLSPGERATLSCRASQSVSSSYLAWYQQKPGQAPRLLIYGASSRATGIPDRFSGSGSGTDFTLTISRLEPEDFAVYYCQQHTVRPPLTFGGGTKVEIK (SEQ ID NO: 26) |
| MAB7-IgG4 | VH4-31 | GSIESGVYYWG (SEQ ID NO: 52) | SIYYSGSTYYNPSLKS (SEQ ID NO: 40) | ARDGVLTLNKRSFDI (SEQ ID NO: 31) | QVQLQESGPGLVKPSQTLSLTCTVSGGSIESGVYYWGWIRQPPGKGLEWIGSIYYSGSTYYNPSLKSRVTISVDTSKNQFSLKLSSVTAADTAVYYCARDGVLTLNKRSFDIWGQGTMVTVSS (SEQ ID NO: 10) | VK3-20 | RASQSVSSSYLA (SEQ ID NO: 71) | GASSRAT (SEQ ID NO: 68) | QQHTVRPPLT (SEQ ID NO: 64) | EIVLTQSPGTLSLSPGERATLSCRASQSVSSSYLAWYQQKPGQAPRLLIYGASSRATGIPDRFSGSGSGTDFTLTISRLEPEDFAVYYCQQHTVRPPLTFGGGTKVEIK (SEQ ID NO: 26) |
| MAB8-IgG4 | VH4-39 | GSIASGSYYWG (SEQ ID NO: ) | SIYYSGQTYYNPSLKS (SEQ ID NO: ) | ARDGVLTLNKRSFDI (SEQ ID NO: ) | QLQLQESGPGLVKPSETLSLTCTVSGGSIASGSYYWGWIRQPPGKGLEWIGSIYYSGQTYYNPSLKSRVTISVDTSKNQFSLKLSSVTAADTAVYYCARDGVLTL | VK3-20 | RASQSVSSSYLA (SEQ ID NO: ) | GASSRAT (SEQ ID NO: ) | QQHTVRPPLT (SEQ ID NO: ) | EIVLTQSPGTLSLSPGERATLSCRASQSVSSSYLAWYQQKPGQAPRLLIYGASSRATGIPDRFSGSGSGTDFT |

TABLE 5-continued

Sequences and germlines (GL) of TIGIT ABPs.

| Ab | VH GL | CDR-H1[1] | CDR-H2[2] | CDR-H3[3] | VH Protein | VL GL | CDR-L1[4] | CDR-L2[5] | CDR-L3[6] | VL Protein |
|---|---|---|---|---|---|---|---|---|---|---|
| | | 53) | NO: 41) | NO: 31) | NKRSFDIWGQGTMVTVSS (SEQ ID NO: 11) | | NO: 71) | 68) | 64) | LTISRLEPEDFAVYY CQQHTVRPPLTFGG GTKVEIK (SEQ ID NO: 26) |
| MAB9-IgG4 | VH4-31 | GSIESG LYYWG (SEQ ID NO: 54) | SIYYSG STYYN PSLKS (SEQ ID NO: 40) | ARDGV LTLNK RSFDI (SEQ ID NO: 31) | QVQLQESGPGLVKPSQTLSLT CTVSGGSIESGLYYWGWIRQP PGKGLEWIGSIYYSGSTYYNP SLKSRVTISVDTSKNQFSLKL SSVTAADTAVYYCARDGVLTL NKRSFDIWGQGTMVTVSS (SEQ ID NO: 12) | VK3-20 | RASQS VSSSY LA (SEQ ID NO: 71) | GASSR AT (SEQ ID NO: 68) | QQHTV RPPLT (SEQ ID NO: 64) | EIVLTQSPGTLSLSP GERATLSCRASQSV SSSYLAWYQQKPGQ APRLLIYGASSRATG IPDRFSGSGSGTDFT LTISRLEPEDFAVYY CQQHTVRPPLTFGG GTKVEIK (SEQ ID NO: 26) |
| MAB10-IgG4 | VH4-31 | GSIESG LYYWG (SEQ ID NO: 54) | SIYYSG STYYN PSLKS (SEQ ID NO: 40) | ARDGV LALNK RSFDI (SEQ ID NO: 32) | QVQLQESGPGLVKPSQTLSLT CTVSGGSIESGLYYWGWIRQP PGKGLEWIGSIYYSGSTYYNP SLKSRATISVDTSKNQFSLKL SSVTAADTAVYYCARDGVLAL NKRSFDIWGQGTMVTVSS (SEQ ID NO: 13) | VK3-20 | RASQS VSSSY LA (SEQ ID NO: 71) | GASSR AT (SEQ ID NO: 68) | QQHTV RPPLT (SEQ ID NO: 64) | EIVLTQSPGTLSLSP GERATLSCRASQSV SSSYLAWYQQKPGQ APRLLIYGASSRATG IPDRFSGSGSGTDFT LTISRLEPEDFAVYY CQQHTVRPPLTFGG GTKVEIK (SEQ ID NO: 26) |
| MAB11-IgG4 | VH4-31 | GSIESG LYYWG (SEQ ID NO: 54) | SIYYSG STYYN PSLKS (SEQ ID NO: 40) | ARDGV LALNK RSFDI (SEQ ID NO: 32) | QVQLQESGPGLVKPSQTLSLT CTVSGGSIESGLYYWGWIRQP PGKGLEWIGSIYYSGSTYYNP SLKSRVTISVDTSKNQFSLKL SSVTAADTAVYYCARDGVLAL NKRSFDIWGQGTMVTVSS (SEQ ID NO: 14) | VK3-20 | RASQS VSSSY LA (SEQ ID NO: 71) | GASSR AT (SEQ ID NO: 68) | QQHTV RPPLT (SEQ ID NO: 64) | EIVLTQSPGTLSLSP GERATLSCRASQSV SSSYLAWYQQKPGQ APRLLIYGASSRATG IPDRFSGSGSGTDFT LTISRLEPEDFAVYY CQQHTVRPPLTFGG GTKVEIK (SEQ ID NO: 26) |
| MAB12-IgG4 | VH4-31 | GSIESG LYYWG (SEQ ID NO: 54) | SIYYSG STYYN PSLKS (SEQ ID NO: 40) | ARDGV LALNK RSFDI (SEQ ID NO: 32) | QVQLQESGPGLVKPSQTLSLT CTASGGSIESGLYYWGWIRQP PGKGLEWIGSIYYSGSTYYNP SLKSRVTISVDTSKNQFSLKL SSVTAADTAVYYCARDGVLAL NKRSFDIWGQGTMVTVSS (SEQ ID NO: 15) | VK3-20 | RASQS VSSSY LA (SEQ ID NO: 71) | GASSR AT (SEQ ID NO: 68) | QQHTV RPPLT (SEQ ID NO: 64) | EIVLTQSPGTLSLSP GERATLSCRASQSV SSSYLAWYQQKPGQ APRLLIYGASSRATG IPDRFSGSGSGTDFT LTISRLEPEDFAVYY CQQHTVRPPLTFGG GTKVEIK (SEQ ID NO: 26) |
| MAB13-IgG4 | VH1-46 | YTFGN YYMH (SEQ ID NO: 58) | IINPSL GLTSY AQKFQ G (SEQ ID NO: 42) | ARGGR TTWIG AFDI (SEQ ID NO: 33) | QVQLVQSGAEVKKPGASVKV SCKASGYTFGNYYMHWVRQ APGQGLEWMGIINPSLGLTSY AQKFQGRVTMTRDTSTSTVY MELSSLRSEDTAVYYCARGG RTTWIGAFDIWGQGTMVTVS S (SEQ ID NO: 16) | VK3-15 | RASQS VSSNL A (SEQ ID NO: 72) | GASTR AT (SEQ ID NO: 69) | QQYVV WPPLT (SEQ ID NO: 65) | EIVMTQSPATLSVSP GERATLSCRASQSV SSNLAWYQQKPGQ APRLLIYGASTRATG IPARFSGSGSGTEFT LTISSLQSEDFAVYY CQQYVVWPPLTFGG GTKVEIK (SEQ ID NO: 27) |
| MAB14-IgG4 | VH1-46 | YTFPA YYMH (SEQ ID NO: 59) | IINPSL GLTSY AQKFQ G (SEQ ID NO: 42) | ARGGR TTWIG AFDI (SEQ ID NO: 33) | QVQLVQSGAEVKKPGASVKV SCKASGYTFPAYYMHWVRQA PGQGLEWMGIINPSLGLTSYA QKFQGRVTMTRDTSTSTVYM ELSSLRSEDTAVYYCARGGRT TWIGAFDIWGQGTMVTVSS (SEQ ID NO: 17) | VK3-15 | RASQS VSSNL A (SEQ ID NO: 72) | GASTR AT (SEQ ID NO: 69) | QQYVV WPPLT (SEQ ID NO: 65) | EIVMTQSPATLSVSP GERATLSCRASQSV SSNLAWYQQKPGQ APRLLIYGASTRATG IPARFSGSGSGTEFT LTISSLQSEDFAVYY CQQYVVWPPLTFGG GTKVEIK (SEQ ID NO: 27) |
| MAB15-IgG4 | VH1-46 | YTFRE YYMH (SEQ ID NO: 60) | IINPSIG LTSYA RKFQG (SEQ ID NO: 43) | ARGGR TTWIG AFDI (SEQ ID NO: 33) | QVQLVQSGAEVKKPGASVKV SCKASGYTFREYYMHWVRQA PGQGLEWMGIINPSIGLTSYA RKFQGRVTMTRDTSTSTVYME LSSLRSEDTAVYYCARGGRTT WIGAFDIWGQGTMVTVSS (SEQ ID NO: 18) | VK3-15 | RASQS VSSNL A (SEQ ID NO: 72) | GASTR AT (SEQ ID NO: 69) | QQYVV WPPLT (SEQ ID NO: 65) | EIVMTQSPATLSVSP GERATLSCRASQSV SSNLAWYQQKPGQ APRLLIYGASTRATG IPARFSGSGSGTEFT LTISSLQSEDFAVYY CQQYVVWPPLTFGG GTKVEIK (SEQ ID NO: 27) |

TABLE 5-continued

Sequences and germlines (GL) of TIGIT ABPs.

| Ab | VH GL | CDR-H1[1] | CDR-H2[2] | CDR-H3[3] | VH Protein | VL GL | CDR-L1[4] | CDR-L2[5] | CDR-L3[6] | VL Protein |
|---|---|---|---|---|---|---|---|---|---|---|
| MAB16-IgG4 | VH1-46 | YTFRE YYMH (SEQ ID NO: 60) | IINPSIG LTSYA RKFQG (SEQ ID NO: 43) | ARGGR TTWIG ALDI (SEQ ID NO: 34) | QVQLVQSGAEVKKPGASVKV SCKASGYTFREYYMHWVRQA PGQGLEWMGIINPSIGLTSYA RKFQGRVTMTRDTSTSTVYME LSSLRSEDTAVYYCARGGRTT WIGALDIWGQGTMVTVSS (SEQ ID NO: 19) | VK3-15 | RASQS VSSNL A (SEQ ID NO: 72) | GASTR AT (SEQ ID NO: 69) | QQYVV WPPLT (SEQ ID NO: 65) | EIVMTQSPATLSVSP GERATLSCRASQSV SSNLAWYQQKPGQ APRLLIYGASTRATG IPARFSGSGSGTEFT LTISSLQSEDFAVYY CQQYVVWPPLTFGG GTKVEIK (SEQ ID NO: 27) |
| MAB17-IgG4 | VH1-46 | YTFPA YYIH (SEQ ID NO: 61) | IINPSL GLTSY ARKFQ G (SEQ ID NO: 44) | ARGGR TTWIG ALDI (SEQ ID NO: 34) | QVQLVQSGAEVKKPGASVKV SCKASGYTFPAYYIHWVRQAP GQGLEWMGIINPSLGLTSYAR KFQGRVTMTRDTSTSTVYME LSSLRSEDTAVYYCARGGRTT WIGALDIWGQGTMVTVSS (SEQ ID NO: 20) | VK3-15 | RASQS VSSNL A (SEQ ID NO: 72) | GASTR AT (SEQ ID NO: 69) | QQYVV WPPLT (SEQ ID NO: 65) | EIVMTQSPATLSVSP GERATLSCRASQSV SSNLAWYQQKPGQ APRLLIYGASTRATG IPARFSGSGSGTEFT LTISSLQSEDFAVYY CQQYVVWPPLTFGG GTKVEIK (SEQ ID NO: 27) |
| MAB18-IgG4 | VH1-46 | YTFPA YYMH (SEQ ID NO: 59) | IINPSL GLTSY ARKFQ G (SEQ ID NO: 44) | ARGGR TTWIG AFDI (SEQ ID NO: 33) | QVQLVQSGAEVKKPGASVKV SCKASGYTFPAYYMHWVRQA PGQGLEWMGIINPSLGLTSYA RKFQGRVTMTRDTSTSTVYM ELSSLRSEDTAVYYCARGGRT TWIGAFDIWGQGTMVTVSS (SEQ ID NO: 21) | VK3-15 | RASQS VSSNL A (SEQ ID NO: 72) | GASTR AT (SEQ ID NO: 69) | QQYVV WPPLT (SEQ ID NO: 65) | EIVMTQSPATLSVSP GERATLSCRASQSV SSNLAWYQQKPGQ APRLLIYGASTRATG IPARFSGSGSGTEFT LTISSLQSEDFAVYY CQQYVVWPPLTFGG GTKVEIK (SEQ ID NO: 27) |
| MAB19-IgG4 | VH1-46 | YTFTSH YMG (SEQ ID NO: 62) | VINPS MGATS YAQKF QG (SEQ ID NO: 45) | ARLHV SGSYY PAYLD Y (SEQ ID NO: 35) | QVQLVQSGAEVKKPGASVKV SCKASGYTFTSHYMGWVRQA PGQGLEWMGVINPSMGATSY AQKFQGRVTMTRDTSTSTVY MELSSLRSEDTAVYYCARLH VSGSYYPAYLDYWGQGTMV TVSS (SEQ ID NO: 22) | VK3-15 | RASQS VSSNL A (SEQ ID NO: 72) | GASTR AT (SEQ ID NO: 69) | QQYIVF PWT (SEQ ID NO: 66) | EIVMTQSPATLSVSP GERATLSCRASQSV SSNLAWYQQKPGQ APRHLIYGASTRAT GIPARFSGSGSGTEF TLTISSLQSEDFAVY YCQQYIVFPWTFGG GTKVEIK (SEQ ID NO: 28) |
| MAB20-IgG4 | VH1-46 | YTFTSH YMG (SEQ ID NO: 62) | IINPSM GATSY AQKFQ G (SEQ ID NO: 46) | ARLHV SGSYY PAYLD Y (SEQ ID NO: 35) | QVQLVQSGAEVKKPGASVKV SCKASGYTFTSHYMGWVRQA PGQGLEWVGIINPSMGATSYA QKFQGRVTMTRDTSTSTVYM ELSSLRSEDTAVYYCARLHVS GSYYPAYLDYWGQGTMVTV SS (SEQ ID NO: 23) | VK3-15 | RASQS VSSNL A (SEQ ID NO: 72) | GASTR AT (SEQ ID NO: 69) | QQYIVF PWT (SEQ ID NO: 66) | EIVMTQSPATLSVSP GERATLSCRASQSV SSNLAWYQQKPGQ APRHLIYGASTRAT GIPARFSGSGSGTEF TLTISSLQSEDFAVY YCQQYIVFPWTFGG GTKVEIK (SEQ ID NO: 28) |
| MAB21-IgG4 | VH1-46 | YTFTSH YMG (SEQ ID NO: 62) | IINPSM GATSY TQKFR G (SEQ ID NO: 47) | ARLHV SGSYY PAYLD Y (SEQ ID NO: 35) | QVQLVQSGAEVKKPGASVKV SCKASGYTFTSHYMGWVRQA PGQGLEWMGIINPSMGATSYT QKFRGRVTMTRDTSTSTVYM ELSSLRSEDTAVYYCARLHVS GSYYPAYLDYWGQGTMVTV SS (SEQ ID NO: 24) | VK3-15 | RASQS VSSNL A (SEQ ID NO: 72) | GASTR AT (SEQ ID NO: 69) | QQYIVF PWT (SEQ ID NO: 66) | EIVMTQSPATLSVSP GERATLSCRASQSV SSNLAWYQQKPGQ APRHLIYGASTRAT GIPARFSGSGSGTEF TLTISSLQSEDFAVY YCQQYIVFPWTFGG GTKVEIK (SEQ ID NO: 28) |

[1]Includes CDR-H1 as defined by both the Chothia and Kabat numbering systems, inclusive of the boundaries of both numbering systems.
[2]According to the Kabat numbering system.
[3]According to the IMGT numbering system.
[4]According to the Kabat and Chothia numbering systems.
[5]According to the Kabat and Chothia numbering systems.
[6]According to the Kabat, Chothia, and IMGT numbering systems.

Example 4: Antibody Characterization

ForteBio $K_D$ Measurements:

Quantitative binding of antibodies to recombinant monomeric human, mouse (SEQ ID NO: 3), cynomolgus monkey TIGIT was measured using biolayer interferometry (BLI) with a FORTEBIO®. Affinity measurements of selected antibodies were performed generally as described in Estep et al., *Mabs*, 2013, 5:270-278, incorporated by reference in its entirety. FORTEBIO affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to a single concentration of antigen (100 nM) for 3 minutes. Afterwards they were transferred to assay buffer for 3 minutes for off-rate measurement. Kinetics were analyzed using the 1:1 binding model. A summary of $K_D$ measurements for antibodies binding a single concentration of human, cynomolgus monkey, and mouse (SEQ ID NO: 3) TIGIT is shown in Table 6 below.

MSD-SET $K_D$ Measurements:

Solution equilibrium affinity measurements of selected antibodies binding to monomeric recombinant human and cynomolgus monkey TIGIT were performed generally as previously described. See Estep et al., supra, incorporated by reference in its entirety. Briefly, solution equilibrium titrations (SET) were performed in PBS+0.1% IgG-Free BSA (PBSF) with antigen (TIGIT monomer) held constant at 10-100 pM and incubated with 3- to 5-fold serial dilutions of Fab or mAbs starting at 10 pM-10 nM. Antibodies (20 nM in PBS) were coated onto standard bind MSD-ECL plates overnight at 4° C. or at room temperature for 30 min. Plates were then blocked by BSA for 30 min with shaking at 700 rpm, followed by three washes with wash buffer (PBSF+ 0.05% Tween 20). SET samples were applied and incubated on the plates for 150 s with shaking at 700 rpm followed by one wash. Antigen captured on a plate was detected with 250 ng/mL sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the $K_D$. To improve throughput, liquid handling robots were used throughout MSD-SET experiments, including SET sample preparation.

Example 5: Evaluation of Blockade of TIGIT Ligands

Quantitative ligand blocking studies were conducted by using a cell surface TIGIT binding assay. Binding of fluorescently labeled PVR-Fc or PVRL2-Fc to human TIGIT expressing Jurkat cells was measured by flow cytometry. A dilution series of each test antibody was incubated with the TIGIT Jurkat cells in order to measure each antibody's ability to block PVR-Fc or PVRL2-Fc binding and determine the $IC_{50}$ values shown in Table 7.

TABLE 7

Ligand blocking $IC_{50}$ Values for Antibody Panel

| Antibody | PVR $IC_{50}$ (nM) | PVRL2 $IC_{50}$ (nM) |
| --- | --- | --- |
| MAB1-IgG4 | 2.2 | 1.4 |
| MAB2-IgG4 | 2.3 | 1.3 |
| MAB3-IgG4 | 1.6 | 1.2 |
| MAB4-IgG4 | 1.9 | 1.6 |
| MAB5-IgG4 | 1.7 | 1.4 |
| MAB6-IgG4 | 3.2 | 1.4 |
| MAB7-IgG4 | 2.6 | 2 |
| MAB8-IgG4 | 2.9 | 1.2 |
| MAB9-IgG4 | 1.9 | 1.1 |
| MAB10-IgG4 | 3.3 | 1 |
| MAB11-IgG4 | 2 | 1.2 |
| MAB12-IgG4 | 1.7 | 1.2 |
| MAB13-IgG4 | 2.1 | 1.8 |
| MAB14-IgG4 | 2.6 | 1.6 |
| MAB15-IgG4 | 2.2 | 1.1 |
| MAB16-IgG4 | 2.1 | 1.3 |
| MAB17-IgG4 | 2.6 | 1.9 |
| MAB18-IgG4 | 1.8 | 1.9 |
| MAB19-IgG4 | 6.4 | 2 |
| MAB20-IgG4 | 2.3 | 1.9 |
| MAB21-IgG4 | 1 | 0.8 |

TABLE 6

$K_D$ Measurements for Human, Cyno, and Mouse (SEQ ID NO: 3) TIGIT

| Antibody | ForteBio $K_D$ (M) Human TIGIT His | ForteBio $K_D$ (M) Cyno TIGIT His | ForteBio $K_D$ (M) Mouse TIGIT His | MSD-SET $K_D$ (M) Human TIGIT His | MSD-SET $K_D$ (M) Cyno TIGIT His |
| --- | --- | --- | --- | --- | --- |
| MAB1 | 5.24E−10 | 2.64E−09 | N.B. | 5.40E−11 | 3.20E−10 |
| MAB2 | 4.57E−10 | 1.57E−09 | N.B. | 2.50E−11 | 2.30E−10 |
| MAB3 | 3.32E−10 | 8.02E−10 | N.B. | 8.10E−12 | 3.50E−11 |
| MAB4 | 2.46E−10 | 3.69E−10 | N.B. | 5.00E−12 | 1.50E−11 |
| MAB5 | 1.96E−10 | 8.98E−10 | N.B. | 4.90E−12 | 4.60E−11 |
| MAB6 | 3.11E−09 | 1.75E−08 | N.B. | N.D | N.D |
| MAB7 | 2.54E−09 | P.F. | N.B. | N.D | N.D |
| MAB8 | 3.13E−09 | 2.58E−08 | N.B. | N.D | N.D |
| MAB9 | 2.83E−09 | 9.35E−09 | N.B. | N.D | N.D |
| MAB10 | 1.71E−09 | 6.55E−09 | P.F. | 1.10E−10 | N.D |
| MAB11 | 2.47E−09 | 8.14E−09 | N.B. | 1.50E−10 | N.D |
| MAB12 | 2.35E−09 | 6.57E−09 | P.F. | 5.60E−11 | N.D |
| MAB13 | 1.44E−09 | N.B. | N.B. | 4.00E−10 | N.D |
| MAB14 | 1.23E−09 | N.B. | N.B. | 3.80E−10 | N.D |
| MAB15 | 5.26E−10 | 7.94E−08 | N.B. | 2.10E−10 | N.D |
| MAB16 | 3.78E−10 | 7.04E−08 | N.B. | 7.00E−11 | N.D |
| MAB17 | 4.29E−10 | 1.10E−07 | N.B. | 4.10E−11 | N.D |
| MAB18 | 4.48E−10 | 7.20E−08 | N.B. | N.D | N.D |
| MAB19 | P.F. | N.B. | N.B. | N.D | N.D |
| MAB20 | P.F. | N.B. | N.B. | 3.00E−11 | N.D |
| MAB21 | P.F. | N.B. | N.B. | 8.00E−11 | N.D |

N.B.: Non-binder or weak binder
P.F.: Poor Fit (good binding response with unreportable $K_D$ based on a 1:1 fitting model)
N.D.: MSD affinity measurement was not performed Example 6: Additional TIGIT Binding Assays to Measure Affinity and Cross-Reactivity of Antibodies to TIGIT The affinity of antibodies binding to human TIGIT was measured with multiple concentrations of antigen in order to more accurately measure binding kinetics. Additionally, quantitative binding of MAB10 to human, mouse (SEQ ID NO: 3), cynomolgus monkey TIGIT was measured using biolayer interferometry (BLI) and flow cytometry. FIG. 1A shows an alignment of TIGIT from different species. The percent identities across the whole TIGIT protein are summarized in Table 8 below.

TABLE 8

Percent identities between TIGIT proteins of different species.

|  | Human | Cynomolgus Monkey | Mouse |
|---|---|---|---|
| Human | 100 | 89.17 | 68.38 |
| Cynomolgus Monkey | 89.17 | 100 | 66.67 |
| Mouse | 68.38 | 66.67 | 100 |

Kinetic Measurements for Antibodies Binding to Human, Cynomolgus Monkey, and Mouse TIGIT The binding affinities and kinetics for antibodies binding to human TIGIT-His were measured using an Octet® QKe instrument (ForteBio) in a method similar to that described above in Example 4 but with multiple concentrations of antigen used. Additionally, binding of MAB10 to cynomolgus monkey and mouse (SEQ ID NO: 3) TIGIT-His was measured. A strategy of capturing anti-TIGIT antibodies on sensors following association/dissociation of monomeric TIGIT proteins was used to avoid avidity effects in the assay. The BLI analysis was performed at 29° C. using 1× kinetics buffer (ForteBio) as assay buffer. Anti-human IgG Fc capture (AHC) biosensors (ForteBio) were first presoaked in assay buffer for over five minutes. Anti-TIGIT antibody (5 µg/mL) was captured on the sensor for 300 seconds. Sensors were then dipped in assay buffer for 120 seconds to establish a baseline before measuring binding to each TIGIT protein. Sensors were then dipped into varying concentrations of human TIGIT-His (12.4 to 0.8 nM or 6.2 to 0.8 nM, 2-fold dilutions in assay buffer), cynomolgus monkey TIGIT-His (24.6 to 1.5 nM or 12.3 to 1.5 nM, 2-fold dilutions in assay buffer, for MAB10 only), or mouse TIGIT-His (303 to 4.7 nM, 2-fold dilutions in assay buffer, for MAB10 only) for 300 seconds or 600 seconds, depending on the experiment, to measure association. Dissociation of TIGIT was measured by dipping the sensors into assay buffer for 600, 1200, or 1800 seconds, depending on the experiment (600 seconds was only used for mouse TIGIT-His). Agitation at all steps was 1000 rpm.

Kinetic parameters were generated with Octet® Data Analysis Software Version 8.2.0.7 using reference subtraction, dissociation based inter-step correction, 1-to-1 binding model, and global fit ($R_{max}$ unlinked by sensor). The association rate constant ($k_a$), dissociation rate constant ($k_d$) and equilibrium constant ($K_D$) values were individually averaged across experiments, and a summary of the data for antibodies binding to human TIGIT are shown in Table 9. A summary of MAB10 binding to monomeric human, cynomolgus monkey, and mouse TIGIT (SEQ ID NO: 3) is shown in Table 10.

TABLE 9

TIGIT Antibody Multi-Concentration Kinetics for Binding Human TIGIT

| Antibody | Average of $k_a$ (1/Ms) | Average of $k_d$ (1/s) | Average of $K_D$ (M) | n |
|---|---|---|---|---|
| MAB2 | 3.2E+05 | 2.3E−04 | 7.1E−10 | 2 |
| MAB4 | 7.0E+05 | 6.3E−05 | 8.1E−11 | 3 |
| MAB5 | 7.7E+05 | 1.4E−04 | 1.9E−10 | 2 |
| MAB9 | 1.6E+06 | 8.5E−04 | 5.6E−10 | 2 |
| MAB10 | 2.0E+06 | 3.8E−04 | 2.4E−10 | 6 |
| MAB11 | 1.3E+06 | 3.5E−04 | 2.8E−10 | 2 |
| MAB12 | 1.5E+06 | 2.4E−04 | 1.6E−10 | 2 |
| MAB15 | 1.1E+06 | 6.6E−04 | 5.8E−10 | 2 |
| MAB16 | 4.5E+05 | 3.5E−04 | 1.1E−09 | 3 |
| MAB18 | 7.5E+05 | 5.9E−04 | 8.1E−10 | 3 |
| MAB20 | 8.9E+05 | 3.8E−04 | 4.6E−10 | 2 |
| MAB21 | 1.4E+06 | 5.0E−04 | 3.6E−10 | 2 |

TABLE 10

MAB10 Kinetic Parameters for Binding Human, Cynomolgus Monkey, and Mouse

| Species | Average $k_a$ (1/Ms) | Average $k_d$ (1/s) | Average $K_D$ (M) | n |
|---|---|---|---|---|
| Human | 2.0E+06 | 3.8E−04 | 2.4E−10 | 6 |
| Cynomolgus Monkey | 7.9E+05 | 4.6E−03 | 6.2E−09 | 5 |
| Mouse | — | — | >7.0E−07* | 3 |

*$K_D$ could not be determined due to minimal binding (very low binding response), indicating that any binding is poorer than the limit of the instrument's sensitivity.

$K_D$ Measurements for Binding to Cells Engineered to Express TIGIT

The $K_D$ for MAB10 binding to cell surface TIGIT in engineered cell lines was measured using flow cytometry. Jurkat cells (acute T cell leukemia, ATCC® TIB-152™) were engineered to stably express human or cynomolgus monkey TIGIT, and CHO-K1 cells were engineered to stably express mouse TIGIT (SEQ ID NO: 3). The $K_D$ values are shown in Table 11. The $K_D$ values for MAB10 binding to cell surface human and cynomolgus monkey TIGIT are very similar.

TABLE 11

Measurement of $K_D$ for MAB10 Binding to Cell Surface TIGIT on Engineered Cells

| Cell Line | Average $K_D$ (M) | n |
|---|---|---|
| Human TIGIT Jurkat | 5.1E−10 | 2 |
| Cynomolgus Monkey TIGIT Jurkat | 4.0E−10 | 1 |
| Mouse TIGIT CHO-K1 | 9.8E−9 | 1 |

$K_D$ Measurements for Binding to Primary Cells

The $K_D$ for MAB10 binding to cell surface TIGIT on primary cells was measured using flow cytometry. For both human and cynomolgus monkey PBMCs, CD8+ T cells had the greatest detectable TIGIT expression, and therefore were used to calculate the binding of MAB10 to primary cells in these species. For analysis purposes, CD8+ T cells were defined as cells with a lymphocyte size and granularity that expressed the following combination of molecular markers: CD3+CD4−CD8+. Similarly, murine Tregs demonstrated the highest binding of MAB10, and were therefore used for these calculations. Murine Tregs were defined as CD4+CD8−CD25+FoxP3+ cells of lymphocyte size and granularity. The $K_D$ values are shown in Table 12. The $K_D$ values for MAB10 binding to cell surface human and cynomolgus monkey TIGIT on primary cells are very similar.

TABLE 12

Measurement of $K_D$ for MAB10 Binding to Cell Surface TIGIT on Primary Cells

| Cells | Average $K_D$ (M) | n |
|---|---|---|
| Human CD8 | 1.3E−9 | 2 |
| Cynomolgus Monkey CD8 | 2.8E−9 | 2 |
| Mouse Tregs | 2.5E−8 | 2 |

Antibody Binding to Human PVRL4

Figure 1B:
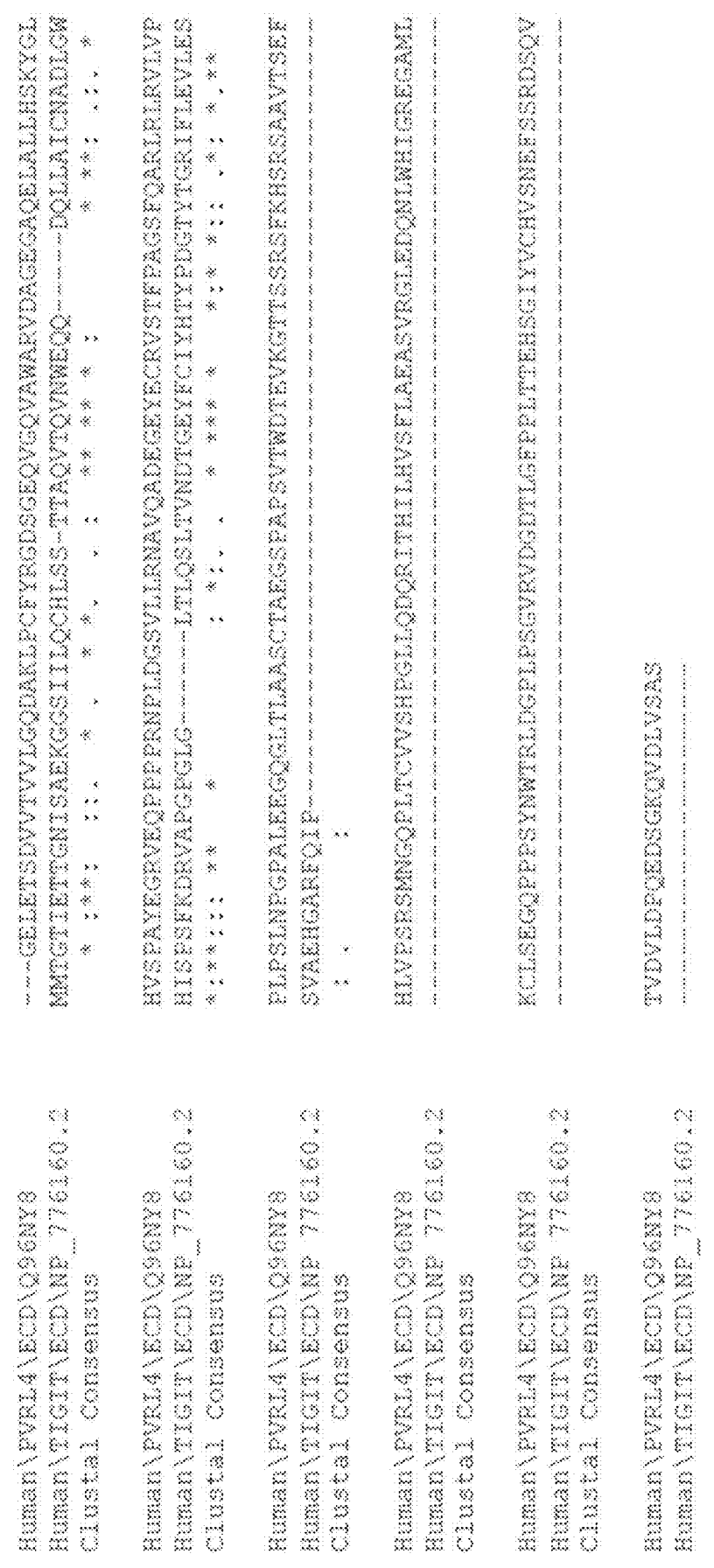

In order to confirm the specificity of anti-TIGIT antibodies, binding to human PVRL4, the Ig family member most closely related to TIGIT (29% identity in extracellular region of homology), was measured by BLI. FIG. 1B shows an alignment of the human TIGIT and PVRL4 extracellular domains. The BLI analysis was performed at 30° C. using 1× kinetics buffer as assay buffer. AHC sensors were first presoaked in assay buffer for greater than 5 minutes. Antibody (5 μg/mL) was captured on the sensor for 300 seconds. Sensors were then dipped in assay buffer for 120 seconds to establish a baseline before measuring binding to human PVRL4-His protein. Sensors were then dipped into human PVRL4-His (200 nM in assay buffer) for 200 seconds to measure association. Dissociation of PVRL4 was then measured by dipping sensors into assay buffer for 200 seconds. Results were analyzed using Octet® Data Analysis Software Version 8.2.0.7. MAB1 through MAB21 did not bind PVRL4, thus demonstrating that the MAbs disclosed herein are highly specific for TIGIT.

Example 7: Production of IL-2 in Jurkat Cells Engineered to Respond to Human TIGIT Signaling Following Treatment with Anti-TIGIT Antibodies An assay for testing the ability of antibodies to inhibit the function of TIGIT was developed using two engineered cell lines. This co-culture assay was developed to mimic the interaction of a TIGIT expressing T cell with a second cell expressing TIGIT ligand (PVR and PVRL2), thus replicating TIGIT's ability to suppress T cell activation. This interaction causes an inhibition of T cell function (e.g. cytokine release) in the TIGIT expressing cell. Jurkat cells (acute T cell leukemia) normally express IL-2 upon stimulation of the T cell receptor (using anti-CD3 and anti-CD28 agonist antibodies). The expression of TIGIT in Jurkat cells would reduce IL-2 expression induced by anti-CD3/CD28 agonist antibodies if PVR and/or PVRL2 was present and bound to TIGIT, thus providing a suppressive signal to the Jurkat cell. Therefore, a Jurkat cell line was engineered to express human TIGIT.

Figure 3:
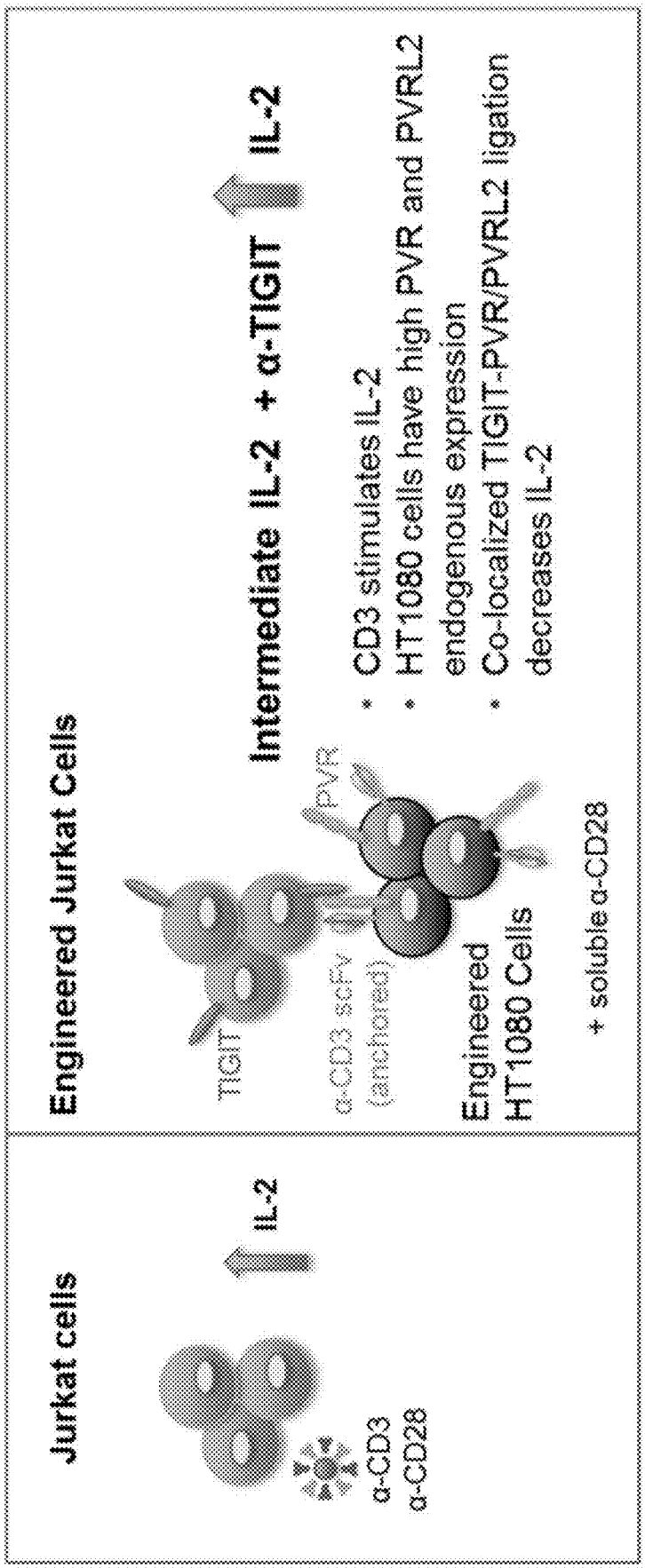
FIG. 3 shows a schematic diagram of the TIGIT Jurkat/anti-CD3 HT-1080 co-culture assay described in Example 7.

A second cell line, HT-1080 (human fibrosarcoma cell line, ATCC® CCL121™), was engineered to express a membrane tethered anti-CD3 single chain Fv (scFv) antibody that can provide an activating signal to the TIGIT Jurkat cells. The activating signal was also enhanced by including soluble anti-CD28 agonist antibody. HT-1080 cells naturally express high levels of PVR and PVRL2, thus providing ligand for TIGIT in a TIGIT Jurkat/anti-CD3 HT-1080 co-culture assay. In this co-culture assay, TIGIT antagonist antibodies increase the production of IL-2 compared to negative control antibodies. An overview of this assay system is shown in FIG. 3.

The co-culture assay was used to determine the $EC_{50}$ of anti-TIGIT antibodies by treatment with a dose range of antibody. $EC_{50}$ was measured for anti-TIGIT antibodies MAB1-MAB21, as well as the hamster anti-mouse antibody SEC1 (see Example 8) and the commercial anti-human anti-TIGIT antibody MBSA43 (available, e.g., from eBioscience, Cat. No. 16-9500). The supernatants were harvested as described above 24 hours post treatment and analyzed by an IL-2 ELISA. A summary of the experimentally determined $EC_{50}$ values in human TIGIT Jurkat cells is in Table 13. As can be seen in Table 13, all of the MABs except for MAB13, MAB14, MAB16, and SEC1, perform better in this assay than the commercial antibody MBSA43.

TABLE 13

Average $EC_{50}$ Values in Human TIGIT Jurkat Co-Culture Assay

| Antibody | Average $EC_{50}$ (nM) |
|---|---|
| MAB1 | 0.22 |
| MAB2 | 0.31 |
| MAB3 | 0.33 |
| MAB4 | 0.34 |
| MAB5 | 0.34 |
| MAB6 | data not available |
| MAB7 | 0.25 |
| MAB8 | 0.24 |
| MAB9 | 0.06 |
| MAB10 | 0.14 |
| MAB11 | 0.24 |
| MAB12 | 0.16 |
| MAB13 | 1.40 |
| MAB14 | 0.71 |
| MAB15 | 0.21 |
| MAB16 | 1.11 |
| MAB17 | 0.13 |
| MAB18 | 0.25 |
| MAB19 | 0.20 |
| MAB20 | 0.68 |
| MAB21 | 0.61 |
| SEC1 (see below) | 8.46 |
| MBSA43 | 0.45 |

Figure 4A:
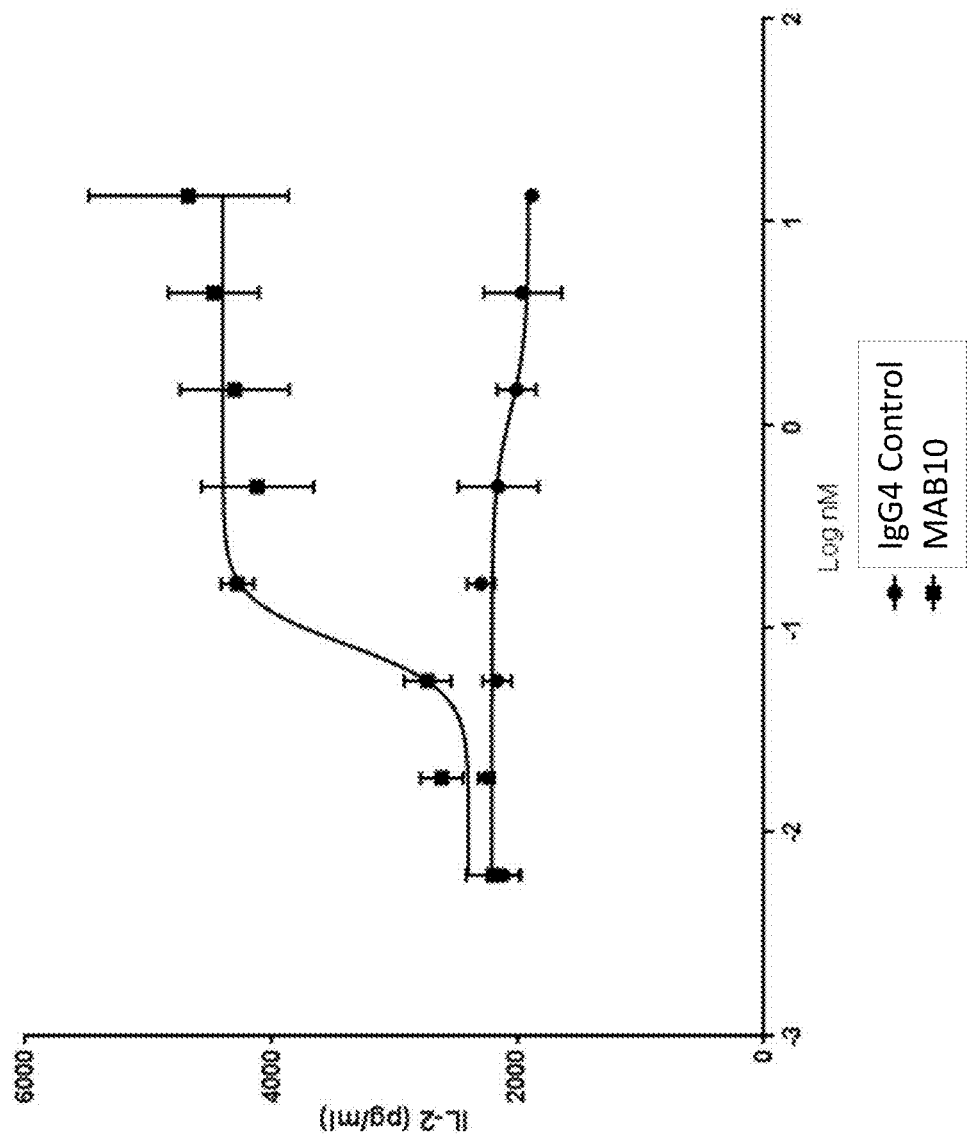
FIG. 4A shows the $EC_{50}$ curves from exemplary experiments comparing the ability of MAB10 and an IgG4 isotype control to induce IL-2 production in engineered Jurkat cells expressing human TIGIT.

Additionally, the Jurkat co-culture assay was repeated with MAB10 using a subcloned isolate of the anti-CD3 scFv HT1080 cells. FIG. 4A shows the $EC_{50}$ curves from an exemplary experiment comparing MAB10 and an IgG4 control. That experiment was conducted 3 times, and the average $EC_{50}$ was 0.11 nM.

Figure 4B:
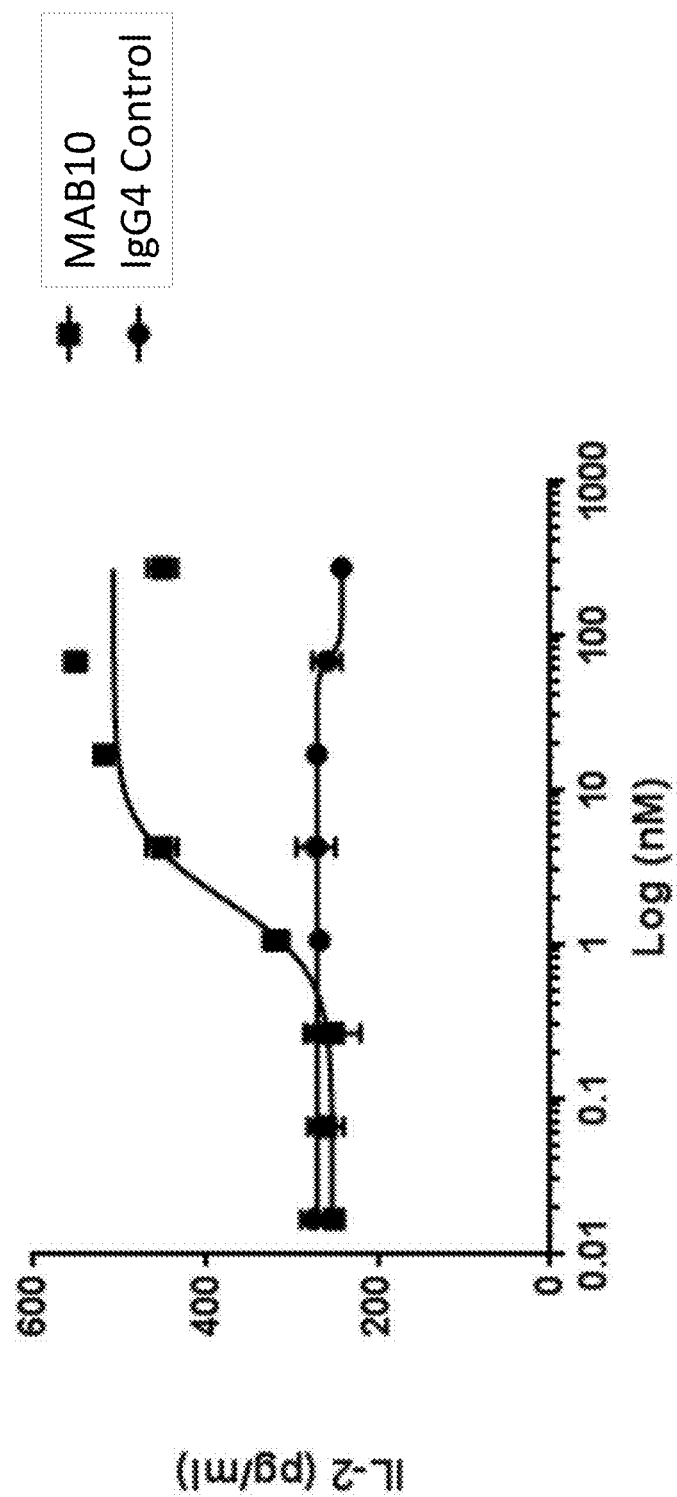
FIG. 4B shows the $EC_{50}$ curves from exemplary experiments comparing the ability of MAB10 and an IgG4 isotype control to induce IL-2 production in engineered Jurkat cells expressing cynomolgus monkey TIGIT.

As described above for human TIGIT expressing Jurkat cells, a co-culture stimulation assay was set up with HT-1080 anti-CD3 scFv cells in the presence of cynomolgus monkey TIGIT expressing Jurkat cells and soluble anti-human CD28. FIG. 4B shows the $EC_{50}$ curves from an exemplary experiment comparing MAB10 and IgG4 control. As shown in FIG. 4B, MAB10 induces IL-2 production in cynomolgus monkey TIGIT expressing Jurkat cells, whereas the IgG4 isotype control does not. The average $EC_{50}$ for MAB10 in the cynomolgus monkey TIGIT Jurkat/anti-CD3 HT-1080 co-culture assay was determined to be 2.87 nM.

Example 8: Characterization of the Anti-TIGIT Antibody "SEC1"

Additional studies were conducted to characterize the hamster anti-TIGIT antibody 10A7 (disclosed, e.g., in U.S. Pat. Pub. No. 20090258013). The antibody 10A7 was reformatted in two different ways for use in this study. The first was to make a chimeric antibody with hamster variable regions and human IgG4 S228P (human S228P heavy chain, SEQ ID NO:73) and kappa constant regions (constant regions used for MAB10, SEQ ID NO:75). The second was to make a chimeric antibody with hamster variable regions and mouse IgG2a N297A and kappa constant regions (heavy chain: SEQ ID NO:77; light chain: SEQ ID NO:79). The variable regions of the antibodies are provided in SEQ ID NOs:74, 76, 78 and 80. The reformatted 10A7 antibodies are referred to herein as "SEC1".

Kinetic Measurements for SEC1 Binding to Recombinant Human, Cynomolgus Monkey, and Mouse TIGIT The binding affinities and kinetics of binding of SEC1 mouse IgG2a N297A to human TIGIT-His, cynomolgus monkey TIGIT-His, and mouse (SEQ ID NO: 3) TIGIT-His were measured using BLI with an Octet QKe instrument. A strategy of capturing SEC1 on sensors followed by association/dissociation of monomeric TIGIT proteins was used to avoid avidity effects in the assay. The BLI analysis was performed at 29° C. using 1× Kinetics Buffer (ForteBio) as assay buffer. Anti-Mouse IgG Fc Capture (AMC) biosensors (ForteBio) were first presoaked in assay buffer for greater than 5 minutes. SEC1 mouse IgG2a N297A (5 μg/mL) was captured on the sensor for 300 seconds. Sensors were then dipped in assay buffer for 120 seconds to establish a baseline before measuring binding to each TIGIT protein. Sensors were then dipped into varying concentrations of human TIGIT-His (33.8 to 1.25 nM, 3 fold dilutions in assay buffer), cynomolgus monkey TIGIT-His (302.8 to 0.42 nM, 3 fold dilutions in assay buffer), or mouse TIGIT-His (33 to 1.22 nM, 3 fold dilutions in assay buffer) for 300 seconds to measure association. Dissociation of TIGIT was then measured by dipping sensors into assay buffer for 600 seconds. Agitation at all steps was 1000 rpm. Kinetic parameters and sensorgrams were generated with Octet® Data Analysis Software using reference subtraction, dissociation based inter-step correction, 1 to 1 binding model, and global fit (Rmax unlinked by sensor). The $K_D$ values are shown in Table 14.

TABLE 14

| SEC1 IgG2a N297A Kinetic Parameters for Binding TIGIT | | | |
|---|---|---|---|
| Species | $k_a$ (1/Ms) | $k_d$ (1/s) | $K_D$ (M) |
| Human | 1.7E+06 | 7.9E−03 | 4.7E−09 |
| Cynomolgus Monkey | | No Binding | |
| Mouse | 1.9E+06 | 6.0E−04 | 3.2E−10 |

$K_D$ Measurements for Binding to Primary Cells

The $K_D$ for SEC1 (IgG4 S228P) binding to cell surface TIGIT on primary cells was measured using flow cytometry as described in Example 6. For both human and cynomolgus monkey PBMCs, CD8+ T cells had the greatest detectable TIGIT expression, and therefore were used to calculate the binding of SEC1 to primary cells in these species. For analysis purposes, CD8+ T cells were defined as cells with a lymphocyte size and granularity that expressed the following combination of molecular markers: CD3+CD4−CD8+. Similarly, murine Tregs demonstrated the highest expression of TIGIT, and were therefore used for these calculations. Murine Tregs were defined as CD4+CD8−CD25+FoxP3+ cells of lymphocyte size and granularity. The $K_D$ values are shown in Table 15.

TABLE 15

| Measurement of $K_D$ for SEC1 Binding to Cell Surface TIGIT on Primary Cells | | |
|---|---|---|
| Cells | Average $K_D$ (M) | n |
| Human CD8 | 3.6E−9 | 1 |
| Cynomolgus Monkey CD8 | No binding | 1 |
| Mouse Tregs | 4.1E−10 | 2 |

Engineered TIGIT Jurkat/Anti-CD3 HT-1080 Assay

SEC1 antagonizes TIGIT function in the engineered human TIGIT Jurkat/anti-CD3 HT-1080 co-culture assay described in Example 7. The experiment was conducted 3 times, and the average $EC_{50}$ was 8.5 nM. In comparison, the average $EC_{50}$ for MAB10 in this assay is 0.14 nM.

Like MAB10, SEC1 has been described as a ligand blocking antibody, and both antibodies inhibit the function of TIGIT in an engineered TIGIT Jurkat/anti-CD3 scFv HT-1080 co-culture assay.

Example 9: Increase in Cytokine Production in Sub-Optimally Stimulated Human T Cells Following Treatment with MAB10

A study was developed in order to determine whether MAB10 is efficacious in a cellular in vitro system using human primary T cells obtained from healthy donors. Two different forms of the assay were used: stimulation of T cells within a mix of PBMCs and stimulation of CD4+ T cells after isolation from PBMCs. TIGIT is expressed in exhausted intra-tumoral CD8+ T cells, NK and regulatory T cells. This study was designed to identify and obtain more readily available TIGIT expressing human primary T cells to use as a surrogate system for the intra-tumoral target cells.

In CD4+ T cells, TIGIT expression is primarily restricted to memory cells (CD45RO+). Suboptimal stimulation of CD4+ T cells permits assaying the efficacy of MAB10 by measuring the increased production of IFN-γ following inhibition of TIGIT-ligand interactions.

Human primary T cells were obtained from healthy donors. Total peripheral blood mononuclear cells (PBMCs) were isolated from leukapheresis preparations and CD4+ T cells were in turn isolated from PBMCs.

PBMCs were purified using Ficoll® density gradients. PBMCs were then used to purify CD4+ cells using negative selection (CD4 T cell isolation kit, Miltenyi) following manufacturer's protocol.

FACS Analysis of Key Markers on Human CD4+ T Cells.

CD4+ T cells were sub-optimally stimulated with plate-bound anti-CD3 antibody (1 μg/mL) and soluble anti-CD28 antibody (2 μg/mL) for 60 hours. For staining and FACS analysis, cells from unstimulated and stimulated samples were used. The following antibodies were used for staining: anti-TIGIT-PE-Cy7, anti-PVR-PE, anti-CD4-APC-eFluor780 and anti-CD45RA-APC, anti-CD45RO PerCP-eFluor710, and CD226-FITC. Cells were analyzed by flow cytometry using a BD LSRFortessa™ instrument.

Sub-optimal stimulation of PBMCs was achieved by addition of low concentrations of anti-CD3 antibody (0.2 μg/mL). Sub-optimal stimulation of CD4+ T cells was achieved by culturing the cells on 96-well flat-bottom plates that had been previously coated with 1 μg/mL of anti-CD3 antibody and 2 μg/mL soluble anti-CD28 antibody. After 60 hours of culture, supernatants were collected and frozen for cytokine quantification using ELISA, AlphaLISA® or multiplex/Luminex® technology. The effect of MAB10 addition was compared to the addition of a non-specific control IgG4 antibody.

Figure 5A:
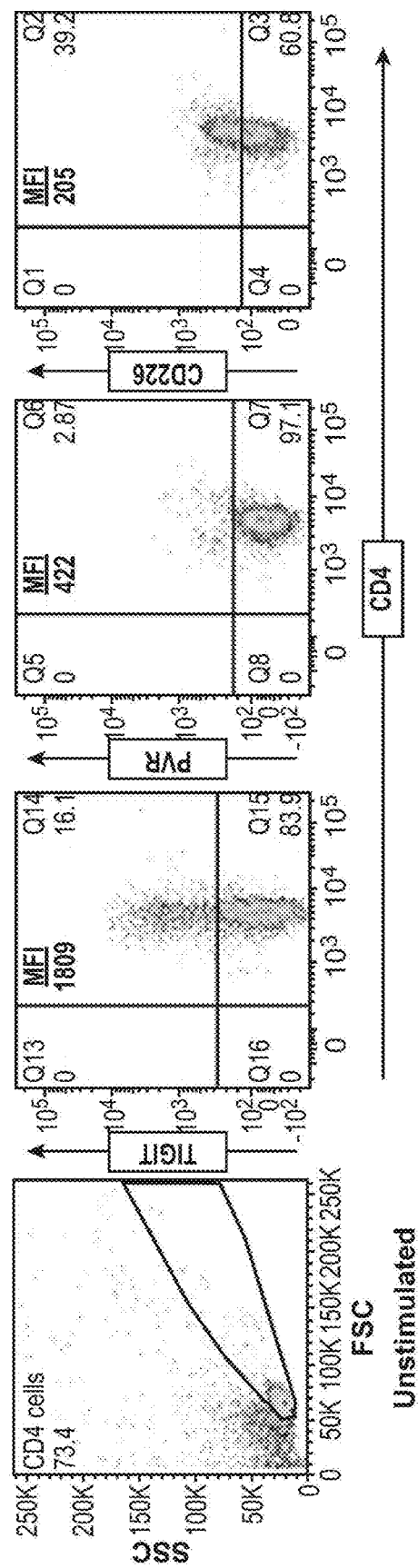
FIG. 5A-5C show TIGIT expression analysis on human CD4+ T cells by FACS.
Figure 5B:
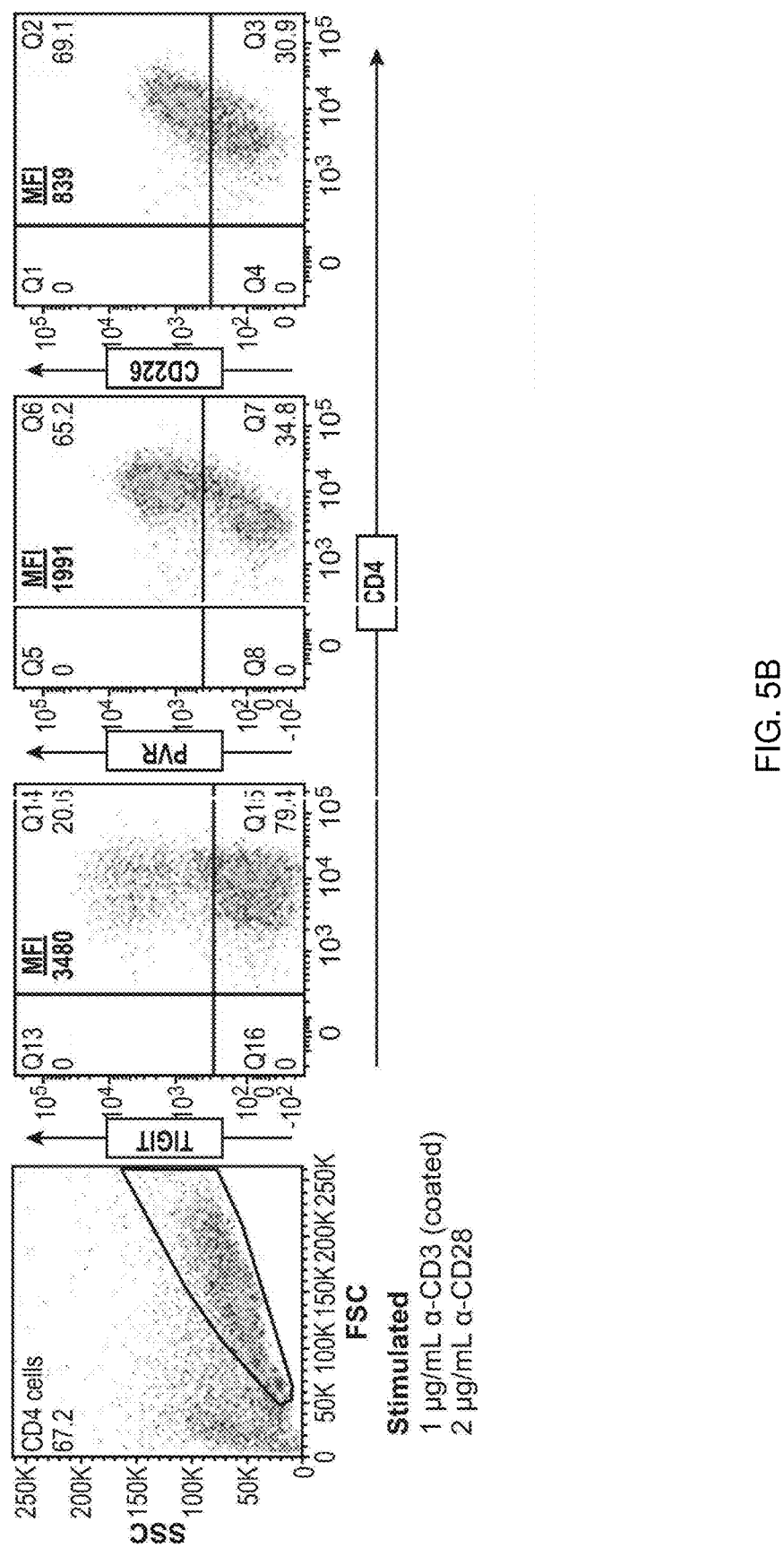
Figure 5C:
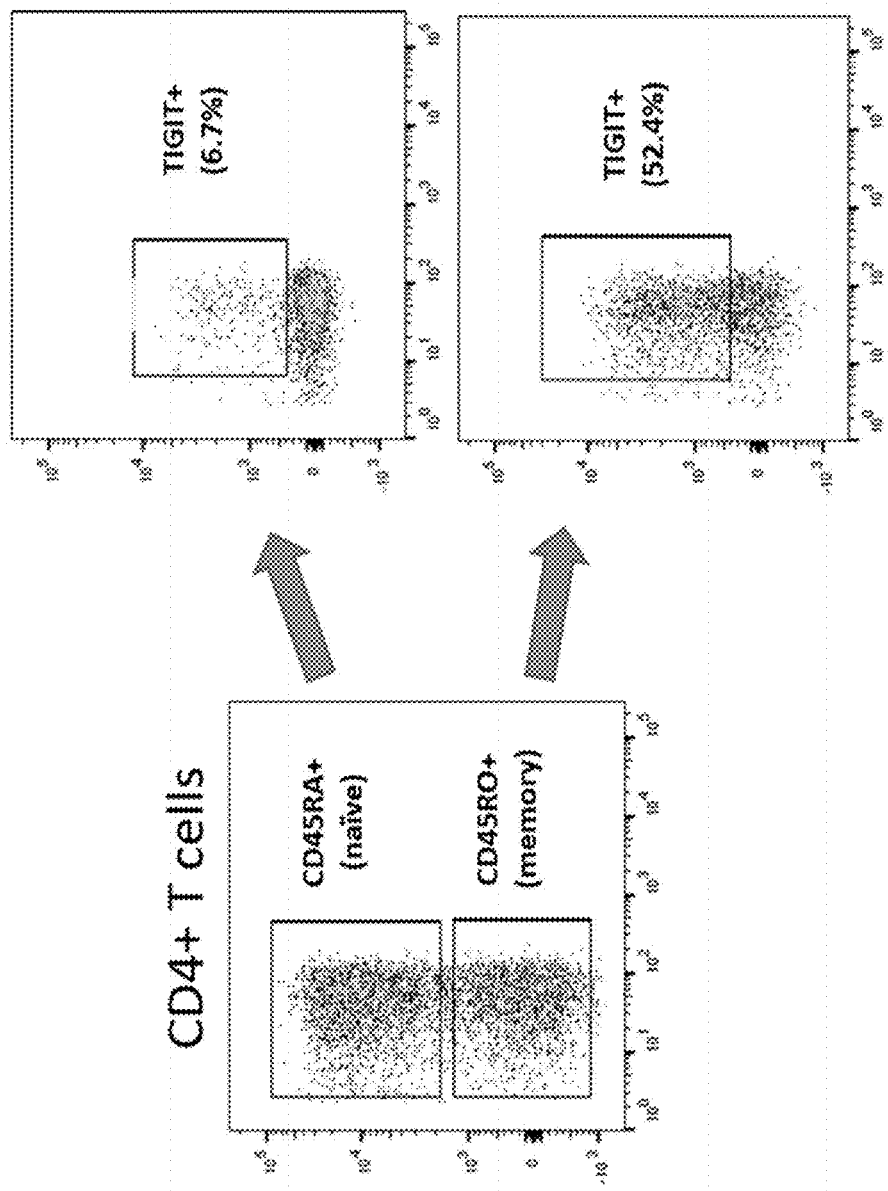

Purified CD4+ T cells were left unstimulated or were stimulated for 60 hours using plate-bound anti-CD3 antibody (1 µg/mL) and soluble anti-CD28 antibody (2 µg/mL). FACS analysis was performed on both unstimulated (FIG. 5A) and stimulated cells (FIG. 5B). Population percentages and mean fluorescence intensity (MFI) were calculated. Expression analysis of cell markers TIGIT, PVR, and CD226 prior and post-activation showed that the percentage of both PVR and CD226 positive cells increases upon activation. For TIGIT, the percentage of TIGIT positive cells only increased moderately with these activation conditions, but the MFI values indicated a clear upregulation of TIGIT expression in the positive cell population. FACS analysis also confirmed that TIGIT expression was restricted primarily to memory cells (CD45RO+). CD4+ T cells from a representative donor were stained for CD45RA (naïve T cell marker) and CD45RO (activated or memory T cell marker) markers to differentiate naïve and memory T cells. Expression levels of TIGIT were analyzed within each of these populations (see FIG. 5C).

Figure 6A:
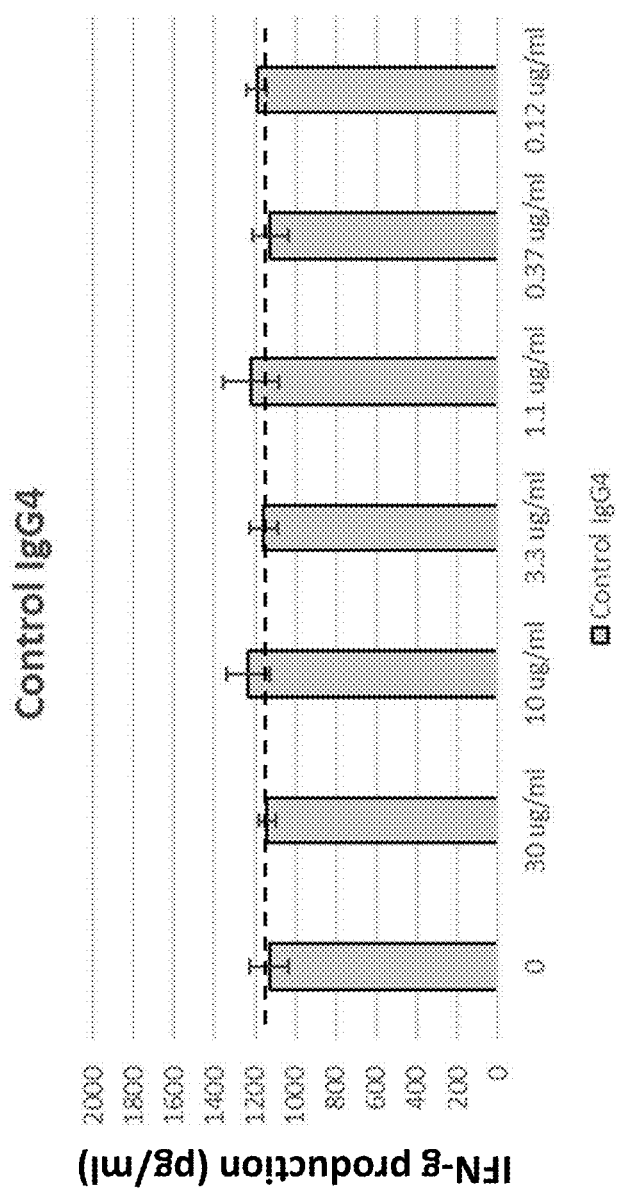
FIGS. 6A-6O show the effect of treatment with MABs on sub-optimally stimulated PBMCs from human donors. MABs were tested for their ability to induce IFN-γ in PBMCs from human donors, including a control IgG4 antibody (FIG. 6A), MAB2 (FIG. 6B), MAB3 (FIG. 6C), MAB4 (FIG. 6D), MAB5 (FIG. 6E), MAB10 (FIG. 6F), MAB11 (FIG. 6G), MAB12 (FIG. 6H), MAB15 (FIG. 6I), MAB16 (FIG. 6J), and SEC1 (hamster anti-mouse TIGIT, FIG. 6K). Treatment of the PBMCs from Donor 1 with MAB10 induces the upregulation of several pro-inflammatory cytokines, including tumor necrosis factor alpha (TNF, FIG. 6L), lymphotoxin alpha (LT-α, FIG. 6M), and interferon gamma (IFN-γ, FIG. 6N).
Figure 6B:
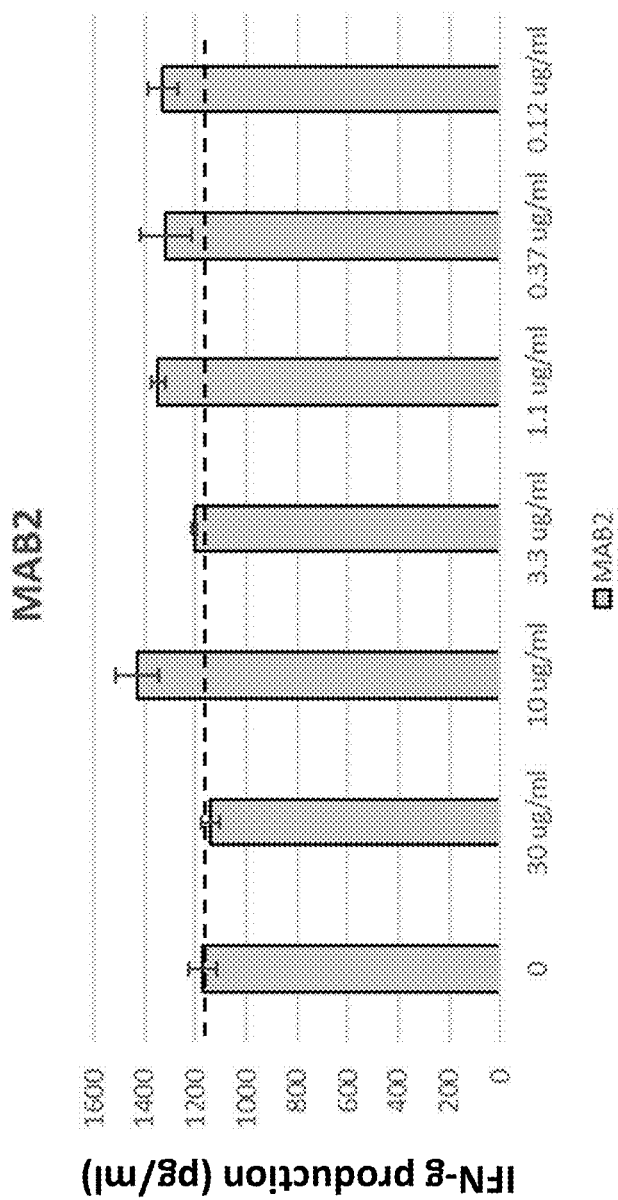
Figure 6C:
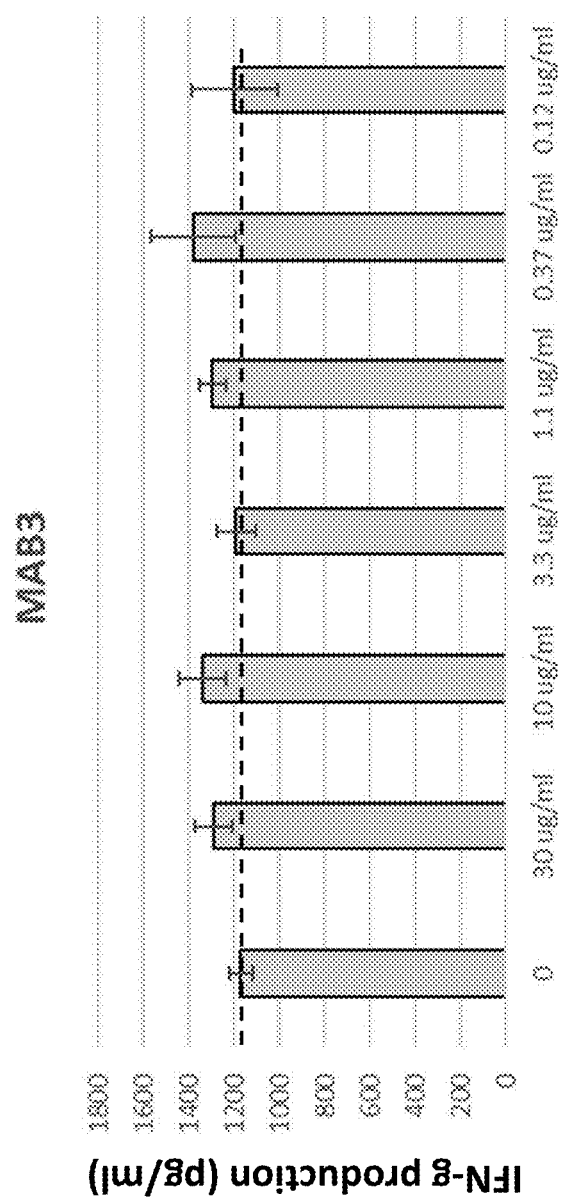
Figure 6D:
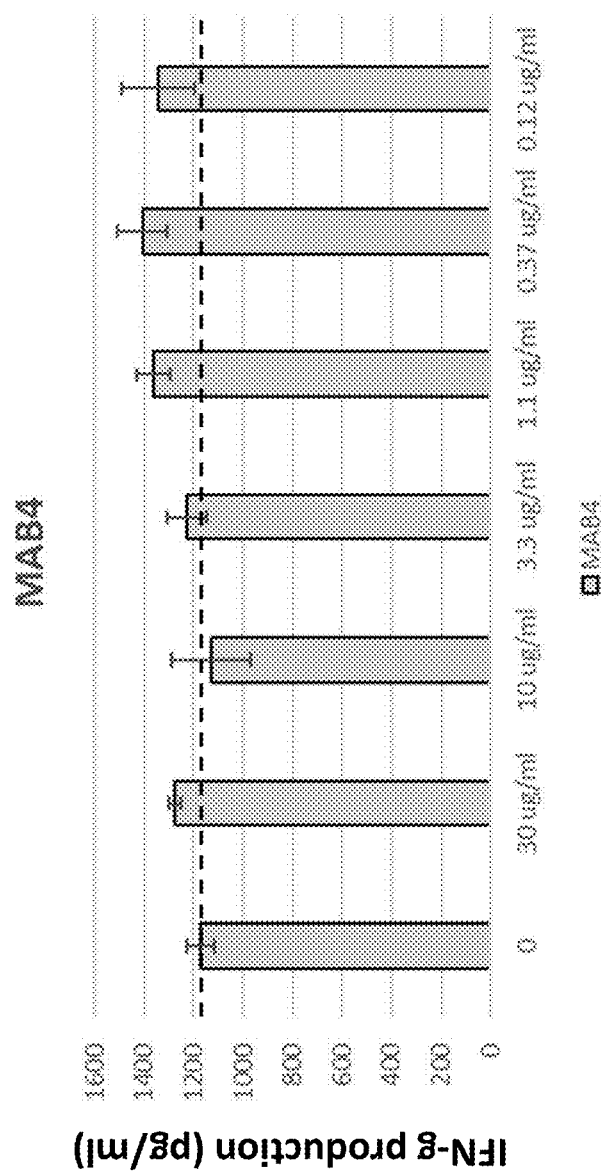
Figure 6E:
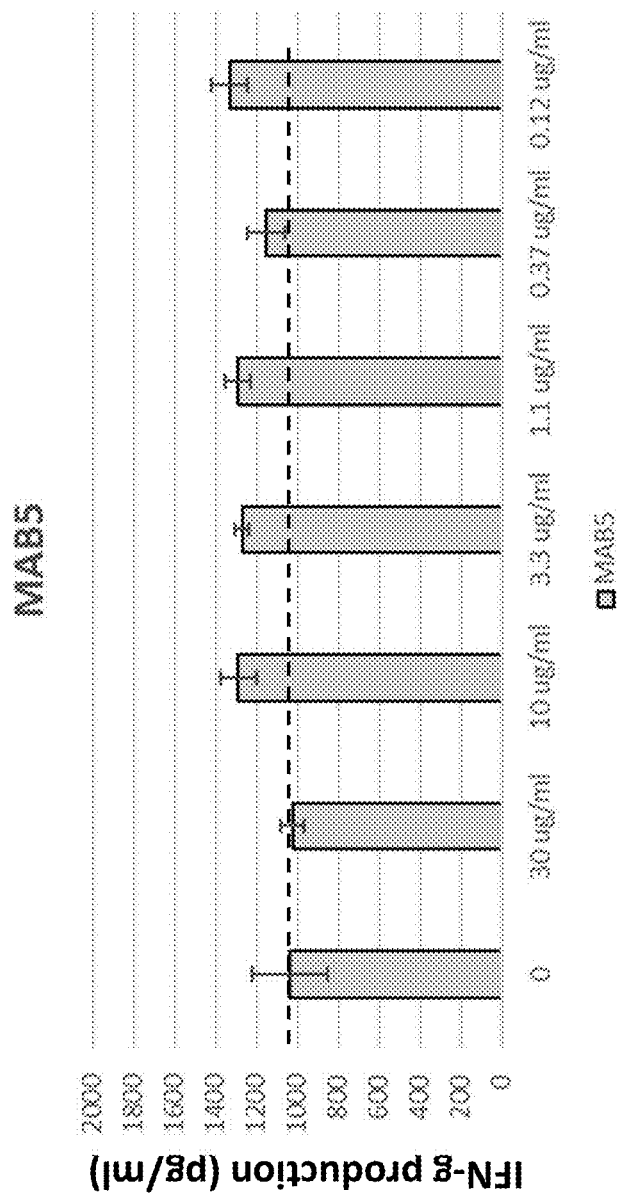
Figure 6F:
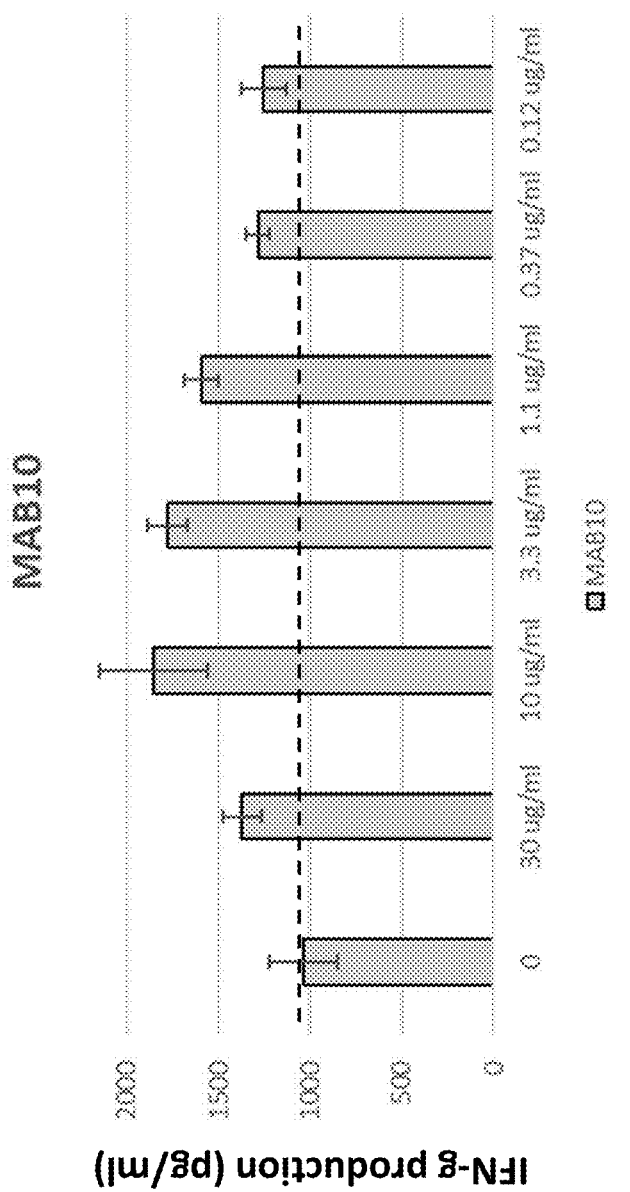
Figure 6G:
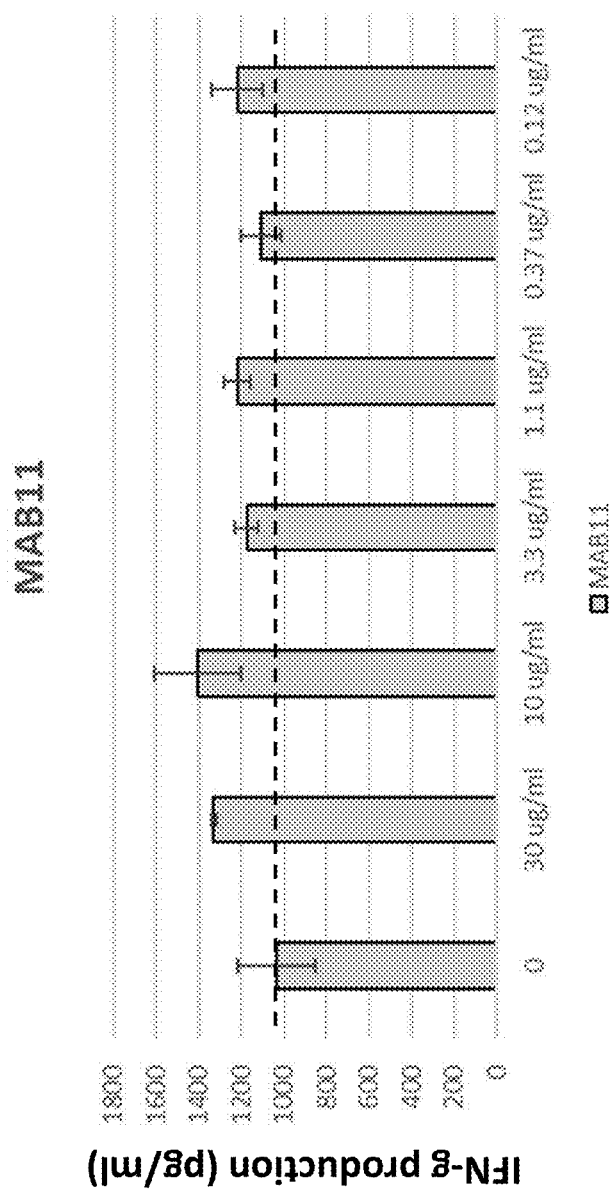
Figure 6H:
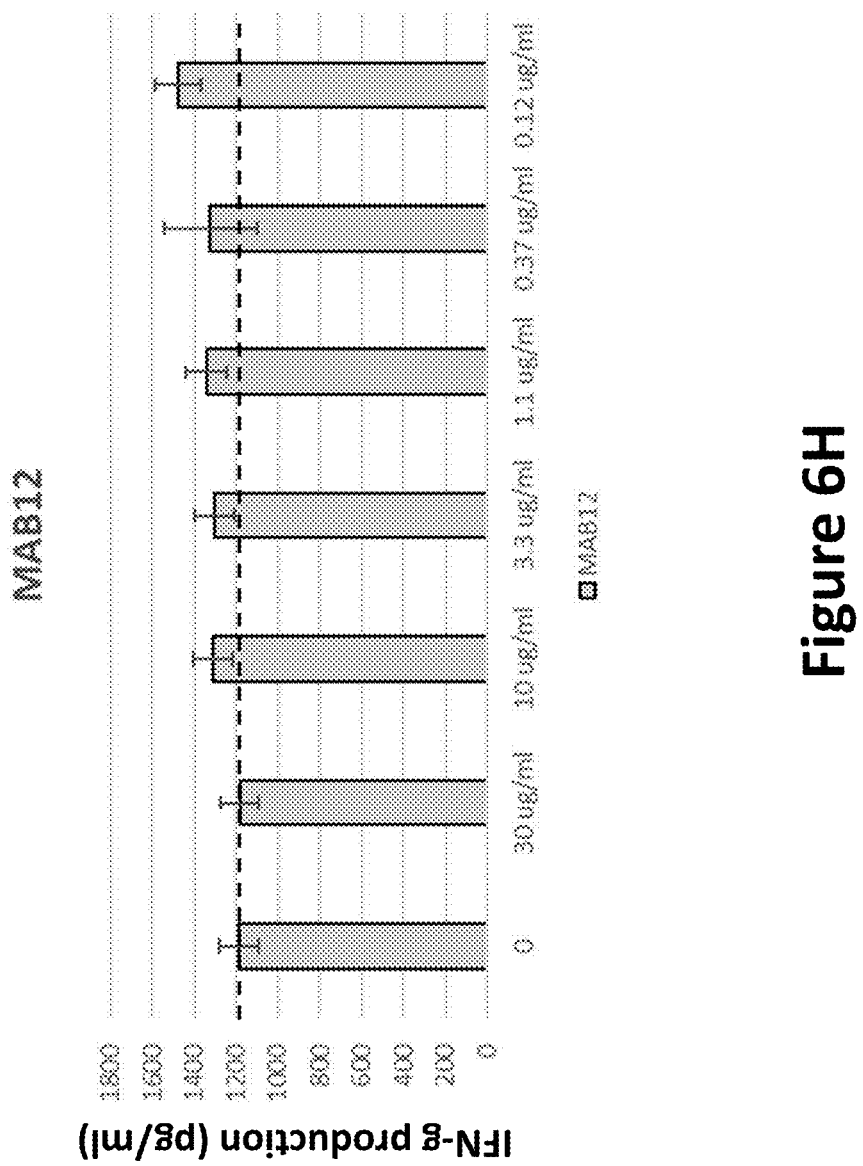
Figure 6I:
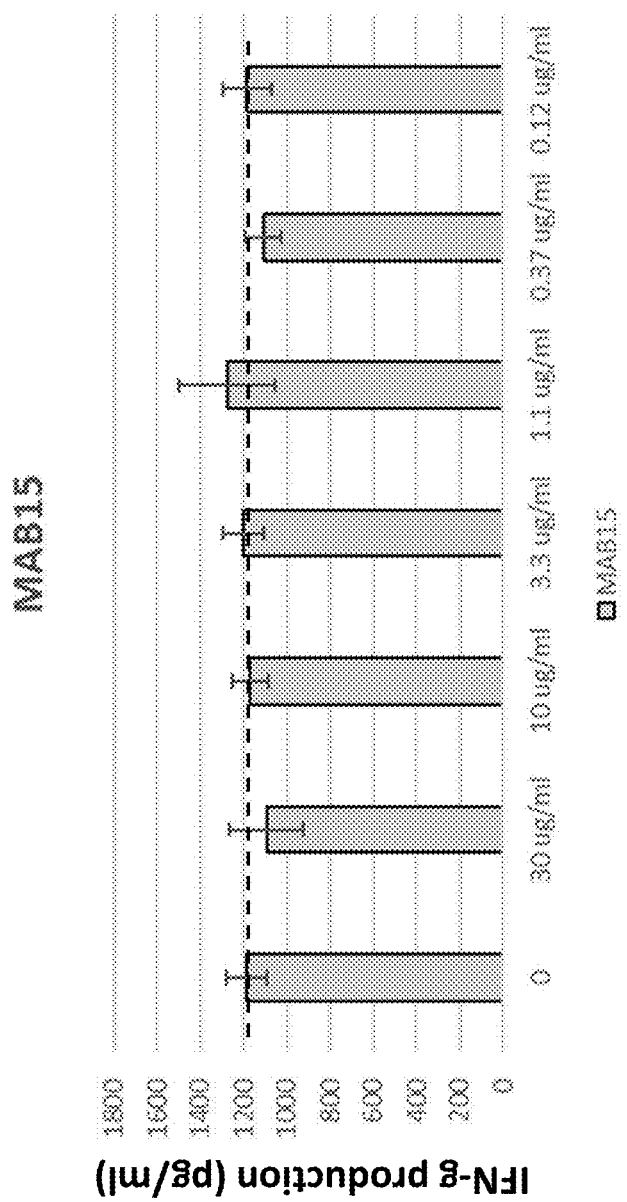
Figure 6J:
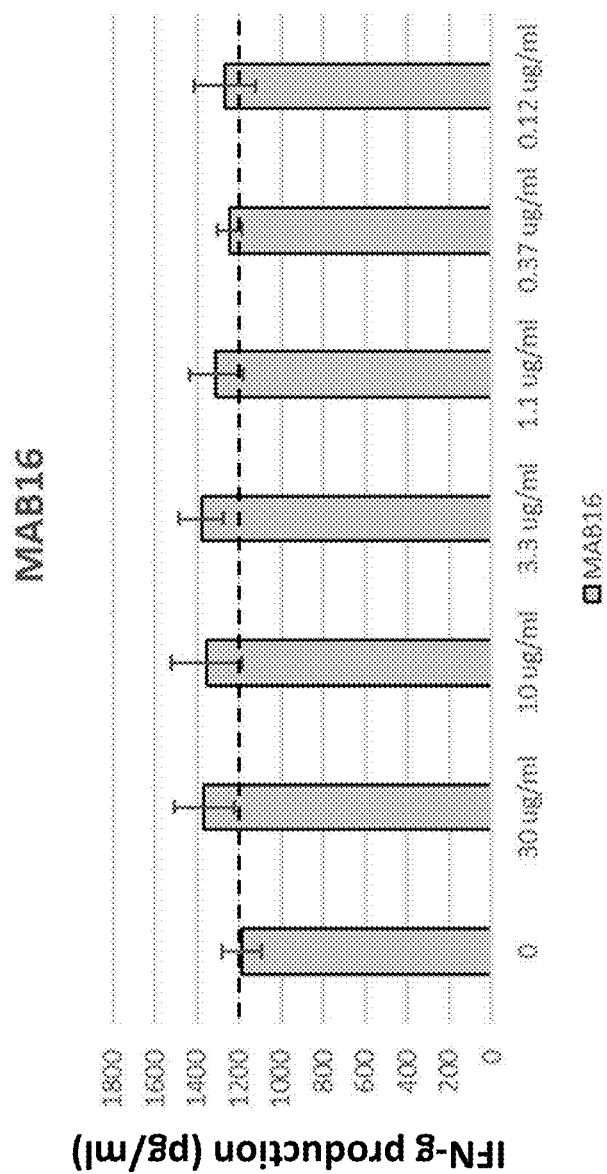
Figure 6K:
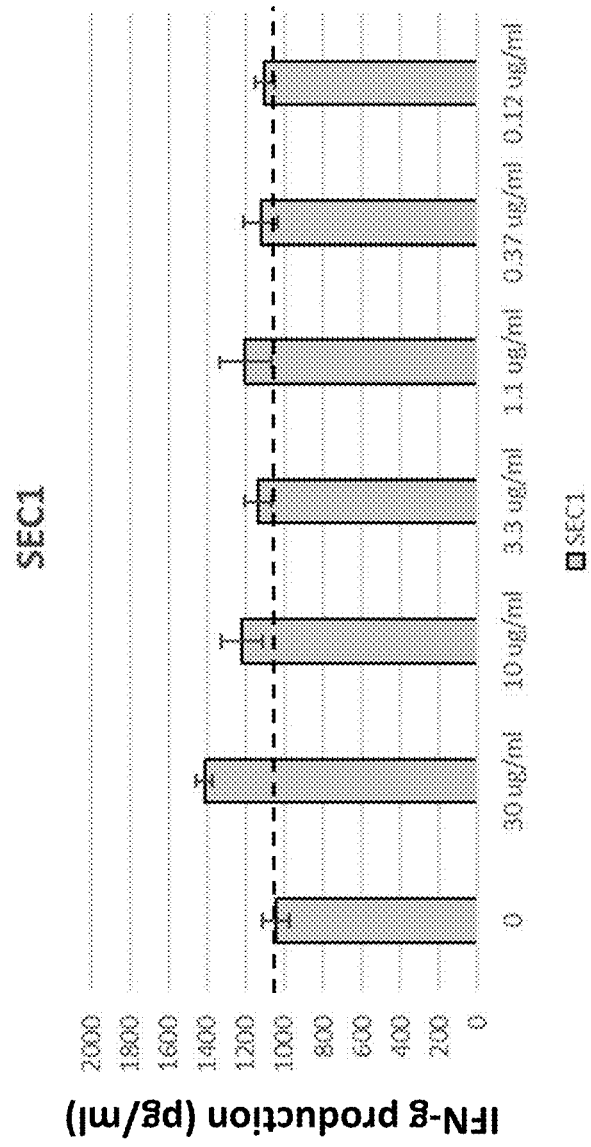
Figure 6L:
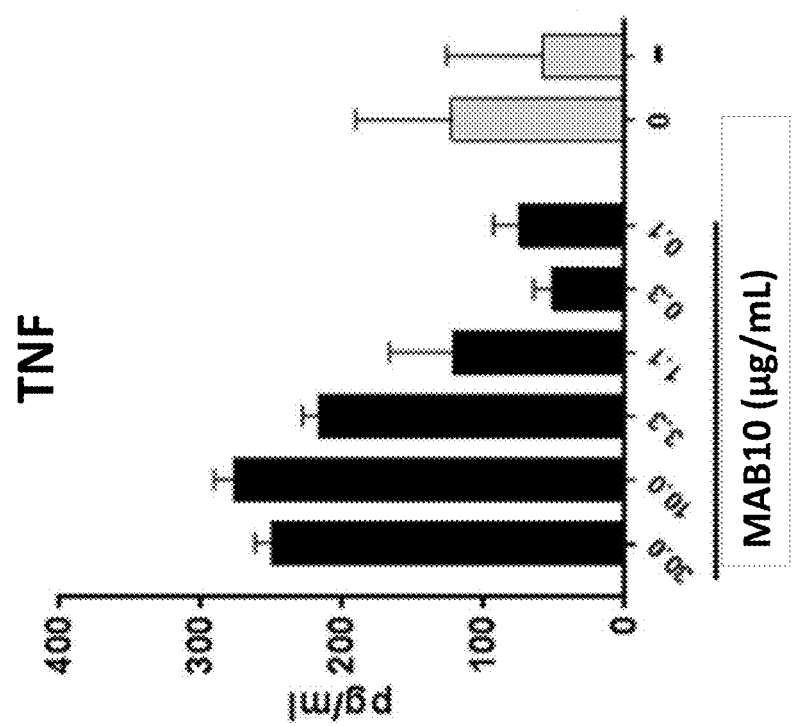
Figure 6N:
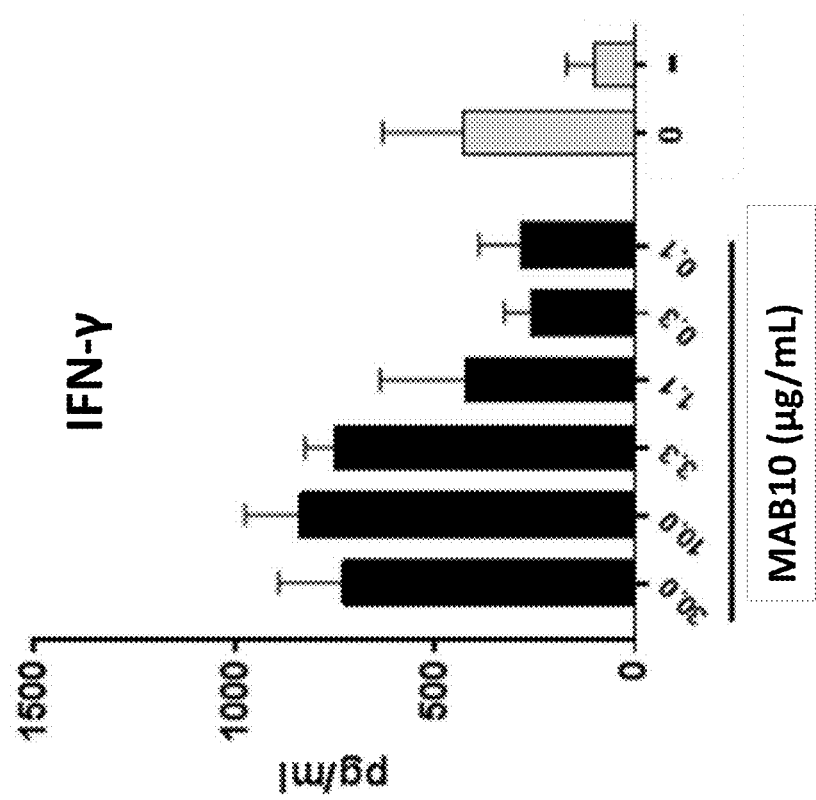
Figure 6O:
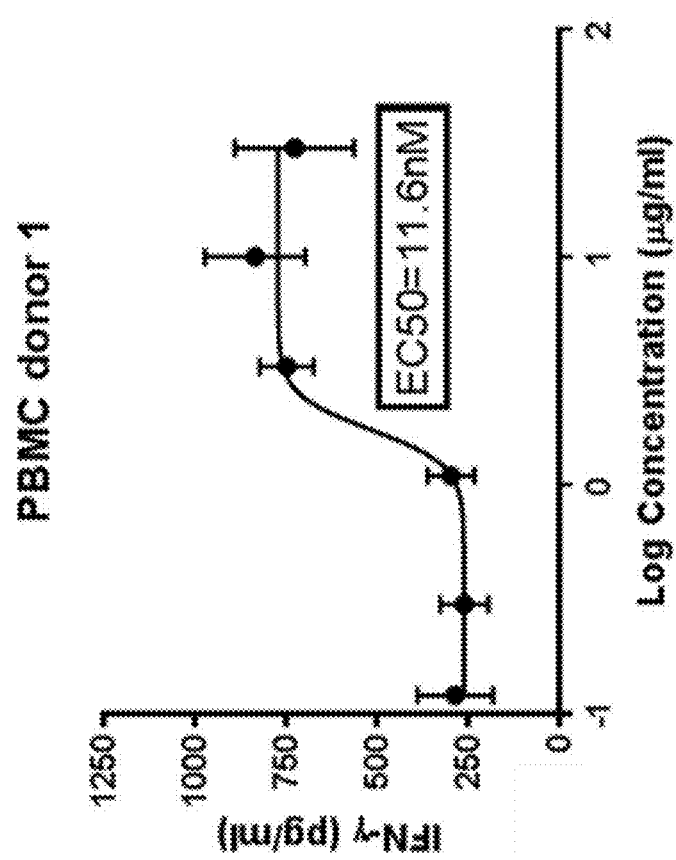
Figure 7A:
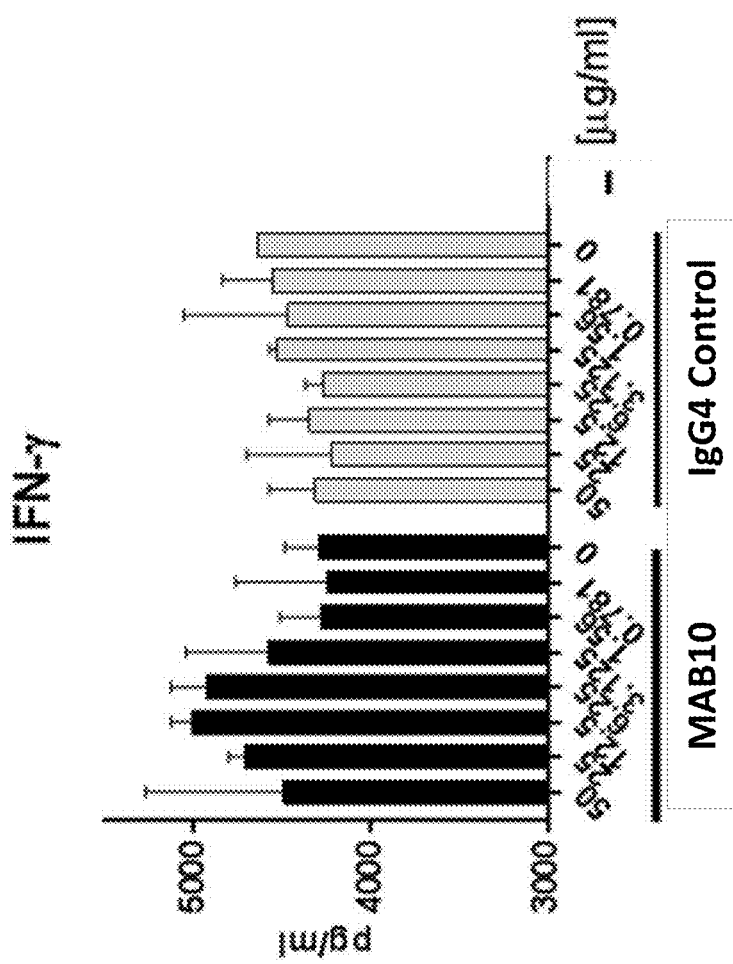
Figure 7B:
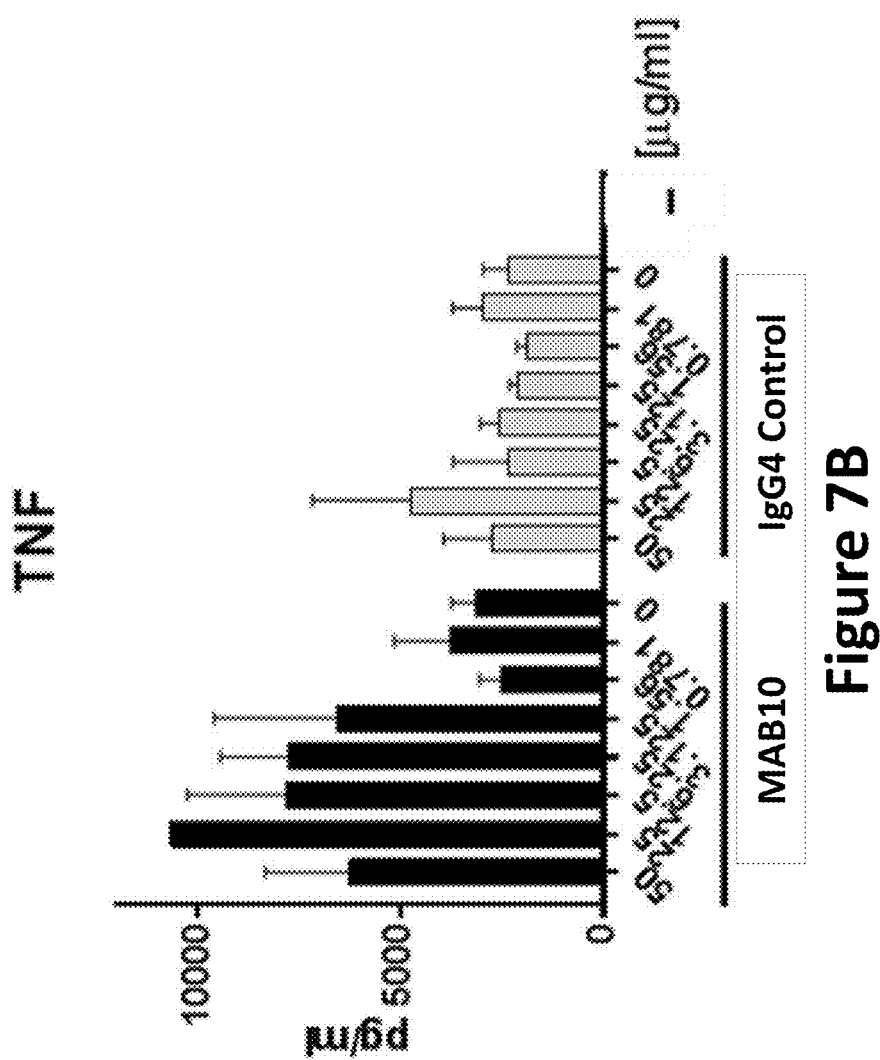
Figure 7D:
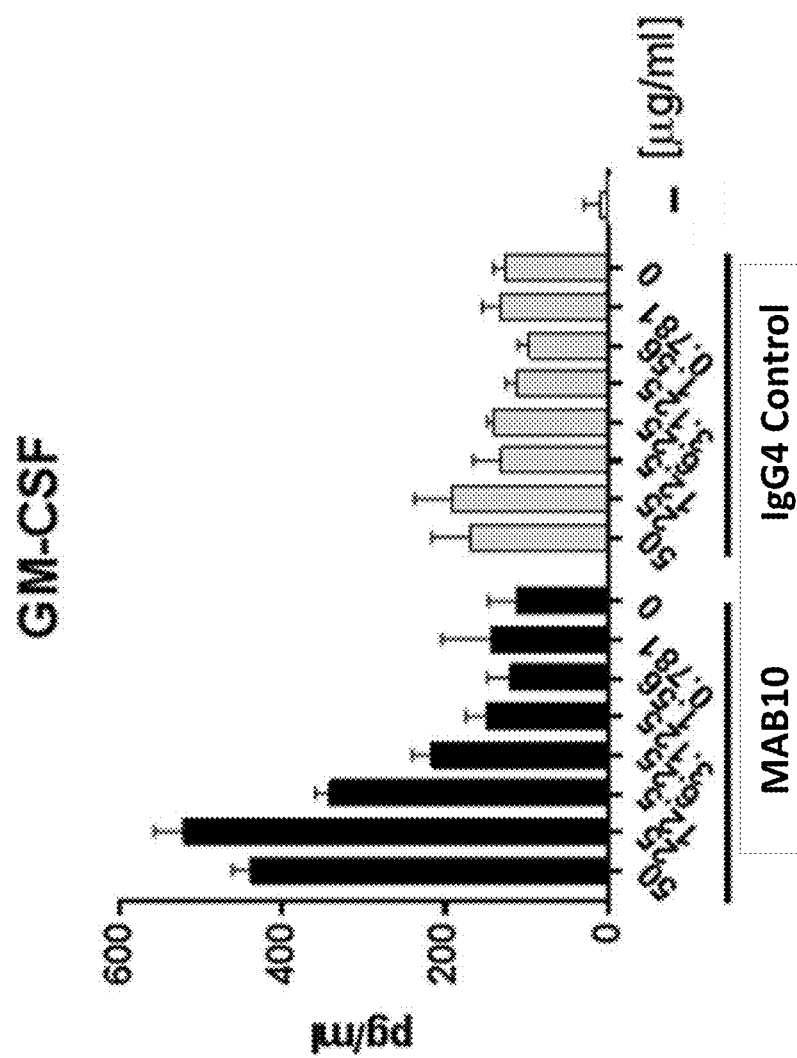

Purified PBMCs obtained from healthy donors were stimulated for 60 hours using soluble anti-CD3 antibody (0.2 µg/mL) in the presence of different concentrations of a MAB or a control IgG4 antibody. Cell culture supernatants were collected and used to measure production of pro-inflammatory cytokines. The analysis of samples from two human donors, illustrated in FIGS. 6A-6K, show that treatment with each of the MABs induces the upregulation IFN-γ. MAB10 was then used to induce the production of several pro-inflammatory cytokines in PBMCs from Donor 1, including tumor necrosis factor alpha (TNF, FIG. 6L), lymphotoxin alpha (LT-α, FIG. 6M), and interferon gamma (IFN-γ, FIG. 6N). A graphical analysis of the $EC_{50}$ for IFN-γ is shown in FIG. 6O. PBMCs from Donor 2 were similarly treated with MAB10 and cytokines induced as shown in FIG. 7A (IFN-γ), FIG. 7B (TNF), FIG. 7C (IL-6), FIG. 7D (GM-CSF), and FIG. 7E (LT-α). $EC_{50}$ value for MAB10 in this assay in the two donors tested was averaged as ~16 nM, by determining the concentration of MAB10 required to induce 50% of the increase in IFN-γ, TNF and LT-α signal. A summary of the TNF data for the two donors (FIG. 6) is shown in Table 16.

TABLE 16

Data Summary for Two Donors (TNF Analyzed)

| Donor | $EC_{10}$ (nM) | $EC_{50}$ (nM) | $EC_{90}$ (nM) |
|---|---|---|---|
| 1 | 5.02 | 12.60 | 31.59 |
| 2 | 18.86 | 20.60 | 22.49 |
| Average | 11.94 | 16.60 | 27.04 |

Purified CD4+ T cells obtained from 3 different healthy donors were stimulated for 60 hours using plate-bound anti-CD3 antibody (1 µg/mL) and soluble anti-CD28 antibody (2 µg/mL) in the presence of different concentrations of a control IgG4 antibody or MAB10. Cell culture supernatants were collected and used to measure levels of IFN-γ production.

Figure 8A:
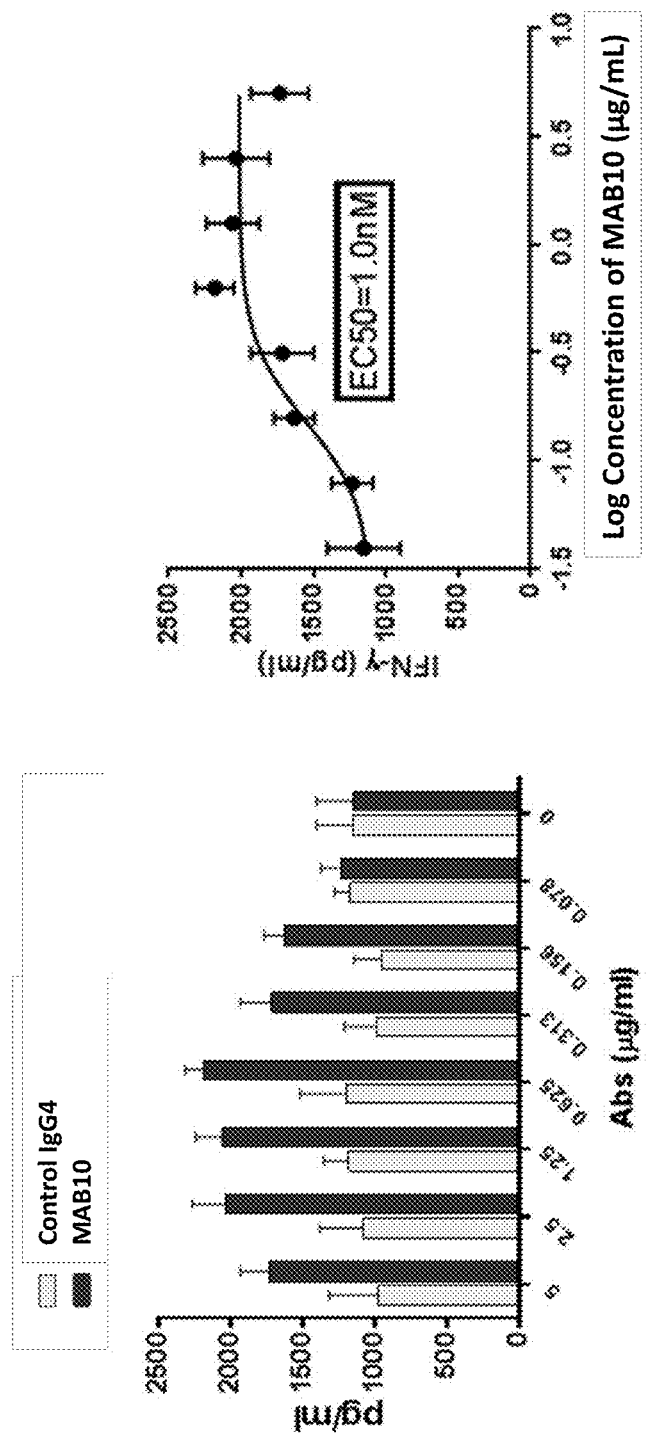
FIGS. 8A-8C provide a series of graphs showing that the antagonist anti-TIGIT antibody MAB10 increases IFN-γ in a CD4+ cell assay using cells obtained from three different donors.
Figure 8B:
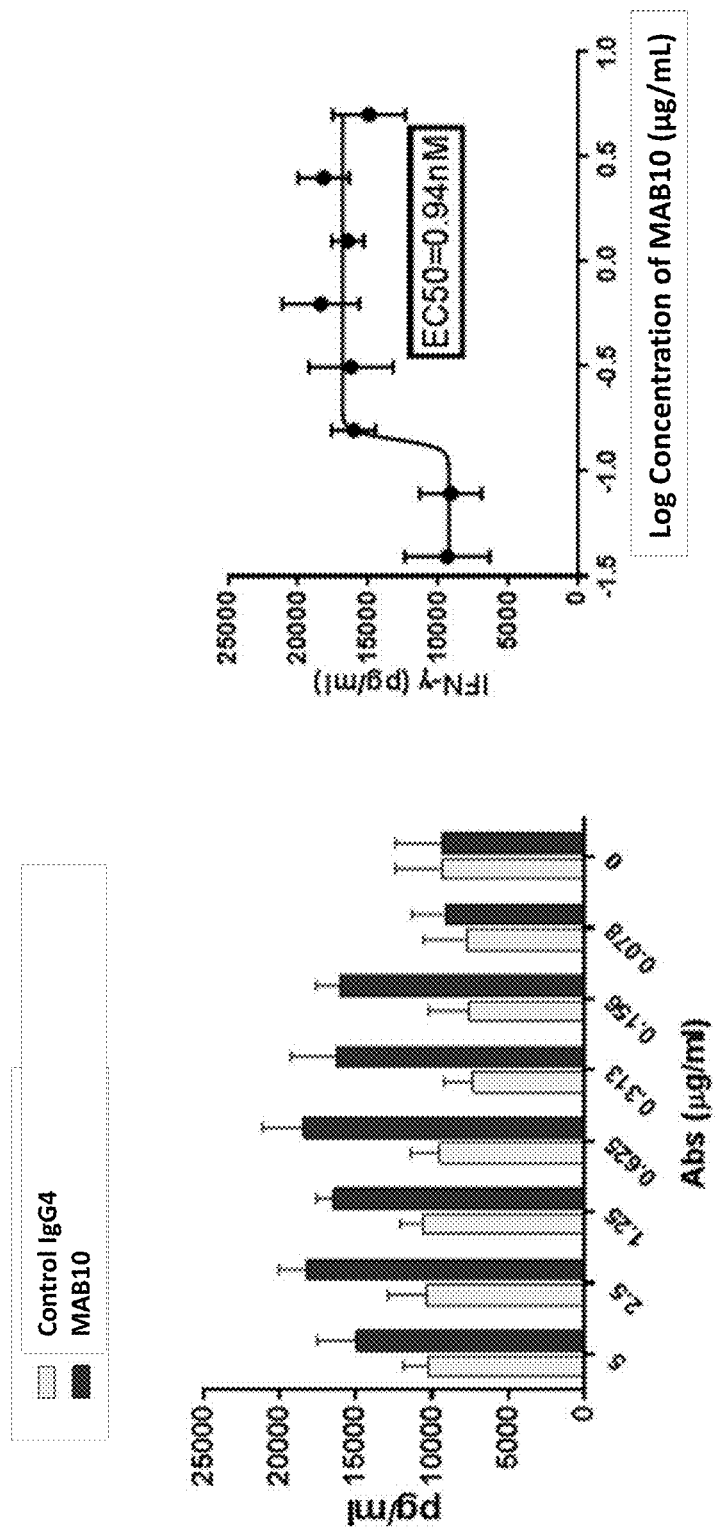
Figure 8C:
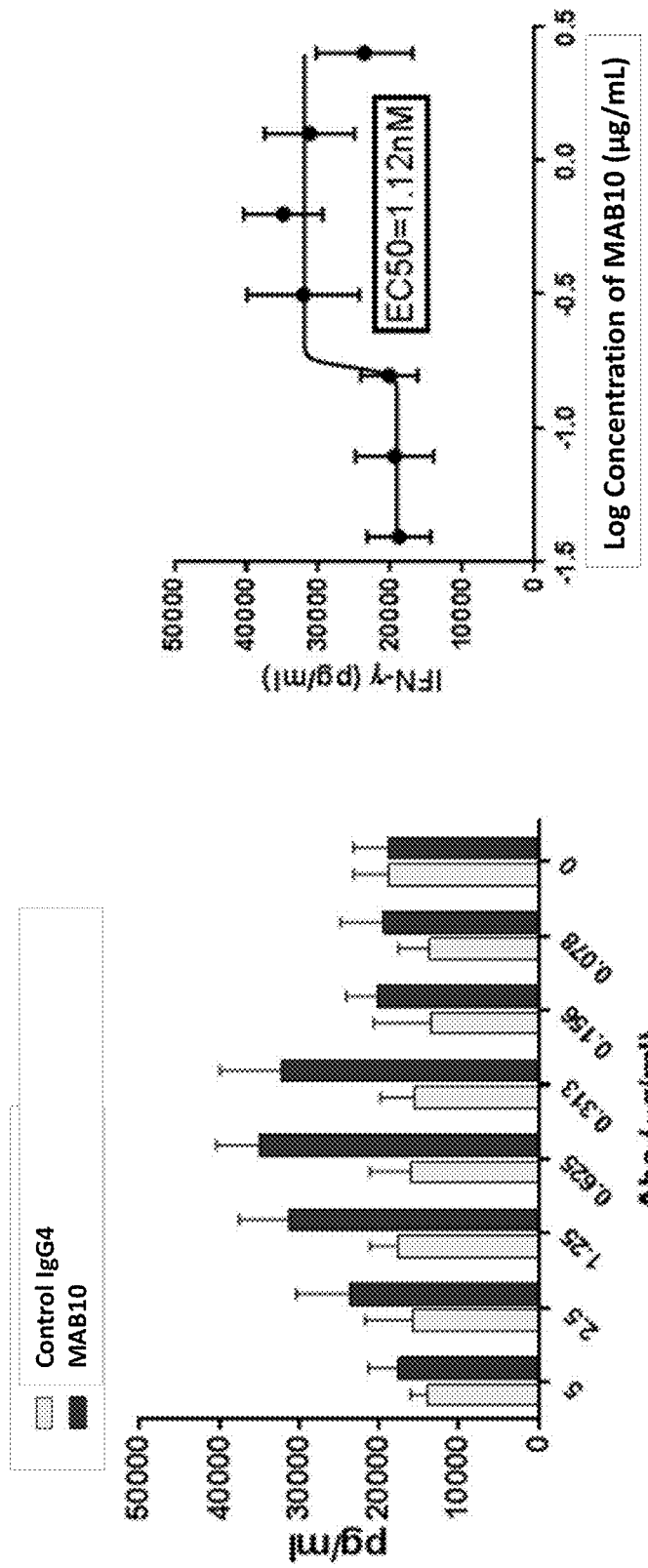

In these sub-optimally stimulated CD4+ T cells, MAB10 addition results in an upregulation of IFN-γ in a dose dependent manner in all three donors, demonstrating the anti-TIGIT antagonistic function of MAB10 (see FIG. 8A (Donor 1), FIG. 8B (Donor 2), and FIG. 8C (Donor 3)). IFN-γ production in cells treated with either MAB10 (black bars) or the IgG4 isotype control (light gray bars) is shown in the left panel of each Figure. $EC_{50}$ average value for MAB10 in this assay was calculated as 1.02 nM by determining the concentration of MAB10 required to induce 50% of the increase in IFN-γ signal (plotted in the right panel of each of FIGS. 8A-8C). The data are summarized in Table 17.

TABLE 17

Data Summary for Three Donors

| Donor | $EC_{10}$ (nM) | $EC_{50}$ (nM) | $EC_{90}$ (nM) |
|---|---|---|---|
| 1 | 0.37 | 1.00 | 2.72 |
| 2 | 0.85 | 0.94 | 1.04 |
| 3 | 1.05 | 1.12 | 1.19 |
| Average | 0.75 | 1.02 | 1.65 |

As described above, addition of MAB10 to sub-optimally stimulated human T cells antagonizes TIGIT function and induces the upregulation of pro-inflammatory cytokines (e.g., IFN-γ and TNF) when compared to a non-specific control IgG4 antibody. This effect is dose-dependent with an estimated $EC_{50}$ of 1 nM for the isolated CD4+ T cell assay. These data demonstrate in vitro efficacy of MAB10 in normal primary human T cells.

Example 10: Characterization of MAB10 in PD-1/TIGIT Combination Bioassay

PD-1 is an immune inhibitory receptor expressed on activated T cells and B cells and plays a critical role in regulating immune responses to tumor antigens and autoantigens. Engagement of PD-1 by either of its ligands, PD-L1 or PD-L2, on an adjacent cell inhibits T-cell receptor (TCR) signaling and TCR-mediated proliferation, transcriptional activation and cytokine production. Therapeutic antibodies and Fc fusion proteins designed to block the PD-1/PD-L1 interaction show promising results in clinical trials for the treatment of a variety of cancers.

The PD-1/TIGIT Combination Bioassay (Promega) is a biologically relevant mechanism of action-based assay that can be used to measure the potency and stability of antibodies and other biologics designed to block the PD-1/PD-L1 and TIGIT/CD155 interactions in combination. The assay consists of two genetically engineered cell lines: PD-1/TIGIT Effector Cells, which are Jurkat T-cells stably expressing human PD-1, TIGIT, and a luciferase reporter, and PD-L1/CD155 APC/CHO-K1 Cells, which are CHO-K1 cells stably expressing human PD-L1, human CD155, and a cell surface protein (in this case, TIGIT) designed to activate cognate TCRs in an antigen-independent manner.

When the two cell types are co-cultured, the PD-1/PD-L1 and TIGIT/CD155 interactions inhibit TCR signaling and luciferase activity. Addition of an antibody, e.g., an ABP disclosed herein or known in the art, that binds TIGIT and blocks ligand binding (e.g., CD155), in combination with a second antibody that blocks the interaction of PD-1 with its ligand (e.g., PD-L1), releases the inhibitory signal and results in TCR signaling and NFAT-mediated luciferase activity.

Figure 9A:
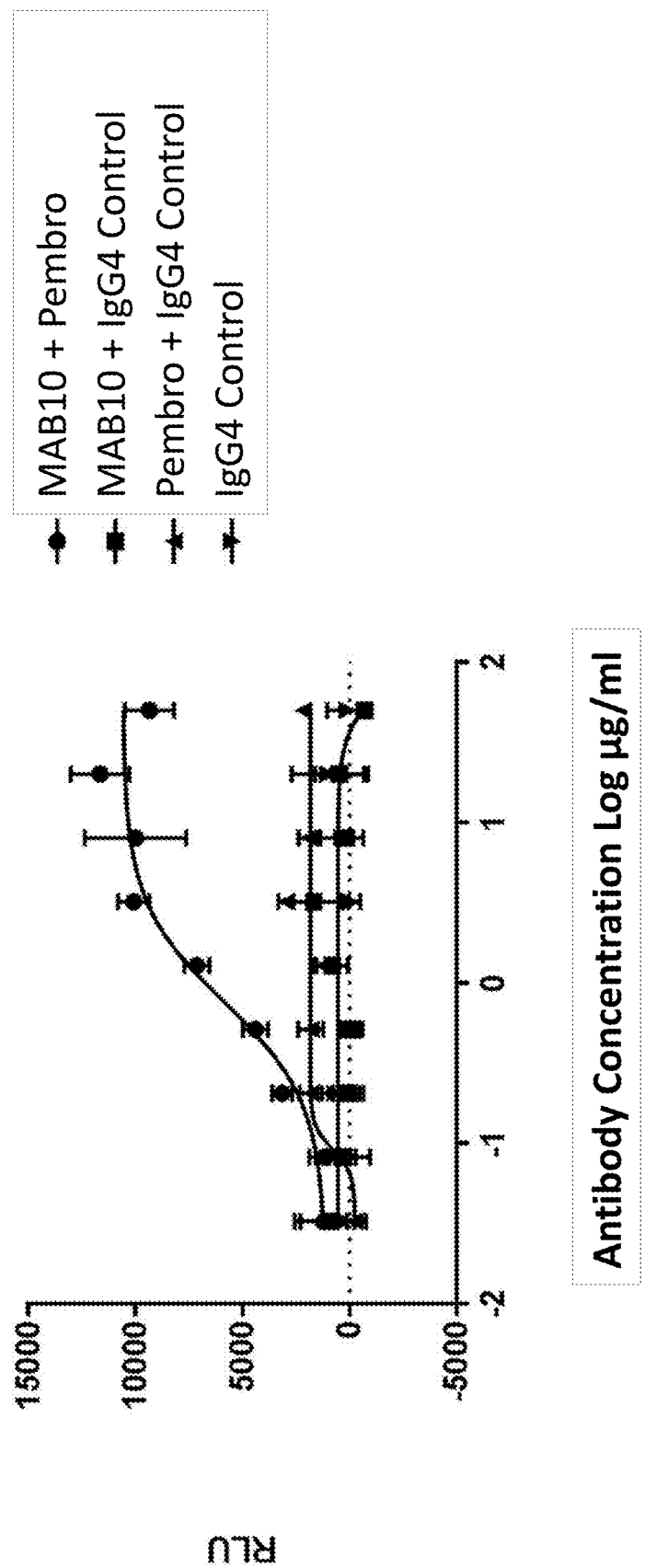
FIG. 9A shows the results of the assay in which a 1:1 ratio of MAB10 and pembrolizumab (anti-PD-1 antibody) were used in a mechanism-of-action based PD-1/TIGIT Combination Bioassay. Concentrations for each antibody were 25, 10, 4, 1.6, 0.64, 0.256, 0.1024, 0.04096, and 0.016384 µg/ml. An untargeted IgG4 was used as a control.

FIG. 9A shows the results of the assay in which a 1:1 ratio of MAB10 and pembrolizumab (anti-PD-1 antibody) was used. Concentrations for each antibody were 25, 10, 4, 1.6, 0.64, 0.256, 0.1024, 0.04096, and 0.016384 µg/ml. An untargeted IgG4 was used as a control. As shown in the Figure, only the combination of MAB10 and pembrolizumab (EC$_{50}$ of 5.06 nM) blocked binding sufficiently to induce luciferase activity in the Jurkat cells. Neither the IgG4 control alone or the IgG4+MAB10 combination induced luciferase activity.

Figure 9B:
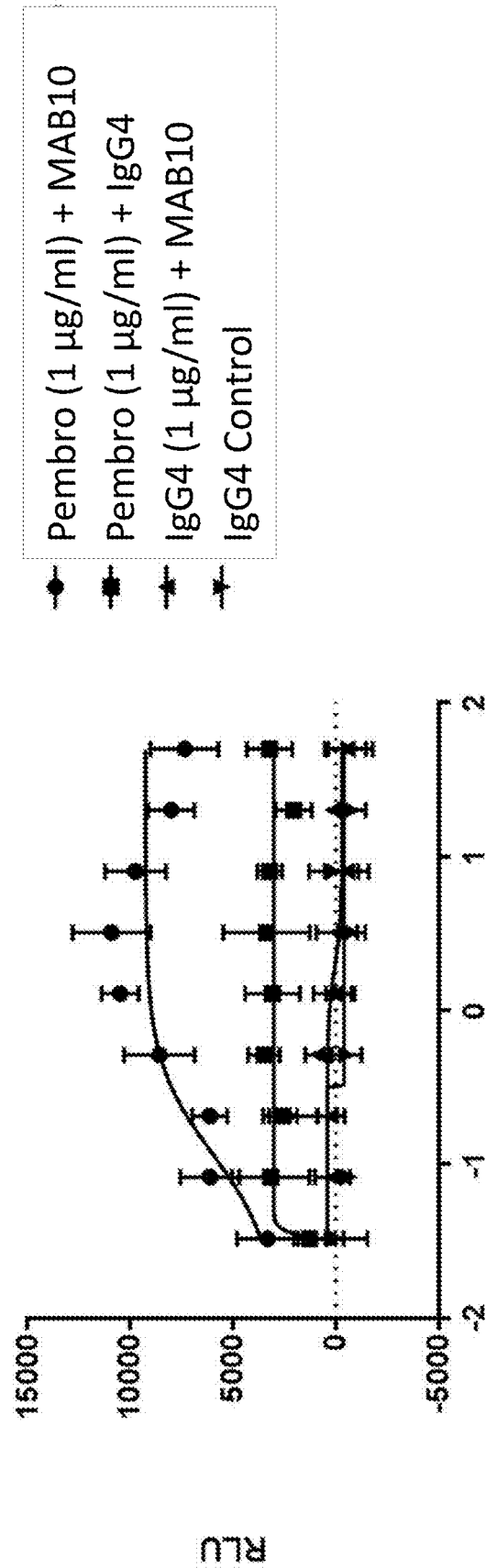
FIG. 9B shows the results of the assay with a fixed dose (1 µg/ml) of pembrolizumab (or IgG4 control) and a varying dose of MAB10 (50, 20, 8, 3.2, 1.28, 0.512, 0.2048, 0.08192, and 0.032768 µg/ml).

The assay was then repeated with a 1 μg/ml fixed dose of pembrolizumab (and a 1 μg/ml fixed dose of the IgG4 control) and a varying dose of MAB10 (50, 20, 8, 3.2, 1.28, 0.512, 0.2048, 0.08192, and 0.032768 μg/ml). As shown in FIG. 9B, while the fixed dose of pembrolizumab resulted in a low level of activation of luciferase induction, the combination of pembrolizumab and MAB10 was much more effective at induction of luciferase, with an EC$_{50}$ of 0.78 nM. As in FIG. 9A, neither the IgG4 control alone or the IgG4+MAB10 combination induced luciferase activity.

Example 11: Combination Therapy of CMV+ T-Cells with MAB10 and Pembrolizumab

A lymphoproliferation assay was used to test for T-cell responses in cytomegalovirus positive (CMV+) T-cells. PBMCs from individual donors that have been screened for CMV antigen reactivity were purchased from Astarte Biologics (Bothell, Wash.). Cell lysates from CMV-infected cells were also purchased from Astarte Biologics. The PBMCs were plated and the antigen-specific stimulation is performed by the addition of cell lysate, which stimulates the CMV+ T-cells in the sample. MAB10, an IgG4 control, and/or the anti-PD-1 antibody pembrolizumab were added. Cells were cultured for five days, and the supernatants were collected and analyzed for the production of the effector cytokine TNF. Further data were collected performing intracellular cytokine staining for other effector molecules including IL-2, IFN-γ, perforin and granzyme-B.

Figure 10A:
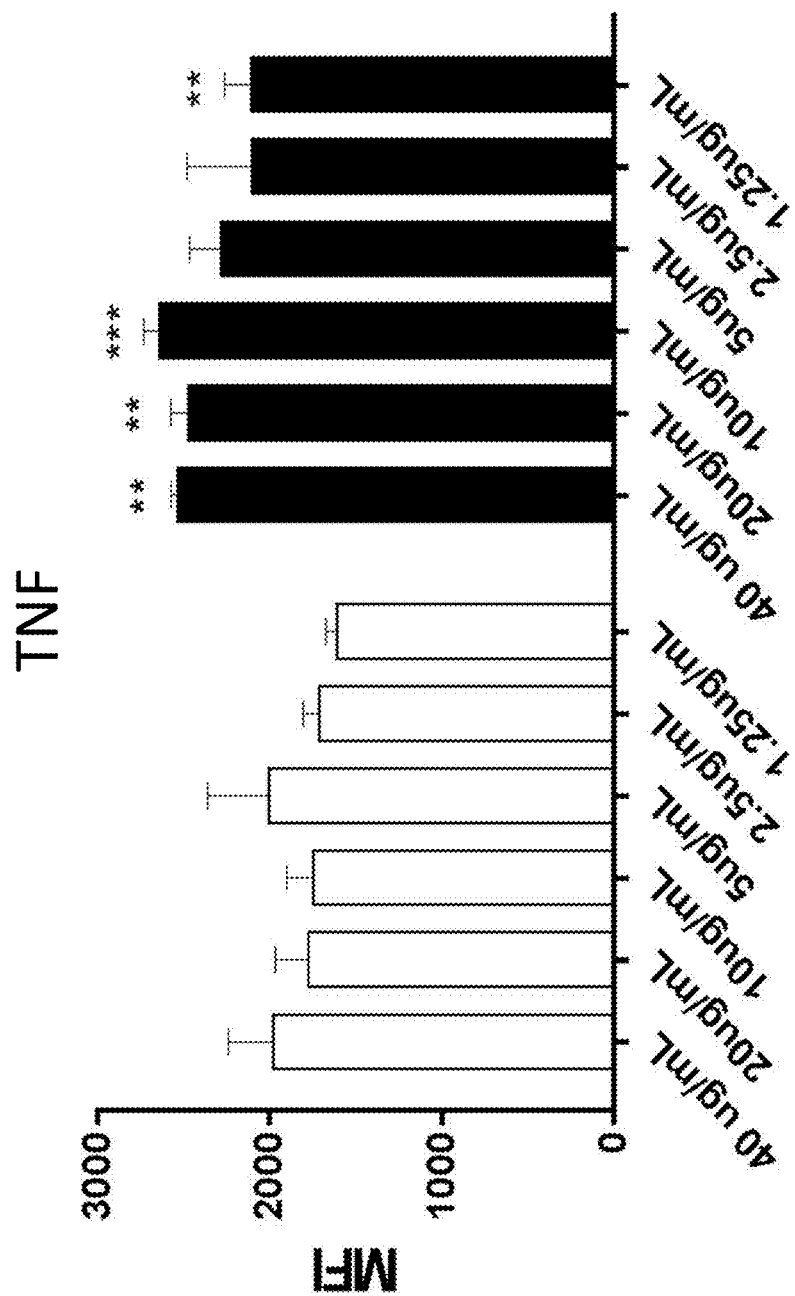
Figure 10C:
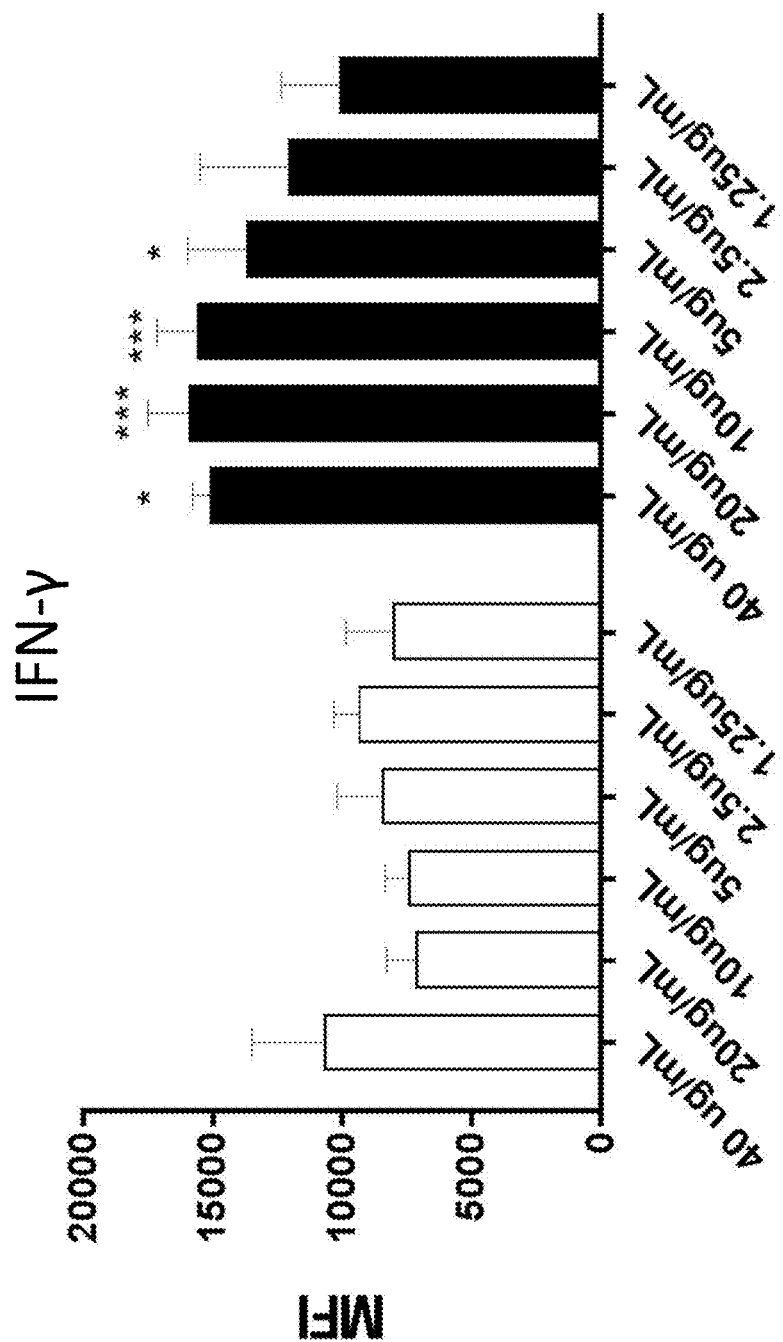
Figure 10D:
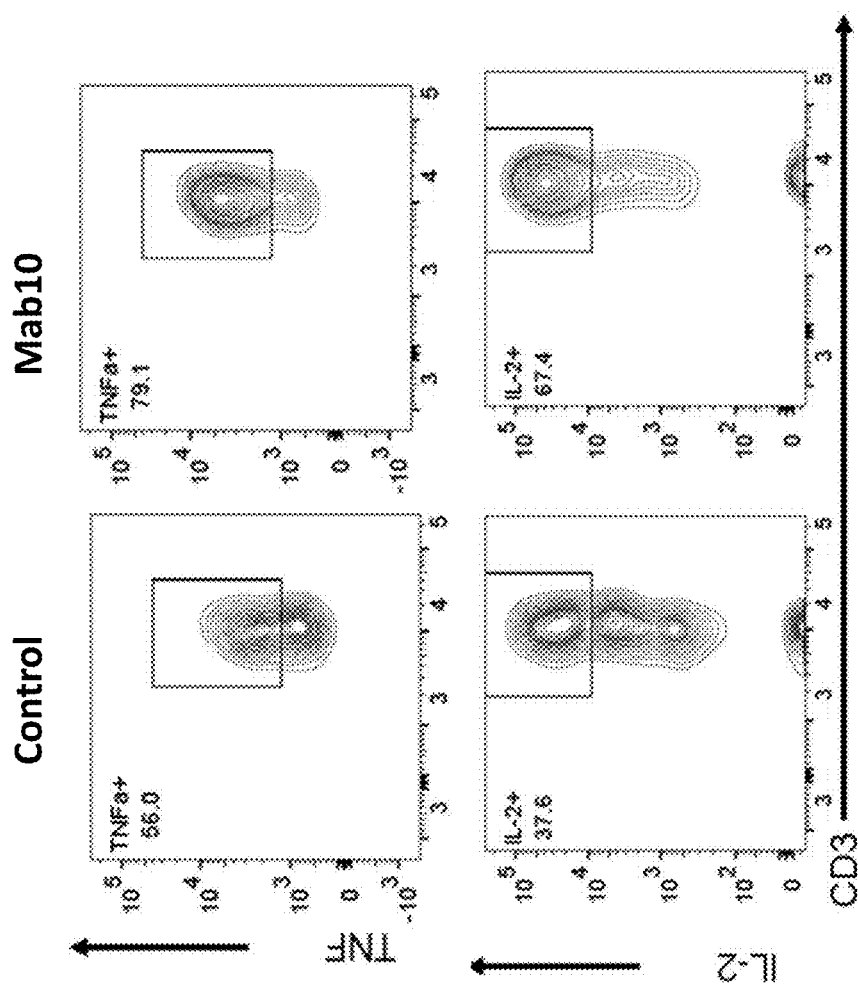

Cells from a single donor (Donor 1) were stimulated and cultured as described above. As shown in FIG. 10, by gating on CD4+ cells, incubation with MAB10 (black bars) increases the production of the effector cytokines in a dose-dependent matter, as measured by intracellular staining, including TNF (FIG. 10A), IL-2 (FIG. 10B), and IFN-γ (FIG. 10C) to a greater extent than cells incubated with the IgG4 control (white bars). Incubation with MAB10 also increases the proportion of antigen-specific activated CD4+ T-cells, as shown in FIG. 10D, in which cells that were treated with 20 μg/ml of the IgG4 control or MAB10 were analyzed by FACS by expression of CD3 (a marker of mature T-cells) and expression of TNF and IL-2.

Figure 11A:
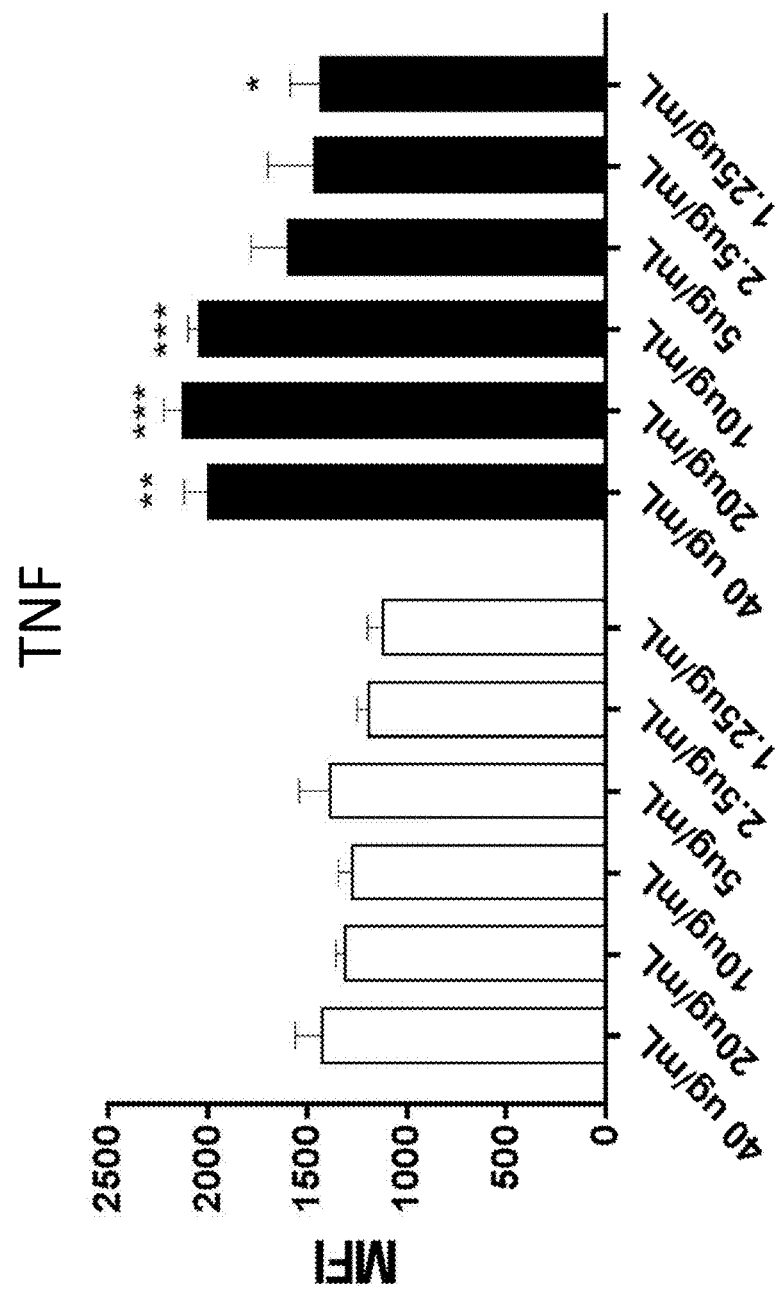
FIGS. 11A-11D are a series of graphs similar to FIG. 10, but using CD8+ cells, and show the production of TNF (FIG. 11A), perforin (FIG. 11B), and granzyme B (FIG. 11C) by such cells treated with MAB10 or the IgG4 control.
Figure 11B:
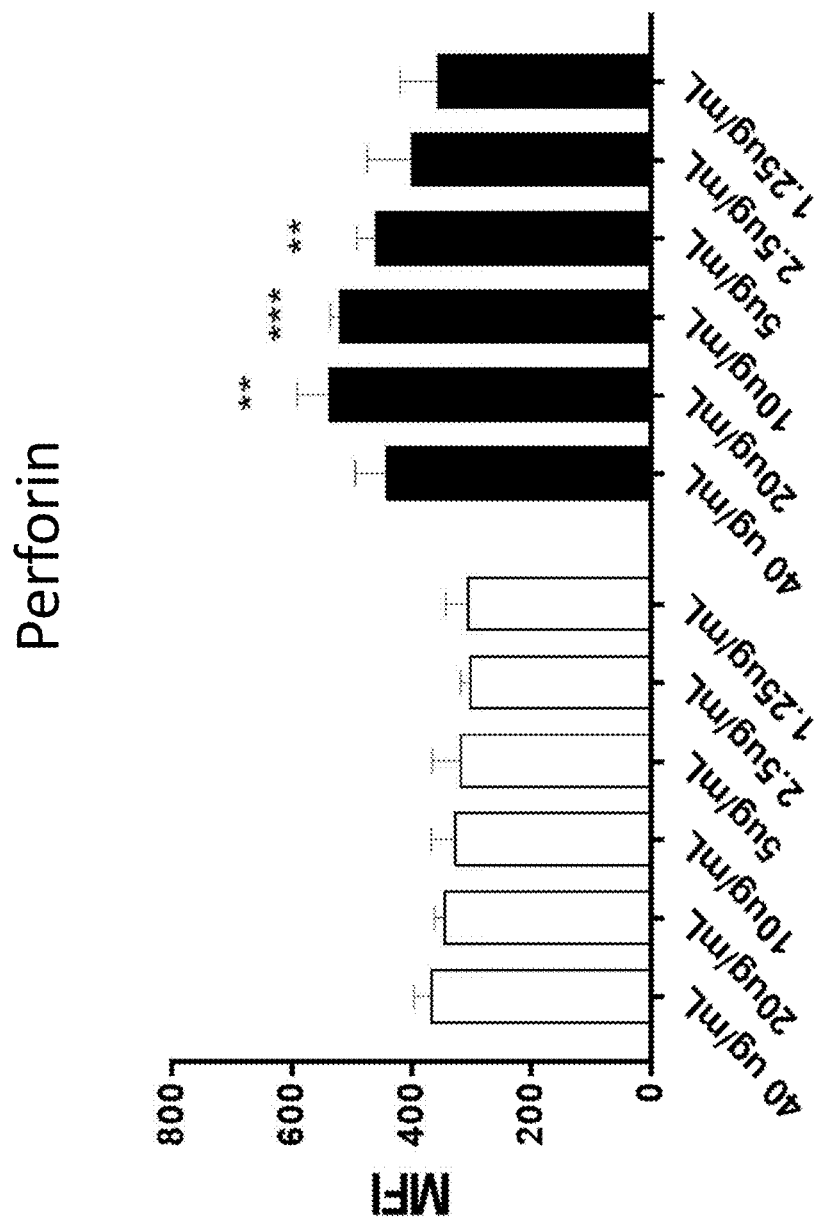
Figure 11C:
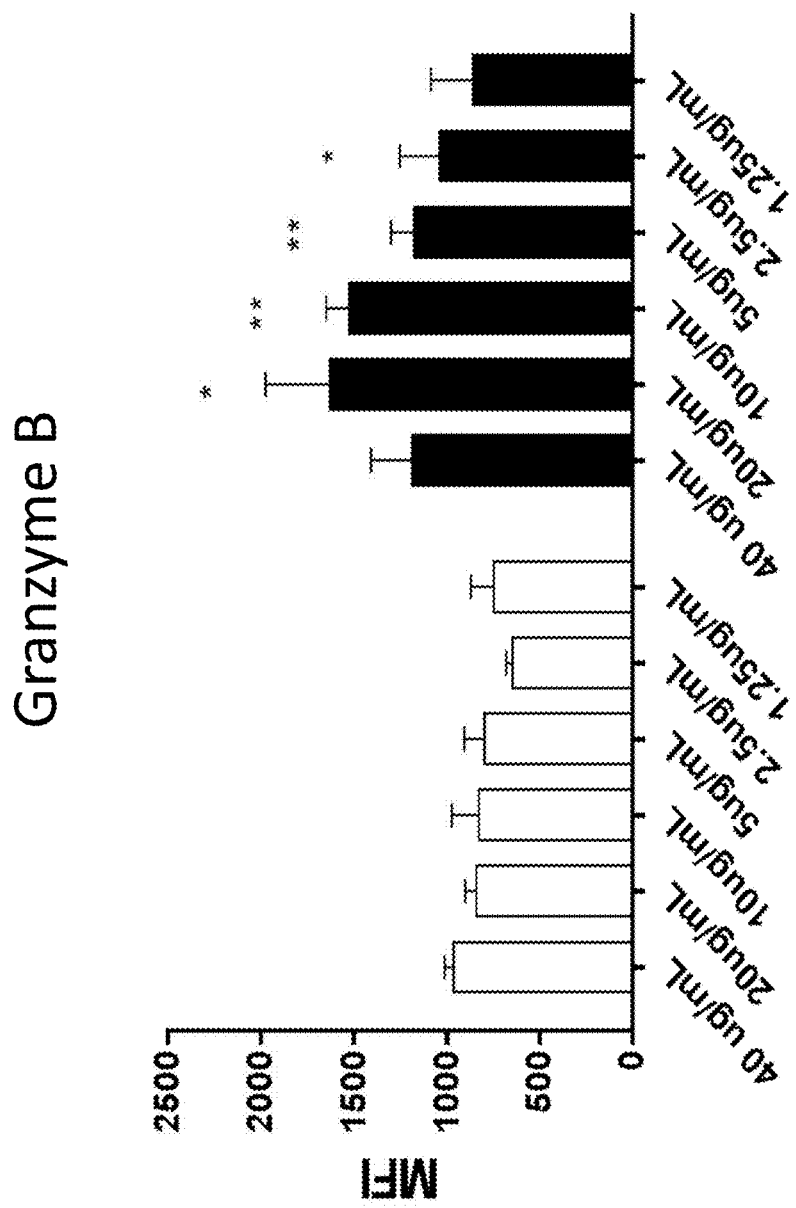
Figure 11D:
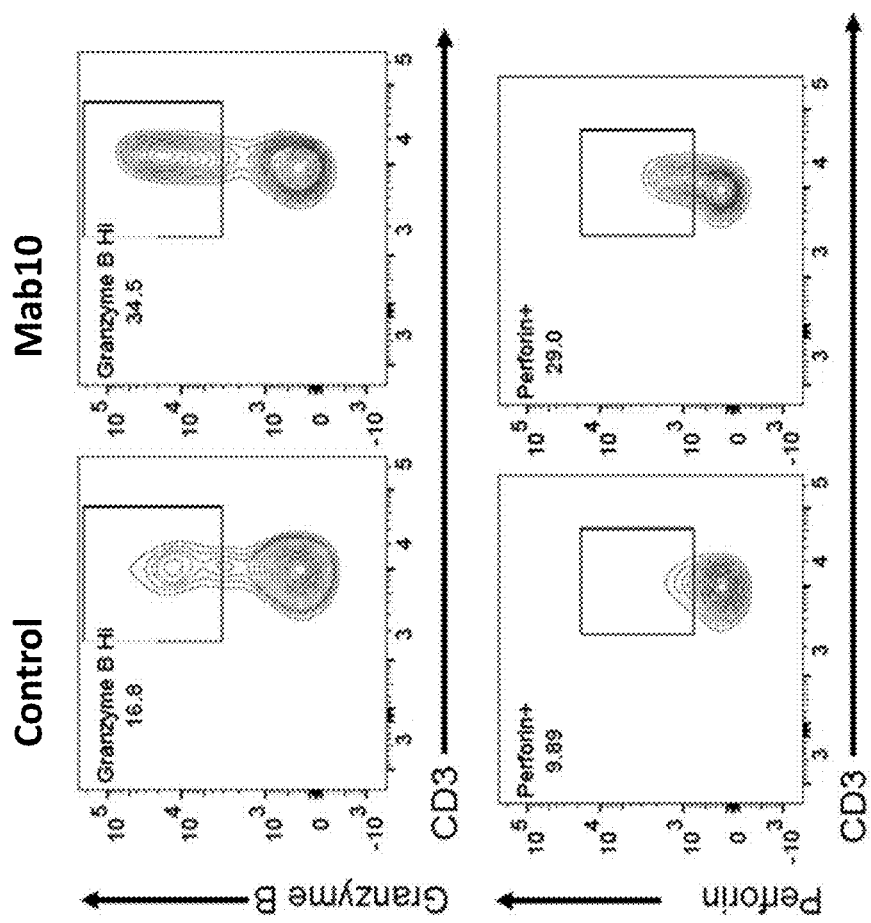

Similar results were obtained by gating on CD8+ cells. As shown in FIG. 11, on gated CD8+ cells, incubation with MAB10 (black bars) increases the production of the effector cytokines in a dose-dependent matter, including TNF (FIG. 11A), perforin (FIG. 11B), and granzyme B (FIG. 11C) compared to cells incubated with the IgG4 control (white bars). Perforin and granzyme B are markers of activated cytotoxic T-lymphocytes. Incubation with MAB10 also increases the proportion of antigen-specific activated CD8+ T-cells, as shown in FIG. 11D. Cells that were treated with 20 jgg/ml of the IgG4 control or MAB10 were analyzed by FACS by expression of CD3 and expression of perforin and granzyme B.

Figure 12A:
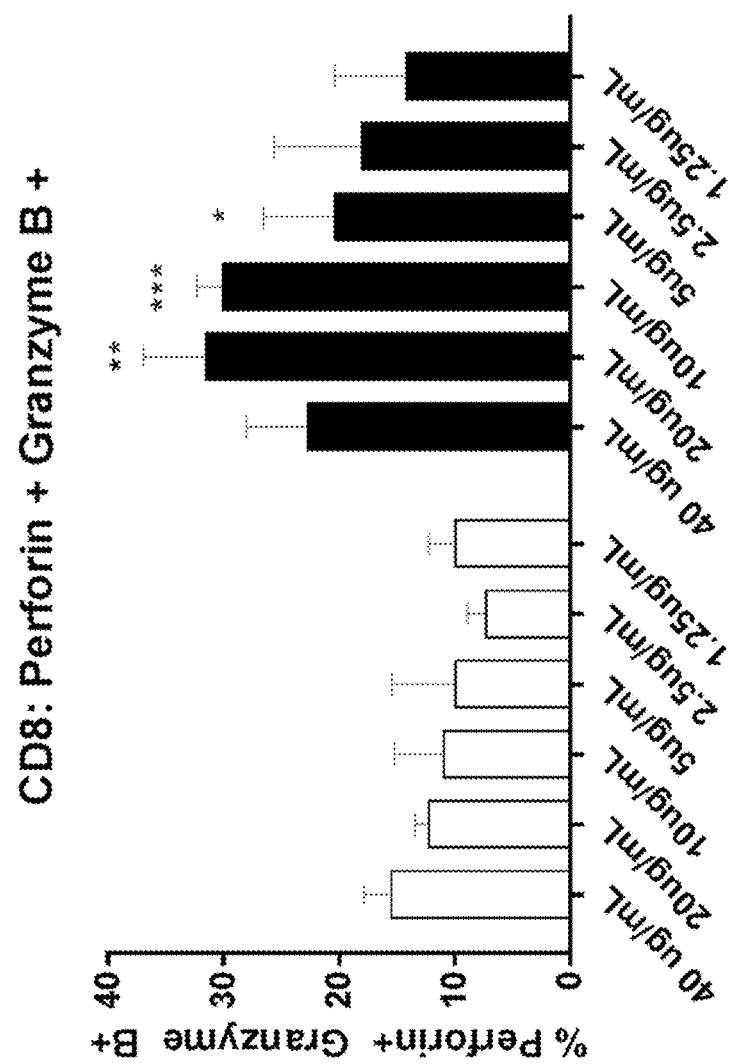
FIGS. 12A-12D show the results of treatment of cells from the same donor, wherein blockade by MAB10 amplifies CMV-specific CD8+ T-cell responses. Cells were incubated with a range of concentrations of MAB10 (black bars) or the IgG4 control (white bars), and the percentage of double positive population perforin+granzyme B+(FIG. 12A) or IFN-γ+TNF+(FIG. 12C) was analyzed. Statistical differences were calculated between MAB10 and IgG4 control groups (same concentration treatments) using Student's T test (*=p<0.05, =p<0.01, *=p<0.005, ****=p<0.001).
Figure 12B:
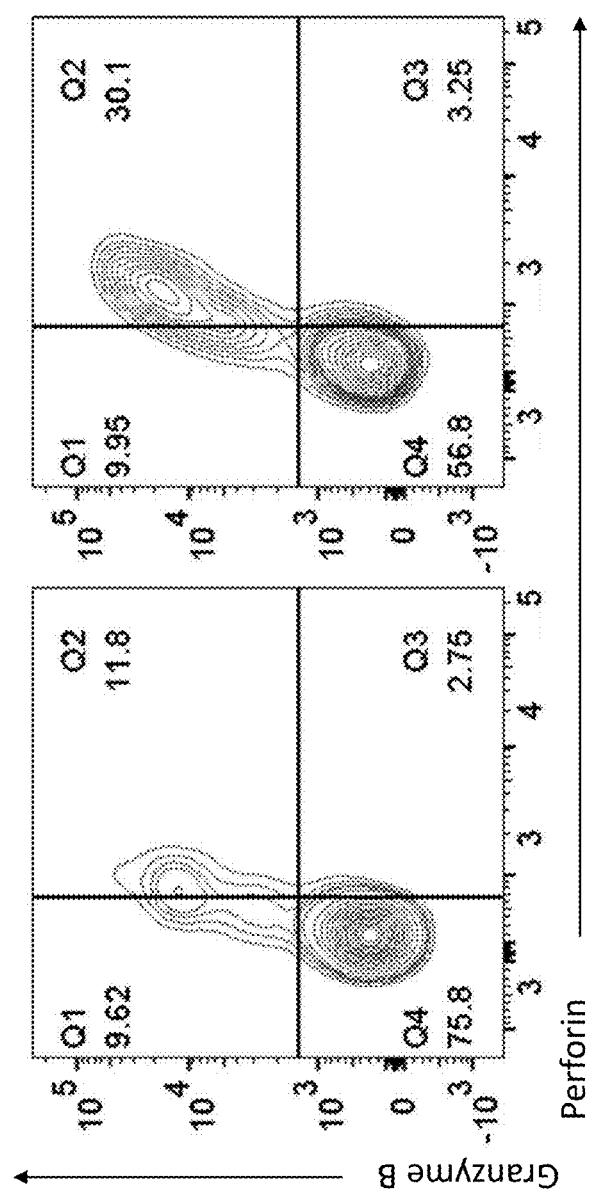
Figure 12C:
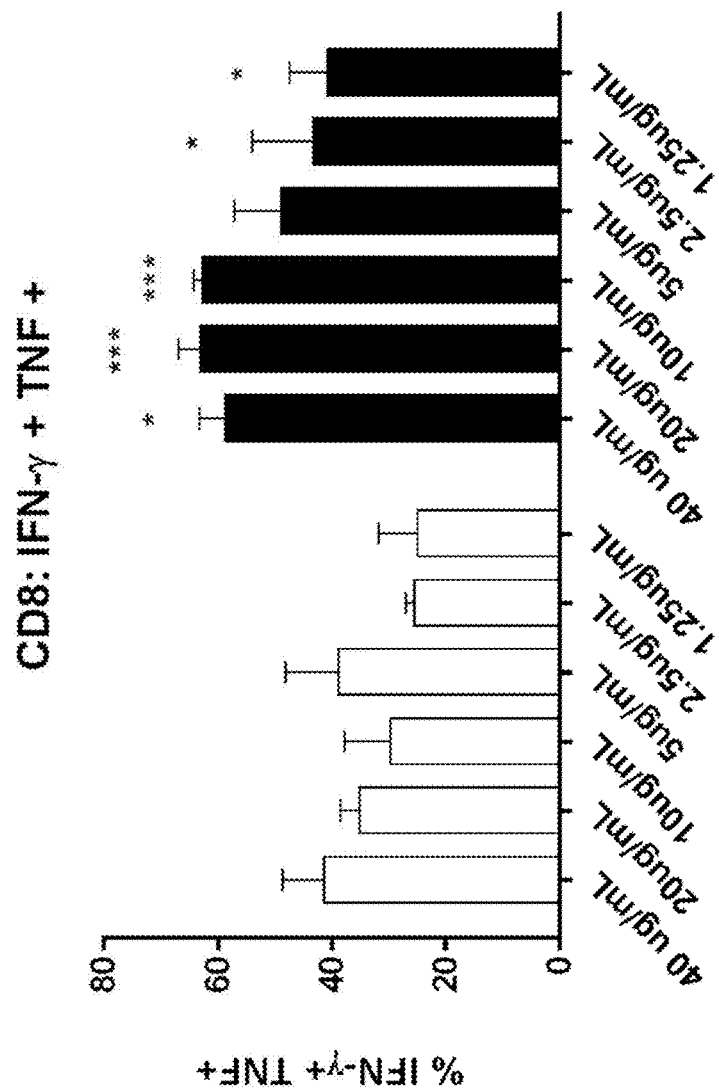
Figure 12D:
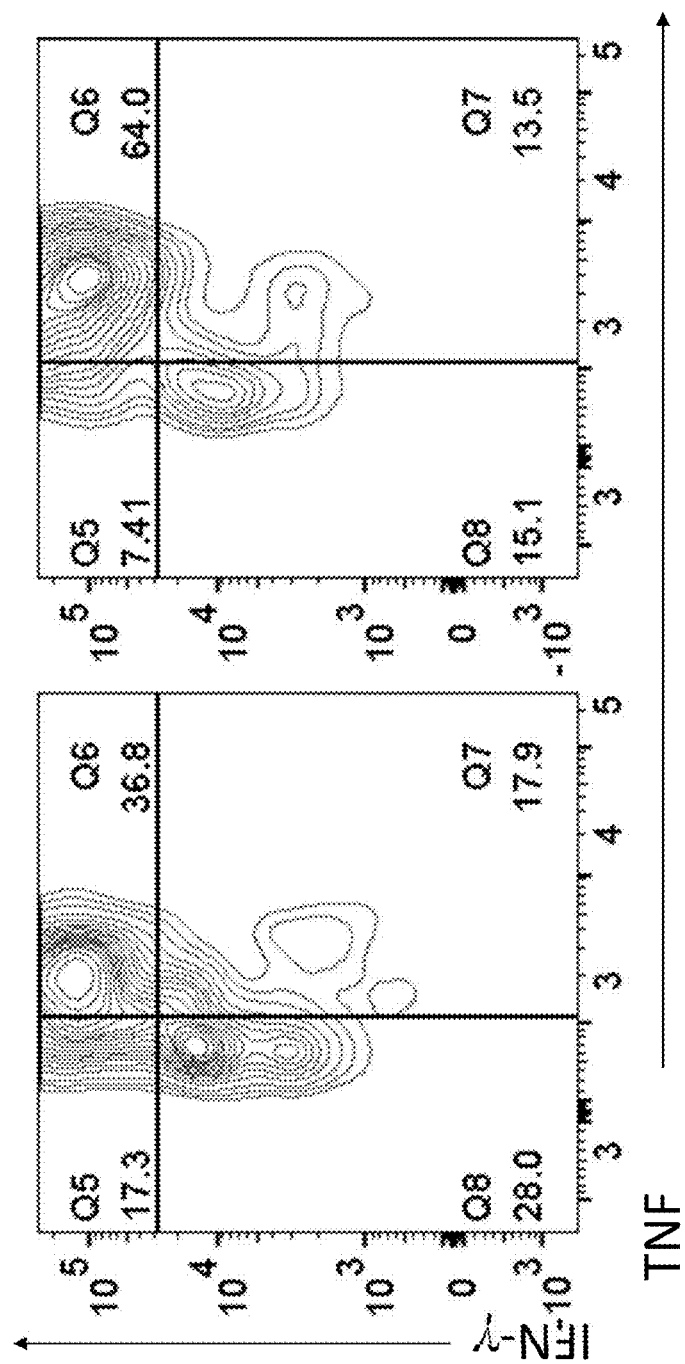

Cells from the same donor were used in a similar set of experiments to show that blockade by MAB10 amplifies CMV-specific CD8+ T-cell responses. Cells were incubated with a range of concentrations of MAB10 (black bars) or the IgG4 control (white bars) and the percentage of double positive population perforin+granzyme B+(FIG. 12A) or IFN-γ+TNF+(FIG. 12C) was analyzed. FIG. 12B (perforin+ granzyme B+ analysis) and 12D (IFN-γ+TNF+ analysis) show the proportion of double positive cells comparing cells treated with 20 μg/ml of the control antibody (left panels) or 20 μg/ml of MAB10 (right panels). The cells treated with MAB10 showed a much greater production of effector cytokines compared with control-treated cells.

Figure 13:
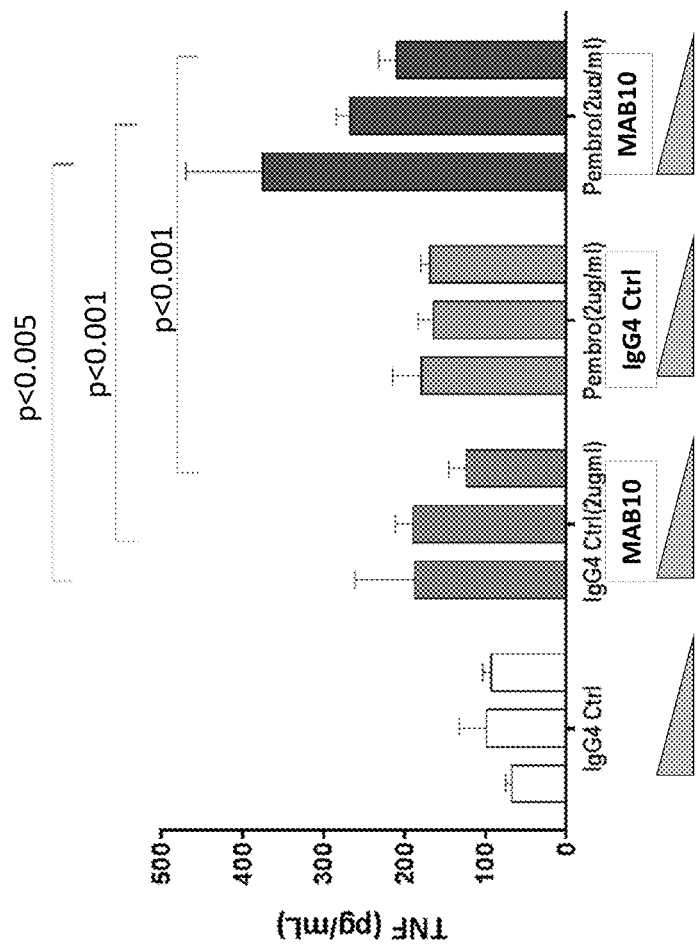
FIG. 13 is a graph showing the combinatorial effect of MAB10 and the PD-1 antibody pembrolizumab on cells from the same donor as used for FIGS. 10-12. Cells were stimulated with CMV lysates and treated with 2 µg/ml pembrolizumab or control IgG4, and 10, 20, or 40 µg/ml control antibody or MAB10, and production of TNF was measured. Four groups of cells were tested, and treated with IgG4 control (white bars, left most group), a constant amount of IgG4 control and a titration of MAB10 (dark gray bars, second group from left), a constant amount of pembrolizumab and a titration of IgG4 control (light gray bars, second group from right), or a constant amount of pembrolizumab and a titration of MAB10 (black bars, right hand group).

The combinatorial effect of MAB10 and the PD-1 antibody pembrolizumab was tested using the same donor as described above. Cells were stimulated with CMV lysates as described above and treated with 2 μg/ml pembrolizumab or control IgG4, and 10, 20, or 40 μg/ml control antibody or MAB10, and production of TNF in the supernatant was measured. As shown in FIG. 13, four groups of cells were tested, treated with IgG4 control (white bars, left most group), a constant amount of IgG4 control and a titration of MAB10 (dark gray bars, second group from left), a constant amount of pembrolizumab and a titration of IgG4 control (light gray bars, second group from right), or a constant amount of pembrolizumab and a titration of MAB10 (black bars, right hand group). The combination of pembrolizumab and MAB10 increased the production of TNF above the effect observed with the single agents.

Figure 14A:
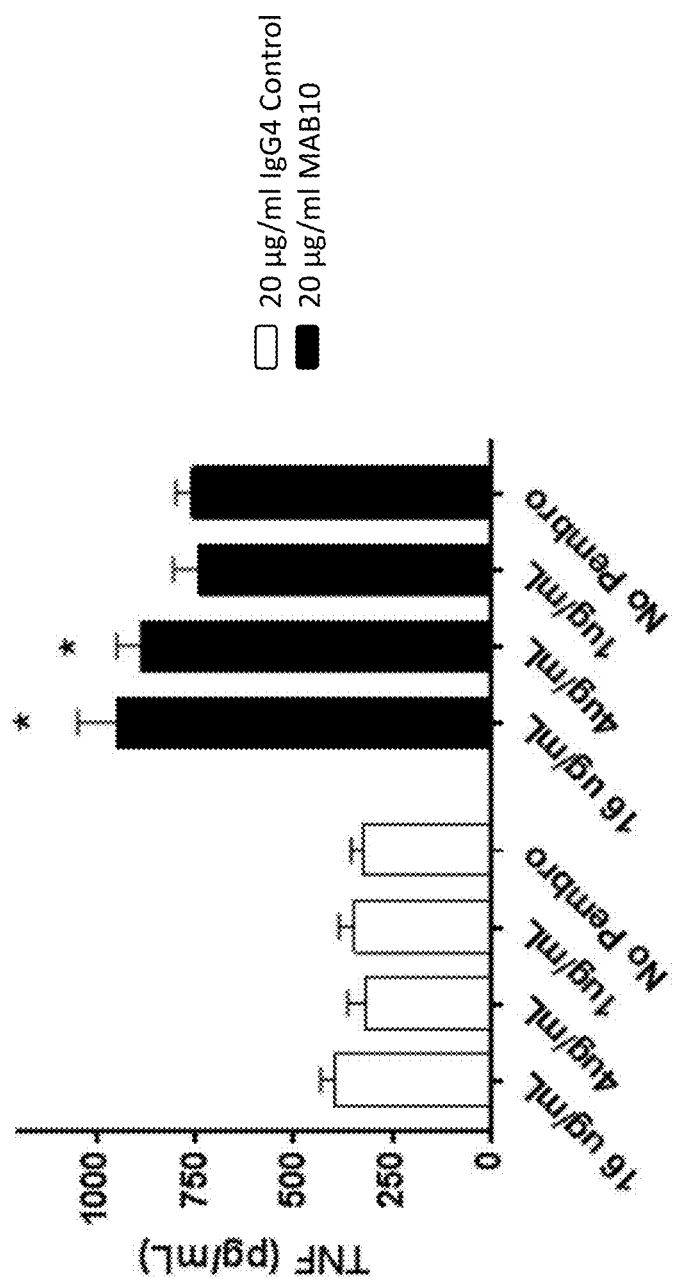
FIGS. 14A-14C are a series of graphs showing the effect of MAB10+pembrolizumab treatment on cells from three different donors. Cells were stimulated with 0.1 µg/ml of CMV lysate and treated with 20 µg/ml of MAB10 or 20 µg/ml of control IgG4 antibody and a titration of pembrolizumab, then the production of TNF was measured.
Figure 14B:
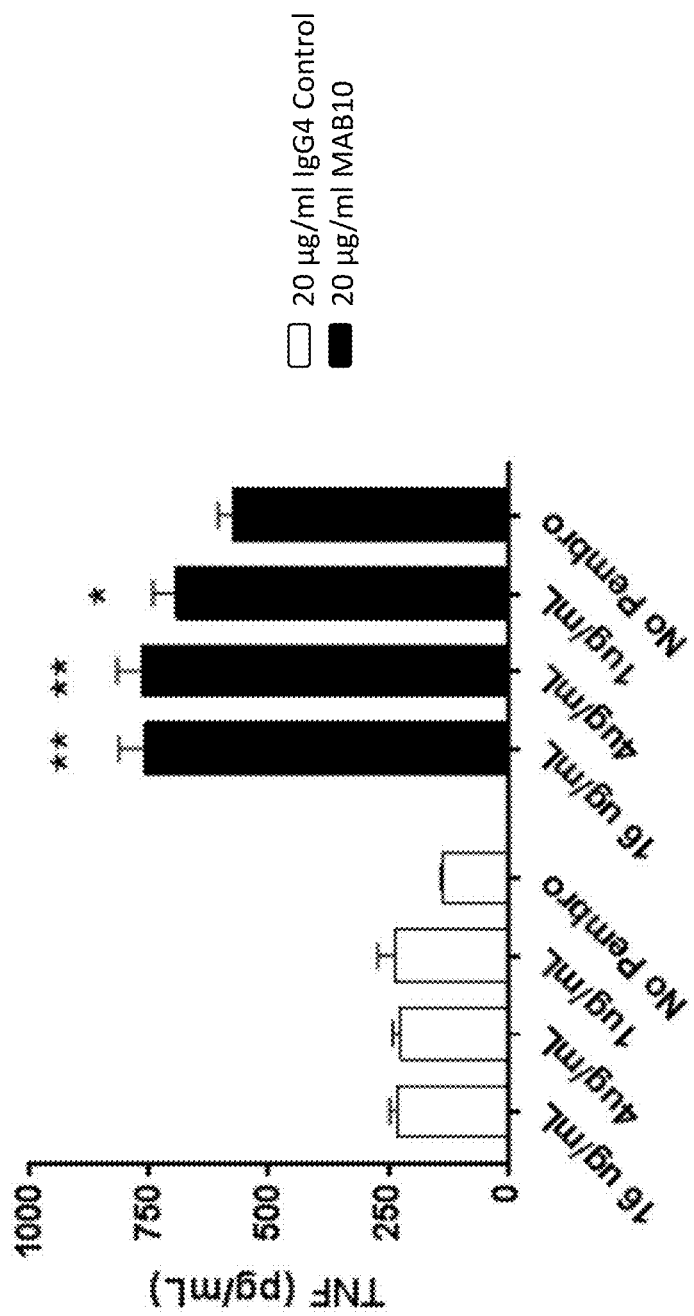
Figure 14C:
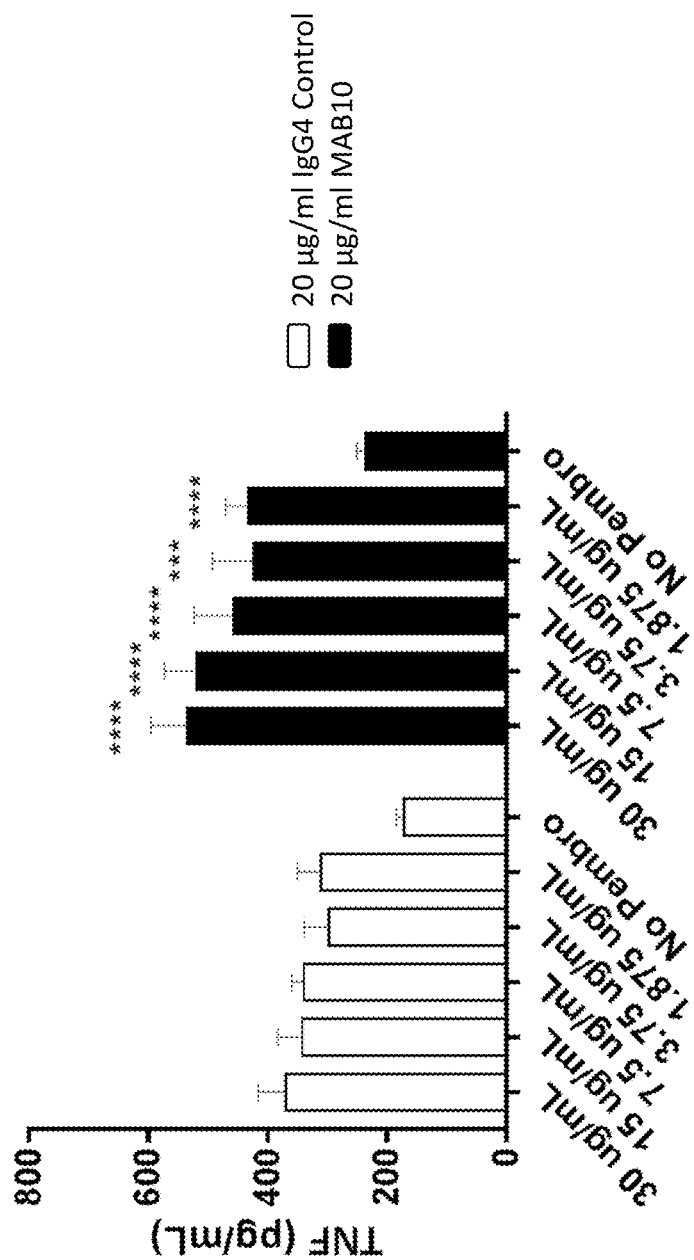

The combination was again tested in three different donors, using the assay described above. Cells were stimulated with CMV lysate and treated with 20 μg/ml of MAB10 or 20 μg/ml of control IgG4 antibody and a titration of pembrolizumab, and production of TNF was measured. As shown in FIG. 14A (Donor 1), FIG. 14B (Donor 2), and FIG. 14C (Donor 3), the addition of MAB10 (black bars), alone or in combination with increasing concentrations of pembrolizumab, results in greater production of TNF compared to the control antibody+pembrolizumab group (white bars). Additionally, MAB10 (black bars) in combination with pembrolizumab also resulted in increased activation compared to MAB10 alone. Statistical differences were calculated between MAB10 alone and MAB10+pembrolizumab groups using Student T test analysis (*=$p<0.05$, =$p<0.01$, *=$p<0.005$, ****=$p<0.001$)

Taken together, the data presented in the Example demonstrate a clear, dose-dependent effect of MAB10 as a single agent in antigen-specific recall assays. In addition, the data show increased efficacy when combining MAB10 and pembrolizumab in multiple donors, indicating the value of the ABPs disclosed herein and PD-1 inhibitors or PD-L1 inhibitors as combination therapies.

INCORPORATION BY REFERENCE

The entire disclosures of all patent and non-patent publications cited herein are each incorporated by reference in their entireties for all purposes.

Other Embodiments

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

APPENDIX A

SEQUENCE REFERENCE TABLE

| SEQ ID NO | Molecule | Region | Sequence |
|---|---|---|---|
| 1 | hTIGIT | | MRWCLLLIWAQGLRQAPLASGMMTGTIETTGNISAE KGGSIILQCHLSSTTAQVTQVNWEQQDQLLAICNAD LGWHISPSFKDRVAPGPGLGLTLQSLTVNDTGEYFCI YHTYPDGTYTGRIFLEVLESSVAEHGARFQIPLLGAM AATLVVICTAVIVVVALTRKKKALRIHSVEGDLRRK SAGQEEWSPSAPSPPGSCVQAEAAPAGLCGEQRGED CAELHDYFNVLSYRSLGNCSFFTETG |
| 2 | cTIGIT | | MRWCLFLIWAQGLRQAPLASGMMTGTIETTGNISAK KGGSVILQCHLSSTMAQVTQVNWEQHDHSLLAIRN AELGWHIYPAFKDRVAPGPGLGLTLQSLTMNDTGEY FCTYHTYPDGTYRGRIFLEVLESSVAEHSARFQIPLL GAMAMMLVVICIAVIVVVLARKKKSLRIHSVESGL QRKSTGQEEQIPSAPSPPGSCVQAEAAPAGLCGEQQ GDDCAELHDYFNVLSYRSLGSCSFFTETG |
| 3 | mTIGIT | | MHGWLLLVWVQGLIQAAFLATGATAGTIDTKRNIS AEEGGSVILQCHFSSDTAEVTQVDWKQQDLLAIYS VDLGWHVASVFSDRVVPGPSLGLTFQSLTMNDTGE YFCTYHTYPGGIYKGRIFLKVQESSVAQFQTAPLGGT MAAVLGLICLMVTGVTVLARKKSIRMHSIESGLGRT EAEPQEWNLRSLSSPGSPVQTQTAPAGPCGEQAEDD YADPQEYFNVLSYRSLESFIAVSKTG |
| 4 | MAB1-IgG4 | VH | QLQLQESGPGLVKPSETLSLTCTVSGGSITSSSYYWG WIRQPPGKGLEWIGSIYYSGATFYNPSLKSRVTISVD TSKNQFSLKLSSVTAADTAVYYCARDANYYGSAWA FDPWGQGTLVTVSS |
| 5 | MAB2-IgG4 | VH | QLQLQESGPGLVKPSETLSLTCTVSGGSISSSKYYWG WIRQPPGKGLEWIGSIYYSGSTFYNPSLKSRVTISVDT SKNQFSLKLSSVTAADTAVYYCARDANYYGSAWAF DPWGQGTLVTVSS |
| 6 | MAB3-IgG4 | VH | QLQLQESGPGLVKPSETLSLTCTVSGGSISSTSHYWG WIRQPPGKGLEWIGSIYYSGSTFYNPSLKSRVTISVDT SKNQFSLKLSSVTAADTAVYYCARDANYYGSAWAF DPWGQGTLVTVSS |
| 7 | MAB4-IgG4 | VH | QLQLQESGPGLVKPSETLSLTCTVSGGSISSTSHYWG WIRQPPGKGLEWIGSIYYSGSTFYNPSLKSRVTISVDT SKNQFSLKLSSVTAADTAVYYCARDANYYGAWAF DPWGQGTLVTVSS |
| 8 | MAB5-IgG4 | VH | QLQLQESGPGLVKPSETLSLTCTVSGGSISSTSHYWG WIRQPPGKGLEWIGSIYYSGSTFYNPSLKGRVTISVD TSKNQFSLKLSSVTAADTAVYYCARDANYYGSAWA FDPWGQGTLVTVSS |
| 9 | MAB6-IgG4 | VH | QLQLQESGPGLVKPSETLSLTCTVSGGSIESGSYYWG WIRQPPGKGLEWIGSIYYSGGTYYNPSLKSRVTISVD TSKNQFSLKLSSVTAADTAVYYCARDGVLTLNKRSF DIWGQGTMVTVSS |
| 10 | MAB7-IgG4 | VH | QVQLQESGPGLVKPSQTLSLTCTVSGGSIESGVYYW GWIRQPPGKGLEWIGSIYYSGSTYYNPSLKSRVTISV DTSKNQFSLKLSSVTAADTAVYYCARDGVLTLNKRS FDIWGQGTMVTVSS |
| 11 | MAB8-IgG4 | VH | QLQLQESGPGLVKPSETLSLTCTVSGGSIASGSYYWG WIRQPPGKGLEWIGSIYYSGQTYYNPSLKSRVTISVD TSKNQFSLKLSSVTAADTAVYYCARDGVLTLNKRSF DIWGQGTMVTVSS |
| 12 | MAB9-IgG4 | VH | QVQLQESGPGLVKPSQTLSLTCTVSGGSIESGLYYW GWIRQPPGKGLEWIGSIYYSGSTYYNPSLKSRVTISV DTSKNQFSLKLSSVTAADTAVYYCARDGVLTLNKRS FDIWGQGTMVTVSS |
| 13 | MAB10-IgG4 | VH | QVQLQESGPGLVKPSQTLSLTCTVSGGSIESGLYYW GWIRQPPGKGLEWIGSIYYSGSTYYNPSLKSRATISV DTSKNQFSLKLSSVTAADTAVYYCARDGVLALNKR SFDIWGQGTMVTVSS |

APPENDIX A-continued

SEQUENCE REFERENCE TABLE

| SEQ ID NO | Molecule | Region | Sequence |
|---|---|---|---|
| 14 | MAB11-IgG4 | VH | QVQLQESGPGLVKPSQTLSLTCTVSGGSIESGLYYWGWIRQPPGKGLEWIGSIYYSGSTYYNPSLKSRVTISVDTSKNQFSLKLSSVTAADTAVYYCARDGVLALNKRSFDIWGQGTMVTVSS |
| 15 | MAB12-IgG4 | VH | QVQLQESGPGLVKPSQTLSLTCTASGGSIESGLYYWGWIRQPPGKGLEWIGSIYYSGSTYYNPSLKSRVTISVDTSKNQFSLKLSSVTAADTAVYYCARDGVLALNKRSFDIWGQGTMVTVSS |
| 16 | MAB13-IgG4 | VH | QVQLVQSGAEVKKPGASVKVSCKASGYTFGNYYMHWVRQAPGQGLEWMGIINPSLGLTSYAQKFQGRVTMTRDTSTSTVYMELSSLRSEDTAVYYCARGGRTTWIGAFDIWGQGTMVTVSS |
| 17 | MAB14-IgG4 | VH | QVQLVQSGAEVKKPGASVKVSCKASGYTFPAYYMHWVRQAPGQGLEWMGIINPSLGLTSYAQKFQGRVTMTRDTSTSTVYMELSSLRSEDTAVYYCARGGRTTWIGAFDIWGQGTMVTVSS |
| 18 | MAB15-IgG4 | VH | QVQLVQSGAEVKKPGASVKVSCKASGYTFREYYMHWVRQAPGQGLEWMGIINPSIGLTSYARKFQGRVTMTRDTSTSTVYMELSSLRSEDTAVYYCARGGRTTWIGAFDIWGQGTMVTVSS |
| 19 | MAB16-IgG4 | VH | QVQLVQSGAEVKKPGASVKVSCKASGYTFREYYMHWVRQAPGQGLEWMGIINPSIGLTSYARKFQGRVTMTRDTSTSTVYMELSSLRSEDTAVYYCARGGRTTWIGALDIWGQGTMVTVSS |
| 20 | MAB17-IgG4 | VH | QVQLVQSGAEVKKPGASVKVSCKASGYTFPAYYIHWVRQAPGQGLEWMGIINPSLGLTSYARKFQGRVTMTRDTSTSTVYMELSSLRSEDTAVYYCARGGRTTWIGALDIWGQGTMVTVSS |
| 21 | MAB18-IgG4 | VH | QVQLVQSGAEVKKPGASVKVSCKASGYTFPAYYMHWVRQAPGQGLEWMGIINPSLGLTSYARKFQGRVTMTRDTSTSTVYMELSSLRSEDTAVYYCARGGRTTWIGAFDIWGQGTMVTVSS |
| 22 | MAB19-IgG4 | VH | QVQLVQSGAEVKKPGASVKVSCKASGYTFTSHYMGWVRQAPGQGLEWMGVINPSMGATSYAQKFQGRVTMTRDTSTSTVYMELSSLRSEDTAVYYCARLHVSGSYYPAYLDYWGQGTMVTVSS |
| 23 | MAB20-IgG4 | VH | QVQLVQSGAEVKKPGASVKVSCKASGYTFTSHYMGWVRQAPGQGLEWVGIINPSMGATSYAQKFQGRVTMTRDTSTSTVYMELSSLRSEDTAVYYCARLHVSGSYYPAYLDYWGQGTMVTVSS |
| 24 | MAB21-IgG4 | VH | QVQLVQSGAEVKKPGASVKVSCKASGYTFTSHYMGWVRQAPGQGLEWMGIINPSMGATSYTQKFRGRVTMTRDTSTSTVYMELSSLRSEDTAVYYCARLHVSGSYYPAYLDYWGQGTMVTVSS |
| 25 | MAB1-IgG4 | VL | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK |
| 25 | MAB2-IgG4 | VL | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK |
| 25 | MAB3-IgG4 | VL | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK |
| 25 | MAB4-IgG4 | VL | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK |
| 25 | MAB5-IgG4 | VL | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK |

APPENDIX A-continued

SEQUENCE REFERENCE TABLE

| SEQ ID NO | Molecule | Region | Sequence |
|---|---|---|---|
| 26 | MAB6-IgG4 | VL | EIVLTQSPGTLSLSPGERATLSCRASQSVSSSYLAWY QQKPGQAPRLLIYGASSRATGIPDRFSGSGSGTDFTL TISRLEPEDFAVYYCQQHTVRPPLTFGGGTKVEIK |
| 26 | MAB7-IgG4 | VL | EIVLTQSPGTLSLSPGERATLSCRASQSVSSSYLAWY QQKPGQAPRLLIYGASSRATGIPDRFSGSGSGTDFTL TISRLEPEDFAVYYCQQHTVRPPLTFGGGTKVEIK |
| 26 | MAB8-IgG4 | VL | EIVLTQSPGTLSLSPGERATLSCRASQSVSSSYLAWY QQKPGQAPRLLIYGASSRATGIPDRFSGSGSGTDFTL TISRLEPEDFAVYYCQQHTVRPPLTFGGGTKVEIK |
| 26 | MAB9-IgG4 | VL | EIVLTQSPGTLSLSPGERATLSCRASQSVSSSYLAWY QQKPGQAPRLLIYGASSRATGIPDRFSGSGSGTDFTL TISRLEPEDFAVYYCQQHTVRPPLTFGGGTKVEIK |
| 26 | MAB10-IgG4 | VL | EIVLTQSPGTLSLSPGERATLSCRASQSVSSSYLAWY QQKPGQAPRLLIYGASSRATGIPDRFSGSGSGTDFTL TISRLEPEDFAVYYCQQHTVRPPLTFGGGTKVEIK |
| 26 | MAB11-IgG4 | VL | EIVLTQSPGTLSLSPGERATLSCRASQSVSSSYLAWY QQKPGQAPRLLIYGASSRATGIPDRFSGSGSGTDFTL TISRLEPEDFAVYYCQQHTVRPPLTFGGGTKVEIK |
| 26 | MAB12-IgG4 | VL | EIVLTQSPGTLSLSPGERATLSCRASQSVSSSYLAWY QQKPGQAPRLLIYGASSRATGIPDRFSGSGSGTDFTL TISRLEPEDFAVYYCQQHTVRPPLTFGGGTKVEIK |
| 27 | MAB13-IgG4 | VL | EIVMTQSPATLSVSPGERATLSCRASQSVSSNLAWY QQKPGQAPRLLIYGASTRATGIPARFSGSGSGTEFTL TISSLQSEDFAVYYCQQYVVWPPLTFGGGTKVEIK |
| 27 | MAB14-IgG4 | VL | EIVMTQSPATLSVSPGERATLSCRASQSVSSNLAWY QQKPGQAPRLLIYGASTRATGIPARFSGSGSGTEFTL TISSLQSEDFAVYYCQQYVVWPPLTFGGGTKVEIK |
| 27 | MAB15-IgG4 | VL | EIVMTQSPATLSVSPGERATLSCRASQSVSSNLAWY QQKPGQAPRLLIYGASTRATGIPARFSGSGSGTEFTL TISSLQSEDFAVYYCQQYVVWPPLTFGGGTKVEIK |
| 27 | MAB16-IgG4 | VL | EIVMTQSPATLSVSPGERATLSCRASQSVSSNLAWY QQKPGQAPRLLIYGASTRATGIPARFSGSGSGTEFTL TISSLQSEDFAVYYCQQYVVWPPLTFGGGTKVEIK |
| 27 | MAB17-IgG4 | VL | EIVMTQSPATLSVSPGERATLSCRASQSVSSNLAWY QQKPGQAPRLLIYGASTRATGIPARFSGSGSGTEFTL TISSLQSEDFAVYYCQQYVVWPPLTFGGGTKVEIK |
| 27 | MAB18-IgG4 | VL | EIVMTQSPATLSVSPGERATLSCRASQSVSSNLAWY QQKPGQAPRLLIYGASTRATGIPARFSGSGSGTEFTL TISSLQSEDFAVYYCQQYVVWPPLTFGGGTKVEIK |
| 28 | MAB19-IgG4 | VL | EIVMTQSPATLSVSPGERATLSCRASQSVSSNLAWY QQKPGQAPRHLIYGASTRATGIPARFSGSGSGTEFTL TISSLQSEDFAVYYCQQYIVFPWTFGGGTKVEIK |
| 28 | MAB20-IgG4 | VL | EIVMTQSPATLSVSPGERATLSCRASQSVSSNLAWY QQKPGQAPRHLIYGASTRATGIPARFSGSGSGTEFTL TISSLQSEDFAVYYCQQYIVFPWTFGGGTKVEIK |
| 28 | MAB21-IgG4 | VL | EIVMTQSPATLSVSPGERATLSCRASQSVSSNLAWY QQKPGQAPRHLIYGASTRATGIPARFSGSGSGTEFTL TISSLQSEDFAVYYCQQYIVFPWTFGGGTKVEIK |
| 29 | MAB1-IgG4 | H3-IMGT | ARDANYYGSAWAFDP |
| 29 | MAB2-IgG4 | H3-IMGT | ARDANYYGSAWAFDP |
| 29 | MAB3-IgG4 | H3-IMGT | ARDANYYGSAWAFDP |

APPENDIX A-continued

SEQUENCE REFERENCE TABLE

| SEQ ID NO | Molecule | Region | Sequence |
|---|---|---|---|
| 30 | MAB4-IgG4 | H3-IMGT | ARDANYYGGAWAFDP |
| 29 | MAB5-IgG4 | H3-IMGT | ARDANYYGSAWAFDP |
| 31 | MAB6-IgG4 | H3-IMGT | ARDGVLTLNKRSFDI |
| 31 | MAB7-IgG4 | H3-IMGT | ARDGVLTLNKRSFDI |
| 31 | MAB8-IgG4 | H3-IMGT | ARDGVLTLNKRSFDI |
| 31 | MAB9-IgG4 | H3-IMGT | ARDGVLTLNKRSFDI |
| 32 | MAB10-IgG4 | H3-IMGT | ARDGVLALNKRSFDI |
| 32 | MAB11-IgG4 | H3-IMGT | ARDGVLALNKRSFDI |
| 32 | MAB12-IgG4 | H3-IMGT | ARDGVLALNKRSFDI |
| 33 | MAB13-IgG4 | H3-IMGT | ARGGRTTWIGAFDI |
| 33 | MAB14-IgG4 | H3-IMGT | ARGGRTTWIGAFDI |
| 33 | MAB15-IgG4 | H3-IMGT | ARGGRTTWIGAFDI |
| 34 | MAB16-IgG4 | H3-IMGT | ARGGRTTWIGALDI |
| 34 | MAB17-IgG4 | H3-IMGT | ARGGRTTWIGALDI |
| 33 | MAB18-IgG4 | H3-IMGT | ARGGRTTWIGAFDI |
| 35 | MAB19-IgG4 | H3-IMGT | ARLHVSGSYYPAYLDY |
| 35 | MAB20-IgG4 | H3-IMGT | ARLHVSGSYYPAYLDY |
| 35 | MAB21-IgG4 | H3-IMGT | ARLHVSGSYYPAYLDY |
| 36 | MAB1-IgG4 | H2-Kabat | SIYYSGATFYNPSLKS |
| 37 | MAB2-IgG4 | H2-Kabat | SIYYSGSTFYNPSLKS |
| 37 | MAB3-IgG4 | H2-Kabat | SIYYSGSTFYNPSLKS |
| 37 | MAB4-IgG4 | H2-Kabat | SIYYSGSTFYNPSLKS |
| 38 | MAB5-IgG4 | H2-Kabat | SIYYSGSTFYNPSLKG |
| 39 | MAB6-IgG4 | H2-Kabat | SIYYSGGTYYNPSLKS |
| 40 | MAB7-IgG4 | H2-Kabat | SIYYSGSTYYNPSLKS |

APPENDIX A-continued

SEQUENCE REFERENCE TABLE

| SEQ ID NO | Molecule | Region | Sequence |
|---|---|---|---|
| 41 | MAB8-IgG4 | H2-Kabat | SIYYSGQTYYNPSLKS |
| 40 | MAB9-IgG4 | H2-Kabat | SIYYSGSTYYNPSLKS |
| 40 | MAB10-IgG4 | H2-Kabat | SIYYSGSTYYNPSLKS |
| 40 | MAB11-IgG4 | H2-Kabat | SIYYSGSTYYNPSLKS |
| 40 | MAB12-IgG4 | H2-Kabat | SIYYSGSTYYNPSLKS |
| 42 | MAB13-IgG4 | H2-Kabat | IINPSLGLTSYAQKFQG |
| 42 | MAB14-IgG4 | H2-Kabat | IINPSLGLTSYAQKFQG |
| 43 | MAB15-IgG4 | H2-Kabat | IINPSIGLTSYARKFQG |
| 43 | MAB16-IgG4 | H2-Kabat | IINPSIGLTSYARKFQG |
| 44 | MAB17-IgG4 | H2-Kabat | IINPSLGLTSYARKFQG |
| 44 | MAB18-IgG4 | H2-Kabat | IINPSLGLTSYARKFQG |
| 45 | MAB19-IgG4 | H2-Kabat | VINPSMGATSYAQKFQG |
| 46 | MAB20-IgG4 | H2-Kabat | IINPSMGATSYAQKFQG |
| 47 | MAB21-IgG4 | H2-Kabat | IINPSMGATSYTQKFRG |
| 48 | MAB1-IgG4 | H1-Chothia + Kabat | GSITSSSYYWG |
| 49 | MAB2-IgG4 | H1-Chothia + Kabat | GSISSSKYYWG |
| 50 | MAB3-IgG4 | H1-Chothia + Kabat | GSISSTSHYWG |
| 50 | MAB4-IgG4 | H1-Chothia + Kabat | GSISSTSHYWG |
| 50 | MAB5-IgG4 | H1-Chothia + Kabat | GSISSTSHYWG |
| 51 | MAB6-IgG4 | H1-Chothia + Kabat | GSIESGSYYWG |
| 52 | MAB7-IgG4 | H1-Chothia + Kabat | GSIESGVYYWG |
| 53 | MAB8-IgG4 | H1-Chothia + Kabat | GSIASGSYYWG |
| 54 | MAB9-IgG4 | H1-Chothia + Kabat | GSIESGLYYWG |
| 54 | MAB10-IgG4 | H1-Chothia + Kabat | GSIESGLYYWG |

APPENDIX A-continued

SEQUENCE REFERENCE TABLE

| SEQ ID NO | Molecule | Region | Sequence |
|---|---|---|---|
| 54 | MAB11-IgG4 | H1-Chothia + Kabat | GSIESGLYYWG |
| 54 | MAB12-IgG4 | H1-Chothia + Kabat | GSIESGLYYWG |
| 55 | IgG4 | Constant, hinge stabilizing | S228PASTKGPSVFPLAPCSRSTSESTAALGCLVKDYFPEPV TVSWNSGALTSGVHTFPAVLQSSGLYSLSSVVTVPSS SLGTKTYTCNVDHKPSNTKVDKRVESKYGPPCPPCP APEFLGGPSVFLFPPKPKDTLMISRTPEVTCVVVDVS QEDPEVQFNWYVDGVEVHNAKTKPREEQFNSTYRV VSVLTVLHQDWLNGKEYKCKVSNKGLPSSIEKTISK AKGQPREPQVYTLPPSQEEMTKNQVSLTCLVKGFYP SDIAVEWESNGQPENNYKTTPPVLDSDGSFFLYSRLT VDKSRWQEGNVFSCSVMHEALHNHYTQKSLSLSLG K |
| 56 | IgG4 | Constant S228P, N297A, C terminal Lys deleted | ASTKGPSVFPLAPCSRSTSESTAALGCLVKDYFPEPV TVSWNSGALTSGVHTFPAVLQSSGLYSLSSVVTVPSS SLGTKTYTCNVDHKPSNTKVDKRVESKYGPPCPPCP APEFLGGPSVFLFPPKPKDTLMISRTPEVTCVVVDVS QEDPEVQFNWYVDGVEVHNAKTKPREEQFASTYRV VSVLTVLHQDWLNGKEYKCKVSNKGLPSSIEKTISK AKGQPREPQVYTLPPSQEEMTKNQVSLTCLVKGFYP SDIAVEWESNGQPENNYKTTPPVLDSDGSFFLYSRLT VDKSRWQEGNVFSCSVMHEALHNHYTQKSLSLSLG |
| 57 | IgG1 | Constant (G1m(3) allotype) | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKTHTCP PCPAPELLGGPSVFLFPPKPKDTLMISRTPEVTCVVV DVSHEDPEVKFNWYVDGVEVHNAKTKPREEQYNST YRVVSVLTVLHQDWLNGKEYKCKVSNKALPAPIEK TISKAKGQPREPQVYTLPPSREEMTKNQVSLTCLVK GFYPSDIAVEWESNGQPENNYKTTPPVLDSDGSFFLY SKLTVDKSRWQQGNVFSCSVMHEALHNHYTQKSLS LSPGK |
| 58 | MAB13-IgG4 | H1-Chothia + Kabat | YTFGNYYMH |
| 59 | MAB14-IgG4 | H1-Chothia + Kabat | YTFPAYYMH |
| 60 | MAB15-IgG4 | H1-Chothia + Kabat | YTFREYYMH |
| 60 | MAB16-IgG4 | H1-Chothia + Kabat | YTFREYYMH |
| 61 | MAB17-IgG4 | H1-Chothia + Kabat | YTFPAYYIH |
| 59 | MAB18-IgG4 | H1-Chothia + Kabat | YTFPAYYMH |
| 62 | MAB19-IgG4 | H1-Chothia + Kabat | YTFTSHYMG |
| 62 | MAB20-IgG4 | H1-Chothia + Kabat | YTFTSHYMG |
| 62 | MAB21-IgG4 | H1-Chothia + Kabat | YTFTSHYMG |
| 63 | MAB1-IgG4 | L3-Chothia/Kabat/IMGT | QQHFNLPT |
| 63 | MAB2-IgG4 | L3-Chothia/Kabat/IMGT | QQHFNLPT |

APPENDIX A-continued

SEQUENCE REFERENCE TABLE

| SEQ ID NO | Molecule | Region | Sequence |
|---|---|---|---|
| 63 | MAB3-IgG4 | L3-Chothia/Kabat/IMGT | QQHFNLPT |
| 63 | MAB4-IgG4 | L3-Chothia/Kabat/IMGT | QQHFNLPT |
| 63 | MAB5-IgG4 | L3-Chothia/Kabat/IMGT | QQHFNLPT |
| 64 | MAB6-IgG4 | L3-Chothia/Kabat/IMGT | QQHTVRPPLT |
| 64 | MAB7-IgG4 | L3-Chothia/Kabat/IMGT | QQHTVRPPLT |
| 64 | MAB8-IgG4 | L3-Chothia/Kabat/IMGT | QQHTVRPPLT |
| 64 | MAB9-IgG4 | L3-Chothia/Kabat/IMGT | QQHTVRPPLT |
| 64 | MAB10-IgG4 | L3-Chothia/Kabat/IMGT | QQHTVRPPLT |
| 64 | MAB11-IgG4 | L3-Chothia/Kabat/IMGT | QQHTVRPPLT |
| 64 | MAB12-IgG4 | L3-Chothia/Kabat/IMGT | QQHTVRPPLT |
| 65 | MAB13-IgG4 | L3-Chothia/Kabat/IMGT | QQYVVWPPLT |
| 65 | MAB14-IgG4 | L3-Chothia/Kabat/IMGT | QQYVVWPPLT |
| 65 | MAB15-IgG4 | L3-Chothia/Kabat/IMGT | QQYVVWPPLT |
| 65 | MAB16-IgG4 | L3-Chothia/Kabat/IMGT | QQYVVWPPLT |
| 65 | MAB17-IgG4 | L3-Chothia/Kabat/IMGT | QQYVVWPPLT |
| 65 | MAB18-IgG4 | L3-Chothia/Kabat/IMGT | QQYVVWPPLT |
| 66 | MAB19-IgG4 | L3-Chothia/Kabat/IMGT | QQYIVFPWT |
| 66 | MAB20-IgG4 | L3-Chothia/Kabat/IMGT | QQYIVFPWT |

APPENDIX A-continued

SEQUENCE REFERENCE TABLE

| SEQ ID NO | Molecule | Region | Sequence |
|---|---|---|---|
| 66 | MAB21-IgG4 | L3-Chothia/Kabat/IMGT | QQYIVFPWT |
| 67 | MAB1-IgG4 | L2-Chothia/Kabat | DASNRAT |
| 67 | MAB2-IgG4 | L2-Chothia/Kabat | DASNRAT |
| 67 | MAB3-IgG4 | L2-Chothia/Kabat | DASNRAT |
| 67 | MAB4-IgG4 | L2-Chothia/Kabat | DASNRAT |
| 67 | MAB5-IgG4 | L2-Chothia/Kabat | DASNRAT |
| 68 | MAB6-IgG4 | L2-Chothia/Kabat | GASSRAT |
| 68 | MAB7-IgG4 | L2-Chothia/Kabat | GASSRAT |
| 68 | MAB8-IgG4 | L2-Chothia/Kabat | GASSRAT |
| 68 | MAB9-IgG4 | L2-Chothia/Kabat | GASSRAT |
| 68 | MAB10-IgG4 | L2-Chothia/Kabat | GASSRAT |
| 68 | MAB11-IgG4 | L2-Chothia/Kabat | GASSRAT |
| 68 | MAB12-IgG4 | L2-Chothia/Kabat | GASSRAT |
| 69 | MAB13-IgG4 | L2-Chothia/Kabat | GASTRAT |
| 69 | MAB14-IgG4 | L2-Chothia/Kabat | GASTRAT |
| 69 | MAB15-IgG4 | L2-Chothia/Kabat | GASTRAT |
| 69 | MAB16-IgG4 | L2-Chothia/Kabat | GASTRAT |
| 69 | MAB17-IgG4 | L2-Chothia/Kabat | GASTRAT |
| 69 | MAB18-IgG4 | L2-Chothia/Kabat | GASTRAT |
| 69 | MAB19-IgG4 | L2-Chothia/Kabat | GASTRAT |
| 69 | MAB20-IgG4 | L2-Chothia/Kabat | GASTRAT |
| 69 | MAB21-IgG4 | L2-Chothia/Kabat | GASTRAT |
| 70 | MAB1-IgG4 | L1-Chothia/Kabat | RASQSVSSYLA |
| 70 | MAB2-IgG4 | L1-Chothia/Kabat | RASQSVSSYLA |

APPENDIX A-continued

SEQUENCE REFERENCE TABLE

| SEQ ID NO | Molecule | Region | Sequence |
|---|---|---|---|
| 70 | MAB3-IgG4 | L1-Chothia/Kabat | RASQSVSSYLA |
| 70 | MAB4-IgG4 | L1-Chothia/Kabat | RASQSVSSYLA |
| 70 | MAB5-IgG4 | L1-Chothia/Kabat | RASQSVSSYLA |
| 71 | MAB6-IgG4 | L1-Chothia/Kabat | RASQSVSSSYLA |
| 71 | MAB7-IgG4 | L1-Chothia/Kabat | RASQSVSSSYLA |
| 71 | MAB8-IgG4 | L1-Chothia/Kabat | RASQSVSSSYLA |
| 71 | MAB9-IgG4 | L1-Chothia/Kabat | RASQSVSSSYLA |
| 71 | MAB10-IgG4 | L1-Chothia/Kabat | RASQSVSSSYLA |
| 71 | MAB11-IgG4 | L1-Chothia/Kabat | RASQSVSSSYLA |
| 71 | MAB12-IgG4 | L1-Chothia/Kabat | RASQSVSSSYLA |
| 72 | MAB13-IgG4 | L1-Chothia/Kabat | RASQSVSSNLA |
| 72 | MAB14-IgG4 | L1-Chothia/Kabat | RASQSVSSNLA |
| 72 | MAB15-IgG4 | L1-Chothia/Kabat | RASQSVSSNLA |
| 72 | MAB16-IgG4 | L1-Chothia/Kabat | RASQSVSSNLA |
| 72 | MAB17-IgG4 | L1-Chothia/Kabat | RASQSVSSNLA |
| 72 | MAB18-IgG4 | L1-Chothia/Kabat | RASQSVSSNLA |
| 72 | MAB19-IgG4 | L1-Chothia/Kabat | RASQSVSSNLA |
| 72 | MAB20-IgG4 | L1-Chothia/Kabat | RASQSVSSNLA |
| 72 | MAB21-IgG4 | L1-Chothia/Kabat | RASQSVSSNLA |
| 73 | SEC1 | Human IgG4 S228P Heavy Chain | EVQLVESGGGLTQPGKSLKLSCEASGFTFSSFTMHW VRQSPGKGLEWVAFIRSGSGIVFYADAVRGRFTISRD NAKNLLFLQMNDLKSEDTAMYYCARRPLGHNTFDS WGQGTLVTVSSASTKGPSVFPLAPCSRSTSESTAALG CLVKDYFPEPVTVSWNSGALTSGVHTFPAVLQSSGL YSLSSVVTVPSSSLGTKTYTCNVDHKPSNTKVDKRV ESKYGPPCPPCPAPEFLGGPSVFLFPPKPKDTLMISRT PEVTCVVVDVSQEDPEVQFNWYVDGVEVHNAKTKP REEQFNSTYRVVSVLTVLHQDWLNGKEYKCKVSNK GLPSSIEKTISKAKGQPREPQVYTLPPSQEEMTKNQV SLTCLVKGFYPSDIAVEWESNGQPENNYKTTPPVLD SDGSFFLYSRLTVDKSRWQEGNVFSCSVMHEALHN HYTQKSLSLSLGK |

APPENDIX A-continued

SEQUENCE REFERENCE TABLE

| SEQ ID NO | Molecule | Region | Sequence |
|---|---|---|---|
| 74 | SEC1 | Heavy Chain Variable Region | EVQLVESGGGLTQPGKSLKLSCEASGFTFSSFTMHW VRQSPGKGLEWVAFIRSGSGIVFYADAVRGRFTISRD NAKNLLFLQMNDLKSEDTAMYYCARRPLGHNTFDS WGQGTLVTVSS |
| 75 | SEC1 | SEC1 Human Kappa Chain | DIVMTQSPSSLAVSPGEKVTMTCKSSQSLYYSGVKE NLLAWYQQKPGQSPKLLIYYASIRFTGVPDRFTGSGS GTDYTLTITSVQAEDMGQYFCQQGINNPLTFGDGTK LEIKRTVAAPSVFIFPPSDEQLKSGTASVVCLLNNFYP REAKVQWKVDNALQSGNSQESVTEQDSKDSTYSLS STLTLSKADYEKHKVYACEVTHQGLSSPVTKSFNRG EC |
| 76 | SEC1 | Light Chain Variable Region | DIVMTQSPSSLAVSPGEKVTMTCKSSQSLYYSGVKE NLLAWYQQKPGQSPKLLIYYASIRFTGVPDRFTGSGS GTDYTLTITSVQAEDMGQYFCQQGINNPLTFGDGTK LEIK |
| 77 | SEC1 | Mouse IgG2a N297A Heavy Chain | EVQLVESGGGLTQPGKSLKLSCEASGFTFSSFTMHW VRQSPGKGLEWVAFIRSGSGIVFYADAVRGRFTISRD NAKNLLFLQMNDLKSEDTAMYYCARRPLGHNTFDS WGQGTLVTVSSAKTTAPSVYPLAPVCGDTTGSSVTL GCLVKGYFPEPVTLTWNSGSLSSGVHTFPAVLQSDL YTLSSSVTVTSSTWPSQSITCNVAHPASSTKVDKKIEP RGPTIKPCPPCKCPAPNLLGGPSVFIFPPKIKDVLMISL SPIVTCVVVDVSEDDPDVQISWFVNNVEVHTAQTQT HREDYASTLRVVSALPIQHQDWMSGKEFKCKVNNK DLPAPIERTISKPKGSVRAPQVYVLPPPEEEMTKKQV TLTCMVTDFMPEDIYVEWTNNGKTELNYKNTEPVL DSDGSYFMYSKLRVEKKNWVERNSYSCSVVHEGLH NHHTTKSFSRTPGK |
| 74 | SEC1 | Heavy Chain Variable region | EVQLVESGGGLTQPGKSLKLSCEASGFTFSSFTMHW VRQSPGKGLEWVAFIRSGSGIVFYADAVRGRFTISRD NAKNLLFLQMNDLKSEDTAMYYCARRPLGHNTFDS WGQGTLVTVSS |
| 78 | SEC1 | Mouse Kappa Chain | DIVMTQSPSSLAVSPGEKVTMTCKSSQSLYYSGVKE NLLAWYQQKPGQSPKLLIYYASIRFTGVPDRFTGSGS GTDYTLTITSVQAEDMGQYFCQQGINNPLTFGDGTK LEIKRADAAPTVSIFPPSSEQLTSGGASVVCFLNNFYP KDINVKWKIDGSERQNGVLNSWTDQDSKDSTYSMS STLTLTKDEYERHNSYTCEATHKTSTSPIVKSFNRNE C |
| 76 | SEC1 | Light Chain Variable Region | DIVMTQSPSSLAVSPGEKVTMTCKSSQSLYYSGVKE NLLAWYQQKPGQSPKLLIYYASIRFTGVPDRFTGSGS GTDYTLTITSVQAEDMGQYFCQQGINNPLTFGDGTK LEIK |
| 79 | MAB1 | Full length IgG4 S228P | QLQLQESGPGLVKPSETLSLTCTVSGGSITSSSYYWG WIRQPPGKGLEWIGSIYYSGATFYNPSLKSRVTISVD TSKNQFSLKLSSVTAADTAVYYCARDANYYGSAWA FDPWGQGTLVTVSSASTKGPSVFPLAPCSRSTSESTA ALGCLVKDYFPEPVTVSWNSGALTSGVHTFPAVLQS SGLYSLSSVVTVPSSSLGTKTYTCNVDHKPSNTKVD KRVESKYGPPCPPCPAPEFLGGPSVFLFPPKPKDTLMI SRTPEVTCVVVDVSQEDPEVQFNWYVDGVEVHNAK TKPREEQFNSTYRVVSVLTVLHQDWLNGKEYKCKV SNKGLPSSIEKTISKAKGQPREPQVYTLPPSQEEMTK NQVSLTCLVKGFYPSDIAVEWESNGQPENNYKTTPP VLDSDGSFFLYSRLTVDKSRWQEGNVFSCSVMHEAL HNHYTQKSLSLSLGK |
| 80 | MAB1 | Full length IgG1 | QLQLQESGPGLVKPSETLSLTCTVSGGSITSSSYYWG WIRQPPGKGLEWIGSIYYSGATFYNPSLKSRVTISVD TSKNQFSLKLSSVTAADTAVYYCARDANYYGSAWA FDPWGQGTLVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK RVEPKSCDKTHTCPPCPAPELLGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSREE |

APPENDIX A-continued

SEQUENCE REFERENCE TABLE

| SEQ ID NO | Molecule | Region | Sequence |
|---|---|---|---|
| | | | MTKNQVSLTCLVKGFYPSDIAVEWESNGQPENNYK TTPPVLDSDGSFFLYSKLTVDKSRWQQGNVFSCSVM HEALHNHYTQKSLSLSPGK |
| 81 | MAB1 | Full length Kappa | EIVLTQSPATLSLSPGERATLSCRASQSVSSYLAWYQ QKPGQAPRLLIYDASNRATGIPARFSGSGSGTDFTLTI SSLEPEDFAVYYCQQHFNLPTFGGGTKVEIKRTVAA PSVFIFPPSDEQLKSGTASVVCLLNNFYPREAKVQWK VDNALQSGNSQESVTEQDSKDSTYSLSSTLTLSKAD YEKHKVYACEVTHQGLSSPVTKSFNRGEC |
| 82 | MAB2 | Full length IgG4 S228P | QLQLQESGPGLVKPSETLSLTCTVSGGSISSSKYYWG WIRQPPGKGLEWIGSIYYSGSTFYNPSLKSRVTISVDT SKNQFSLKLSSVTAADTAVYYCARDANYYGSAWAF DPWGQGTLVTVSSASTKGPSVFPLAPCSRSTSESTAA LGCLVKDYFPEPVTVSWNSGALTSGVHTFPAVLQSS GLYSLSSVVTVPSSSLGTKTYTCNVDHKPSNTKVDK RVESKYGPPCPPCPAPEFLGGPSVFLFPPKPKDTLMIS RTPEVTCVVVDVSQEDPEVQFNWYVDGVEVHNAKT KPREEQFNSTYRVVSVLTVLHQDWLNGKEYKCKVS NKGLPSSIEKTISKAKGQPREPQVYTLPPSQEEMTKN QVSLTCLVKGFYPSDIAVEWESNGQPENNYKTTPPV LDSDGSFFLYSRLTVDKSRWQEGNVFSCSVMHEALH NHYTQKSLSLSLGK |
| 83 | MAB2 | Full length IgG1 | QLQLQESGPGLVKPSETLSLTCTVSGGSISSSKYYWG WIRQPPGKGLEWIGSIYYSGSTFYNPSLKSRVTISVDT SKNQFSLKLSSVTAADTAVYYCARDANYYGSAWAF DPWGQGTLVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK RVEPKSCDKTHTCPPCPAPELLGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSREE MTKNQVSLTCLVKGFYPSDIAVEWESNGQPENNYK TTPPVLDSDGSFFLYSKLTVDKSRWQQGNVFSCSVM HEALHNHYTQKSLSLSPGK |
| 81 | MAB2 | Full length Kappa | EIVLTQSPATLSLSPGERATLSCRASQSVSSYLAWYQ QKPGQAPRLLIYDASNRATGIPARFSGSGSGTDFTLTI SSLEPEDFAVYYCQQHFNLPTFGGGTKVEIKRTVAA PSVFIFPPSDEQLKSGTASVVCLLNNFYPREAKVQWK VDNALQSGNSQESVTEQDSKDSTYSLSSTLTLSKAD YEKHKVYACEVTHQGLSSPVTKSFNRGEC |
| 84 | MAB3 | Full length IgG4 S228P | QLQLQESGPGLVKPSETLSLTCTVSGGSISSTSHYWG WIRQPPGKGLEWIGSIYYSGSTFYNPSLKSRVTISVDT SKNQFSLKLSSVTAADTAVYYCARDANYYGSAWAF DPWGQGTLVTVSSASTKGPSVFPLAPCSRSTSESTAA LGCLVKDYFPEPVTVSWNSGALTSGVHTFPAVLQSS GLYSLSSVVTVPSSSLGTKTYTCNVDHKPSNTKVDK RVESKYGPPCPPCPAPEFLGGPSVFLFPPKPKDTLMIS RTPEVTCVVVDVSQEDPEVQFNWYVDGVEVHNAKT KPREEQFNSTYRVVSVLTVLHQDWLNGKEYKCKVS NKGLPSSIEKTISKAKGQPREPQVYTLPPSQEEMTKN QVSLTCLVKGFYPSDIAVEWESNGQPENNYKTTPPV LDSDGSFFLYSRLTVDKSRWQEGNVFSCSVMHEALH NHYTQKSLSLSLGK |
| 85 | MAB3 | Full length IgG1 | QLQLQESGPGLVKPSETLSLTCTVSGGSISSTSHYWG WIRQPPGKGLEWIGSIYYSGSTFYNPSLKSRVTISVDT SKNQFSLKLSSVTAADTAVYYCARDANYYGSAWAF DPWGQGTLVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK RVEPKSCDKTHTCPPCPAPELLGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSREE MTKNQVSLTCLVKGFYPSDIAVEWESNGQPENNYK TTPPVLDSDGSFFLYSKLTVDKSRWQQGNVFSCSVM HEALHNHYTQKSLSLSPGK |

APPENDIX A-continued

SEQUENCE REFERENCE TABLE

| SEQ ID NO | Molecule | Region | Sequence |
|---|---|---|---|
| 81 | MAB3 | Full length Kappa | EIVLTQSPATLSLSPGERATLSCRASQSVSSYLAWYQ QKPGQAPRLLIYDASNRATGIPARFSGSGSGTDFTLTI SSLEPEDFAVYYCQQHFNLPTFGGGTKVEIKRTVAA PSVFIFPPSDEQLKSGTASVVCLLNNFYPREAKVQWK VDNALQSGNSQESVTEQDSKDSTYSLSSTLTLSKAD YEKHKVYACEVTHQGLSSPVTKSFNRGEC |
| 86 | MAB4 | Full length IgG4 S228P | QLQLQESGPGLVKPSETLSLTCTVSGGSISSTSHYWG WIRQPPGKGLEWIGSIYYSGSTFYNPSLKSRVTISVDT SKNQFSLKLSSVTAADTAVYYCARDANYYGGAWAF DPWGQGTLVTVSSASTKGPSVFPLAPCSRSTSESTAA LGCLVKDYFPEPVTVSWNSGALTSGVHTFPAVLQSS GLYSLSSVVTVPSSSLGTKTYTCNVDHKPSNTKVDK RVESKYGPPCPPCPAPEFLGGPSVFLFPPKPKDTLMIS RTPEVTCVVVDVSQEDPEVQFNWYVDGVEVHNAKT KPREEQFNSTYRVVSVLTVLHQDWLNGKEYKCKVS NKGLPSSIEKTISKAKGQPREPQVYTLPPSQEEMTKN QVSLTCLVKGFYPSDIAVEWESNGQPENNYKTTPPV LDSDGSFFLYSRLTVDKSRWQEGNVFSCSVMHEALH NHYTQKSLSLSLGK |
| 87 | MAB4 | Full length IgG1 | QLQLQESGPGLVKPSETLSLTCTVSGGSISSTSHYWG WIRQPPGKGLEWIGSIYYSGSTFYNPSLKSRVTISVDT SKNQFSLKLSSVTAADTAVYYCARDANYYGGAWAF DPWGQGTLVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK RVEPKSCDKTHTCPPCPAPELLGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSREE MTKNQVSLTCLVKGFYPSDIAVEWESNGQPENNYK TTPPVLDSDGSFFLYSKLTVDKSRWQQGNVFSCSVM HEALHNHYTQKSLSLSPGK |
| 81 | MAB4 | Full length Kappa | EIVLTQSPATLSLSPGERATLSCRASQSVSSYLAWYQ QKPGQAPRLLIYDASNRATGIPARFSGSGSGTDFTLTI SSLEPEDFAVYYCQQHFNLPTFGGGTKVEIKRTVAA PSVFIFPPSDEQLKSGTASVVCLLNNFYPREAKVQWK VDNALQSGNSQESVTEQDSKDSTYSLSSTLTLSKAD YEKHKVYACEVTHQGLSSPVTKSFNRGEC |
| 88 | MAB5 | Full length IgG4 S228P | QLQLQESGPGLVKPSETLSLTCTVSGGSISSTSHYWG WIRQPPGKGLEWIGSIYYSGSTFYNPSLKGRVTISVD TSKNQFSLKLSSVTAADTAVYYCARDANYYGSAWA FDPWGQGTLVTVSSASTKGPSVFPLAPCSRSTSESTA ALGCLVKDYFPEPVTVSWNSGALTSGVHTFPAVLQS SGLYSLSSVVTVPSSSLGTKTYTCNVDHKPSNTKVD KRVESKYGPPCPPCPAPEFLGGPSVFLFPPKPKDTLMI SRTPEVTCVVVDVSQEDPEVQFNWYVDGVEVHNAK TKPREEQFNSTYRVVSVLTVLHQDWLNGKEYKCKV SNKGLPSSIEKTISKAKGQPREPQVYTLPPSQEEMTK NQVSLTCLVKGFYPSDIAVEWESNGQPENNYKTTPP VLDSDGSFFLYSRLTVDKSRWQEGNVFSCSVMHEAL HNHYTQKSLSLSLGK |
| 89 | MAB5 | Full length IgG1 | QLQLQESGPGLVKPSETLSLTCTVSGGSISSTSHYWG WIRQPPGKGLEWIGSIYYSGSTFYNPSLKGRVTISVD TSKNQFSLKLSSVTAADTAVYYCARDANYYGSAWA FDPWGQGTLVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK RVEPKSCDKTHTCPPCPAPELLGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSREE MTKNQVSLTCLVKGFYPSDIAVEWESNGQPENNYK TTPPVLDSDGSFFLYSKLTVDKSRWQQGNVFSCSVM HEALHNHYTQKSLSLSPGK |
| 81 | MAB5 | Full length Kappa | EIVLTQSPATLSLSPGERATLSCRASQSVSSYLAWYQ QKPGQAPRLLIYDASNRATGIPARFSGSGSGTDFTLTI SSLEPEDFAVYYCQQHFNLPTFGGGTKVEIKRTVAA PSVFIFPPSDEQLKSGTASVVCLLNNFYPREAKVQWK |

APPENDIX A-continued

SEQUENCE REFERENCE TABLE

| SEQ ID NO | Molecule | Region | Sequence |
|---|---|---|---|
| | | | VDNALQSGNSQESVTEQDSKDSTYSLSSTLTLSKAD YEKHKVYACEVTHQGLSSPVTKSFNRGEC |
| 90 | MAB6 | Full length IgG4 S228P | QLQLQESGPGLVKPSETLSLTCTVSGGSIESGSYYWG WIRQPPGKGLEWIGSIYYSGGTYYNPSLKSRVTISVD TSKNQFSLKLSSVTAADTAVYYCARDGVLTLNKRSF DIWGQGTMVTVSSASTKGPSVFPLAPCSRSTSESTAA LGCLVKDYFPEPVTVSWNSGALTSGVHTFPAVLQSS GLYSLSSVVTVPSSSLGTKTYTCNVDHKPSNTKVDK RVESKYGPPCPPCPAPEFLGGPSVFLFPPKPKDTLMIS RTPEVTCVVVDVSQEDPEVQFNWYVDGVEVHNAKT KPREEQFNSTYRVVSVLTVLHQDWLNGKEYKCKVS NKGLPSSIEKTISKAKGQPREPQVYTLPPSQEEMTKN QVSLTCLVKGFYPSDIAVEWESNGQPENNYKTTPPV LDSDGSFFLYSRLTVDKSRWQEGNVFSCSVMHEALH NHYTQKSLSLSLGK |
| 91 | MAB6 | Full length IgG1 | QLQLQESGPGLVKPSETLSLTCTVSGGSIESGSYYWG WIRQPPGKGLEWIGSIYYSGGTYYNPSLKSRVTISVD TSKNQFSLKLSSVTAADTAVYYCARDGVLTLNKRSF DIWGQGTMVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK RVEPKSCDKTHTCPPCPAPELLGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSREE MTKNQVSLTCLVKGFYPSDIAVEWESNGQPENNYK TTPPVLDSDGSFFLYSKLTVDKSRWQQGNVFSCSVM HEALHNHYTQKSLSLSPGK |
| 92 | MAB6 | Full length Kappa | EIVLTQSPGTLSLSPGERATLSCRASQSVSSSYLAWY QQKPGQAPRLLIYGASSRATGIPDRFSGSGSGTDFTL TISRLEPEDFAVYYCQQHTVRPPLTFGGGTKVEIKRT VAAPSVFIFPPSDEQLKSGTASVVCLLNNFYPREAKV QWKVDNALQSGNSQESVTEQDSKDSTYSLSSTLTLS KADYEKHKVYACEVTHQGLSSPVTKSFNRGEC |
| 93 | MAB7 | Full length IgG4 S228P | QVQLQESGPGLVKPSQTLSLTCTVSGGSIESGVYYW GWIRQPPGKGLEWIGSIYYSGSTYYNPSLKSRVTISV DTSKNQFSLKLSSVTAADTAVYYCARDGVLTLNKRS FDIWGQGTMVTVSSASTKGPSVFPLAPCSRSTSESTA ALGCLVKDYFPEPVTVSWNSGALTSGVHTFPAVLQS SGLYSLSSVVTVPSSSLGTKTYTCNVDHKPSNTKVD KRVESKYGPPCPPCPAPEFLGGPSVFLFPPKPKDTLMI SRTPEVTCVVVDVSQEDPEVQFNWYVDGVEVHNAK TKPREEQFNSTYRVVSVLTVLHQDWLNGKEYKCKV SNKGLPSSIEKTISKAKGQPREPQVYTLPPSQEEMTK NQVSLTCLVKGFYPSDIAVEWESNGQPENNYKTTPP VLDSDGSFFLYSRLTVDKSRWQEGNVFSCSVMHEAL HNHYTQKSLSLSLGK |
| 94 | MAB7 | Full length IgG1 | QVQLQESGPGLVKPSQTLSLTCTVSGGSIESGVYYW GWIRQPPGKGLEWIGSIYYSGSTYYNPSLKSRVTISV DTSKNQFSLKLSSVTAADTAVYYCARDGVLTLNKRS FDIWGQGTMVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK RVEPKSCDKTHTCPPCPAPELLGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSREE MTKNQVSLTCLVKGFYPSDIAVEWESNGQPENNYK TTPPVLDSDGSFFLYSKLTVDKSRWQQGNVFSCSVM HEALHNHYTQKSLSLSPGK |
| 92 | MAB7 | Full length Kappa | EIVLTQSPGTLSLSPGERATLSCRASQSVSSSYLAWY QQKPGQAPRLLIYGASSRATGIPDRFSGSGSGTDFTL TISRLEPEDFAVYYCQQHTVRPPLTFGGGTKVEIKRT VAAPSVFIFPPSDEQLKSGTASVVCLLNNFYPREAKV QWKVDNALQSGNSQESVTEQDSKDSTYSLSSTLTLS KADYEKHKVYACEVTHQGLSSPVTKSFNRGEC |

APPENDIX A-continued

SEQUENCE REFERENCE TABLE

| SEQ ID NO | Molecule | Region | Sequence |
|---|---|---|---|
| 95 | MAB8 | Full length IgG4 S228P | QLQLQESGPGLVKPSETLSLTCTVSGGSIASGSYYWG WIRQPPGKGLEWIGSIYYSGQTYYNPSLKSRVTISVD TSKNQFSLKLSSVTAADTAVYYCARDGVLTLNKRSF DIWGQGTMVTVSSASTKGPSVFPLAPCSRSTSESTAA LGCLVKDYFPEPVTVSWNSGALTSGVHTFPAVLQSS GLYSLSSVVTVPSSSLGTKTYTCNVDHKPSNTKVDK RVESKYGPPCPPCPAPEFLGGPSVFLFPPKPKDTLMIS RTPEVTCVVVDVSQEDPEVQFNWYVDGVEVHNAKT KPREEQFNSTYRVVSVLTVLHQDWLNGKEYKCKVS NKGLPSSIEKTISKAKGQPREPQVYTLPPSQEEMTKN QVSLTCLVKGFYPSDIAVEWESNGQPENNYKTTPPV LDSDGSFFLYSRLTVDKSRWQEGNVFSCSVMHEALH NHYTQKSLSLSLGK |
| 96 | MAB8 | Full length IgG1 | QLQLQESGPGLVKPSETLSLTCTVSGGSIASGSYYWG WIRQPPGKGLEWIGSIYYSGQTYYNPSLKSRVTISVD TSKNQFSLKLSSVTAADTAVYYCARDGVLTLNKRSF DIWGQGTMVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK RVEPKSCDKTHTCPPCPAPELLGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSREE MTKNQVSLTCLVKGFYPSDIAVEWESNGQPENNYK TTPPVLDSDGSFFLYSKLTVDKSRWQQGNVFSCSVM HEALHNHYTQKSLSLSPGK |
| 92 | MAB8 | Full length Kappa | EIVLTQSPGTLSLSPGERATLSCRASQSVSSSYLAWY QQKPGQAPRLLIYGASSRATGIPDRFSGSGSGTDFTL TISRLEPEDFAVYYCQQHTVRPPLTFGGGTKVEIKRT VAAPSVFIFPPSDEQLKSGTASVVCLLNNFYPREAKV QWKVDNALQSGNSQESVTEQDSKDSTYSLSSTLTLS KADYEKHKVYACEVTHQGLSSPVTKSFNRGEC |
| 97 | MAB9 | Full length IgG4 S228P | QVQLQESGPGLVKPSQTLSLTCTVSGGSIESGLYYW GWIRQPPGKGLEWIGSIYYSGSTYYNPSLKSRVTISV DTSKNQFSLKLSSVTAADTAVYYCARDGVLTLNKRS FDIWGQGTMVTVSSASTKGPSVFPLAPCSRSTSESTA ALGCLVKDYFPEPVTVSWNSGALTSGVHTFPAVLQS SGLYSLSSVVTVPSSSLGTKTYTCNVDHKPSNTKVD KRVESKYGPPCPPCPAPEFLGGPSVFLFPPKPKDTLMI SRTPEVTCVVVDVSQEDPEVQFNWYVDGVEVHNAK TKPREEQFNSTYRVVSVLTVLHQDWLNGKEYKCKV SNKGLPSSIEKTISKAKGQPREPQVYTLPPSQEEMTK NQVSLTCLVKGFYPSDIAVEWESNGQPENNYKTTPP VLDSDGSFFLYSRLTVDKSRWQEGNVFSCSVMHEAL HNHYTQKSLSLSLGK |
| 98 | MAB9 | Full length IgG1 | QVQLQESGPGLVKPSQTLSLTCTVSGGSIESGLYYW GWIRQPPGKGLEWIGSIYYSGSTYYNPSLKSRVTISV DTSKNQFSLKLSSVTAADTAVYYCARDGVLTLNKRS FDIWGQGTMVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK RVEPKSCDKTHTCPPCPAPELLGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSREE MTKNQVSLTCLVKGFYPSDIAVEWESNGQPENNYK TTPPVLDSDGSFFLYSKLTVDKSRWQQGNVFSCSVM HEALHNHYTQKSLSLSPGK |
| 92 | MAB9 | Full length Kappa | EIVLTQSPGTLSLSPGERATLSCRASQSVSSSYLAWY QQKPGQAPRLLIYGASSRATGIPDRFSGSGSGTDFTL TISRLEPEDFAVYYCQQHTVRPPLTFGGGTKVEIKRT VAAPSVFIFPPSDEQLKSGTASVVCLLNNFYPREAKV QWKVDNALQSGNSQESVTEQDSKDSTYSLSSTLTLS KADYEKHKVYACEVTHQGLSSPVTKSFNRGEC |
| 99 | MAB10 | Full length IgG4 S228P | QVQLQESGPGLVKPSQTLSLTCTVSGGSIESGLYYW GWIRQPPGKGLEWIGSIYYSGSTYYNPSLKSRATISV DTSKNQFSLKLSSVTAADTAVYYCARDGVLALNKR SFDIWGQGTMVTVSSASTKGPSVFPLAPCSRSTSEST |

APPENDIX A-continued

SEQUENCE REFERENCE TABLE

| SEQ ID NO | Molecule | Region | Sequence |
|---|---|---|---|
| | | | AALGCLVKDYFPEPVTVSWNSGALTSGVHTFPAVLQ SSGLYSLSSVVTVPSSSLGTKTYTCNVDHKPSNTKVD KRVESKYGPPCPPCPAPEFLGGPSVFLFPPKPKDTLMI SRTPEVTCVVVDVSQEDPEVQFNWYVDGVEVHNAK TKPREEQFNSTYRVVSVLTVLHQDWLNGKEYKCKV SNKGLPSSIEKTISKAKGQPREPQVYTLPPSQEEMTK NQVSLTCLVKGFYPSDIAVEWESNGQPENNYKTTPP VLDSDGSFFLYSRLTVDKSRWQEGNVFSCSVMHEAL HNHYTQKSLSLSLGK |
| 100 | MAB10 | Full length IgG1 | QVQLQESGPGLVKPSQTLSLTCTVSGGSIESGLYYW GWIRQPPGKGLEWIGSIYYSGSTYYNPSLKSRATISV DTSKNQFSLKLSSVTAADTAVYYCARDGVLALNKR SFDIWGQGTMVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVD KRVEPKSCDKTHTCPPCPAPELLGGPSVFLFPPKPKD TLMISRTPEVTCVVVDVSHEDPEVKFNWYVDGVEV HNAKTKPREEQYNSTYRVVSVLTVLHQDWLNGKEY KCKVSNKALPAPIEKTISKAKGQPREPQVYTLPPSRE EMTKNQVSLTCLVKGFYPSDIAVEWESNGQPENNY KTTPPVLDSDGSFFLYSKLTVDKSRWQQGNVFSCSV MHEALHNHYTQKSLSLSPGK |
| 92 | MAB10 | Full length Kappa | EIVLTQSPGTLSLSPGERATLSCRASQSVSSSYLAWY QQKPGQAPRLLIYGASSRATGIPDRFSGSGSGTDFTL TISRLEPEDFAVYYCQQHTVRPPLTFGGGTKVEIKRT VAAPSVFIFPPSDEQLKSGTASVVCLLNNFYPREAKV QWKVDNALQSGNSQESVTEQDSKDSTYSLSSTLTLS KADYEKHKVYACEVTHQGLSSPVTKSFNRGEC |
| 101 | MAB11 | Full length IgG4 S228P | QVQLQESGPGLVKPSQTLSLTCTVSGGSIESGLYYW GWIRQPPGKGLEWIGSIYYSGSTYYNPSLKSRVTISV DTSKNQFSLKLSSVTAADTAVYYCARDGVLALNKR SFDIWGQGTMVTVSSASTKGPSVFPLAPCSRSTSEST AALGCLVKDYFPEPVTVSWNSGALTSGVHTFPAVLQ SSGLYSLSSVVTVPSSSLGTKTYTCNVDHKPSNTKVD KRVESKYGPPCPPCPAPEFLGGPSVFLFPPKPKDTLMI SRTPEVTCVVVDVSQEDPEVQFNWYVDGVEVHNAK TKPREEQFNSTYRVVSVLTVLHQDWLNGKEYKCKV SNKGLPSSIEKTISKAKGQPREPQVYTLPPSQEEMTK NQVSLTCLVKGFYPSDIAVEWESNGQPENNYKTTPP VLDSDGSFFLYSRLTVDKSRWQEGNVFSCSVMHEAL HNHYTQKSLSLSLGK |
| 102 | MAB11 | Full length IgG1 | QVQLQESGPGLVKPSQTLSLTCTVSGGSIESGLYYW GWIRQPPGKGLEWIGSIYYSGSTYYNPSLKSRVTISV DTSKNQFSLKLSSVTAADTAVYYCARDGVLALNKR SFDIWGQGTMVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVD KRVEPKSCDKTHTCPPCPAPELLGGPSVFLFPPKPKD TLMISRTPEVTCVVVDVSHEDPEVKFNWYVDGVEV HNAKTKPREEQYNSTYRVVSVLTVLHQDWLNGKEY KCKVSNKALPAPIEKTISKAKGQPREPQVYTLPPSRE EMTKNQVSLTCLVKGFYPSDIAVEWESNGQPENNY KTTPPVLDSDGSFFLYSKLTVDKSRWQQGNVFSCSV MHEALHNHYTQKSLSLSPGK |
| 92 | MAB11 | Full length Kappa | EIVLTQSPGTLSLSPGERATLSCRASQSVSSSYLAWY QQKPGQAPRLLIYGASSRATGIPDRFSGSGSGTDFTL TISRLEPEDFAVYYCQQHTVRPPLTFGGGTKVEIKRT VAAPSVFIFPPSDEQLKSGTASVVCLLNNFYPREAKV QWKVDNALQSGNSQESVTEQDSKDSTYSLSSTLTLS KADYEKHKVYACEVTHQGLSSPVTKSFNRGEC |
| 103 | MAB12 | Full length IgG4 S228P | QVQLQESGPGLVKPSQTLSLTCTASGGSIESGLYYW GWIRQPPGKGLEWIGSIYYSGSTYYNPSLKSRVTISV DTSKNQFSLKLSSVTAADTAVYYCARDGVLALNKR SFDIWGQGTMVTVSSASTKGPSVFPLAPCSRSTSEST AALGCLVKDYFPEPVTVSWNSGALTSGVHTFPAVLQ SSGLYSLSSVVTVPSSSLGTKTYTCNVDHKPSNTKVD KRVESKYGPPCPPCPAPEFLGGPSVFLFPPKPKDTLMI SRTPEVTCVVVDVSQEDPEVQFNWYVDGVEVHNAK |

APPENDIX A-continued

SEQUENCE REFERENCE TABLE

| SEQ ID NO | Molecule | Region | Sequence |
|---|---|---|---|
| | | | TKPREEQFNSTYRVVSVLTVLHQDWLNGKEYKCKV SNKGLPSSIEKTISKAKGQPREPQVYTLPPSQEEMTK NQVSLTCLVKGFYPSDIAVEWESNGQPENNYKTTPP VLDSDGSFFLYSRLTVDKSRWQEGNVFSCSVMHEAL HNHYTQKSLSLSLGK |
| 104 | MAB12 | Full length IgG1 | QVQLQESGPGLVKPSQTLSLTCTASGGSIESGLYYW GWIRQPPGKGLEWIGSIYYSGSTYYNPSLKSRVTISV DTSKNQFSLKLSSVTAADTAVYYCARDGVLALNKR SFDIWGQGTMVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVD KRVEPKSCDKTHTCPPCPAPELLGGPSVFLFPPKPKD TLMISRTPEVTCVVVDVSHEDPEVKFNWYVDGVEV HNAKTKPREEQYNSTYRVVSVLTVLHQDWLNGKEY KCKVSNKALPAPIEKTISKAKGQPREPQVYTLPPSRE EMTKNQVSLTCLVKGFYPSDIAVEWESNGQPENNY KTTPPVLDSDGSFFLYSKLTVDKSRWQQGNVFSCSV MHEALHNHYTQKSLSLSPGK |
| 92 | MAB12 | Full length Kappa | EIVLTQSPGTLSLSPGERATLSCRASQSVSSSYLAWY QQKPGQAPRLLIYGASSRATGIPDRFSGSGSGTDFTL TISRLEPEDFAVYYCQQHTVRPPLTFGGGTKVEIKRT VAAPSVFIFPPSDEQLKSGTASVVCLLNNFYPREAKV QWKVDNALQSGNSQESVTEQDSKDSTYSLSSTLTLS KADYEKHKVYACEVTHQGLSSPVTKSFNRGEC |
| 105 | MAB13 | Full length IgG4 S228P | QVQLVQSGAEVKKPGASVKVSCKASGYTFGNYYM HWVRQAPGQGLEWMGIINPSLGLTSYAQKFQGRVT MTRDTSTSTVYMELSSLRSEDTAVYYCARGGRTTWI GAFDIWGQGTMVTVSSASTKGPSVFPLAPCSRSTSES TAALGCLVKDYFPEPVTVSWNSGALTSGVHTFPAVL QSSGLYSLSSVVTVPSSSLGTKTYTCNVDHKPSNTKV DKRVESKYGPPCPPCPAPEFLGGPSVFLFPPKPKDTL MISRTPEVTCVVVDVSQEDPEVQFNWYVDGVEVHN AKTKPREEQFNSTYRVVSVLTVLHQDWLNGKEYKC KVSNKGLPSSIEKTISKAKGQPREPQVYTLPPSQEEM TKNQVSLTCLVKGFYPSDIAVEWESNGQPENNYKTT PPVLDSDGSFFLYSRLTVDKSRWQEGNVFSCSVMHE ALHNHYTQKSLSLSLGK |
| 106 | MAB13 | Full length IgG1 | QVQLVQSGAEVKKPGASVKVSCKASGYTFGNYYM HWVRQAPGQGLEWMGIINPSLGLTSYAQKFQGRVT MTRDTSTSTVYMELSSLRSEDTAVYYCARGGRTTWI GAFDIWGQGTMVTVSSASTKGPSVFPLAPSSKSTSG GTAALGCLVKDYFPEPVTVSWNSGALTSGVHTFPAV LQSSGLYSLSSVVTVPSSSLGTQTYICNVNHKPSNTK VDKRVEPKSCDKTHTCPPCPAPELLGGPSVFLFPPKP KDTLMISRTPEVTCVVVDVSHEDPEVKFNWYVDGV EVHNAKTKPREEQYNSTYRVVSVLTVLHQDWLNGK EYKCKVSNKALPAPIEKTISKAKGQPREPQVYTLPPS REEMTKNQVSLTCLVKGFYPSDIAVEWESNGQPENN YKTTPPVLDSDGSFFLYSKLTVDKSRWQQGNVFSCS VMHEALHNHYTQKSLSLSPGK |
| 107 | MAB13 | Full length Kappa | EIVMTQSPATLSVSPGERATLSCRASQSVSSNLAWY QQKPGQAPRLLIYGASTRATGIPARFSGSGSGTEFTL TISSLQSEDFAVYYCQQYVVWPPLTFGGGTKVEIKR TVAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC |
| 108 | MAB14 | Full length IgG4 S228P | QVQLVQSGAEVKKPGASVKVSCKASGYTFPAYYMH WVRQAPGQGLEWMGIINPSLGLTSYAQKFQGRVTM TRDTSTSTVYMELSSLRSEDTAVYYCARGGRTTWIG AFDIWGQGTMVTVSSASTKGPSVFPLAPCSRSTSEST AALGCLVKDYFPEPVTVSWNSGALTSGVHTFPAVLQ SSGLYSLSSVVTVPSSSLGTKTYTCNVDHKPSNTKVD KRVESKYGPPCPPCPAPEFLGGPSVFLFPPKPKDTLMI SRTPEVTCVVVDVSQEDPEVQFNWYVDGVEVHNAK TKPREEQFNSTYRVVSVLTVLHQDWLNGKEYKCKV SNKGLPSSIEKTISKAKGQPREPQVYTLPPSQEEMTK |

APPENDIX A-continued

SEQUENCE REFERENCE TABLE

| SEQ ID NO | Molecule | Region | Sequence |
|---|---|---|---|
| | | | NQVSLTCLVKGFYPSDIAVEWESNGQPENNYKTTPP VLDSDGSFFLYSRLTVDKSRWQEGNVFSCSVMHEAL HNHYTQKSLSLSLGK |
| 109 | MAB14 | Full length IgG1 | QVQLVQSGAEVKKPGASVKVSCKASGYTFPAYYMH WVRQAPGQGLEWMGIINPSLGLTSYAQKFQGRVTM TRDTSTSTVYMELSSLRSEDTAVYYCARGGRTTWIG AFDIWGQGTMVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVD KRVEPKSCDKTHTCPPCPAPELLGGPSVFLFPPKPKD TLMISRTPEVTCVVVDVSHEDPEVKFNWYVDGVEV HNAKTKPREEQYNSTYRVVSVLTVLHQDWLNGKEY KCKVSNKALPAPIEKTISKAKGQPREPQVYTLPPSRE EMTKNQVSLTCLVKGFYPSDIAVEWESNGQPENNY KTTPPVLDSDGSFFLYSKLTVDKSRWQQGNVFSCSV MHEALHNHYTQKSLSLSPGK |
| 107 | MAB14 | Full length Kappa | EIVMTQSPATLSVSPGERATLSCRASQSVSSNLAWY QQKPGQAPRLLIYGASTRATGIPARFSGSGSGTEFTL TISSLQSEDFAVYYCQQYVVWPPLTFGGGTKVEIKR TVAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC |
| 110 | MAB15 | Full length IgG4 S228P | QVQLVQSGAEVKKPGASVKVSCKASGYTFREYYMH WVRQAPGQGLEWMGIINPSIGLTSYARKFQGRVTMT RDTSTSTVYMELSSLRSEDTAVYYCARGGRTTWIGA FDIWGQGTMVTVSSASTKGPSVFPLAPCSRSTSESTA ALGCLVKDYFPEPVTVSWNSGALTSGVHTFPAVLQS SGLYSLSSVVTVPSSSLGTKTYTCNVDHKPSNTKVD KRVESKYGPPCPPCPAPEFLGGPSVFLFPPKPKDTLMI SRTPEVTCVVVDVSQEDPEVQFNWYVDGVEVHNAK TKPREEQFNSTYRVVSVLTVLHQDWLNGKEYKCKV SNKGLPSSIEKTISKAKGQPREPQVYTLPPSQEEMTK NQVSLTCLVKGFYPSDIAVEWESNGQPENNYKTTPP VLDSDGSFFLYSRLTVDKSRWQEGNVFSCSVMHEAL HNHYTQKSLSLSLGK |
| 111 | MAB15 | Full length IgG1 | QVQLVQSGAEVKKPGASVKVSCKASGYTFREYYMH WVRQAPGQGLEWMGIINPSIGLTSYARKFQGRVTMT RDTSTSTVYMELSSLRSEDTAVYYCARGGRTTWIGA FDIWGQGTMVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK RVEPKSCDKTHTCPPCPAPELLGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSREE MTKNQVSLTCLVKGFYPSDIAVEWESNGQPENNYK TTPPVLDSDGSFFLYSKLTVDKSRWQQGNVFSCSVM HEALHNHYTQKSLSLSPGK |
| 107 | MAB15 | Full length Kappa | EIVMTQSPATLSVSPGERATLSCRASQSVSSNLAWY QQKPGQAPRLLIYGASTRATGIPARFSGSGSGTEFTL TISSLQSEDFAVYYCQQYVVWPPLTFGGGTKVEIKR TVAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC |
| 112 | MAB16 | Full length IgG4 S228P | QVQLVQSGAEVKKPGASVKVSCKASGYTFREYYMH WVRQAPGQGLEWMGIINPSIGLTSYARKFQGRVTMT RDTSTSTVYMELSSLRSEDTAVYYCARGGRTTWIGA LDIWGQGTMVTVSSASTKGPSVFPLAPCSRSTSESTA ALGCLVKDYFPEPVTVSWNSGALTSGVHTFPAVLQS SGLYSLSSVVTVPSSSLGTKTYTCNVDHKPSNTKVD KRVESKYGPPCPPCPAPEFLGGPSVFLFPPKPKDTLMI SRTPEVTCVVVDVSQEDPEVQFNWYVDGVEVHNAK TKPREEQFNSTYRVVSVLTVLHQDWLNGKEYKCKV SNKGLPSSIEKTISKAKGQPREPQVYTLPPSQEEMTK NQVSLTCLVKGFYPSDIAVEWESNGQPENNYKTTPP VLDSDGSFFLYSRLTVDKSRWQEGNVFSCSVMHEAL HNHYTQKSLSLSLGK |

APPENDIX A-continued

SEQUENCE REFERENCE TABLE

| SEQ ID NO | Molecule | Region | Sequence |
|---|---|---|---|
| 113 | MAB16 | Full length IgG1 | QVQLVQSGAEVKKPGASVKVSCKASGYTFREYYMH WVRQAPGQGLEWMGIINPSIGLTSYARKFQGRVTMT RDTSTSTVYMELSSLRSEDTAVYYCARGGRTTWIGA LDIWGQGTMVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK RVEPKSCDKTHTCPPCPAPELLGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSREE MTKNQVSLTCLVKGFYPSDIAVEWESNGQPENNYK TTPPVLDSDGSFFLYSKLTVDKSRWQQGNVFSCSVM HEALHNHYTQKSLSLSPGK |
| 107 | MAB16 | Full length Kappa | EIVMTQSPATLSVSPGERATLSCRASQSVSSNLAWY QQKPGQAPRLLIYGASTRATGIPARFSGSGSGTEFTL TISSLQSEDFAVYYCQQYVVWPPLTFGGGTKVEIKR TVAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC |
| 114 | MAB17 | Full length IgG4 S228P | QVQLVQSGAEVKKPGASVKVSCKASGYTFPAYYIH WVRQAPGQGLEWMGIINPSLGLTSYARKFQGRVTM TRDTSTSTVYMELSSLRSEDTAVYYCARGGRTTWIG ALDIWGQGTMVTVSSASTKGPSVFPLAPCSRSTSEST AALGCLVKDYFPEPVTVSWNSGALTSGVHTFPAVLQ SSGLYSLSSVVTVPSSSLGTKTYTCNVDHKPSNTKVD KRVESKYGPPCPPCPAPEFLGGPSVFLFPPKPKDTLMI SRTPEVTCVVVDVSQEDPEVQFNWYVDGVEVHNAK TKPREEQFNSTYRVVSVLTVLHQDWLNGKEYKCKV SNKGLPSSIEKTISKAKGQPREPQVYTLPPSQEEMTK NQVSLTCLVKGFYPSDIAVEWESNGQPENNYKTTPP VLDSDGSFFLYSRLTVDKSRWQEGNVFSCSVMHEAL HNHYTQKSLSLSLGK |
| 115 | MAB17 | Full length IgG1 | QVQLVQSGAEVKKPGASVKVSCKASGYTFPAYYIH WVRQAPGQGLEWMGIINPSLGLTSYARKFQGRVTM TRDTSTSTVYMELSSLRSEDTAVYYCARGGRTTWIG ALDIWGQGTMVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVD KRVEPKSCDKTHTCPPCPAPELLGGPSVFLFPPKPKD TLMISRTPEVTCVVVDVSHEDPEVKFNWYVDGVEV HNAKTKPREEQYNSTYRVVSVLTVLHQDWLNGKEY KCKVSNKALPAPIEKTISKAKGQPREPQVYTLPPSRE EMTKNQVSLTCLVKGFYPSDIAVEWESNGQPENNY KTTPPVLDSDGSFFLYSKLTVDKSRWQQGNVFSCSV MHEALHNHYTQKSLSLSPGK |
| 107 | MAB17 | Full length Kappa | EIVMTQSPATLSVSPGERATLSCRASQSVSSNLAWY QQKPGQAPRLLIYGASTRATGIPARFSGSGSGTEFTL TISSLQSEDFAVYYCQQYVVWPPLTFGGGTKVEIKR TVAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC |
| 116 | MAB18 | Full length IgG4 S228P | QVQLVQSGAEVKKPGASVKVSCKASGYTFPAYYMH WVRQAPGQGLEWMGIINPSLGLTSYARKFQGRVTM TRDTSTSTVYMELSSLRSEDTAVYYCARGGRTTWIG AFDIWGQGTMVTVSSASTKGPSVFPLAPCSRSTSEST AALGCLVKDYFPEPVTVSWNSGALTSGVHTFPAVLQ SSGLYSLSSVVTVPSSSLGTKTYTCNVDHKPSNTKVD KRVESKYGPPCPPCPAPEFLGGPSVFLFPPKPKDTLMI SRTPEVTCVVVDVSQEDPEVQFNWYVDGVEVHNAK TKPREEQFNSTYRVVSVLTVLHQDWLNGKEYKCKV SNKGLPSSIEKTISKAKGQPREPQVYTLPPSQEEMTK NQVSLTCLVKGFYPSDIAVEWESNGQPENNYKTTPP VLDSDGSFFLYSRLTVDKSRWQEGNVFSCSVMHEAL HNHYTQKSLSLSLGK |
| 117 | MAB18 | Full length IgG1 | QVQLVQSGAEVKKPGASVKVSCKASGYTFPAYYMH WVRQAPGQGLEWMGIINPSLGLTSYARKFQGRVTM TRDTSTSTVYMELSSLRSEDTAVYYCARGGRTTWIG AFDIWGQGTMVTVSSASTKGPSVFPLAPSSKSTSGGT |

APPENDIX A-continued

SEQUENCE REFERENCE TABLE

| SEQ ID NO | Molecule | Region | Sequence |
|---|---|---|---|
| | | | AALGCLVKDYFPEPVTVSWNSGALTSGVHTFPAVLQ SSGLYSLSSVVTVPSSSLGTQTYICNVNHKPSNTKVD KRVEPKSCDKTHTCPPCPAPELLGGPSVFLFPPKPKD TLMISRTPEVTCVVVDVSHEDPEVKFNWYVDGVEV HNAKTKPREEQYNSTYRVVSVLTVLHQDWLNGKEY KCKVSNKALPAPIEKTISKAKGQPREPQVYTLPPSRE EMTKNQVSLTCLVKGFYPSDIAVEWESNGQPENNY KTTPPVLDSDGSFFLYSKLTVDKSRWQQGNVFSCSV MHEALHNHYTQKSLSLSPGK |
| 107 | MAB18 | Full length Kappa | EIVMTQSPATLSVSPGERATLSCRASQSVSSNLAWY QQKPGQAPRLLIYGASTRATGIPARFSGSGSGTEFTL TISSLQSEDFAVYYCQQYVVWPPLTFGGGTKVEIKR TVAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC |
| 118 | MAB19 | Full length IgG4 S228P | QVQLVQSGAEVKKPGASVKVSCKASGYTFTSHYMG WVRQAPGQGLEWMGVINPSMGATSYAQKFQGRVT MTRDTSTSTVYMELSSLRSEDTAVYYCARLHVSGSY YPAYLDYWGQGTMVTVSSASTKGPSVFPLAPCSRST SESTAALGCLVKDYFPEPVTVSWNSGALTSGVHTFP AVLQSSGLYSLSSVVTVPSSSLGTKTYTCNVDHKPSN TKVDKRVESKYGPPCPPCPAPEFLGGPSVFLFPPKPK DTLMISRTPEVTCVVVDVSQEDPEVQFNWYVDGVE VHNAKTKPREEQFNSTYRVVSVLTVLHQDWLNGKE YKCKVSNKGLPSSIEKTISKAKGQPREPQVYTLPPSQ EEMTKNQVSLTCLVKGFYPSDIAVEWESNGQPENNY KTTPPVLDSDGSFFLYSRLTVDKSRWQEGNVFSCSV MHEALHNHYTQKSLSLSLGK |
| 119 | MAB19 | Full length IgG1 | QVQLVQSGAEVKKPGASVKVSCKASGYTFTSHYMG WVRQAPGQGLEWMGVINPSMGATSYAQKFQGRVT MTRDTSTSTVYMELSSLRSEDTAVYYCARLHVSGSY YPAYLDYWGQGTMVTVSSASTKGPSVFPLAPSSKST SGGTAALGCLVKDYFPEPVTVSWNSGALTSGVHTFP AVLQSSGLYSLSSVVTVPSSSLGTQTYICNVNHKPSN TKVDKRVEPKSCDKTHTCPPCPAPELLGGPSVFLFPP KPKDTLMISRTPEVTCVVVDVSHEDPEVKFNWYVD GVEVHNAKTKPREEQYNSTYRVVSVLTVLHQDWLN GKEYKCKVSNKALPAPIEKTISKAKGQPREPQVYTLP PSREEMTKNQVSLTCLVKGFYPSDIAVEWESNGQPE NNYKTTPPVLDSDGSFFLYSKLTVDKSRWQQGNVFS CSVMHEALHNHYTQKSLSLSPGK |
| 120 | MAB19 | Full length Kappa | EIVMTQSPATLSVSPGERATLSCRASQSVSSNLAWY QQKPGQAPRHLIYGASTRATGIPARFSGSGSGTEFTL TISSLQSEDFAVYYCQQYIVFPWTFGGGTKVEIKRTV AAPSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEC |
| 121 | MAB20 | Full length IgG4 S228P | QVQLVQSGAEVKKPGASVKVSCKASGYTFTSHYMG WVRQAPGQGLEWVGIINPSMGATSYAQKFQGRVTM TRDTSTSTVYMELSSLRSEDTAVYYCARLHVSGSYY PAYLDYWGQGTMVTVSSASTKGPSVFPLAPCSRSTS ESTAALGCLVKDYFPEPVTVSWNSGALTSGVHTFPA VLQSSGLYSLSSVVTVPSSSLGTKTYTCNVDHKPSNT KVDKRVESKYGPPCPPCPAPEFLGGPSVFLFPPKPKD TLMISRTPEVTCVVVDVSQEDPEVQFNWYVDGVEV HNAKTKPREEQFNSTYRVVSVLTVLHQDWLNGKEY KCKVSNKGLPSSIEKTISKAKGQPREPQVYTLPPSQE EMTKNQVSLTCLVKGFYPSDIAVEWESNGQPENNY KTTPPVLDSDGSFFLYSRLTVDKSRWQEGNVFSCSV MHEALHNHYTQKSLSLSLGK |
| 122 | MAB20 | Full length IgG1 | QVQLVQSGAEVKKPGASVKVSCKASGYTFTSHYMG WVRQAPGQGLEWVGIINPSMGATSYAQKFQGRVTM TRDTSTSTVYMELSSLRSEDTAVYYCARLHVSGSYY PAYLDYWGQGTMVTVSSASTKGPSVFPLAPSSKSTS GGTAALGCLVKDYFPEPVTVSWNSGALTSGVHTFPA VLQSSGLYSLSSVVTVPSSSLGTQTYICNVNHKPSNT KVDKRVEPKSCDKTHTCPPCPAPELLGGPSVFLFPPK PKDTLMISRTPEVTCVVVDVSHEDPEVKFNWYVDG |

APPENDIX A-continued

SEQUENCE REFERENCE TABLE

| SEQ ID NO | Molecule | Region | Sequence |
|---|---|---|---|
| | | | VEVHNAKTKPREEQYNSTYRVVSVLTVLHQDWLNG KEYKCKVSNKALPAPIEKTISKAKGQPREPQVYTLPP SREEMTKNQVSLTCLVKGFYPSDIAVEWESNGQPEN NYKTTPPVLDSDGSFFLYSKLTVDKSRWQQGNVFSC SVMHEALHNHYTQKSLSLSPGK |
| 120 | MAB20 | Full length Kappa | EIVMTQSPATLSVSPGERATLSCRASQSVSSNLAWY QQKPGQAPRHLIYGASTRATGIPARFSGSGSGTEFTL TISSLQSEDFAVYYCQQYIVFPWTFGGGTKVEIKRTV AAPSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEC |
| 123 | MAB21 | Full length IgG4 S228P | QVQLVQSGAEVKKPGASVKVSCKASGYTFTSHYMG WVRQAPGQGLEWMGIINPSMGATSYTQKFRGRVTM TRDTSTSTVYMELSSLRSEDTAVYYCARLHVSGSYY PAYLDYWGQGTMVTVSSASTKGPSVFPLAPCSRSTS ESTAALGCLVKDYFPEPVTVSWNSGALTSGVHTFPA VLQSSGLYSLSSVVTVPSSSLGTKTYTCNVDHKPSNT KVDKRVESKYGPPCPPCPAPEFLGGPSVFLFPPKPKD TLMISRTPEVTCVVVDVSQEDPEVQFNWYVDGVEV HNAKTKPREEQFNSTYRVVSVLTVLHQDWLNGKEY KCKVSNKGLPSSIEKTISKAKGQPREPQVYTLPPSQE EMTKNQVSLTCLVKGFYPSDIAVEWESNGQPENNY KTTPPVLDSDGSFFLYSRLTVDKSRWQEGNVFSCSV MHEALHNHYTQKSLSLSLGK |
| 124 | MAB21 | Full length IgG1 | QVQLVQSGAEVKKPGASVKVSCKASGYTFTSHYMG WVRQAPGQGLEWMGIINPSMGATSYTQKFRGRVTM TRDTSTSTVYMELSSLRSEDTAVYYCARLHVSGSYY PAYLDYWGQGTMVTVSSASTKGPSVFPLAPSSKSTS GGTAALGCLVKDYFPEPVTVSWNSGALTSGVHTFPA VLQSSGLYSLSSVVTVPSSSLGTQTYICNVNHKPSNT KVDKRVEPKSCDKTHTCPPCPAPELLGGPSVFLFPPK PKDTLMISRTPEVTCVVVDVSHEDPEVKFNWYVDG VEVHNAKTKPREEQYNSTYRVVSVLTVLHQDWLNG KEYKCKVSNKALPAPIEKTISKAKGQPREPQVYTLPP SREEMTKNQVSLTCLVKGFYPSDIAVEWESNGQPEN NYKTTPPVLDSDGSFFLYSKLTVDKSRWQQGNVFSC SVMHEALHNHYTQKSLSLSPGK |
| 120 | MAB21 | Full length Kappa | EIVMTQSPATLSVSPGERATLSCRASQSVSSNLAWY QQKPGQAPRHLIYGASTRATGIPARFSGSGSGTEFTL TISSLQSEDFAVYYCQQYIVFPWTFGGGTKVEIKRTV AAPSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEC |
| 125 | IgG1 | Constant (Glm(17, 1) allotype, N297A | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSCDKTHTCP PCPAPELLGGPSVFLFPPKPKDTLMISRTPEVTCVVV DVSHEDPEVKFNWYVDGVEVHNAKTKPREEQYAST YRVVSVLTVLHQDWLNGKEYKCKVSNKALPAPIEK TISKAKGQPREPQVYTLPPSRDELTKNQVSLTCLVKG FYPSDIAVEWESNGQPENNYKTTPPVLDSDGSFFLYS KLTVDKSRWQQGNVFSCSVMHEALHNHYTQKSLSL SPGK |
| 126 | Kappa | Constant | RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC |
| 127 | Linker | | GGGGS |

128. . . 137 - See other portions of this disclosure and the electronic version of the Sequence Listing submitted herewith.

| 138 | mTIGIT2 | | MHGWLLLVWVQGLIQAAFLATAIGATAGTIDTKRNI SAEEGGSVILQCHFSSDTAEVTQVDWKQQDQLLAIY SVDLGWHVASVFSDRVVPGPSLGLTFQSLTMNDTGE YFCTYHTYPGGIYKGRIFLKVQESSDDRNGLAQFQT |

APPENDIX A-continued

SEQUENCE REFERENCE TABLE

| SEQ ID NO | Molecule | Region | Sequence |
|---|---|---|---|
| | | | APLGGTMAAVLGLICLMVTGVTVLARKDKSIRMHSI ESGLGRTEAEPQEWNLRSLSSPGSPVQTQTAPAGPC GEQAEDDYADPQEYFNVLSYRSLESFIAVSKTG |

What is claimed is:

1. A method of treating a cancer in a human subject in need thereof, comprising administering to the subject:
   a) an effective amount of an isolated antibody or antigen-binding fragment thereof that specifically binds human TIGIT (hTIGIT) as set forth in SEQ ID NO: 1, comprising a heavy chain variable ($V_H$) domain comprising from N-terminus to C-terminus, CDR-H1, CDR-H2, and CDR-H3; and a light chain variable ($V_L$) domain comprising from N-terminus to C-terminus CDR-L1, CDR-L2, and CDR-L3, wherein the CDRs of the $V_H$ and $V_L$ are selected from the group consisting of:
   (1) a CDR-H3 having the sequence A-R-D-A-N-Y-Y-G-$X_1$-A-W-A-F-D-P, wherein X1 is S or G (SEQ ID NO: 131), a CDR-H2 having the sequence S-I-Y-Y-S-G-$X_2$-T-F-Y-N-P-S-L-K-$X_3$, wherein $X_2$ is S or A, and $X_3$ is S or G (SEQ ID NO: 132), a CDR-H1 having the sequence G-S-I-$X_4$-S-$X_5$-$X_6$-$X_7$-Y-W-G, wherein $X_4$ is S or T, $X_5$ is S or T, $X_6$ is S or K, and $X_7$ is H or Y (SEQ ID NO: 133), a CDR-L3 having the sequence QQHFNLPT (SEQ ID NO: 63), a CDR-L2 having the sequence DASNRAT (SEQ ID NO: 67), and a CDR-L1 having the sequence RASQSVSSYLA (SEQ ID NO: 70);

(2) a CDR-H3 having the sequence A-R-G-G-R-T-T-W-I-C-A-$X_1$-D-I, wherein $X_1$ is F or L (SEQ ID NO: 134), a CDR-H2 having the sequence I-I-N-P-S-$X_2$-G-L-T-S-Y-A-$X_3$-K-F-Q-G, wherein $X_2$ is L or I, and $X_3$ is Q or R (SEQ ID NO: 135), a CDR-H1 having the sequence Y-T-F-$X_4$-$X_5$-Y-Y-$X_6$-H, wherein $X_4$ is G, P or R, $X_5$ is N, A or E, and $X_6$ is M or I (SEQ ID NO: 136), a CDR-L3 having the sequence QQYWWPPLT (SEQ ID NO:65), a CDR-L2 having the sequence GASTRAT (SEQ ID NO:69), and a CDR-L1 having the sequence RASQSVSSNLA (SEQ ID NO:72);

(3) a CDR-H3 having the sequence ARLHVSGSYYPAY-LDY (SEQ ID NO: 35), a CDR-H2 having the sequence $X_1$-I-N-P-S-M-G-A-T-S-Y-$X_2$-Q-K-F-$_x$3-G, wherein $X_1$ is V or I, $X_2$ is A or T, and $X_3$ is Q or R (SEQ ID NO: 137), a CDR-H1 having the sequence YTFTSHYMG (SEQ ID NO: 62), a CDR-L3 having the sequence QQYIVFPWT (SEQ ID NO: 66), a CDR-L2 having the sequence GASTRAT (SEQ ID NO: 69), and a CDR-L1 having the sequence RASQSVSSNLA, (SEQ ID NO: 72); and (4) a CDR-H3 having the sequence A-R-D-G-V-L-$X_1$-L-N-K-R-S-F-D-I, wherein $X_1$ is A or T (SEQ ID NO: 128), a CDR-H2 having the sequence S-I-Y-Y-S-G-$X_2$-T-Y-Y-N-P-S-L-K-S, wherein $X_2$ is S, Q or G (SEQ ID NO: 129), a CDR-H1 having the sequence G-S-I-$X_3$-S-G-$X_4$-Y-Y-W-G, wherein $X_3$ is E or A, and $X_4$ is L, V or S (SEQ ID NO: 130), a CDR-L3 having the sequence QQHTVRPPLT (SEQ ID NO: 64), a CDR-L2 having the sequence GASSRAT (SEQ ID NO: 68); and a CDR-L1 having the sequence RASQSVSSSYLA (SEQ ID NO: 71), or a pharmaceutical composition comprising an effective amount of the antibody or antigen-binding fragment thereof and a pharmaceutically acceptable carrier; and b) at least one additional therapeutic agent selected from an immunomodulatory agent, a chemotherapeutic agent, an immunostimulatory agent, radiation, and combinations thereof.

2. The method of claim 1, wherein the immunomodulatory agent is an agent that inhibits the interaction between PD-1 and PD-L1, and wherein the agent that inhibits the interaction between PD-1 and PD-L1 is selected from an antibody, a peptidomimetic, or a small molecule.

3. The method of claim 2, wherein the agent that inhibits the interaction between PD-1 and PD-L1 is selected from the group consisting of pembrolizumab, nivolumab, atezolizumab, avelumab, durvalumab and BMS-936559.

4. The method of claim 1, wherein the immunostimulatory agent is selected from (a) an agent that blocks signaling of an inhibitory receptor of an immune cell or a ligand thereof; (b) an agonist to a stimulatory receptor of an immune cell; (c) a cytokine; (d) an oncolytic virus; (e) a T cell expressing a chimeric antigen receptor; (f) a bi- or multi-specific T cell directed antibody; (g) an anti-TGF-β antibody; (h) a TGF-β trap; (i) a vaccine to a cancer-associated antigen, including such antigen or a nucleic acid encoding such antigen and (j) combinations thereof.

5. The method of claim 4, wherein the immunostimulatory agent is an agent that blocks signaling of an inhibitory receptor of an immune cell or a ligand thereof and the inhibitory receptor or ligand thereof is selected from CTLA-4, PD-L2, LAG-3, Tim3, neuritin, BTLA, CECAM-1, CECAM-5, VISTA, LAIR1, CD160, 2B4, TGF-R, KIR, and combinations thereof.

6. The method of claim 4, wherein the immunostimulatory agent is an agonist to a stimulatory receptor of an immune cell, and the stimulatory receptor of an immune cell is selected from OX40, CD2, CD27, CDS, ICAM-1, LFA-1 (CD11a/CD18), ICOS (CD278), 4-1BB (CD137), GITR, CD28, CD30, CD40, BAFFR, HVEM, CD7, LIGHT, NKG2C, SLAMF7, NKp80, CD160, B7-H3, CD83 ligand, and combinations thereof.

7. The method of claim 1, wherein the cancer is selected from the group consisting of acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

8. The method of claim 1, wherein the cancer comprises a brain tumor.

* * * * *

SEQUENCE LISTING

<160> NUMBER OF SEQ ID NOS: 142

<210> SEQ ID NO 1
<211> LENGTH: 244
<212> TYPE: PRT
<213> ORGANISM: Homo sapiens
<220> FEATURE:
<221> NAME/KEY: misc_feature
<222> LOCATION: (1)..(244)
<223> OTHER INFORMATION: hTIGIT

<400> SEQUENCE: 1

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 2
<211> LENGTH: 245

```
<212> TYPE: PRT
<213> ORGANISM: Macaca fascicularis
<220> FEATURE:
<221> NAME/KEY: misc_feature
<222> LOCATION: (1)..(245)
<223> OTHER INFORMATION: cTIGIT

<400> SEQUENCE: 2

Met Arg Trp Cys Leu Phe Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Lys Lys Gly Gly Ser Val Ile Leu Gln Cys His Leu Ser
        35                  40                  45

Ser Thr Met Ala Gln Val Thr Gln Val Asn Trp Glu Gln His Asp His
    50                  55                  60

Ser Leu Leu Ala Ile Arg Asn Ala Glu Leu Gly Trp His Ile Tyr Pro
65                  70                  75                  80

Ala Phe Lys Asp Arg Val Ala Pro Gly Pro Gly Leu Gly Leu Thr Leu
                85                  90                  95

Gln Ser Leu Thr Met Asn Asp Thr Gly Glu Tyr Phe Cys Thr Tyr His
            100                 105                 110

Thr Tyr Pro Asp Gly Thr Tyr Arg Gly Arg Ile Phe Leu Glu Val Leu
        115                 120                 125

Glu Ser Ser Val Ala Glu His Ser Ala Arg Phe Gln Ile Pro Leu Leu
    130                 135                 140

Gly Ala Met Ala Met Met Leu Val Val Ile Cys Ile Ala Val Ile Val
145                 150                 155                 160

Val Val Val Leu Ala Arg Lys Lys Lys Ser Leu Arg Ile His Ser Val
                165                 170                 175

Glu Ser Gly Leu Gln Arg Lys Ser Thr Gly Gln Glu Gln Ile Pro
            180                 185                 190

Ser Ala Pro Ser Pro Pro Gly Ser Cys Val Gln Ala Glu Ala Ala Pro
    195                 200                 205

Ala Gly Leu Cys Gly Glu Gln Gln Gly Asp Asp Cys Ala Glu Leu His
    210                 215                 220

Asp Tyr Phe Asn Val Leu Ser Tyr Arg Ser Leu Gly Ser Cys Ser Phe
225                 230                 235                 240

Phe Thr Glu Thr Gly
            245

<210> SEQ ID NO 3
<211> LENGTH: 241
<212> TYPE: PRT
<213> ORGANISM: Mus musculus
<220> FEATURE:
<221> NAME/KEY: misc_feature
<222> LOCATION: (1)..(241)
<223> OTHER INFORMATION: mTIGIT

<400> SEQUENCE: 3

Met His Gly Trp Leu Leu Leu Val Trp Val Gln Gly Leu Ile Gln Ala
1               5                   10                  15

Ala Phe Leu Ala Thr Gly Ala Thr Ala Gly Thr Ile Asp Thr Lys Arg
            20                  25                  30

Asn Ile Ser Ala Glu Glu Gly Gly Ser Val Ile Leu Gln Cys His Phe
        35                  40                  45

Ser Ser Asp Thr Ala Glu Val Thr Gln Val Asp Trp Lys Gln Gln Asp
```

```
                    50                  55                  60
Gln Leu Leu Ala Ile Tyr Ser Val Asp Leu Gly Trp His Val Ala Ser
 65                  70                  75                  80

Val Phe Ser Asp Arg Val Val Pro Gly Pro Ser Leu Gly Leu Thr Phe
                     85                  90                  95

Gln Ser Leu Thr Met Asn Asp Thr Gly Glu Tyr Phe Cys Thr Tyr His
                    100                 105                 110

Thr Tyr Pro Gly Gly Ile Tyr Lys Gly Arg Ile Phe Leu Lys Val Gln
                    115                 120                 125

Glu Ser Ser Val Ala Gln Phe Gln Thr Ala Pro Leu Gly Gly Thr Met
                    130                 135                 140

Ala Ala Val Leu Gly Leu Ile Cys Leu Met Val Thr Gly Val Thr Val
145                 150                 155                 160

Leu Ala Arg Lys Lys Ser Ile Arg Met His Ser Ile Glu Ser Gly Leu
                    165                 170                 175

Gly Arg Thr Glu Ala Glu Pro Gln Glu Trp Asn Leu Arg Ser Leu Ser
                    180                 185                 190

Ser Pro Gly Ser Pro Val Gln Thr Gln Thr Ala Pro Ala Gly Pro Cys
                    195                 200                 205

Gly Glu Gln Ala Glu Asp Asp Tyr Ala Asp Pro Gln Glu Tyr Phe Asn
                    210                 215                 220

Val Leu Ser Tyr Arg Ser Leu Glu Ser Phe Ile Ala Val Ser Lys Thr
225                 230                 235                 240

Gly

<210> SEQ ID NO 4
<211> LENGTH: 123
<212> TYPE: PRT
<213> ORGANISM: Artificial Sequence
<220> FEATURE:
<223> OTHER INFORMATION: Synthetic - MAB1-IgG4; VH

<400> SEQUENCE: 4

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Thr Ser Ser
                    20                  25                  30

Ser Tyr Tyr Trp Gly Trp Ile Arg Gln Pro Pro Gly Lys Gly Leu Glu
                35                  40                  45

Trp Ile Gly Ser Ile Tyr Tyr Ser Gly Ala Thr Phe Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                    85                  90                  95

Cys Ala Arg Asp Ala Asn Tyr Tyr Gly Ser Ala Trp Ala Phe Asp Pro
                    100                 105                 110

Trp Gly Gln Gly Thr Leu Val Thr Val Ser Ser
                    115                 120

<210> SEQ ID NO 5
<211> LENGTH: 123
<212> TYPE: PRT
<213> ORGANISM: Artificial Sequence
<220> FEATURE:
<223> OTHER INFORMATION: Synthetic - MAB2-IgG4; VH
```

```
<400> SEQUENCE: 5

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Lys Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser
        115                 120

<210> SEQ ID NO 6
<211> LENGTH: 123
<212> TYPE: PRT
<213> ORGANISM: Artificial Sequence
<220> FEATURE:
<223> OTHER INFORMATION: Synthetic - MAB3-IgG4; VH

<400> SEQUENCE: 6

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser
        115                 120

<210> SEQ ID NO 7
<211> LENGTH: 123
<212> TYPE: PRT
<213> ORGANISM: Artificial Sequence
<220> FEATURE:
<223> OTHER INFORMATION: Synthetic - MAB4-IgG4; VH

<400> SEQUENCE: 7

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45
```

Trp Ile Gly Ser Ile Tyr Tyr Ser Gly Ser Thr Phe Tyr Asn Pro Ser
            50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Gly Ala Trp Ala Phe Asp Pro
                100                 105                 110

Trp Gly Gln Gly Thr Leu Val Thr Val Ser Ser
            115                 120

<210> SEQ ID NO 8
<211> LENGTH: 123
<212> TYPE: PRT
<213> ORGANISM: Artificial Sequence
<220> FEATURE:
<223> OTHER INFORMATION: Synthetic - MAB5-IgG4; VH

<400> SEQUENCE: 8

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
            50                  55                  60

Leu Lys Gly Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
                100                 105                 110

Trp Gly Gln Gly Thr Leu Val Thr Val Ser Ser
            115                 120

<210> SEQ ID NO 9
<211> LENGTH: 123
<212> TYPE: PRT
<213> ORGANISM: Artificial Sequence
<220> FEATURE:
<223> OTHER INFORMATION: Synthetic - MAB6-IgG4; VH

<400> SEQUENCE: 9

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Glu Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Gly Thr Tyr Tyr Asn Pro Ser
            50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
                100                 105                 110

```
Trp Gly Gln Gly Thr Met Val Thr Val Ser Ser
        115                 120

<210> SEQ ID NO 10
<211> LENGTH: 123
<212> TYPE: PRT
<213> ORGANISM: Artificial Sequence
<220> FEATURE:
<223> OTHER INFORMATION: Synthetic - MAB7-IgG4; VH

<400> SEQUENCE: 10

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Val Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser
        115                 120

<210> SEQ ID NO 11
<211> LENGTH: 123
<212> TYPE: PRT
<213> ORGANISM: Artificial Sequence
<220> FEATURE:
<223> OTHER INFORMATION: Synthetic - MAB8-IgG4; VH

<400> SEQUENCE: 11

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ala Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Gln Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser
        115                 120

<210> SEQ ID NO 12
<211> LENGTH: 123
<212> TYPE: PRT
<213> ORGANISM: Artificial Sequence
<220> FEATURE:
<223> OTHER INFORMATION: Synthetic - MAB9-IgG4; VH
```

<400> SEQUENCE: 12

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser
        115                 120

<210> SEQ ID NO 13
<211> LENGTH: 123
<212> TYPE: PRT
<213> ORGANISM: Artificial Sequence
<220> FEATURE:
<223> OTHER INFORMATION: Synthetic - MAB10-IgG4; VH

<400> SEQUENCE: 13

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Gly Val Leu Ala Leu Asn Lys Arg Ser Phe Asp Ile
            100                 105                 110

Trp Gly Gln Gly Thr Met Val Thr Val Ser Ser
        115                 120

<210> SEQ ID NO 14
<211> LENGTH: 123
<212> TYPE: PRT
<213> ORGANISM: Artificial Sequence
<220> FEATURE:
<223> OTHER INFORMATION: Synthetic - MAB11-IgG4; VH

<400> SEQUENCE: 14

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

```
Trp Ile Gly Ser Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Ala Leu Asn Lys Arg Ser Phe Asp Ile
            100                 105                 110

Trp Gly Gln Gly Thr Met Val Thr Val Ser Ser
        115                 120

<210> SEQ ID NO 15
<211> LENGTH: 123
<212> TYPE: PRT
<213> ORGANISM: Artificial Sequence
<220> FEATURE:
<223> OTHER INFORMATION: Synthetic - MAB12-IgG4; VH

<400> SEQUENCE: 15

Gln Val Gln Leu Gln Glu Ser Gly Pro Gly Leu Val Lys Pro Ser Gln
1               5                   10                  15

Thr Leu Ser Leu Thr Cys Thr Ala Ser Gly Gly Ser Ile Glu Ser Gly
                20                  25                  30

Leu Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Ala Leu Asn Lys Arg Ser Phe Asp Ile
            100                 105                 110

Trp Gly Gln Gly Thr Met Val Thr Val Ser Ser
        115                 120

<210> SEQ ID NO 16
<211> LENGTH: 121
<212> TYPE: PRT
<213> ORGANISM: Artificial Sequence
<220> FEATURE:
<223> OTHER INFORMATION: Synthetic - MAB13-IgG4; VH

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
                20                  25                  30

Tyr Met His Trp Val Arg Gln Ala Pro Gly Gln Gly Leu Glu Trp Met
            35                  40                  45

Gly Ile Ile Asn Pro Ser Leu Gly Leu Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
```

```
                    100                 105                 110
Gln Gly Thr Met Val Thr Val Ser Ser
            115                 120

<210> SEQ ID NO 17
<211> LENGTH: 121
<212> TYPE: PRT
<213> ORGANISM: Artificial Sequence
<220> FEATURE:
<223> OTHER INFORMATION: Synthetic - MAB14-IgG4; VH

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
            20                  25                  30

Tyr Met His Trp Val Arg Gln Ala Pro Gly Gln Gly Leu Glu Trp Met
        35                  40                  45

Gly Ile Ile Asn Pro Ser Leu Gly Leu Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
            100                 105                 110

Gln Gly Thr Met Val Thr Val Ser Ser
            115                 120

<210> SEQ ID NO 18
<211> LENGTH: 121
<212> TYPE: PRT
<213> ORGANISM: Artificial Sequence
<220> FEATURE:
<223> OTHER INFORMATION: Synthetic - MAB15-IgG4; VH

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Glu Tyr
            20                  25                  30

Tyr Met His Trp Val Arg Gln Ala Pro Gly Gln Gly Leu Glu Trp Met
        35                  40                  45

Gly Ile Ile Asn Pro Ser Ile Gly Leu Thr Ser Tyr Ala Arg Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
            100                 105                 110

Gln Gly Thr Met Val Thr Val Ser Ser
            115                 120

<210> SEQ ID NO 19
<211> LENGTH: 121
<212> TYPE: PRT
<213> ORGANISM: Artificial Sequence
<220> FEATURE:
```

<223> OTHER INFORMATION: Synthetic - MAB16-IgG4; VH

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Glu Tyr
            20                  25                  30

Tyr Met His Trp Val Arg Gln Ala Pro Gly Gln Gly Leu Glu Trp Met
        35                  40                  45

Gly Ile Ile Asn Pro Ser Ile Gly Leu Thr Ser Tyr Ala Arg Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Leu Asp Ile Trp Gly
            100                 105                 110

Gln Gly Thr Met Val Thr Val Ser Ser
        115                 120

<210> SEQ ID NO 20
<211> LENGTH: 121
<212> TYPE: PRT
<213> ORGANISM: Artificial Sequence
<220> FEATURE:
<223> OTHER INFORMATION: Synthetic - MAB17-IgG4; VH

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
            20                  25                  30

Tyr Ile His Trp Val Arg Gln Ala Pro Gly Gln Gly Leu Glu Trp Met
        35                  40                  45

Gly Ile Ile Asn Pro Ser Leu Gly Leu Thr Ser Tyr Ala Arg Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Leu Asp Ile Trp Gly
            100                 105                 110

Gln Gly Thr Met Val Thr Val Ser Ser
        115                 120

<210> SEQ ID NO 21
<211> LENGTH: 121
<212> TYPE: PRT
<213> ORGANISM: Artificial Sequence
<220> FEATURE:
<223> OTHER INFORMATION: Synthetic - MAB18-IgG4; VH

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
            20                  25                  30

Tyr Met His Trp Val Arg Gln Ala Pro Gly Gln Gly Leu Glu Trp Met

```
                35                  40                  45
Gly Ile Ile Asn Pro Ser Leu Gly Leu Thr Ser Tyr Ala Arg Lys Phe
        50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Gly Arg Thr Thr Trp Ile Gly Ala Phe Asp Ile Trp Gly
                100                 105                 110
Gln Gly Thr Met Val Thr Val Ser Ser
        115                 120

<210> SEQ ID NO 22
<211> LENGTH: 123
<212> TYPE: PRT
<213> ORGANISM: Artificial Sequence
<220> FEATURE:
<223> OTHER INFORMATION: Synthetic - MAB19-IgG4; VH

<400> SEQUENCE: 22

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser His
                20                  25                  30
Tyr Met Gly Trp Val Arg Gln Ala Pro Gly Gln Gly Leu Glu Trp Met
                35                  40                  45
Gly Val Ile Asn Pro Ser Met Gly Ala Thr Ser Tyr Ala Gln Lys Phe
        50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Leu His Val Ser Gly Ser Tyr Tyr Pro Ala Tyr Leu Asp Tyr
                100                 105                 110
Trp Gly Gln Gly Thr Met Val Thr Val Ser Ser
        115                 120

<210> SEQ ID NO 23
<211> LENGTH: 123
<212> TYPE: PRT
<213> ORGANISM: Artificial Sequence
<220> FEATURE:
<223> OTHER INFORMATION: Synthetic - MAB20-IgG4; VH

<400> SEQUENCE: 23

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser His
                20                  25                  30
Tyr Met Gly Trp Val Arg Gln Ala Pro Gly Gln Gly Leu Glu Trp Val
                35                  40                  45
Gly Ile Ile Asn Pro Ser Met Gly Ala Thr Ser Tyr Ala Gln Lys Phe
        50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
```

```
Ala Arg Leu His Val Ser Gly Ser Tyr Tyr Pro Ala Tyr Leu Asp Tyr
            100                 105                 110

Trp Gly Gln Gly Thr Met Val Thr Val Ser Ser
        115                 120

<210> SEQ ID NO 24
<211> LENGTH: 123
<212> TYPE: PRT
<213> ORGANISM: Artificial Sequence
<220> FEATURE:
<223> OTHER INFORMATION: Synthetic - MAB21-IgG4; VH

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met Gly Trp Val Arg Gln Ala Pro Gly Gln Gly Leu Glu Trp Met
        35                  40                  45

Gly Ile Ile Asn Pro Ser Met Gly Ala Thr Ser Tyr Thr Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
            100                 105                 110

Trp Gly Gln Gly Thr Met Val Thr Val Ser Ser
        115                 120

<210> SEQ ID NO 25
<211> LENGTH: 106
<212> TYPE: PRT
<213> ORGANISM: Artificial Sequence
<220> FEATURE:
<223> OTHER INFORMATION: Synthetic - MAB1-IgG4, MAB2-IgG4, MAB3-IgG4,
      MAB4-IgG4, MAB5-IgG4; VL

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln His Phe Asn Leu Pro Thr
                85                  90                  95

Phe Gly Gly Gly Thr Lys Val Glu Ile Lys
        100                 105

<210> SEQ ID NO 26
<211> LENGTH: 109
<212> TYPE: PRT
<213> ORGANISM: Artificial Sequence
<220> FEATURE:
<223> OTHER INFORMATION: Synthetic - MAB6-IgG4, MAB7-IgG4, MAB8-IgG4,
```

-continued

MAB9-IgG4, MAB10-IgG4, MAB11-IgG4, MAB12-IgG4; VL

<400> SEQUENCE: 26

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Thr Val Arg Pro
                85                  90                  95

Pro Leu Thr Phe Gly Gly Gly Thr Lys Val Glu Ile Lys
            100                 105
```

<210> SEQ ID NO 27
<211> LENGTH: 108
<212> TYPE: PRT
<213> ORGANISM: Artificial Sequence
<220> FEATURE:
<223> OTHER INFORMATION: Synthetic - MAB13-IgG4, MAB14-IgG4, MAB15-IgG4, MAB16-IgG4, MAB17-IgG4, MAB18-IgG4; VL

<400> SEQUENCE: 27

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Val Val Trp Pro Pro
                85                  90                  95

Leu Thr Phe Gly Gly Gly Thr Lys Val Glu Ile Lys
            100                 105
```

<210> SEQ ID NO 28
<211> LENGTH: 107
<212> TYPE: PRT
<213> ORGANISM: Artificial Sequence
<220> FEATURE:
<223> OTHER INFORMATION: Synthetic - MAB19-IgG4, MAB20-IgG4, MAB21-IgG4; VL

<400> SEQUENCE: 28

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg His Leu Ile
        35                  40                  45

Tyr Gly Ala Ser Thr Arg Ala Thr Gly Ile Pro Ala Arg Phe Ser Gly
    50                  55                  60
```

```
Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ile Val Phe Pro Trp
                85                  90                  95

Thr Phe Gly Gly Gly Thr Lys Val Glu Ile Lys
            100                 105
```

<210> SEQ ID NO 29
<211> LENGTH: 15
<212> TYPE: PRT
<213> ORGANISM: Artificial Sequence
<220> FEATURE:
<223> OTHER INFORMATION: Synthetic - MAB1-IgG4, MAB2-IgG4, MAB3-IgG4,
      MAB5-IgG4; H3-IMGT

<400> SEQUENCE: 29

```
Ala Arg Asp Ala Asn Tyr Tyr Gly Ser Ala Trp Ala Phe Asp Pro
1               5                   10                  15
```

<210> SEQ ID NO 30
<211> LENGTH: 15
<212> TYPE: PRT
<213> ORGANISM: Artificial Sequence
<220> FEATURE:
<223> OTHER INFORMATION: Synthetic - MAB4-IgG4; H3-IMGT

<400> SEQUENCE: 30

```
Ala Arg Asp Ala Asn Tyr Tyr Gly Gly Ala Trp Ala Phe Asp Pro
1               5                   10                  15
```

<210> SEQ ID NO 31
<211> LENGTH: 15
<212> TYPE: PRT
<213> ORGANISM: Artificial Sequence
<220> FEATURE:
<223> OTHER INFORMATION: Synthetic - MAB6-IgG4, MAB7-IgG4, MAB8-IgG4,
      MAB9-IgG4; H3-IMGT

<400> SEQUENCE: 31

```
Ala Arg Asp Gly Val Leu Thr Leu Asn Lys Arg Ser Phe Asp Ile
1               5                   10                  15
```

<210> SEQ ID NO 32
<211> LENGTH: 15
<212> TYPE: PRT
<213> ORGANISM: Artificial Sequence
<220> FEATURE:
<223> OTHER INFORMATION: Synthetic - MAB10-IgG4, MAB11-IgG4, MAB12-IgG4;
      H3-IMGT

<400> SEQUENCE: 32

```
Ala Arg Asp Gly Val Leu Ala Leu Asn Lys Arg Ser Phe Asp Ile
1               5                   10                  15
```

<210> SEQ ID NO 33
<211> LENGTH: 14
<212> TYPE: PRT
<213> ORGANISM: Artificial Sequence
<220> FEATURE:
<223> OTHER INFORMATION: Synthetic - MAB13-IgG4, MAB14-IgG4, MAB15-IgG4,
      MAB18-IgG4; H3-IMGT

<400> SEQUENCE: 33

```
Ala Arg Gly Gly Arg Thr Thr Trp Ile Gly Ala Phe Asp Ile
1               5                   10
```

<210> SEQ ID NO 34
<211> LENGTH: 14
<212> TYPE: PRT
<213> ORGANISM: Artificial Sequence
<220> FEATURE:
<223> OTHER INFORMATION: Synthetic - MAB16-IgG4, MAB17-IgG4; H3-IMGT

<400> SEQUENCE: 34

Ala Arg Gly Gly Arg Thr Thr Trp Ile Gly Ala Leu Asp Ile
1               5                   10

<210> SEQ ID NO 35
<211> LENGTH: 16
<212> TYPE: PRT
<213> ORGANISM: Artificial Sequence
<220> FEATURE:
<223> OTHER INFORMATION: Synthetic - MAB19-IgG4, MAB20-IgG4, MAB21-IgG4;
      H3-IMGT

<400> SEQUENCE: 35

Ala Arg Leu His Val Ser Gly Ser Tyr Tyr Pro Ala Tyr Leu Asp Tyr
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic - MAB1-IgG4; H2-Kabat

<400> SEQUENCE: 36

Ser Ile Tyr Tyr Ser Gly Ala Thr Phe Tyr Asn Pro Ser Leu Lys Ser
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Synthetic - MAB2-IgG4, MAB3-IgG4, MAB4-IgG4;
      H2-Kabat

<400> SEQUENCE: 37

Ser Ile Tyr Tyr Ser Gly Ser Thr Phe Tyr Asn Pro Ser Leu Lys Ser
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Synthetic - MAB5-IgG4; H2-Kabat

<400> SEQUENCE: 38

Ser Ile Tyr Tyr Ser Gly Ser Thr Phe Tyr Asn Pro Ser Leu Lys Gly
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Synthetic - MAB6-IgG4; H2-Kabat

<400> SEQUENCE: 39

Ser Ile Tyr Tyr Ser Gly Gly Thr Tyr Tyr Asn Pro Ser Leu Lys Ser
1               5                   10                  15

```
<210> SEQ ID NO 40
<211> LENGTH: 16
<212> TYPE: PRT
<213> ORGANISM: Artificial Sequence
<220> FEATURE:
<223> OTHER INFORMATION: Synthetic - MAB7-IgG4, MAB9-IgG4, MAB10-IgG4,
      MAB11-IgG4, MAB12-IgG4; H2-Kabat

<400> SEQUENCE: 40

Ser Ile Tyr Tyr Ser Gly Ser Thr Tyr Tyr Asn Pro Ser Leu Lys Ser
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Synthetic - MAB8-IgG4; H2-Kabat

<400> SEQUENCE: 41

Ser Ile Tyr Tyr Ser Gly Gln Thr Tyr Tyr Asn Pro Ser Leu Lys Ser
1               5                   10                  15

<210> SEQ ID NO 42
<211> LENGTH: 17
<212> TYPE: PRT
<213> ORGANISM: Artificial Sequence
<220> FEATURE:
<223> OTHER INFORMATION: Synthetic - MAB13-IgG4, MAB14-IgG4; H2-Kabat

<400> SEQUENCE: 42

Ile Ile Asn Pro Ser Leu Gly Leu Thr Ser Tyr Ala Gln Lys Phe Gln
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: Synthetic - MAB15-IgG4, MAB16-IgG4; H2-Kabat

<400> SEQUENCE: 43

Ile Ile Asn Pro Ser Ile Gly Leu Thr Ser Tyr Ala Arg Lys Phe Gln
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: Synthetic - MAB17-IgG4, MAB18-IgG4; H2-Kabat

<400> SEQUENCE: 44

Ile Ile Asn Pro Ser Leu Gly Leu Thr Ser Tyr Ala Arg Lys Phe Gln
1               5                   10                  15

Gly

<210> SEQ ID NO 45
<211> LENGTH: 17
<212> TYPE: PRT
<213> ORGANISM: Artificial Sequence
<220> FEATURE:
```

<223> OTHER INFORMATION: Synthetic - MAB19-IgG4; H2-Kabat

<400> SEQUENCE: 45

Val Ile Asn Pro Ser Met Gly Ala Thr Ser Tyr Ala Gln Lys Phe Gln
1               5                   10                  15
Gly

<210> SEQ ID NO 46
<211> LENGTH: 17
<212> TYPE: PRT
<213> ORGANISM: Artificial Sequence
<220> FEATURE:
<223> OTHER INFORMATION: Synthetic - MAB20-IgG4; H2-Kabat

<400> SEQUENCE: 46

Ile Ile Asn Pro Ser Met Gly Ala Thr Ser Tyr Ala Gln Lys Phe Gln
1               5                   10                  15
Gly

<210> SEQ ID NO 47
<211> LENGTH: 17
<212> TYPE: PRT
<213> ORGANISM: Artificial Sequence
<220> FEATURE:
<223> OTHER INFORMATION: Synthetic - MAB21-IgG4; H2-Kabat

<400> SEQUENCE: 47

Ile Ile Asn Pro Ser Met Gly Ala Thr Ser Tyr Thr Gln Lys Phe Arg
1               5                   10                  15
Gly

<210> SEQ ID NO 48
<211> LENGTH: 11
<212> TYPE: PRT
<213> ORGANISM: Artificial Sequence
<220> FEATURE:
<223> OTHER INFORMATION: Synthetic - MAB1-IgG4; H1-Chothia + Kabat

<400> SEQUENCE: 48

Gly Ser Ile Thr Ser Ser Ser Tyr Tyr Trp Gly
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic - MAB2-IgG4; H1-Chothia + Kabat

<400> SEQUENCE: 49

Gly Ser Ile Ser Ser Ser Lys Tyr Tyr Trp Gly
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic - MAB3-IgG4, MAB4-IgG4, MAB5-IgG4;
    H1-Chothia + Kabat

<400> SEQUENCE: 50

Gly Ser Ile Ser Ser Thr Ser His Tyr Trp Gly
1               5                   10

```
<210> SEQ ID NO 51
<211> LENGTH: 11
<212> TYPE: PRT
<213> ORGANISM: Artificial Sequence
<220> FEATURE:
<223> OTHER INFORMATION: Synthetic - MAB6-IgG4; H1-Chothia + Kabat

<400> SEQUENCE: 51

Gly Ser Ile Glu Ser Gly Ser Tyr Tyr Trp Gly
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic - MAB7-IgG4; H1-Chothia + Kabat

<400> SEQUENCE: 52

Gly Ser Ile Glu Ser Gly Val Tyr Tyr Trp Gly
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic - MAB8-IgG4; H1-Chothia + Kabat

<400> SEQUENCE: 53

Gly Ser Ile Ala Ser Gly Ser Tyr Tyr Trp Gly
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic - MAB9-IgG4, MAB10-IgG4, MAB11-IgG4,
      MAB12-IgG4; H1-Chothia + Kabat

<400> SEQUENCE: 54

Gly Ser Ile Glu Ser Gly Leu Tyr Tyr Trp Gly
1               5                   10

<210> SEQ ID NO 55
<211> LENGTH: 327
<212> TYPE: PRT
<213> ORGANISM: Artificial Sequence
<220> FEATURE:
<223> OTHER INFORMATION: Synthetic - IgG4; Constant, S228P hinge
      stabilizing

<400> SEQUENCE: 55

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80
```

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 56
<211> LENGTH: 326
<212> TYPE: PRT
<213> ORGANISM: Artificial Sequence
<220> FEATURE:
<223> OTHER INFORMATION: Synthetic - IgG4; Constant S228P, N297A, C
      terminal Lys deleted

<400> SEQUENCE: 56

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

```
Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Ala Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 57
<211> LENGTH: 330
<212> TYPE: PRT
<213> ORGANISM: Artificial Sequence
<220> FEATURE:
<223> OTHER INFORMATION: Synthetic - IgG1; Constant (G1m(3) allotype)

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 58
<211> LENGTH: 9
<212> TYPE: PRT
<213> ORGANISM: Artificial Sequence
<220> FEATURE:
<223> OTHER INFORMATION: Synthetic - MAB13-IgG4; H1-Chothia + Kabat

<400> SEQUENCE: 58

Tyr Thr Phe Gly Asn Tyr Tyr Met His
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic - MAB14-IgG4, MAB18-IgG4;
      H1-Chothia + Kabat

<400> SEQUENCE: 59

Tyr Thr Phe Pro Ala Tyr Tyr Met His
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic - MAB15-IgG4, MAB16-IgG4;
      H1-Chothia + Kabat

<400> SEQUENCE: 60

Tyr Thr Phe Arg Glu Tyr Tyr Met His
1               5

```
<210> SEQ ID NO 61
<211> LENGTH: 9
<212> TYPE: PRT
<213> ORGANISM: Artificial Sequence
<220> FEATURE:
<223> OTHER INFORMATION: Synthetic - MAB17-IgG4; H1-Chothia + Kabat

<400> SEQUENCE: 61

Tyr Thr Phe Pro Ala Tyr Tyr Ile His
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic - MAB19-IgG4, MAB20-IgG4, MAB21-IgG4;
      H1-Chothia + Kabat

<400> SEQUENCE: 62

Tyr Thr Phe Thr Ser His Tyr Met Gly
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic - MAB1-IgG4, MAB2-IgG4, MAB3-IgG4,
      MAB4-IgG4, MAB5-IgG4; L3 - Chothia/Kabat/IMGT

<400> SEQUENCE: 63

Gln Gln His Phe Asn Leu Pro Thr
1               5

<210> SEQ ID NO 64
<211> LENGTH: 10
<212> TYPE: PRT
<213> ORGANISM: Artificial Sequence
<220> FEATURE:
<223> OTHER INFORMATION: Synthetic - MAB6-IgG4, MAB7-IgG4, MAB8-IgG4,
      MAB9-IgG4, MAB10-IgG4, MAB11-IgG4, MAB12-IgG4;
      L3 - Chothia/Kabat/IMGT

<400> SEQUENCE: 64

Gln Gln His Thr Val Arg Pro Pro Leu Thr
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic - MAB13-IgG4, MAB14-IgG4, MAB15-IgG4,
      MAB16-IgG4, MAB17-IgG4, MAB18-IgG4; L3 - Chothia/Kabat/IMGT

<400> SEQUENCE: 65

Gln Gln Tyr Val Val Trp Pro Pro Leu Thr
1               5                   10

<210> SEQ ID NO 66
<211> LENGTH: 9
<212> TYPE: PRT
<213> ORGANISM: Artificial Sequence
<220> FEATURE:
<223> OTHER INFORMATION: Synthetic - MAB19-IgG4, MAB20-IgG4, MAB21-IgG4;
      L3 - Chothia/Kabat/IMGT

<400> SEQUENCE: 66
```

```
Gln Gln Tyr Ile Val Phe Pro Trp Thr
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic - MAB1-IgG4, MAB2-IgG4, MAB3-IgG4,
      MAB4-IgG4, MAB5-IgG4; L2 - Chothia/Kabat

<400> SEQUENCE: 67

Asp Ala Ser Asn Arg Ala Thr
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic - MAB6-IgG4, MAB7-IgG4, MAB8-IgG4,
      MAB9-IgG4, MAB10-IgG4, MAB11-IgG4, MAB12-IgG4; L2 - Chothia/Kabat

<400> SEQUENCE: 68

Gly Ala Ser Ser Arg Ala Thr
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic - MAB13-IgG4, MAB14-IgG4, MAB15-IgG4,
      MAB16-IgG4, MAB17-IgG4, MAB18-IgG4, MAB19-IgG4, MAB20-IgG4,
      MAB21-IgG4; L2 - Chothia/Kabat

<400> SEQUENCE: 69

Gly Ala Ser Thr Arg Ala Thr
1               5

<210> SEQ ID NO 70
<211> LENGTH: 11
<212> TYPE: PRT
<213> ORGANISM: Artificial Sequence
<220> FEATURE:
<223> OTHER INFORMATION: Synthetic - MAB1-IgG4, MAB2-IgG4, MAB3-IgG4,
      MAB4-IgG4; L1 - Chothia/Kabat

<400> SEQUENCE: 70

Arg Ala Ser Gln Ser Val Ser Ser Tyr Leu Ala
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic - MAB6-IgG4, MAB7-IgG4, MAB8-IgG4,
      MAB9-IgG4, MAB10-IgG4, MAB11-IgG4, MAB12-IgG4; L1 - Chothia/Kabat

<400> SEQUENCE: 71

Arg Ala Ser Gln Ser Val Ser Ser Ser Tyr Leu Ala
1               5                   10

<210> SEQ ID NO 72
<211> LENGTH: 11
<212> TYPE: PRT
```

```
<213> ORGANISM: Artificial Sequence
<220> FEATURE:
<223> OTHER INFORMATION: Synthetic - MAB13-IgG4, MAB14-IgG4, MAB15-IgG4,
      MAB16-IgG4, MAB17-IgG4, MAB18-IgG4, MAB19-IgG4, MAB20-IgG4,
      MAB21-IgG4; L1 - Chothia/Kabat

<400> SEQUENCE: 72

Arg Ala Ser Gln Ser Val Ser Ser Asn Leu Ala
1               5                   10

<210> SEQ ID NO 73
<211> LENGTH: 446
<212> TYPE: PRT
<213> ORGANISM: Artificial Sequence
<220> FEATURE:
<223> OTHER INFORMATION: Synthetic - SEC1; Human IgG4 S228P Heavy Chain

<400> SEQUENCE: 73

Glu Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
                20                  25                  30

Thr Met His Trp Val Arg Gln Ser Pro Gly Lys Gly Leu Glu Trp Val
            35                  40                  45

Ala Phe Ile Arg Ser Gly Ser Gly Ile Val Phe Tyr Ala Asp Ala Val
        50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
```

```
                    305                 310                 315                 320
Lys Val Ser Asn Lys Gly Leu Pro Ser Ile Glu Lys Thr Ile Ser
                    325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 74
<211> LENGTH: 119
<212> TYPE: PRT
<213> ORGANISM: Homo sapiens
<220> FEATURE:
<221> NAME/KEY: misc_feature
<222> LOCATION: (1)..(119)
<223> OTHER INFORMATION: SEC1; Heavy Chain Variable Region

<400> SEQUENCE: 74

Glu Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
            20                  25                  30

Thr Met His Trp Val Arg Gln Ser Pro Gly Lys Gly Leu Glu Trp Val
        35                  40                  45

Ala Phe Ile Arg Ser Gly Ser Gly Ile Val Phe Tyr Ala Asp Ala Val
    50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser
        115

<210> SEQ ID NO 75
<211> LENGTH: 220
<212> TYPE: PRT
<213> ORGANISM: Homo sapiens
<220> FEATURE:
<221> NAME/KEY: misc_feature
<222> LOCATION: (1)..(220)
<223> OTHER INFORMATION: SEC1 Human Kappa Chain

<400> SEQUENCE: 75

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30
```

Gly Val Lys Glu Asn Leu Leu Ala Trp Tyr Gln Gln Lys Pro Gly Gln
            35                  40                  45

Ser Pro Lys Leu Leu Ile Tyr Tyr Ala Ser Ile Arg Phe Thr Gly Val
    50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 76
<211> LENGTH: 113
<212> TYPE: PRT
<213> ORGANISM: Homo sapiens
<220> FEATURE:
<221> NAME/KEY: misc_feature
<222> LOCATION: (1)..(113)
<223> OTHER INFORMATION: SEC1; Light Chain Variable Region

<400> SEQUENCE: 76

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
            35                  40                  45

Ser Pro Lys Leu Leu Ile Tyr Tyr Ala Ser Ile Arg Phe Thr Gly Val
    50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys

<210> SEQ ID NO 77
<211> LENGTH: 449
<212> TYPE: PRT
<213> ORGANISM: Artificial Sequence
<220> FEATURE:
<223> OTHER INFORMATION: Synthetic - SEC1; Mouse IgG2a N297A Heavy Chain

<400> SEQUENCE: 77

Glu Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
            20                  25                  30

Thr Met His Trp Val Arg Gln Ser Pro Gly Lys Gly Leu Glu Trp Val
        35                  40                  45

Ala Phe Ile Arg Ser Gly Ser Gly Ile Val Phe Tyr Ala Asp Ala Val
    50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Ala Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys

Lys Asn Trp Val Glu Arg Asn Ser Tyr Ser Cys Ser Val Val His Glu
                420                 425                 430

Gly Leu His Asn His His Thr Thr Lys Ser Phe Ser Arg Thr Pro Gly
        435                 440                 445

Lys

<210> SEQ ID NO 78
<211> LENGTH: 220
<212> TYPE: PRT
<213> ORGANISM: Mus musculus
<220> FEATURE:
<221> NAME/KEY: misc_feature
<222> LOCATION: (1)..(220)
<223> OTHER INFORMATION: SEC1; Mouse Kappa Chain

<400> SEQUENCE: 78

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
            85                  90                  95

Gly Ile Asn Asn Pro Leu Thr Phe Gly Asp Gly Thr Lys Leu Glu Ile
        100                 105                 110

Lys Arg Ala Asp Ala Ala Pro Thr Val Ser Ile Phe Pro Pro Ser Ser
    115                 120                 125

Glu Gln Leu Thr Ser Gly Gly Ala Ser Val Val Cys Phe Leu Asn Asn
130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
            165                 170                 175

Ser Thr Tyr Ser Met Ser Ser Thr Leu Thr Leu Thr Lys Asp Glu Tyr
        180                 185                 190

Glu Arg His Asn Ser Tyr Thr Cys Glu Ala Thr His Lys Thr Ser Thr
    195                 200                 205

Ser Pro Ile Val Lys Ser Phe Asn Arg Asn Glu Cys
210                 215                 220

<210> SEQ ID NO 79
<211> LENGTH: 450
<212> TYPE: PRT
<213> ORGANISM: Artificial Sequence
<220> FEATURE:
<223> OTHER INFORMATION: Synthetic - MAB1; Full length IgG4 S228P

<400> SEQUENCE: 79

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Ser
            20                  25                  30

-continued

```
Ser Tyr Tyr Trp Gly Trp Ile Arg Gln Pro Gly Lys Gly Leu Glu
         35                  40                  45

Trp Ile Gly Ser Ile Tyr Tyr Ser Gly Ala Thr Phe Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Ala Asn Tyr Tyr Gly Ser Ala Trp Ala Phe Asp Pro
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445
```

Gly Lys
    450

<210> SEQ ID NO 80
<211> LENGTH: 453
<212> TYPE: PRT
<213> ORGANISM: Artificial Sequence
<220> FEATURE:
<223> OTHER INFORMATION: Synthetic - MAB1; Full length IgG1

<400> SEQUENCE: 80

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ala Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

```
Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 81
<211> LENGTH: 213
<212> TYPE: PRT
<213> ORGANISM: Artificial Sequence
<220> FEATURE:
<223> OTHER INFORMATION: Synthetic - MAB1, MAB2, MAB3, MAB4, MAB5; Full
      length Kappa

<400> SEQUENCE: 81

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln His Phe Asn Leu Pro Thr
            85                  90                  95

Phe Gly Gly Gly Thr Lys Val Glu Ile Lys Arg Thr Val Ala Ala Pro
        100                 105                 110

Ser Val Phe Ile Phe Pro Pro Ser Asp Glu Gln Leu Lys Ser Gly Thr
    115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
    195                 200                 205

Asn Arg Gly Glu Cys
    210

<210> SEQ ID NO 82
<211> LENGTH: 450
<212> TYPE: PRT
<213> ORGANISM: Artificial Sequence
```

<220> FEATURE:
<223> OTHER INFORMATION: Synthetic - MAB2; Full length IgG4 S228P

<400> SEQUENCE: 82

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Lys Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Ala Asn Tyr Tyr Gly Ser Ala Trp Ala Phe Asp Pro
        100                 105                 110

Trp Gly Gln Gly Thr Leu Val Thr Val Ser Ser Ala Ser Thr Lys Gly
    115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Lys Thr Tyr Thr Cys Asn Val
    195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
        260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Gln Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400
```

-continued

```
Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 83
<211> LENGTH: 453
<212> TYPE: PRT
<213> ORGANISM: Artificial Sequence
<220> FEATURE:
<223> OTHER INFORMATION: Synthetic - MAB2; Full length IgG1

<400> SEQUENCE: 83

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Lys Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 84
<211> LENGTH: 450
<212> TYPE: PRT
<213> ORGANISM: Artificial Sequence
<220> FEATURE:
<223> OTHER INFORMATION: Synthetic - MAB3; Full length IgG4 S228P

<400> SEQUENCE: 84

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

```
Asp His Lys Pro Ser Asn Thr Lys Val Asp Lys Arg Val Glu Ser Lys
        210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 85
<211> LENGTH: 453
<212> TYPE: PRT
<213> ORGANISM: Artificial Sequence
<220> FEATURE:
<223> OTHER INFORMATION: Synthetic - MAB3; Full length IgG1

<400> SEQUENCE: 85

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110
```

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 86
<211> LENGTH: 450
<212> TYPE: PRT
<213> ORGANISM: Artificial Sequence
<220> FEATURE:
<223> OTHER INFORMATION: Synthetic - MAB4; Full length IgG4 S228P

<400> SEQUENCE: 86

Gln Leu Gln Leu Gln Glu Ser Gly Pro Gly Leu Val Lys Pro Ser Glu
1               5                   10                  15

-continued

Thr Leu Ser Leu Thr Cys Thr Val Ser Gly Gly Ser Ile Ser Ser Thr
              20                  25                  30

Ser His Tyr Trp Gly Trp Ile Arg Gln Pro Pro Gly Lys Gly Leu Glu
              35                  40                  45

Trp Ile Gly Ser Ile Tyr Tyr Ser Gly Ser Thr Phe Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
              85                  90                  95

Cys Ala Arg Asp Ala Asn Tyr Tyr Gly Ala Trp Ala Phe Asp Pro
             100                 105                 110

Trp Gly Gln Gly Thr Leu Val Thr Val Ser Ser Ala Ser Thr Lys Gly
             115                 120                 125

Pro Ser Val Phe Pro Leu Ala Pro Cys Ser Arg Ser Thr Ser Glu Ser
 130                 135                 140

Thr Ala Ala Leu Gly Cys Leu Val Lys Asp Tyr Phe Pro Glu Pro Val
 145                 150                 155                 160

Thr Val Ser Trp Asn Ser Gly Ala Leu Thr Ser Gly Val His Thr Phe
             165                 170                 175

Pro Ala Val Leu Gln Ser Ser Gly Leu Tyr Ser Leu Ser Ser Val Val
             180                 185                 190

Thr Val Pro Ser Ser Ser Leu Gly Thr Lys Thr Tyr Thr Cys Asn Val
             195                 200                 205

Asp His Lys Pro Ser Asn Thr Lys Val Asp Lys Arg Val Glu Ser Lys
 210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
             245                 250                 255

Ser Arg Thr Pro Glu Val Thr Cys Val Val Val Asp Val Ser Gln Glu
             260                 265                 270

Asp Pro Glu Val Gln Phe Asn Trp Tyr Val Asp Gly Val Glu Val His
             275                 280                 285

Asn Ala Lys Thr Lys Pro Arg Glu Glu Gln Phe Asn Ser Thr Tyr Arg
 290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
             325                 330                 335

Lys Thr Ile Ser Lys Ala Lys Gly Gln Pro Arg Glu Pro Gln Val Tyr
             340                 345                 350

Thr Leu Pro Pro Ser Gln Glu Glu Met Thr Lys Asn Gln Val Ser Leu
             355                 360                 365

Thr Cys Leu Val Lys Gly Phe Tyr Pro Ser Asp Ile Ala Val Glu Trp
 370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
             405                 410                 415

Lys Ser Arg Trp Gln Glu Gly Asn Val Phe Ser Cys Ser Val Met His
             420                 425                 430

-continued

```
Glu Ala Leu His Asn His Tyr Thr Gln Lys Ser Leu Ser Leu
            435                 440                 445
Gly Lys
    450

<210> SEQ ID NO 87
<211> LENGTH: 453
<212> TYPE: PRT
<213> ORGANISM: Artificial Sequence
<220> FEATURE:
<223> OTHER INFORMATION: Synthetic - MAB4; Full length IgG1

<400> SEQUENCE: 87

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
50                  55                  60

Leu Lys Ser Arg Val Thr Ile Ser Val Asp Thr Ser Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Gly Ala Trp Ala Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

```
Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 88
<211> LENGTH: 450
<212> TYPE: PRT
<213> ORGANISM: Artificial Sequence
<220> FEATURE:
<223> OTHER INFORMATION: Synthetic - MAB5; Full length IgG4 S228P

<400> SEQUENCE: 88

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Gly Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser Gln Glu
        260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 89
<211> LENGTH: 453
<212> TYPE: PRT
<213> ORGANISM: Artificial Sequence
<220> FEATURE:
<223> OTHER INFORMATION: Synthetic - MAB5; Full length IgG1

<400> SEQUENCE: 89

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Gly Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 90
<211> LENGTH: 450
<212> TYPE: PRT
<213> ORGANISM: Artificial Sequence
<220> FEATURE:
<223> OTHER INFORMATION: Synthetic - MAB6; Full length IgG4 S228P

<400> SEQUENCE: 90

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Glu Ser Gly
            20                  25                  30

Ser Tyr Tyr Trp Gly Trp Ile Arg Gln Pro Pro Gly Lys Gly Leu Glu
        35                  40                  45

```
Trp Ile Gly Ser Ile Tyr Tyr Ser Gly Gly Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
210                 215                 220

Tyr Gly Pro Pro Cys Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly Lys
450
```

```
<210> SEQ ID NO 91
<211> LENGTH: 453
<212> TYPE: PRT
<213> ORGANISM: Artificial Sequence
<220> FEATURE:
<223> OTHER INFORMATION: Synthetic - MAB6; Full length IgG1

<400> SEQUENCE: 91
```

| | | | | | | | | | | | | | | | |
|---|---|---|---|---|---|---|---|---|---|---|---|---|---|---|---|
| Gln | Leu | Gln | Leu | Gln | Glu | Ser | Gly | Pro | Gly | Leu | Val | Lys | Pro | Ser | Glu |
| 1 | | | | 5 | | | | | 10 | | | | | 15 | |
| Thr | Leu | Ser | Leu | Thr | Cys | Thr | Val | Ser | Gly | Gly | Ser | Ile | Glu | Ser | Gly |
| | | | 20 | | | | | 25 | | | | | 30 | | |
| Ser | Tyr | Tyr | Trp | Gly | Trp | Ile | Arg | Gln | Pro | Pro | Gly | Lys | Gly | Leu | Glu |
| | | 35 | | | | | 40 | | | | | 45 | | | |
| Trp | Ile | Gly | Ser | Ile | Tyr | Tyr | Ser | Gly | Gly | Thr | Tyr | Tyr | Asn | Pro | Ser |
| | 50 | | | | | 55 | | | | | 60 | | | | |
| Leu | Lys | Ser | Arg | Val | Thr | Ile | Ser | Val | Asp | Thr | Ser | Lys | Asn | Gln | Phe |
| 65 | | | | | 70 | | | | | 75 | | | | | 80 |
| Ser | Leu | Lys | Leu | Ser | Ser | Val | Thr | Ala | Ala | Asp | Thr | Ala | Val | Tyr | Tyr |
| | | | | 85 | | | | | 90 | | | | | 95 | |
| Cys | Ala | Arg | Asp | Gly | Val | Leu | Thr | Leu | Asn | Lys | Arg | Ser | Phe | Asp | Ile |
| | | | 100 | | | | | 105 | | | | | 110 | | |
| Trp | Gly | Gln | Gly | Thr | Met | Val | Thr | Val | Ser | Ser | Ala | Ser | Thr | Lys | Gly |
| | | 115 | | | | | 120 | | | | | 125 | | | |
| Pro | Ser | Val | Phe | Pro | Leu | Ala | Pro | Ser | Ser | Lys | Ser | Thr | Ser | Gly | Gly |
| | 130 | | | | | 135 | | | | | 140 | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Gln | Thr | Tyr | Ile | Cys | Asn | Val |
| | | 195 | | | | | 200 | | | | | 205 | | | |
| Asn | His | Lys | Pro | Ser | Asn | Thr | Lys | Val | Asp | Lys | Arg | Val | Glu | Pro | Lys |
| | 210 | | | | | 215 | | | | | 220 | | | | |
| Ser | Cys | Asp | Lys | Thr | His | Thr | Cys | Pro | Pro | Cys | Pro | Ala | Pro | Glu | Leu |
| 225 | | | | | 230 | | | | | 235 | | | | | 240 |
| Leu | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | 260 | | | | | 265 | | | | | 270 | | |
| Ser | His | Glu | Asp | Pro | Glu | Val | Lys | Phe | Asn | Trp | Tyr | Val | Asp | Gly | Val |
| | | 275 | | | | | 280 | | | | | 285 | | | |
| Glu | Val | His | Asn | Ala | Lys | Thr | Lys | Pro | Arg | Glu | Glu | Gln | Tyr | Asn | Ser |
| | 290 | | | | | 295 | | | | | 300 | | | | |
| Thr | Tyr | Arg | Val | Val | Ser | Val | Leu | Thr | Val | Leu | His | Gln | Asp | Trp | Leu |
| 305 | | | | | 310 | | | | | 315 | | | | | 320 |
| Asn | Gly | Lys | Glu | Tyr | Lys | Cys | Lys | Val | Ser | Asn | Lys | Ala | Leu | Pro | Ala |
| | | | | 325 | | | | | 330 | | | | | 335 | |
| Pro | Ile | Glu | Lys | Thr | Ile | Ser | Lys | Ala | Lys | Gly | Gln | Pro | Arg | Glu | Pro |
| | | | 340 | | | | | 345 | | | | | 350 | | |
| Gln | Val | Tyr | Thr | Leu | Pro | Pro | Ser | Arg | Glu | Glu | Met | Thr | Lys | Asn | Gln |
| | | 355 | | | | | 360 | | | | | 365 | | | |
| Val | Ser | Leu | Thr | Cys | Leu | Val | Lys | Gly | Phe | Tyr | Pro | Ser | Asp | Ile | Ala |

```
                    370                 375                 380
Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
            450

<210> SEQ ID NO 92
<211> LENGTH: 216
<212> TYPE: PRT
<213> ORGANISM: Artificial Sequence
<220> FEATURE:
<223> OTHER INFORMATION: Synthetic - MAB6, MAB7, MAB8, MAB9, MAB10,
      MAB11, MAB12; Full length Kappa

<400> SEQUENCE: 92

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Thr Val Arg Pro
                85                  90                  95

Pro Leu Thr Phe Gly Gly Gly Thr Lys Val Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
            210                 215

<210> SEQ ID NO 93
<211> LENGTH: 450
<212> TYPE: PRT
<213> ORGANISM: Artificial Sequence
<220> FEATURE:
<223> OTHER INFORMATION: Synthetic - MAB7; Full length IgG4 S228P

<400> SEQUENCE: 93
```

-continued

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Val Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
                100                 105                 110

Trp Gly Gln Gly Thr Met Val Thr Val Ser Ser Ala Ser Thr Lys Gly
            115                 120                 125

Pro Ser Val Phe Pro Leu Ala Pro Cys Ser Arg Ser Thr Ser Glu Ser
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
            210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415
```

```
Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 94
<211> LENGTH: 453
<212> TYPE: PRT
<213> ORGANISM: Artificial Sequence
<220> FEATURE:
<223> OTHER INFORMATION: Synthetic - MAB7; Full length IgG1

<400> SEQUENCE: 94

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Val Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320
```

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 95
<211> LENGTH: 450
<212> TYPE: PRT
<213> ORGANISM: Artificial Sequence
<220> FEATURE:
<223> OTHER INFORMATION: Synthetic - MAB8; Full length IgG4 S228P

<400> SEQUENCE: 95

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ala Ser Gly
            20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Gln Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
            210                 215                 220

```
Tyr Gly Pro Pro Cys Pro Cys Pro Ala Pro Glu Phe Leu Gly Gly
225                 230                 235                 240

Pro Ser Val Phe Leu Phe Pro Pro Lys Pro Lys Asp Thr Leu Met Ile
        245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 96
<211> LENGTH: 453
<212> TYPE: PRT
<213> ORGANISM: Artificial Sequence
<220> FEATURE:
<223> OTHER INFORMATION: Synthetic - MAB8; Full length IgG1

<400> SEQUENCE: 96

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ala Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Gln Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser Ala Ser Thr Lys Gly
        115                 120                 125
```

```
Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
        450

<210> SEQ ID NO 97
<211> LENGTH: 450
<212> TYPE: PRT
<213> ORGANISM: Artificial Sequence
<220> FEATURE:
<223> OTHER INFORMATION: Synthetic - MAB9; Full length IgG4 S228P

<400> SEQUENCE: 97

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30
```

Leu Tyr Tyr Trp Gly Trp Ile Arg Gln Pro Pro Gly Lys Gly Leu Glu
         35                  40                  45

Trp Ile Gly Ser Ile Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Gly Val Leu Thr Leu Asn Lys Arg Ser Phe Asp Ile
             100                 105                 110

Trp Gly Gln Gly Thr Met Val Thr Val Ser Ser Ala Ser Thr Lys Gly
         115                 120                 125

Pro Ser Val Phe Pro Leu Ala Pro Cys Ser Arg Ser Thr Ser Glu Ser
     130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                 165                 170                 175

Pro Ala Val Leu Gln Ser Ser Gly Leu Tyr Ser Leu Ser Ser Val Val
             180                 185                 190

Thr Val Pro Ser Ser Ser Leu Gly Thr Lys Thr Tyr Thr Cys Asn Val
         195                 200                 205

Asp His Lys Pro Ser Asn Thr Lys Val Asp Lys Arg Val Glu Ser Lys
     210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser Gln Glu
             260                 265                 270

Asp Pro Glu Val Gln Phe Asn Trp Tyr Val Asp Gly Val Glu Val His
         275                 280                 285

Asn Ala Lys Thr Lys Pro Arg Glu Glu Gln Phe Asn Ser Thr Tyr Arg
     290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Gln Glu Glu Met Thr Lys Asn Gln Val Ser Leu
         355                 360                 365

Thr Cys Leu Val Lys Gly Phe Tyr Pro Ser Asp Ile Ala Val Glu Trp
     370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                 405                 410                 415

Lys Ser Arg Trp Gln Glu Gly Asn Val Phe Ser Cys Ser Val Met His
             420                 425                 430

Glu Ala Leu His Asn His Tyr Thr Gln Lys Ser Leu Ser Leu Ser Leu
         435                 440                 445

Gly Lys

-continued

450

<210> SEQ ID NO 98
<211> LENGTH: 453
<212> TYPE: PRT
<213> ORGANISM: Artificial Sequence
<220> FEATURE:
<223> OTHER INFORMATION: Synthetic - MAB9; Full length IgG1

<400> SEQUENCE: 98

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
```

```
                355                 360                 365
Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 99
<211> LENGTH: 450
<212> TYPE: PRT
<213> ORGANISM: Artificial Sequence
<220> FEATURE:
<223> OTHER INFORMATION: Synthetic - MAB10; Full length IgG4 S228P

<400> SEQUENCE: 99

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
                20                  25                  30

Leu Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
        50                  55                  60

Leu Lys Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Ala Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
```

```
                260                 265                 270
Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
        435                 440                 445

Gly Lys
    450

<210> SEQ ID NO 100
<211> LENGTH: 453
<212> TYPE: PRT
<213> ORGANISM: Artificial Sequence
<220> FEATURE:
<223> OTHER INFORMATION: Synthetic - MAB10; Full length IgG1

<400> SEQUENCE: 100

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
                20                  25                  30

Leu Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
    50                  55                  60

Leu Lys Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Ala Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
```

```
                165                 170                 175
Pro Ala Val Leu Gln Ser Ser Gly Leu Tyr Ser Leu Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 101
<211> LENGTH: 450
<212> TYPE: PRT
<213> ORGANISM: Artificial Sequence
<220> FEATURE:
<223> OTHER INFORMATION: Synthetic - MAB11; Full length IgG4 S228P

<400> SEQUENCE: 101

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
```

```
            65                  70                  75                  80
        Ser Leu Lys Leu Ser Ser Val Thr Ala Ala Asp Thr Ala Val Tyr Tyr
                        85                  90                  95

Cys Ala Arg Asp Gly Val Leu Ala Leu Asn Lys Arg Ser Phe Asp Ile
                        100                 105                 110

Trp Gly Gln Gly Thr Met Val Thr Val Ser Ser Ala Ser Thr Lys Gly
                        115                 120                 125

Pro Ser Val Phe Pro Leu Ala Pro Cys Ser Arg Ser Thr Ser Glu Ser
                130                 135                 140

Thr Ala Leu Gly Cys Leu Val Lys Asp Tyr Phe Pro Glu Pro Val
        145                 150                 155                 160

Thr Val Ser Trp Asn Ser Gly Ala Leu Thr Ser Gly Val His Thr Phe
                        165                 170                 175

Pro Ala Val Leu Gln Ser Ser Gly Leu Tyr Ser Leu Ser Ser Val Val
                        180                 185                 190

Thr Val Pro Ser Ser Ser Leu Gly Thr Lys Thr Tyr Thr Cys Asn Val
                        195                 200                 205

Asp His Lys Pro Ser Asn Thr Lys Val Asp Lys Arg Val Glu Ser Lys
                        210                 215                 220

Tyr Gly Pro Pro Cys Pro Cys Pro Ala Pro Glu Phe Leu Gly Gly
        225                 230                 235                 240

Pro Ser Val Phe Leu Phe Pro Pro Lys Pro Lys Asp Thr Leu Met Ile
                        245                 250                 255

Ser Arg Thr Pro Glu Val Thr Cys Val Val Val Asp Val Ser Gln Glu
                        260                 265                 270

Asp Pro Glu Val Gln Phe Asn Trp Tyr Val Asp Gly Val Glu Val His
                        275                 280                 285

Asn Ala Lys Thr Lys Pro Arg Glu Glu Gln Phe Asn Ser Thr Tyr Arg
                        290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Gly Leu Pro Ser Ser Ile Glu
                        325                 330                 335

Lys Thr Ile Ser Lys Ala Lys Gly Gln Pro Arg Glu Pro Gln Val Tyr
                        340                 345                 350

Thr Leu Pro Pro Ser Gln Glu Glu Met Thr Lys Asn Gln Val Ser Leu
                        355                 360                 365

Thr Cys Leu Val Lys Gly Phe Tyr Pro Ser Asp Ile Ala Val Glu Trp
                        370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Arg Leu Thr Val Asp
                        405                 410                 415

Lys Ser Arg Trp Gln Glu Gly Asn Val Phe Ser Cys Ser Val Met His
                        420                 425                 430

Glu Ala Leu His Asn His Tyr Thr Gln Lys Ser Leu Ser Leu Ser Leu
                        435                 440                 445

Gly Lys
            450

<210> SEQ ID NO 102
<211> LENGTH: 453
<212> TYPE: PRT
<213> ORGANISM: Artificial Sequence
```

<220> FEATURE:
<223> OTHER INFORMATION: Synthetic - MAB11; Full length IgG1

<400> SEQUENCE: 102

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Gly Val Leu Ala Leu Asn Lys Arg Ser Phe Asp Ile
        100                 105                 110

Trp Gly Gln Gly Thr Met Val Thr Val Ser Ser Ala Ser Thr Lys Gly
    115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Leu Gly Thr Gln Thr Tyr Ile Cys Asn Val
    195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400
```

```
Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 103
<211> LENGTH: 450
<212> TYPE: PRT
<213> ORGANISM: Artificial Sequence
<220> FEATURE:
<223> OTHER INFORMATION: Synthetic - MAB12; Full length IgG4 S228P

<400> SEQUENCE: 103

Gln Val Gln Leu Gln Glu Ser Gly Pro Gly Leu Val Lys Pro Ser Gln
1               5                   10                  15

Thr Leu Ser Leu Thr Cys Thr Ala Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Ala Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
                435                 440                 445

Gly Lys
    450

<210> SEQ ID NO 104
<211> LENGTH: 453
<212> TYPE: PRT
<213> ORGANISM: Artificial Sequence
<220> FEATURE:
<223> OTHER INFORMATION: Synthetic - MAB12; Full length IgG1

<400> SEQUENCE: 104

Gln Val Gln Leu Gln Glu Ser Gly Pro Gly Leu Val Lys Pro Ser Gln
1               5                   10                  15

Thr Leu Ser Leu Thr Cys Thr Ala Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Ala Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

```
Asn His Lys Pro Ser Asn Thr Lys Val Asp Lys Arg Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 105
<211> LENGTH: 448
<212> TYPE: PRT
<213> ORGANISM: Artificial Sequence
<220> FEATURE:
<223> OTHER INFORMATION: Synthetic - MAB13; Full length IgG4 S228P

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Leu Gly Leu Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
            100                 105                 110
```

Gln Gly Thr Met Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 106
<211> LENGTH: 451
<212> TYPE: PRT
<213> ORGANISM: Artificial Sequence
<220> FEATURE:
<223> OTHER INFORMATION: Synthetic - MAB13; Full length IgG1

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
            20                  25                  30

-continued

```
Tyr Met His Trp Val Arg Gln Ala Pro Gly Gln Gly Leu Glu Trp Met
         35                  40                  45
Gly Ile Ile Asn Pro Ser Leu Gly Leu Thr Ser Tyr Ala Gln Lys Phe
 50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Gly Gly Arg Thr Thr Trp Ile Gly Ala Phe Asp Ile Trp Gly
                100                 105                 110
Gln Gly Thr Met Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
```

Pro Gly Lys
    450

<210> SEQ ID NO 107
<211> LENGTH: 215
<212> TYPE: PRT
<213> ORGANISM: Artificial Sequence
<220> FEATURE:
<223> OTHER INFORMATION: Synthetic - MAB13, MAB14, MAB15, MAB16, MAB17,
      MAB18; Full length Kappa

<400> SEQUENCE: 107

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Val Val Trp Pro Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 108
<211> LENGTH: 448
<212> TYPE: PRT
<213> ORGANISM: Artificial Sequence
<220> FEATURE:
<223> OTHER INFORMATION: Synthetic - MAB14; Full length IgG4 S228P

<400> SEQUENCE: 108

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
            20                  25                  30

Tyr Met His Trp Val Arg Gln Ala Pro Gly Gln Gly Leu Glu Trp Met
        35                  40                  45

Gly Ile Ile Asn Pro Ser Leu Gly Leu Thr Ser Tyr Ala Gln Lys Phe
50                  55                  60

Gln Gly Arg Val Thr Met Thr Arg Asp Thr Ser Thr Ser Thr Val Tyr

```
              65                  70                  75                  80
Met Glu Leu Ser Ser Leu Arg Ser Glu Asp Thr Ala Val Tyr Tyr Cys
                    85                  90                  95

Ala Arg Gly Gly Arg Thr Thr Trp Ile Gly Ala Phe Asp Ile Trp Gly
                100                 105                 110

Gln Gly Thr Met Val Thr Val Ser Ser Ala Ser Thr Lys Gly Pro Ser
                115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
                195                 200                 205

Lys Pro Ser Asn Thr Lys Val Asp Lys Arg Val Glu Ser Lys Tyr Gly
                210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445

<210> SEQ ID NO 109
<211> LENGTH: 451
<212> TYPE: PRT
<213> ORGANISM: Artificial Sequence
<220> FEATURE:
<223> OTHER INFORMATION: Synthetic - MAB14; Full length IgG1
```

<400> SEQUENCE: 109

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
            20                  25                  30

Tyr Met His Trp Val Arg Gln Ala Pro Gly Gln Gly Leu Glu Trp Met
        35                  40                  45

Gly Ile Ile Asn Pro Ser Leu Gly Leu Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
        450

<210> SEQ ID NO 110
<211> LENGTH: 448
<212> TYPE: PRT
<213> ORGANISM: Artificial Sequence
<220> FEATURE:
<223> OTHER INFORMATION: Synthetic - MAB15; Full length IgG4 S228P

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Glu Tyr
            20                  25                  30

Tyr Met His Trp Val Arg Gln Ala Pro Gly Gln Gly Leu Glu Trp Met
        35                  40                  45

Gly Ile Ile Asn Pro Ser Ile Gly Leu Thr Ser Tyr Ala Arg Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445

<210> SEQ ID NO 111
<211> LENGTH: 451
<212> TYPE: PRT
<213> ORGANISM: Artificial Sequence
<220> FEATURE:
<223> OTHER INFORMATION: Synthetic - MAB15; Full length IgG1

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Glu Tyr
                20                  25                  30

Tyr Met His Trp Val Arg Gln Ala Pro Gly Gln Gly Leu Glu Trp Met
                35                  40                  45

Gly Ile Ile Asn Pro Ser Ile Gly Leu Thr Ser Tyr Ala Arg Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
                100                 105                 110

Gln Gly Thr Met Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
                210                 215                 220

Asp Lys Thr His Thr Cys Pro Pro Cys Pro Ala Pro Glu Leu Leu Gly
225                 230                 235                 240
```

```
Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 112
<211> LENGTH: 448
<212> TYPE: PRT
<213> ORGANISM: Artificial Sequence
<220> FEATURE:
<223> OTHER INFORMATION: Synthetic - MAB16; Full length IgG4 S228P

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Glu Tyr
            20                  25                  30

Tyr Met His Trp Val Arg Gln Ala Pro Gly Gln Gly Leu Glu Trp Met
            35                  40                  45

Gly Ile Ile Asn Pro Ser Ile Gly Leu Thr Ser Tyr Ala Arg Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Leu Asp Ile Trp Gly
            100                 105                 110

Gln Gly Thr Met Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
            130                 135                 140
```

-continued

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Thr Val
        180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly Lys
        435                 440                 445

<210> SEQ ID NO 113
<211> LENGTH: 451
<212> TYPE: PRT
<213> ORGANISM: Artificial Sequence
<220> FEATURE:
<223> OTHER INFORMATION: Synthetic - MAB16; Full length IgG1

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Glu Tyr
            20                  25                  30

Tyr Met His Trp Val Arg Gln Ala Pro Gly Gln Gly Leu Glu Trp Met
        35                  40                  45

Gly Ile Ile Asn Pro Ser Ile Gly Leu Thr Ser Tyr Ala Arg Lys Phe
    50                  55                  60
```

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Gly Gly Arg Thr Thr Trp Ile Gly Ala Leu Asp Ile Trp Gly
        100                 105                 110

Gln Gly Thr Met Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 114
<211> LENGTH: 448

<212> TYPE: PRT
<213> ORGANISM: Artificial Sequence
<220> FEATURE:
<223> OTHER INFORMATION: Synthetic - MAB17; Full length IgG4 S228P

<400> SEQUENCE: 114

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
            20                  25                  30

Tyr Ile His Trp Val Arg Gln Ala Pro Gly Gln Gly Leu Glu Trp Met
        35                  40                  45

Gly Ile Ile Asn Pro Ser Leu Gly Leu Thr Ser Tyr Ala Arg Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Leu Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380
```

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly Lys
    435                 440                 445
```

<210> SEQ ID NO 115
<211> LENGTH: 451
<212> TYPE: PRT
<213> ORGANISM: Artificial Sequence
<220> FEATURE:
<223> OTHER INFORMATION: Synthetic - MAB17; Full length IgG1

<400> SEQUENCE: 115

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
            20                  25                  30

Tyr Ile His Trp Val Arg Gln Ala Pro Gly Gln Gly Leu Glu Trp Met
        35                  40                  45

Gly Ile Ile Asn Pro Ser Leu Gly Leu Thr Ser Tyr Ala Arg Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Leu Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 116
<211> LENGTH: 448
<212> TYPE: PRT
<213> ORGANISM: Artificial Sequence
<220> FEATURE:
<223> OTHER INFORMATION: Synthetic - MAB18; Full length IgG4 S228P

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
            20                  25                  30

Tyr Met His Trp Val Arg Gln Ala Pro Gly Gln Gly Leu Glu Trp Met
        35                  40                  45

Gly Ile Ile Asn Pro Ser Leu Gly Leu Thr Ser Tyr Ala Arg Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205
```

-continued

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Asp Val Ser Gln Glu Asp Pro
        260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 117
<211> LENGTH: 451
<212> TYPE: PRT
<213> ORGANISM: Artificial Sequence
<220> FEATURE:
<223> OTHER INFORMATION: Synthetic - MAB18; Full length IgG1

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
            20                  25                  30

Tyr Met His Trp Val Arg Gln Ala Pro Gly Gln Gly Leu Glu Trp Met
        35                  40                  45

Gly Ile Ile Asn Pro Ser Leu Gly Leu Thr Ser Tyr Ala Arg Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 118
<211> LENGTH: 450
<212> TYPE: PRT
<213> ORGANISM: Artificial Sequence
<220> FEATURE:
<223> OTHER INFORMATION: Synthetic - MAB19; Full length IgG4 S228P

<400> SEQUENCE: 118

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

```
Tyr Met Gly Trp Val Arg Gln Ala Pro Gly Gln Gly Leu Glu Trp Met
     35                  40                  45
Gly Val Ile Asn Pro Ser Met Gly Ala Thr Ser Tyr Ala Gln Lys Phe
 50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Leu His Val Ser Gly Ser Tyr Tyr Pro Ala Tyr Leu Asp Tyr
             100                 105                 110
Trp Gly Gln Gly Thr Met Val Thr Val Ser Ser Ala Ser Thr Lys Gly
         115                 120                 125
Pro Ser Val Phe Pro Leu Ala Pro Cys Ser Arg Ser Thr Ser Glu Ser
130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Lys Thr Tyr Thr Cys Asn Val
        195                 200                 205
Asp His Lys Pro Ser Asn Thr Lys Val Asp Lys Arg Val Glu Ser Lys
    210                 215                 220
Tyr Gly Pro Pro Cys Pro Pro Cys Pro Ala Pro Glu Phe Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser Gln Glu
            260                 265                 270
Asp Pro Glu Val Gln Phe Asn Trp Tyr Val Asp Gly Val Glu Val His
        275                 280                 285
Asn Ala Lys Thr Lys Pro Arg Glu Glu Gln Phe Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Gln Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
            420                 425                 430
Glu Ala Leu His Asn His Tyr Thr Gln Lys Ser Leu Ser Leu Ser Leu
        435                 440                 445
Gly Lys
```

<210> SEQ ID NO 119
<211> LENGTH: 453
<212> TYPE: PRT
<213> ORGANISM: Artificial Sequence
<220> FEATURE:
<223> OTHER INFORMATION: Synthetic - MAB19; Full length IgG1

<400> SEQUENCE: 119

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met Gly Trp Val Arg Gln Ala Pro Gly Gln Gly Leu Glu Trp Met
        35                  40                  45

Gly Val Ile Asn Pro Ser Met Gly Ala Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
```

```
            355                 360                 365
Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 120
<211> LENGTH: 214
<212> TYPE: PRT
<213> ORGANISM: Artificial Sequence
<220> FEATURE:
<223> OTHER INFORMATION: Synthetic - MAB19, MAB20, MAB21; Full length
      Kappa

<400> SEQUENCE: 120

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro His Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ile Val Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 121
<211> LENGTH: 450
<212> TYPE: PRT
<213> ORGANISM: Artificial Sequence
<220> FEATURE:
```

<223> OTHER INFORMATION: Synthetic - MAB20; Full length IgG4 S228P

<400> SEQUENCE: 121

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met Gly Trp Val Arg Gln Ala Pro Gly Gln Gly Leu Glu Trp Val
        35                  40                  45

Gly Ile Ile Asn Pro Ser Met Gly Ala Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
            100                 105                 110

Trp Gly Gln Gly Thr Met Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

Leu Asp Ser Asp Gly Ser Phe Phe Leu Tyr Ser Arg Leu Thr Val Asp
        405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
        435                 440                 445

Gly Lys
    450

<210> SEQ ID NO 122
<211> LENGTH: 453
<212> TYPE: PRT
<213> ORGANISM: Artificial Sequence
<220> FEATURE:
<223> OTHER INFORMATION: Synthetic - MAB20; Full length IgG1

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met Gly Trp Val Arg Gln Ala Pro Gly Gln Gly Leu Glu Trp Val
        35                  40                  45

Gly Ile Ile Asn Pro Ser Met Gly Ala Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 123
<211> LENGTH: 450
<212> TYPE: PRT
<213> ORGANISM: Artificial Sequence
<220> FEATURE:
<223> OTHER INFORMATION: Synthetic - MAB21; Full length IgG4 S228P

<400> SEQUENCE: 123

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met Gly Trp Val Arg Gln Ala Pro Gly Gln Gly Leu Glu Trp Met
        35                  40                  45

Gly Ile Ile Asn Pro Ser Met Gly Ala Thr Ser Tyr Thr Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
            100                 105                 110

Trp Gly Gln Gly Thr Met Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205
```

```
Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
    450

<210> SEQ ID NO 124
<211> LENGTH: 453
<212> TYPE: PRT
<213> ORGANISM: Artificial Sequence
<220> FEATURE:
<223> OTHER INFORMATION: Synthetic - MAB21; Full length IgG1

<400> SEQUENCE: 124

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Tyr Met Gly Trp Val Arg Gln Ala Pro Gly Gln Gly Leu Glu Trp Met
            35                  40                  45

Gly Ile Ile Asn Pro Ser Met Gly Ala Thr Ser Tyr Thr Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
                100                 105                 110
```

Trp Gly Gln Gly Thr Met Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 125
<211> LENGTH: 330
<212> TYPE: PRT
<213> ORGANISM: Artificial Sequence
<220> FEATURE:
<223> OTHER INFORMATION: Synthetic - IgG1; Constant (G1m(17,1) allotype,
      N297A

<400> SEQUENCE: 125

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
         20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 126
<211> LENGTH: 107
<212> TYPE: PRT
<213> ORGANISM: Artificial Sequence
<220> FEATURE:
<223> OTHER INFORMATION: Synthetic - Kappa; Constant

<400> SEQUENCE: 126

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

```
Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 127
<211> LENGTH: 5
<212> TYPE: PRT
<213> ORGANISM: Artificial Sequence
<220> FEATURE:
<223> OTHER INFORMATION: Synthetic - Linker

<400> SEQUENCE: 127

Gly Gly Gly Gly Ser
1               5

<210> SEQ ID NO 128
<211> LENGTH: 15
<212> TYPE: PRT
<213> ORGANISM: Artificial Sequence
<220> FEATURE:
<223> OTHER INFORMATION: Synthetic - CDR-H3
<220> FEATURE:
<221> NAME/KEY: misc_feature
<222> LOCATION: (7)..(7)
<223> OTHER INFORMATION: Xaa is Ala or Thr

<400> SEQUENCE: 128

Ala Arg Asp Gly Val Leu Xaa Leu Asn Lys Arg Ser Phe Asp Ile
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Synthetic - CDR-H2
<220> FEATURE:
<221> NAME/KEY: misc_feature
<222> LOCATION: (7)..(7)
<223> OTHER INFORMATION: Xaa is Ser, Gln or Gly

<400> SEQUENCE: 129

Ser Ile Tyr Tyr Ser Gly Xaa Thr Tyr Tyr Asn Pro Ser Leu Lys Ser
1               5                   10                  15

<210> SEQ ID NO 130
<211> LENGTH: 11
<212> TYPE: PRT
<213> ORGANISM: Artificial Sequence
<220> FEATURE:
<223> OTHER INFORMATION: Synthetic - CDR-H1
<220> FEATURE:
<221> NAME/KEY: misc_feature
<222> LOCATION: (4)..(4)
<223> OTHER INFORMATION: Xaa is Glu or Ala
<220> FEATURE:
<221> NAME/KEY: misc_feature
<222> LOCATION: (7)..(7)
<223> OTHER INFORMATION: Xaa is Leu , Val or Ser

<400> SEQUENCE: 130

Gly Ser Ile Xaa Ser Gly Xaa Tyr Tyr Trp Gly
```

```
<210> SEQ ID NO 131
<211> LENGTH: 15
<212> TYPE: PRT
<213> ORGANISM: Artificial Sequence
<220> FEATURE:
<223> OTHER INFORMATION: Synthetic - CDR-H3
<220> FEATURE:
<221> NAME/KEY: misc_feature
<222> LOCATION: (9)..(9)
<223> OTHER INFORMATION: Xaa is Ser or Gly

<400> SEQUENCE: 131

Ala Arg Asp Ala Asn Tyr Tyr Gly Xaa Ala Trp Ala Phe Asp Pro
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Synthetic - CDR-H2
<220> FEATURE:
<221> NAME/KEY: misc_feature
<222> LOCATION: (7)..(7)
<223> OTHER INFORMATION: Xaa is Ser or Ala
<220> FEATURE:
<221> NAME/KEY: misc_feature
<222> LOCATION: (16)..(16)
<223> OTHER INFORMATION: Xaa is Ser or Gly

<400> SEQUENCE: 132

Ser Ile Tyr Tyr Ser Gly Xaa Thr Phe Tyr Asn Pro Ser Leu Lys Xaa
1               5                   10                  15

<210> SEQ ID NO 133
<211> LENGTH: 11
<212> TYPE: PRT
<213> ORGANISM: Artificial Sequence
<220> FEATURE:
<223> OTHER INFORMATION: Synthetic - CDR-H1
<220> FEATURE:
<221> NAME/KEY: misc_feature
<222> LOCATION: (4)..(4)
<223> OTHER INFORMATION: Xaa is Ser or Thr
<220> FEATURE:
<221> NAME/KEY: misc_feature
<222> LOCATION: (6)..(6)
<223> OTHER INFORMATION: Xaa is Ser or Thr
<220> FEATURE:
<221> NAME/KEY: misc_feature
<222> LOCATION: (7)..(7)
<223> OTHER INFORMATION: Xaa is Ser or Lys
<220> FEATURE:
<221> NAME/KEY: misc_feature
<222> LOCATION: (8)..(8)
<223> OTHER INFORMATION: Xaa is His or Tyr

<400> SEQUENCE: 133

Gly Ser Ile Xaa Ser Xaa Xaa Xaa Tyr Trp Gly
1               5                   10

<210> SEQ ID NO 134
<211> LENGTH: 14
<212> TYPE: PRT
<213> ORGANISM: Artificial Sequence
<220> FEATURE:
<223> OTHER INFORMATION: Synthetic - CDR-H3
<220> FEATURE:
<221> NAME/KEY: misc_feature
<222> LOCATION: (12)..(12)
```

```
<223> OTHER INFORMATION: Xaa is Phe or Leu

<400> SEQUENCE: 134

Ala Arg Gly Gly Arg Thr Thr Trp Ile Gly Ala Xaa Asp Ile
1               5                   10

<210> SEQ ID NO 135
<211> LENGTH: 17
<212> TYPE: PRT
<213> ORGANISM: Artificial Sequence
<220> FEATURE:
<223> OTHER INFORMATION: Synthetic - CDR-H2
<220> FEATURE:
<221> NAME/KEY: misc_feature
<222> LOCATION: (6)..(6)
<223> OTHER INFORMATION: Xaa is Leu or Ile
<220> FEATURE:
<221> NAME/KEY: misc_feature
<222> LOCATION: (13)..(13)
<223> OTHER INFORMATION: Xaa is Gln or Arg

<400> SEQUENCE: 135

Ile Ile Asn Pro Ser Xaa Gly Leu Thr Ser Tyr Ala Xaa Lys Phe Gln
1               5                   10                  15

Gly

<210> SEQ ID NO 136
<211> LENGTH: 9
<212> TYPE: PRT
<213> ORGANISM: Artificial Sequence
<220> FEATURE:
<223> OTHER INFORMATION: Synthetic - CDR-H1
<220> FEATURE:
<221> NAME/KEY: misc_feature
<222> LOCATION: (4)..(4)
<223> OTHER INFORMATION: Xaa is Gly , Pro or Arg
<220> FEATURE:
<221> NAME/KEY: misc_feature
<222> LOCATION: (5)..(5)
<223> OTHER INFORMATION: Xaa is is Asn, Ala or Glu
<220> FEATURE:
<221> NAME/KEY: misc_feature
<222> LOCATION: (8)..(8)
<223> OTHER INFORMATION: Xaa is Met or Ile

<400> SEQUENCE: 136

Tyr Thr Phe Xaa Xaa Tyr Tyr Xaa His
1               5

<210> SEQ ID NO 137
<211> LENGTH: 17
<212> TYPE: PRT
<213> ORGANISM: Artificial Sequence
<220> FEATURE:
<223> OTHER INFORMATION: Synthetic - CDR-H2
<220> FEATURE:
<221> NAME/KEY: misc_feature
<222> LOCATION: (1)..(1)
<223> OTHER INFORMATION: Xaa is Val or Ile
<220> FEATURE:
<221> NAME/KEY: misc_feature
<222> LOCATION: (12)..(12)
<223> OTHER INFORMATION: Xaa is Ala or Thr
<220> FEATURE:
<221> NAME/KEY: misc_feature
<222> LOCATION: (16)..(16)
<223> OTHER INFORMATION: Xaa Gln or Arg

<400> SEQUENCE: 137

Xaa Ile Asn Pro Ser Met Gly Ala Thr Ser Tyr Xaa Gln Lys Phe Xaa
1               5                   10                  15
```

Gly

<210> SEQ ID NO 138
<211> LENGTH: 249
<212> TYPE: PRT
<213> ORGANISM: Mus musculus
<220> FEATURE:
<221> NAME/KEY: misc_feature
<223> OTHER INFORMATION: mTIGIT2

<400> SEQUENCE: 138

```
Met His Gly Trp Leu Leu Val Trp Val Gln Gly Leu Ile Gln Ala
1               5                   10                  15

Ala Phe Leu Ala Thr Ala Ile Gly Ala Thr Ala Gly Thr Ile Asp Thr
                20                  25                  30

Lys Arg Asn Ile Ser Ala Glu Glu Gly Gly Ser Val Ile Leu Gln Cys
                35                  40                  45

His Phe Ser Ser Asp Thr Ala Glu Val Thr Gln Val Asp Trp Lys Gln
            50                  55                  60

Gln Asp Gln Leu Leu Ala Ile Tyr Ser Val Asp Leu Gly Trp His Val
65                  70                  75                  80

Ala Ser Val Phe Ser Asp Arg Val Val Pro Gly Pro Ser Leu Gly Leu
                    85                  90                  95

Thr Phe Gln Ser Leu Thr Met Asn Asp Thr Gly Glu Tyr Phe Cys Thr
                100                 105                 110

Tyr His Thr Tyr Pro Gly Gly Ile Tyr Lys Gly Arg Ile Phe Leu Lys
            115                 120                 125

Val Gln Glu Ser Ser Asp Asp Arg Asn Gly Leu Ala Gln Phe Gln Thr
130                 135                 140

Ala Pro Leu Gly Gly Thr Met Ala Ala Val Leu Gly Leu Ile Cys Leu
145                 150                 155                 160

Met Val Thr Gly Val Thr Val Leu Ala Arg Lys Asp Lys Ser Ile Arg
                165                 170                 175

Met His Ser Ile Glu Ser Gly Leu Gly Arg Thr Glu Ala Glu Pro Gln
                180                 185                 190

Glu Trp Asn Leu Arg Ser Leu Ser Ser Pro Gly Ser Pro Val Gln Thr
            195                 200                 205

Gln Thr Ala Pro Ala Gly Pro Cys Gly Glu Gln Ala Glu Asp Tyr
        210                 215                 220

Ala Asp Pro Gln Glu Tyr Phe Asn Val Leu Ser Tyr Arg Ser Leu Glu
225                 230                 235                 240

Ser Phe Ile Ala Val Ser Lys Thr Gly
                245
```

<210> SEQ ID NO 139
<211> LENGTH: 120
<212> TYPE: PRT
<213> ORGANISM: Homo sapiens

<400> SEQUENCE: 139

```
Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
                20                  25                  30

Val Thr Gln Val Asn Trp Glu Gln Gln Asp Gln Leu Leu Ala Ile Cys
                35                  40                  45
```

Asn Ala Asp Leu Gly Trp His Ile Ser Pro Ser Phe Lys Asp Arg Val
 50                  55                  60

Ala Pro Gly Pro Gly Leu Gly Leu Thr Leu Gln Ser Leu Thr Val Asn
 65                  70                  75                  80

Asp Thr Gly Glu Tyr Phe Cys Ile Tyr His Thr Tyr Pro Asp Gly Thr
                 85                  90                  95

Tyr Thr Gly Arg Ile Phe Leu Glu Val Leu Glu Ser Ser Val Ala Glu
                100                 105                 110

His Gly Ala Arg Phe Gln Ile Pro
            115                 120

<210> SEQ ID NO 140
<211> LENGTH: 121
<212> TYPE: PRT
<213> ORGANISM: Macaca fascicularis

<400> SEQUENCE: 140

Met Met Thr Gly Thr Ile Glu Thr Thr Gly Asn Ile Ser Ala Lys Lys
 1               5                  10                  15

Gly Gly Ser Val Ile Leu Gln Cys His Leu Ser Ser Thr Met Ala Gln
                 20                  25                  30

Val Thr Gln Val Asn Trp Glu Gln Gln Asp His Ser Leu Leu Ala Ile
             35                  40                  45

Arg Asn Ala Glu Leu Gly Trp His Ile Tyr Pro Ala Phe Lys Asp Arg
 50                  55                  60

Val Ala Pro Gly Pro Gly Leu Gly Leu Thr Leu Gln Ser Leu Thr Met
 65                  70                  75                  80

Asn Asp Thr Gly Glu Tyr Phe Cys Thr Tyr His Thr Tyr Pro Asp Gly
                 85                  90                  95

Thr Tyr Arg Gly Arg Ile Phe Leu Glu Val Leu Glu Ser Ser Val Ala
                100                 105                 110

Glu His Ser Ala Arg Phe Gln Ile Pro
            115                 120

<210> SEQ ID NO 141
<211> LENGTH: 121
<212> TYPE: PRT
<213> ORGANISM: Rattus norvegicus

<400> SEQUENCE: 141

Ala Phe Leu Ala Gly Ala Thr Ala Gly Thr Met Glu Thr Lys Gly
 1               5                  10                  15

Asn Ile Ser Ala Glu Glu Gly Gly Ser Val Val Leu Gln Cys His Phe
                 20                  25                  30

Ser Ser Asp Thr Ala Glu Val Thr Gln Val Asn Trp Glu Gln Arg Asp
             35                  40                  45

Gln Leu Leu Ala Val Tyr Ser Val Asp Leu Gly Trp Tyr Val Pro Ser
 50                  55                  60

Val Phe Ser Asp Arg Val Val Pro Gly Pro Ser Leu Gly Leu Thr Phe
 65                  70                  75                  80

Gln Ser Leu Thr Thr Asn Asp Thr Gly Glu Tyr Phe Cys Thr Tyr His
                 85                  90                  95

Thr Tyr Pro Gly Gly Ile Tyr Lys Gly Arg Ile Phe Leu Lys Val Gln
                100                 105                 110

Glu Ser Ser Ala His Phe Gln Ile Ala
            115                 120

<210> SEQ ID NO 142
<211> LENGTH: 318
<212> TYPE: PRT
<213> ORGANISM: Homo sapiens

<400> SEQUENCE: 142

```
Gly Glu Leu Glu Thr Ser Asp Val Val Thr Val Val Leu Gly Gln Asp
1               5                   10                  15

Ala Lys Leu Pro Cys Phe Tyr Arg Gly Asp Ser Gly Glu Gln Val Gly
            20                  25                  30

Gln Val Ala Trp Ala Arg Val Asp Ala Gly Glu Gly Ala Gln Glu Leu
        35                  40                  45

Ala Leu Leu His Ser Lys Tyr Gly Leu His Val Ser Pro Ala Tyr Glu
    50                  55                  60

Gly Arg Val Glu Gln Pro Pro Pro Arg Asn Pro Leu Asp Gly Ser
65                  70                  75                  80

Val Leu Leu Arg Asn Ala Val Gln Ala Asp Glu Gly Glu Tyr Glu Cys
                85                  90                  95

Arg Val Ser Thr Phe Pro Ala Gly Ser Phe Gln Ala Arg Leu Arg Leu
            100                 105                 110

Arg Val Leu Val Pro Pro Leu Pro Ser Leu Asn Pro Gly Pro Ala Leu
            115                 120                 125

Glu Glu Gly Gln Gly Leu Thr Leu Ala Ala Ser Cys Thr Ala Glu Gly
    130                 135                 140

Ser Pro Ala Pro Ser Val Thr Trp Asp Thr Glu Val Lys Gly Thr Thr
145                 150                 155                 160

Ser Ser Arg Ser Phe Lys His Ser Arg Ser Ala Ala Val Thr Ser Glu
                165                 170                 175

Phe His Leu Val Pro Ser Arg Ser Met Asn Gly Gln Pro Leu Thr Cys
            180                 185                 190

Val Val Ser His Pro Gly Leu Leu Gln Asp Gln Arg Ile Thr His Ile
            195                 200                 205

Leu His Val Ser Phe Leu Ala Glu Ala Ser Val Arg Gly Leu Glu Asp
    210                 215                 220

Gln Asn Leu Trp His Ile Gly Arg Glu Gly Ala Met Leu Lys Cys Leu
225                 230                 235                 240

Ser Glu Gly Gln Pro Pro Pro Ser Tyr Asn Trp Thr Arg Leu Asp Gly
                245                 250                 255

Pro Leu Pro Ser Gly Val Arg Val Asp Gly Asp Thr Leu Gly Phe Pro
            260                 265                 270

Pro Leu Thr Thr Glu His Ser Gly Ile Tyr Val Cys His Val Ser Asn
            275                 280                 285

Glu Phe Ser Ser Arg Asp Ser Gln Val Thr Val Asp Val Leu Asp Pro
    290                 295                 300

Gln Glu Asp Ser Gly Lys Gln Val Asp Leu Val Ser Ala Ser
305                 310                 315
```